United States Patent [19]

Kim

[11] Patent Number: 4,644,061

[45] Date of Patent: Feb. 17, 1987

[54] CARBAPENEM ANTIBIOTICS

[75] Inventor: Choung U. Kim, Manlius, N.Y.

[73] Assignee: Bristol-Myers Company, New York, N.Y.

[21] Appl. No.: 705,780

[22] Filed: Feb. 22, 1985

Related U.S. Application Data

[63] Continuation-in-part of Ser. No. 530,011, Sep. 9, 1983, abandoned, which is a continuation-in-part of Ser. No. 425,755, Sep. 28, 1982, abandoned.

[51] Int. Cl.$^4$ .................... C07D 487/04; A61K 31/40
[52] U.S. Cl. .................................... 540/350; 540/302
[58] Field of Search ................. 260/245.2 T; 514/210; 540/302, 350

[56] References Cited

U.S. PATENT DOCUMENTS 4,552,873 11/1985 Miyadera et al. ............ 260/245.2 T Primary Examiner—Nicholas S. Rizzo
Attorney, Agent, or Firm—David M. Morse

[57] ABSTRACT

Disclosed are novel carbapenem derivatives characterized by a 2-substituent of the formula

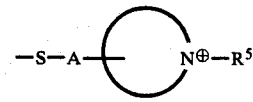

in which A represents a $C_1$–$C_6$ straight or branched chain alkylene group; $R^5$ represents an optionally substituted aliphatic, cycloaliphatic, cycloaliphatic-aliphatic, aryl, araliphatic, heteroaryl, heteroaraliphatic, heterocyclyl or heterocyclyl-aliphatic radial and

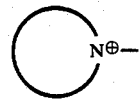

represents a nitrogen-containing aromatic heterocycle attached to the alkylene group A at a ring carbon atom and quaternized by substituent $R^5$. Such derivatives are useful as potent antibacterial agents.

58 Claims, No Drawings

CARBAPENEM ANTIBIOTICS

CROSS-REFERENCE TO RELATED APPLICATIONS

This application is a continuation-in-part of my copending application Ser. No. 530,011 filed Sept. 9, 1983 which in turn was a continuation-in-part of application Ser. No. 425,755 filed Sept. 28, 1982, both now abandoned.

BACKGROUND OF THE INVENTION

1. Field of the Invention

The present invention is directed to new carbapenem antibiotics in which the 2-substituent has the formula

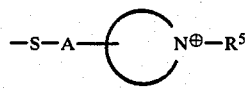

in which A represents a $C_1$-$C_6$ straight or branched chain alkylene group; $R^5$ represents an optionally substituted aliphatic, cycloaliphatic, cycloaliphatic-aliphatic, aryl, araliphatic, heteroaryl, heteroaraliphatic, heterocyclyl or heterocyclyl-aliphatic radical; and

represents a nitrogen-containing aromatic heterocycle attached to the alkylene group A at a ring carbon atom and quaternized by substituent $R^5$.

2. Description of the Prior Art

A number of β-lactam derivatives containing the carbapenem nucleus

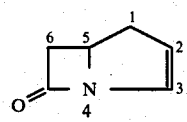

have been disclosed in the literature. These carbapenem derivatives have been reported to possess utility as antibacterial agents and/or β-lactamase inhibitors.

The initial carbapenem compounds were natural products such as thienamycin of the formula

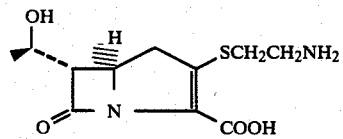

obtained by fermentation of *Streptomyces cattleya* (U.S. Pat. No. 3,950,357). Thienamycin is an exceptionally potent broad-spectrum antibiotic which possesses notable activity against various Pseudomonas species, organisms which have been notoriously resistant to β-lactam antibiotics.

Other natural products containing the carbapenem nucleus include olivanic acid derivatives such as antibiotic MM 13902 of the formula

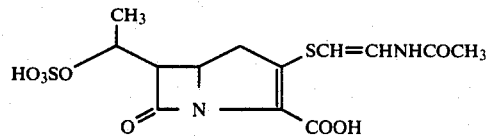

disclosed in U.S. Pat. No. 4,113,856, antibiotic MM 17880 of the formula

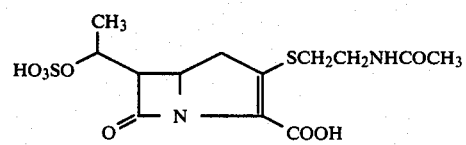

disclosed in U.S. Pat. No. 4,162,304, antibiotic MM 4550A of the formula

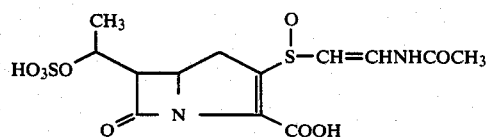

disclosed in U.S. Pat. No. 4,172,129 and antibiotic 890A9 of the formula

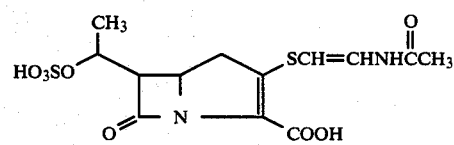

disclosed in U.S. Pat. No. 4,264,735. In addition to the natural products, the compound desacetyl 890A10 of the formula

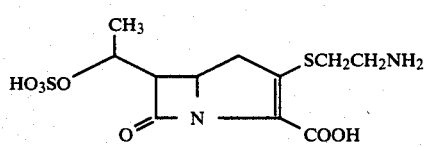

is disclosed in U.S. Pat. No. 4,264,734 as being prepared by an enzymatic deacylation of the corresponding N-acetyl compound. Various derivatives of the naturally-occuring olivanic acids have also been synthesized, e.g. the compounds of the formula

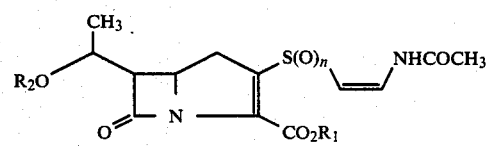

wherein $CO_2R_1$ is a free, salted or esterified carboxyl group, n is 0 or 1 and $R_2$ is H, an acyl group or a group of the formula $R_3O_3S$ wherein $R_3$ is a salting ion or a methyl or ethyl group, disclosed in European Patent Application No. 8885.

U.S. Pat. No. 4,235,922 (see also European Patent Application 2058) discloses the carbapenem derivative of the formula

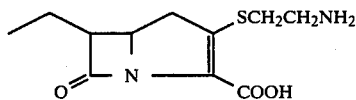

while U.K. Patent Application No. 1,598,062 reports isolation of the compound

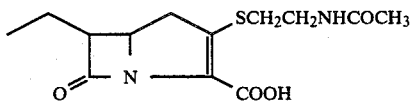

from a Streptomyces fermentation broth.

Carbapenems which are unsubstituted in the 6-position have also been synthesized. Thus, U.S. Pat. No. 4,210,661 discloses compounds of the formula

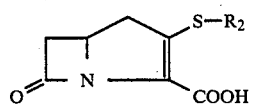

wherein $R_2$ is phenyl or substituted phenyl, U.S. Pat. No. 4,267,177 discloses compounds of the formula

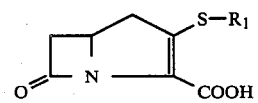

wherein $R_1$ is an optionally substituted pyridyl group, U.S. Pat. No. 4,255,441 discloses compounds of the formula

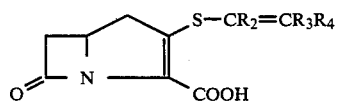

wherein $R_2$ and $R_3$ are H or alkyl and $R_4$ is $NH\text{-}CO_nR_6$ in which $R_6$ is alkyl, phenyl or substituted phenyl and n is 1 or 2, and U.S. Pat. No. 4,282,236 discloses compounds of the formula

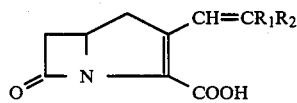

wherein $R_1$ is H or alkyl and $R_2$ is CN or $CO_2R_3$ in which $R_3$ is H, alkyl, aryl or aralkyl.

Carbapenems of the general formula

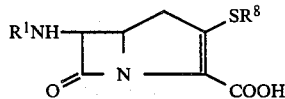

wherein $R^1$ is H or acyl and $R^8$ is H or substituted or unsubstituted: alkyl, alkenyl, alkynyl, cycloalkyl, cycloalkylalkyl, alkylcycloalkyl, aryl, aralkyl, aralkenyl, aralkynyl, heteroaryl, heteroaralkyl, heterocyclyl or heterocyclyalkyl, are disclosed in U.S. Pat. No. 4,218,463. There is no disclosure of any heteroaralkyl $R^8$ substituents of the type

in which A is alkylene and

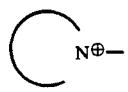

is a quaternized nitrogen-containing aromatic heterocycle attached to the alkylene group A at a ring carbon atom.

The natural product thienamycin has the absolute configuration 5R, 6S, 8R. This isomer, as well as the remaining seven thienamycin isomers, may be obtained via total synthesis as disclosed in U.S. Pat. No. 4,234,596. Total synthesis procedures for thienamycin are also disclosed, for example, in U.S. Pat. Nos. 4,287,123, 4,269,772, 4,282,148, 4,273,709, 4,290,947 and European Patent Application No. 7973. A key intermediate in the disclosed synthetic methods is

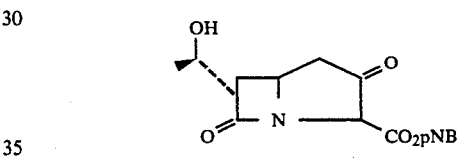

wherein pNB represents p-nitrobenzyl.

Because of the exceptional biological activity of thienamycin, a large number of derivatives have been prepared and disclosed in the literature. Among these are (1) N-formimidoyl thienamycin of the formula

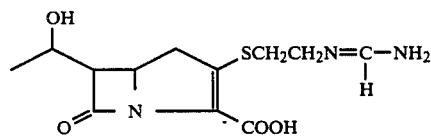

disclosed in European Patent Application No. 6639; (2) N-heterocyclic derivatives of thienamycin having the formula

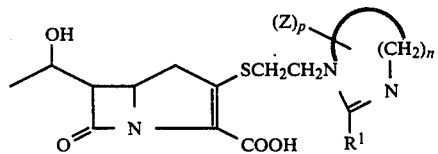

and

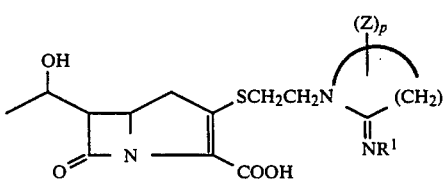

wherein: the bifunctional ring may contain additional unsaturation in the ring; and wherein n is an integer selected from 1-6; p is 0, 1 or 2; $R^1$ is H, alkyl or aryl; and Z is imino, oxo, H, amino or alkyl, disclosed in U.S. Pat. No. 4,189,493; (3) substituted N-methylene derivatives of thienamycin having the formula

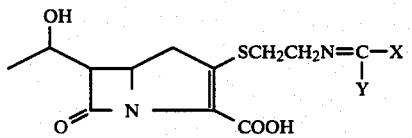

wherein X and Y are H, R, OR, SR or $NR^1R^2$ in which R is substituted or unsubstituted: alkyl, alkenyl, alkynyl, cycloalkyl, cycloalkylalkyl, aryl, aralkyl, heteroaryl, heteroaralkyl, heterocyclyl or heterocyclylalkyl, and $R^1$ and $R^2$ are H or R, disclosed in U.S. Pat. No. 4,194,047; (4) compounds of the formula

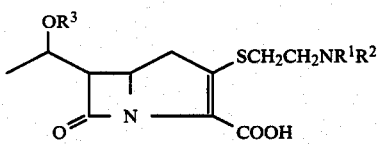

wherein $R^3$ is aryl, alkyl, acyl or aralkyl and $R^1$ and $R^2$ are independently selected from H and acyl (including acyl of the type

in which $R^{11}$ may inter alia be alkyl substituted by a quaternary ammonium group, e.g.

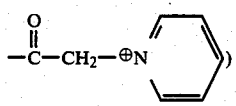

disclosed in U.S. Pat.No. 4,226,870; (5) compounds of the formula

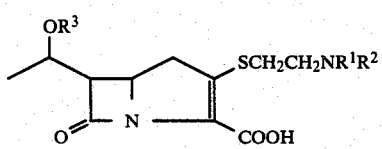

wherein $R^3$ is H, acyl or an univalent optionally substituted hydrocarbon radical; $R^1$ is optionally substituted alkyl, alkenyl, alkynyl, cycloalkyl, cycloalkenyl, cycloalkenylalkyl, cycloalkylalkyl, aryl, aralkyl, heteroaryl or heteroaralkyl and $R^2$ is acyl (including acyl of the type

in which R is alkyl substituted by a quaternary ammonium group, e.g.

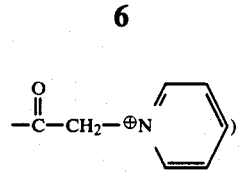

disclosed in U.K. Pat. No. 1,604,276 (see also U.S. Pat. No. 4,235,917); (6) compounds of the formula

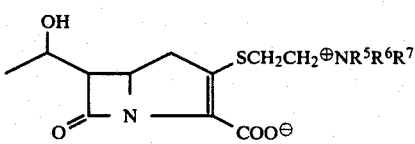

wherein $R^5$, $R^6$ and $R^7$ are independently selected from H and substituted or unsubstituted: alkyl, alkenyl, alkynyl, cycloalkyl, cycloalkenyl, cycloalkenylalkyl, cycloalkylalkyl, aryl, aralkyl, heteroaryl or heteroaralkyl, are disclosed in U.S. Pat. No. 4,235,920; (7) compounds of the formula

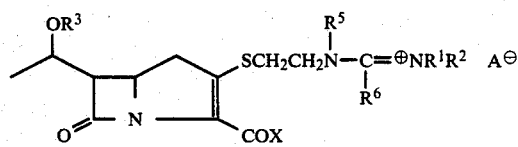

wherein each of $R^1$ and $R^2$, independently of the other, is a radical of the type defined for R, a hydrogen atom, or a nitro, hydroxyl, $C_{1-6}$ alkoxyl, amino, $C_{1-6}$ alkylamino, di($C_{1-6}$ alkyl)amino or tri($C_{1-6}$ alkylamino) radical, an extra anion being present in the latter case; or $R^1$ and $R^2$ are joined together to form, together with the nitrogen atom to which they are attached, a substituted or unsubstituted monocyclic or bicyclic heteroaryl or heterocyclyl residue containing 4–10 ring atoms, one or more of which may be an additional hetero atom selected from oxygen, sulphur and nitrogen; R is a cyano group or a substituted or unsubstituted carbamoyl, carboxyl, ($C_{1-10}$ alkoxy)carbonyl, $C_{1-10}$ alkyl, $C_{2-10}$ alkenyl, $C_{2-10}$ alkynyl, $C_{3-10}$ cycloalkyl, $C_{4-12}$ cycloalkylalkyl, $C_{5-12}$ cycloalkylalkenyl, $C_{3-10}$ cycloalkenyl, $C_{5-12}$ cycloalkenylalkyl, $C_{4-12}$ cycloalkenylalkyl, $C_{6-10}$ aryl, $C_{7-16}$ aralkyl, $C_{8-16}$ aralkenyl, $C_{8-16}$ aralkynyl or monocyclic or bicyclic heteroaryl, heteroaralkyl, heterocyclyl or heterocyclylalkyl comprising 4 to 10 ring atoms one or more of which is a hetero atom selected from oxygen, sulphur and nitrogen and in which the alkyl residue of the heteroaralkyl or heterocyclylalkyl radical contains from 1 to 6 carbon atoms; the substituent or substituents on R, $R^1$, $R^2$ or on the ring formed by joining $R^1$ and $R^2$ are chlorine; bromine; iodine; fluorine; azido; $C_{1-4}$ alkyl; mercapto; sulpho; phosphono; cyanothio (—SCN); nitro; cyano; amino; hydrazino; amino or hydrazino having up to three $C_{1-6}$ alkyl substituents; hydroxy; $C_{1-6}$ alkoxy; $C_{1-6}$ alkylthio; carboxyl; oxo; ($C_{1-6}$ alkoxy)carbonyl; $C_{2-10}$ acyloxy; carbamoyl; ($C_{1-4}$ alkyl)carbamoyl or di($C_{1-4}$ alkyl)carbamoyl; $R_3$ is a hydrogen atom, an acyl radical or a radical of the type defined for $R^4$; $R^4$ is $C_{1-10}$ alkyl; substituted carbonylmethyl; ($C_{1-6}$ alkoxy)-($C_{1-6}$ alkyl), ($C_{3-6}$ cycloalkoxy)($C_{1-6}$ alkyl); $C_{2-12}$ alkanoyloxyalkyl; partially or completely halogenated $C_{1-6}$ alkyl in which the halogen(s) is/are chlorine, bromine or fluorine; aminoalkyl; $C_{2-10}$ alkenyl; $C_{2-10}$ alkynyl; acyl; $C_{3-14}$ alkoxycarbonylalkyl;

$C_{4-21}$ dialkylaminoacetoxyalkyl; $C_{2-13}$ alkanoylaminoalkyl; ar-($C_{1-3}$ alkyl) in which the aryl residue contains from 6 to 10 carbon atoms; monocyclic or bicyclic heteroaralkyl or heterocyclylalkyl containing 4 to 10 ring atoms, 1 to 3 carbon atoms in the alkyl residue, and 1–4 hetero atoms selected from oxygen, sulphur and/or nitrogen; nuclear-substituted aralkyl or heteroaralkyl in which the substituent is chlorine, fluorine, bromine, iodine or $C_{1-6}$ alkyl; aryl or nuclear-substituted aryl containing 6 to 10 ring carbon atoms and in which any nuclear substituent is hydroxy, $C_{1-6}$ alkyl, chlorine, fluorine or bromine; aralkoxyalkyl; $C_{2-12}$ alkylthioalkyl; $C_{4-12}$ cycloalkylthioalkyl; ($C_{2-10}$ acylthio)-($C_{1-6}$ alkyl); or phenylalkenyl in which alkenyl has 2–6 carbon atoms; $R^5$ is substituted or unsubstituted $C_{1-10}$ alkyl; $C_{2-10}$ alkenyl or alkynyl; ring substituted and unsubstituted cycloalkyl, cycloalkenyl, cycloalkenylalkyl, and cycloalkylalkyl having 3–6 ring carbon atoms and up to 6 carbon atoms in any chain; $C_{6-10}$ aryl; aralkyl having 6–10 ring carbon atoms and 1–6 carbon atoms in the alkyl chain; monocyclic or bicyclic heteroaryl or heteroaralkyl containing 4–10 ring atoms, one or more of which is oxygen, nitrogen or sulphur, and 1–6 carbon atoms in the alkyl chain; and the ring or chain substituent(s) is/are chlorine, bromine, iodine, fluorine, azido, cyano, amino, $C_{1-6}$ alkylamino; di($C_{1-6}$ alkyl)amino or tri($C_{1-6}$ alkylamino) radical, an extra anion being present in the latter case, hydroxy, $C_{1-6}$ alkoxy, $C_{1-6}$ alkylthioalkyl; carboxyl; oxo, ($C_{1-6}$ alkoxy)carbonyl; $C_{2-10}$ acyloxy; carbamoyl; ($C_{1-4}$ alkyl)carbamoyl; di($C_{1-4}$ alkyl)carbamoyl; cyanothio (—SCN) or nitro; $R^6$ is hydrogen, hydroxy, mercapto, R, —OR, —SR or $NR^1R^2$, where R, $R^1$ and $R^2$ are as defined above; X is hydroxy, mercapto, amino, acyloxy —$OR^4$, —$SR^4$, —$NHR^4$, $$-\underset{\underset{R^4}{|}}{N}-R^4,$$

—OM, OQ or, when the compound is in zwitterionic form, —O⁻, in which case A⁻ is absent; A, when the compound is not in zwitterionic form, is a counter ion; M is a pharmaceutically acceptable cation; and Q is a blocking group as herein defined, are disclosed in U.K. Pat. No. 1,604,275; and (8) compounds of the formula

[Structure: β-lactam with OH-CH(CH$_3$)- substituent, SCH$_2$CH$_2$NH— linked to ⊕N-R heterocycle, COO⁻]

wherein

[Structure: ⊕N-R ring]

attached to the amino nitrogen group of thienamycin represents a mono- or polycyclic N-containing heterocyclic group and R is H, substituted or unsubstituted: alkyl, aryl, alkenyl, heterocyclylalkenyl, aralkenyl, heterocyclylalkyl, aralkyl, —$NR_2$, COOR, $CONR_2$, —OR, or CN, are disclosed in European Patent Application No. 21082. Among the compounds disclosed in U.S. Pat. No. 4,235,920 is

[Structure: carbapenem with OH-CH(CH$_3$)- group, SCH$_2$CH$_2$⊕N(CH$_3$)$_3$ A⁻, COOH]

wherein A is a pharmaceutically acceptable anion. The above-mentioned quaternary amine derivative is also described in *Recent Advances in the Chemistry of β-Lactam Antibiotics*, Royal Society of Chemistry, London, 1981, pg 240–254, where its antibacterial activity on average is reported as approximately ½ to ⅔ that of thienamycin.

Carbapenem derivatives having a wide variety of 6-substituents in addition to those mentioned above have also been synthesized. Thus, for example, (1) European Patent Application No. 40408 discloses compounds of the formula

[Structure: carbapenem with $CH_3-CH(R_1)$- group, $SR_{51}$, COOH]

wherein $R_1$ is H, methyl or hydroxyl and $R_{51}$ is a monovalent organic group including inter alia heterocyclicalkyl; (2) European Patent Application No. 8514 discloses compounds of the formula

[Structure: carbapenem with $R_2$- group, S—$R_1$, COOH]

wherein $R_1$ is an optionally substituted pyrimidinyl group and $R_2$ is hydrogen or a group $CR_3R_4R_5$ wherein $R_3$ is hydrogen or hydroxy, $R_4$ is hydrogen or alkyl and $R_5$ is hydrogen, alkyl, benzyl or phenyl, or $R_5$ and $R_4$ together form a carbocyclic ring; (3) European Patent Application No. 38869 discloses compounds of the formula

[Structure: carbapenem with $R^6$, $R^7$ substituents, $SR^8$, COOH]

wherein $R^6$, $R^7$, and $R^8$ are independently selected from the group consisting of hydrogen, substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the aliphatic portion has 1–6 carbon atoms; heteroaryl, heteroaralkyl, heterocyclyl and heterocyclylalkyl; wherein the substituent or substituents relative to the above-named radicals are selected from the group consisting of:

—X° halo (chloro, bromo, fluoro)

—OH hydroxy

—OR$^1$ alkoxy, aryloxy

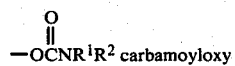  —OCNR$^1$R$^2$ carbamoyloxy

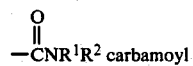  —CNR$^1$R$^2$ carbamoyl

—NR$^1$R$^2$ amino

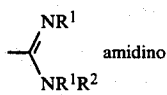 amidino

—NO$_2$ nitro

—N(R$^1$)$_3$$^\oplus$ tri-substituted amino (R$^1$ group independently chosen)

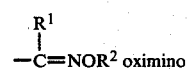  —C=NOR$^2$ oximino

—SR$^1$ alkyl- and arylthio

—SO$_2$NR$^1$R$^2$ sulfonamido

  —NHCNR$^1$R$^2$ ureido

  —R$^1$CNR$^2$— amido

—CO$_2$H carboxy

—CO$_2$R$^1$ carboxylate

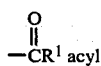  —CR$^1$ acyl

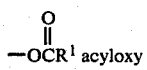  —OCR$^1$ acyloxy

—SH mercapto

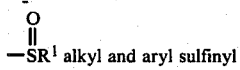  —SR$^1$ alkyl and aryl sulfinyl

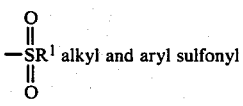  —SR$^1$ alkyl and aryl sulfonyl

—CN cyano
—N$_3$ azido wherein, relative to the above listed substituents on R$^6$, R$^7$, and R$^8$, the groups R$^1$ and R$^2$ are independently selected from: hydrogen, alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the aliphatic portion has 1–6 carbon atoms; heteroaryl, heteroaralkyl, heterocyclyl and heterocyclylalkyl and wherein the hetero atom or atoms in the above-named heterocyclic moieties are selected from the group consisting of 1–4 oxygen, nitrogen or sulphur atoms and wherein the alkyl moieties associated with said heterocyclic moieties have 1–6 carbon atoms. (See also European Patent Application Nos. 1627, 1628, 10317, 17992, 37080, 37081 and 37082); (4) European Patent Application No. 24832 discloses compounds of the formula

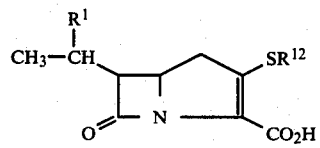

wherein R$^1$ is H or a group selected from OH, OSO$_3$H or a salt or C$_{1-4}$ alkyl ester thereof, OR$^2$, SR$^3$, OCOR$^2$, OCO$_2$R$^3$ or OCONHR$^3$, where R$^2$ is a C$_{1-6}$ alkyl group or an optionally substituted benzyl group and R$^3$ is a C$_{1-6}$ alkyl group or an optionally substituted benzyl or phenyl group and R$^{12}$ is C$_{1-6}$ alkyl, C$_{2-6}$ alkenyl, C$_{3-6}$ alkynyl wherein the triple bond is not present on the carbon adjacent to the sulfur atom, aralkyl, C$_{1-6}$ alkanoyl, aralkanoyl, aryloxyalkanoyl or arylcarbonyl, any of such R$^{12}$ groups being optionally substituted, as antibacterial agents.

European Patent Application No. 44170 discloses carbapenem derivatives of the formula

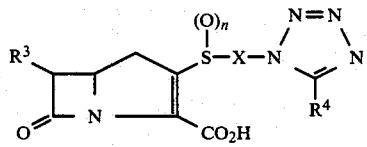

wherein R$^3$ is hydrogen or an organic group bonded via a carbon atom to the carbapenem ring, n is 0 or 1, X is a saturated or unsaturated hydrocarbon radical optionally substituted by bromo or chloro, and R$^4$ is a C$_{1-6}$ alkyl, C$_2$–C$_6$ alkenyl, C$_1$–C$_{10}$ aralkyl or aryl group, any of such groups R$^4$ being optionally substituted. There is no disclosure, however, of any compounds wherein the tetrazole ring is bonded to X via a quaternized nitrogen atom, i.e. a positively charged nitrogen which is not attached to a hydrogen atom.

European Patent Application No. 38,869 mentioned above discloses synthesis of the carbapenem derivatives via intermediates of the general formula

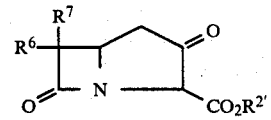

wherein R$^6$ and R$^7$ are as defined above and R$_2'$ is a readily removable carboxyl protecting group. Also disclosed as intermediates are compounds of the formula

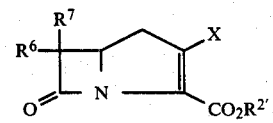

wherein X is described as a leaving group.

At the Gordon Research Conference on Medicinal Chemistry held at New London, N.H. on Aug. 2–6, 1982, a handout was distributed in which a variety of carbapenem antibiotics were disclosed. Among the compounds disclosed on page 9 of the handout is the carbapenem of the formula

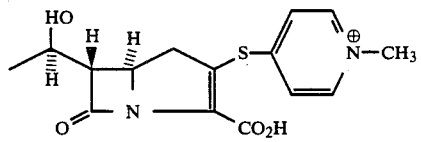

which differs from the compounds of the present invention in that the quaternized heteroaromatic ring in the 2-substituent is bonded directly to the sulfur atom instead of to the carbon atom of an alkylene group.

European Patent Application No. 50,334 discloses carbapenem derivatives of the general formula

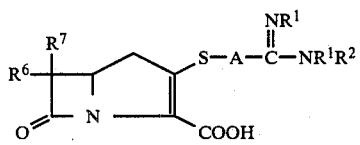

wherein $R^6$ and $R^7$ are, inter alia, independently selected from the group consisting of hydrogen, alkyl, alkenyl, aryl and aralkyl; A is a direct, single bond connecting the indicated S and C atoms, or A is a cyclic or acyclic connecting group selected, inter alia, from alkyl, cycloalkyl, aryl, heteroaryl or heteroalkyl; $R^1$ and $R^2$, which define the carbamimidoyl function are, inter alia, independently selected from hydrogen, alkyl and aryl; additionally, said carbamimidoyl is characterized by cyclic structures achieved by the joinder of the two nitrogen atoms via their substituents and by their joinder to connecting group A; additionally "carbamimidiums" are disclosed by quaternization of one of the nitrogen atoms of said carbamimidoyl. On page 12 of this application, there is disclosed as a possible 2-substituent the group

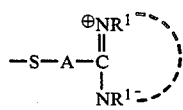

wherein $R^1$ is defined as hydrogen, substituted and unsubstituted: alkyl, cycloalkyl, cycloalkylalkyl, alkylcycloalkyl, aryl, arylalkyl, heterocyclyl or heterocyclylalkyl and the two nitrogen atoms "participate in cyclic structures which are indicated by the dotted lines". No specific disclosure is provided of any cyclized carbamimidoyl groups containing a quaternized nitrogen atom, but page 22 does disclose a cyclized carbamimidoyl group of the formula

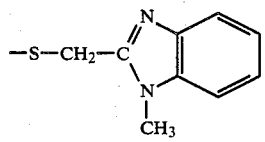

Based on the indicated definitions of substituent $R^1$, applicant does not believe that European Patent Application No. 50,334 generically discloses any of his compounds. However, since the language in the reference application is so vague as to the nature of the intended cyclic structures, applicant is making this reference of record in the present application.

While, as indicated above, the prior art has described carbapenem derivatives having a 2-substituent of the general formula —S—A—Het wherein A represents an alkylene group and Het represents a heterocyclic or heteroaromatic group, there has been no disclosure of which applicants are aware teaching carbapenems wherein Het is a radical of the formula

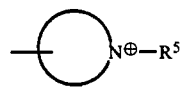

in which $R^5$ is an optionally substituted aliphatic, cycloaliphatic, cycloaliphatic-aliphatic, aryl, araliphatic, heteroaryl, heteroaraliphatic, heterocyclyl or heterocyclylaliphatic radical and

represents a quaternized nitrogen-containing aromatic heterocycle bonded to the alkylene carbon via a ring carbon atom. As mentioned above, the carbapenem having

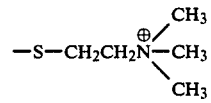

as the 2-substituent has been reported as well as the carbapenem having a quaternized heteroaromatic ring bonded directly to the sulfur 2-substituent.

Despite the vast number of carbapenem derivatives disclosed in the literature, there is still a need for new carbapenems since known derivatives may be improved upon in terms of spectrum of activity, potency, stability and/or toxic side effects.

SUMMARY OF THE INVENTION

The present invention provides a novel series of carbapenem derivatives characterized by a 2-substituent of the formula

in which A represents a $C_1$–$C_6$ straight or branched chain alkylene group; $R^5$ represents an optionally substituted aliphatic, cycloaliphatic, cycloaliphatic-aliphatic, aryl, araliphatic, heteroaryl, heteroaraliphatic, heterocyclyl or heterocyclylaliphatic radical; and

represents a quaternized nitrogen-containing aromatic heterocycle bonded to the alkylene group A via a ring carbon atom. More specifically, the present invention provides carbapenem derivatives of the formula

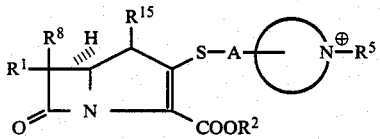

wherein $R^8$ is hydrogen and $R^1$ is selected from the group consisting of hydrogen; substituted and unsubstituted: alkyl, alkenyl and alkynyl, having from 1–10 carbon atoms; cycloalkyl and cycloalkylalkyl, having 3–6 carbon atoms in the cycloalkyl ring and 1–6 carbon atoms in the alkyl moieties; phenyl; aralkyl, aralkenyl and aralkynyl wherein the aryl moiety is phenyl and the aliphatic portion has 1–6 carbon atoms; heteroaryl, heteroaralkyl, heterocyclyl and heterocyclylalkyl wherein the hetero atom or atoms in the above-named heterocyclic moieties are selected from the group consisting of 1–4 oxygen, nitrogen or sulfur atoms and the alkyl moieties associated with said heterocyclic moieties have 1–6 carbon atoms; wherein the substituent or substituents relative to the above-named radicals are independently selected from the group consisting of

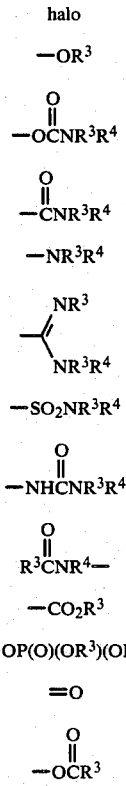

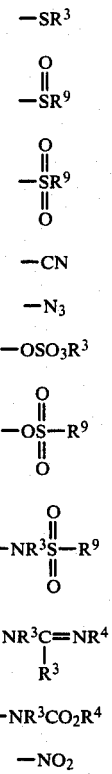

wherein, relative to the above-named substituents, the groups $R^3$ and $R^4$ are independently selected from hydrogen; alkyl, alkenyl and alkynyl, having from 1–10 carbon atoms; cycloalkyl, cycloalkylalkyl and alkylcycloalkyl, having 3–6 carbon atoms in the cycloalkyl ring and 1–6 carbon atoms in the alkyl moieties; phenyl; aralkyl, aralkenyl and aralkynyl wherein the aryl moiety is phenyl and the aliphatic portion has 1–6 carbon atoms; and heteroaryl, heteroaralkyl, heterocyclyl and heterocyclylalkyl wherein the hetero atom or atoms in the above-named heterocyclic moieties are selected from the group consisting of 1–4 oxygen, nitrogen or sulfur atoms and the alkyl moieties associated with said heterocyclic moieties have 1–6 carbon atoms, or $R^3$ and $R^4$ taken together with the nitrogen to which at least one is attached may form a 5- or 6-membered nitrogen-containing heterocyclic ring; $R^9$ is as defined for $R^3$ except that it may not be hydrogen; or wherein $R^1$ and $R^8$ taken together represent $C_2$–$C_{10}$ alkylidene or $C_2$–$C_{10}$ alkylidene substituted by hydroxy; $R^5$ is selected from the group consisting of substituted and unsubstituted: alkyl, alkenyl and alkynyl, having from 1–10 carbon atoms; cycloalkyl and cycloalkylalkyl, having 3–6 carbon atoms in the cycloalkyl ring and 1–6 carbon atoms in the alkyl moieties; phenyl; aralkyl, aralkenyl and aralkynyl wherein the aryl moiety is phenyl and the aliphatic portion has 1–6 carbon atoms; heteroaryl, heteroaralkyl, heterocyclyl and heterocyclylalkyl wherein the hetero atom or atoms in the above-named heterocyclic moieties are selected from the group consisting of 1–4 oxygen, nitrogen or sulfur atoms and the alkyl moieties associated with said heterocyclic moieties have 1–6 carbon atoms; wherein the above-named $R^5$ radicals are optionally substituted by 1–3 substituents independently selected from:

$C_1$-$C_6$ alkyl optionally substituted by amino, fluoro, chloro, carboxyl, hydroxy or carbamoyl;

fluoro, chloro or bromo;

—$OR^3$;

—$OCO_2R^3$;

—$OCOR^3$;

—$OCONR^3R^4$;

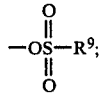

—oxo;

—$NR^3R^4$;

$R^3CONR^4$—;

—$NR^3CO_2R^4$;

—$NR^3CONR^3R^4$;

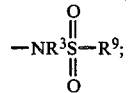

—$SR^3$;

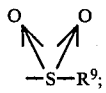

—$SO_3R^3$;

—$CO_2R^3$;

—$CONR^3R^4$;

—CN; or phenyl optionally substituted by 1-3 fluoro, chloro, bromo, $C_1$-$C_6$ alkyl, —$OR^3$, —$NR^3R^4$, —$SO_3R^4$, —$CO_2R^3$ or —$CONR^3R^4$, wherein $R^3$, $R^4$ and $R^9$ in such $R^5$ substitutents are as defined above;

or $R^5$ may be attached to

at another point on the ring so as to form a fused heterocyclic or heteroaromatic ring, which ring may contain additional, preferably up to 2, hetero atoms selected from O, N and S; $R^{15}$ is selected from the group consisting of hydrogen; substituted and unsubstituted: alkyl, alkenyl and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen and sulfur atoms and the alkyl moieties associated with said heterocyclic moieties have 1-6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1-6 carbon atoms; A is $C_1$-$C_6$ straight or branched chain alkylene; $R^2$ is hydrogen, an anionic charge or a conventional readily removable carboxyl protecting group, providing that when $R^2$ is hydrogen or a protecting group, there is also present a counter ion; and

represents a substituted or unsubstituted mono-, bi- or polycyclic aromatic heterocyclic radical containing at least one nitrogen in the ring and attached to A through a ring carbon atom and having a ring nitrogen which is quaternized by the group $R^5$; and pharmaceutically acceptable salts thereof.

The compounds of formula I are potent antibacterial agents or intermediates useful in the preparation of such agents.

Also included in the invention are processes for preparing the novel carbapenem derivatives described above and pharmaceutical compositions containing the biologically active carbapenem derivatives in combination with pharmaceutically acceptable carriers or diluents.

DETAILED DESCRIPTION

The novel compounds of general formula I above contain the carbapenem nucleus

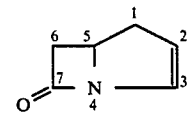

and may thus be named as 1-carba-2-penem-3-carboxylic acid derivatives. Alternatively, the compounds may be considered to have the basic structure

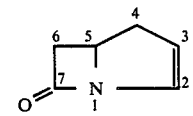

and named as 7-oxo-1-azabicyclo(3.2.0)hept-2-ene-2-carboxylic acid derivatives. While the present invention includes compounds wherein the relative stereochemistry of the 5,6-protons is cis as well as trans, the preferred compounds have the 5R,6S (trans) stereochemistry as in the case of thienamycin.

The compounds of formula I may be unsubstituted in the 6-position or substituted by substituent groups previously disclosed for other carbapenem derivatives. More specifically, $R^8$ may be hydrogen and $R^1$ may be hydrogen or a non-hydrogen substituent disclosed, for example, in European Patent Application No. 38,869 (see definition of $R_6$). Alternatively, $R^8$ and $R^1$ taken together may be $C_2$-$C_{10}$ alkylidene or $C_2$-$C_{10}$ alkylidene substituted, for example, by hydroxy.

The compounds of formula I may also be unsubstituted at the 1-position ($R^{15}$=H) or substituted by substituent groups previously disclosed for other carbapenem derivatives. More specifically, $R^{15}$ may be hydrogen or any of the non-hydrogen 1-substituents disclosed for example, in European Patent Application No. 54,917 (see definition of $R^1$ or $R^2$ therein) or in U.S. Pat. No. 4,350,631. Preferred non-hydrogen $R^{15}$ substituents include $C_1$-$C_6$ alkyl, most preferably methyl; phenyl; and phenyl($C_1$-$C_6$)alkyl. The non-hydrogen $R^{15}$ substituent may be in either the α- or β-configuration, and it is intended that the present invention include the individual α- and β-isomers, as well as mixtures thereof. The most preferred 1-substituted compounds are those having the β-configuration, especially those having the β-methyl substituent.

To elaborate on the definitions for $R^1$, $R^8$ and $R^{15}$:

(a) The aliphatic "alkyl", "alkenyl" and "alkynyl" groups may be straight or branched chain having 1-10 carbon atoms; preferred are 1-6, most preferably 1-4, carbon groups; when part of another substituent, e.g. as in cycloalkylalkyl, or heteroaralkyl or aralkenyl, the alkyl, alkenyl and alkynyl group preferably contains 1-6, most preferably 1-4, carbon atoms.

(b) "heteroaryl" includes mono-, bi- and polycyclic aromatic heterocyclic groups containing 1-4 O, N or S atoms; preferred are 5- or 6-membered heterocyclic rings such as thienyl, furyl, thiadiazolyl, oxadiazolyl, triazolyl, isothiazolyl, thiazolyl, imidazolyl, isoxazolyl, tetrazolyl, oxazolyl, pyridyl, pyrazinyl, pyrimidinyl, pyridazinyl, pyrrolyl, pyrazolyl, etc.

(c) "heterocyclyl" includes mono-, bi- and polycyclic saturated or unsaturated non-aromatic heterocyclic groups containing 1-4 O, N or S atoms; preferred are 5- or 6-membered heterocyclic rings such as morpholinyl, piperazinyl, piperidyl, pyrazolinyl, pyrazolidinyl, imidazolinyl, imidazolidinyl, pyrrolinyl, pyrrolidinyl, etc.

(d) "halo" includes chloro, bromo, fluoro and iodo and is preferably chloro, fluoro or bromo.

The term "conventional readily removable carboxyl protecting group" refers to a known ester group which has been employed to block a carboxyl group during the chemical reaction steps described below and which can be removed, if desired, by methods which do not result in any appreciable destruction of the remaining portion of the molecule, e.g. by chemical or enzymatic hydrolysis, treatment with chemical reducing agents under mild conditions, irradiation with ultraviolet light or catalytic hydrogenation. Examples of such ester protecting groups include benzhydryl, allyl, p-nitrobenzyl, 2-naphthylmethyl, benzyl, trichloroethyl, silyl such as trimethylsilyl, phenacyl, p-methoxybenzyl, acetonyl, o-nitrobenzyl, 4-pyridylmethyl and $C_1$-$C_6$ alkyl such as methyl, ethyl or t-butyl. Included within such protecting groups are those which are hydrolyzed under physiological conditions such as pivaloyloxymethyl, acetoxymethyl, phthalidyl, indanyl and methoxymethyl. A particularly advantageous carboxyl protecting group is p-nitrobenzyl which may be readily removed by catalytic hydrogenolysis.

The pharmaceutically acceptable salts referred to above include the nontoxic acid addition salts, e.g. salts with mineral acids such as hydrochloric, hydrobromic, hydroiodic, phosphoric, sulfuric, etc. and salts with organic acids such as maleic, acetic, citric, succinic, benzoic, tartaric, fumaric, mandelic, ascorbic, lactic, gluconic and malic. Compounds of formula I in the form of acid addition salts may be written as

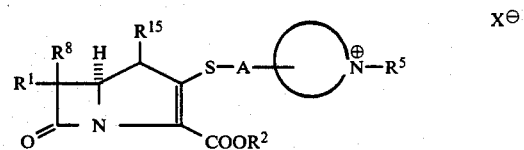

$R^2$=H or protecting group where $X^\ominus$ represents the acid anion. The counter anion $X^\ominus$ may be selected so as to provide pharmaceutically acceptable salts for therapeutic administration but, in the case of intermediate compounds of formula I, $X^\ominus$ may also be a toxic anion. In such a case the ion can be subsequently removed or substituted by a pharmaceutically acceptable anion to form an active end product for therapeutic use. When acidic or basic groups are present in the $R^1$ or $R^5$ group or on the

radical, the present invention may also include suitable base or acid salts of these functional groups, e.g. acid addition salts in the case of a basic group and metal salts (e.g. sodium, potassium, calcium and aluminum), the ammonium salt and salts with nontoxic amines (e.g. trialkylamines, procaine, dibenzylamine, 1-ephenamine, N-benzyl-β-phenethylamine, N,N'-dibenzylethylenediamine, etc.) in the case of an acidic group.

Compounds of formula I wherein $R^2$ is hydrogen, an anionic charge or a physiologically hydrolyzable ester group together with pharmaceutically acceptable salts thereof are useful as antibacterial agents. The remaining compounds of formula I are valuable intermediates which can be converted into the above-mentioned biologically active compounds.

A preferred embodiment of the present invention comprises compounds of formula I wherein $R^8$ is hydrogen and $R^1$ is hydrogen, $CH_3CH_2$—

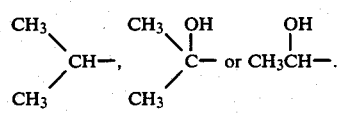

Among this subclass, the preferred compounds are those in which $R^1$ is

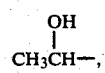

most preferably compounds having the absolute configuration 5R, 6S, 8R.

Another preferred embodiment comprises compounds of formula I in which $R^1$ and $R^8$ taken together form an alkylidene radical of the formula

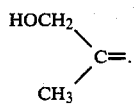

The alkylene (i.e. substituent "A") radical in the compounds of formula I may be straight or branched chain and may contain from 1 to 6 carbon atoms. A preferred embodiment comprises those compounds in which A is —$(CH_2)_n$— in which n is 1 or 2 and a particularly preferred embodiment comprises those compounds where A is —$CH_2$—.

The alkylene moiety "A" is attached via a ring carbon atom to an N-substituted quaternized aromatic heterocycle of the general formula

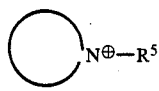

wherein the $R^5$ substituent is preferably an optionally substituted $C_1$-$C_6$ alkyl, $C_2$-$C_{10}$ alkenyl, $C_2$-$C_{10}$ alkynyl, $C_3$-$C_6$ cycloalkyl, $C_3$-$C_6$ cycloalkyl-$C_1$-$C_6$ alkyl, phenyl, phenyl-$C_1$-$C_6$ alkyl, phenyl-$C_2$-$C_6$ alkenyl, phenyl-$C_2$-$C_6$ alkynyl, heteroaryl, heteroaralkyl in which the alkyl moiety has 1-6 carbon atoms, heterocyclyl or heterocyclylalkyl in which the alkyl moiety has 1-6 carbon atoms. The heteroaryl (or heteroaryl portion of heteroaralkyl) $R^5$ substituent may be a mono-, bi- or polycyclic aromatic heterocyclic group containing 1-4 O, N or S atoms; preferred are 5- or 6-membered heterocyclic rings such as thienyl, furyl, thiadiazolyl, oxadiazolyl, triazolyl, isothiazolyl, thiazolyl, imidazolyl, isoxazolyl, tetrazolyl, oxazolyl, pyridyl, pyrazinyl, pyrimidinyl, pyridazinyl, pyrrolyl and pyrazolyl. The heterocyclyl (or heterocyclyl portion of heterocyclylalkyl) $R^5$ substituent may be a mono-, bi- or polycyclic saturated or unsaturated non-aromatic heterocyclic group containing 1-4 O, N or S atoms; preferred are 5- or 6-membered heterocyclic rings such as morpholinyl, piperazinyl, piperidyl, pyrazolinyl, pyrazolidinyl, imidazolinyl, imidazolidinyl, pyrrolinyl and pyrrolidinyl.

The $R^5$ substituent may be optionally substituted by 1-3 substituents independently selected from:

(a) $C_1$-$C_6$ alkyl optionally substituted by, preferably 1-3, amino, fluoro, chloro, carboxyl, hydroxy or carbamoyl groups;
(b) fluoro, chloro or bromo;
(c) —$OR^3$;
(d) —$OCO_2R^3$;
(e) —$OCOR^3$;
(f) —$OCONR^3R^4$;
(g) —$OS(O)_2R^9$ (—OS(=O)(=O)—$R^9$);
(h) -oxo;
(i) —$NR^3R^4$;
(j) $R^3CONR^4$—;
(k) —$NR^3CO_2R^4$;
(l) —$NR^3CONR^3R^4$;
(m) —$NR^3S(O)_2R^9$ (—NR³S(=O)(=O)R⁹);
(n) —$SR^3$;
(o) —$SOR^9$;
(p) —$S(O)_2R^9$;
(q) —$SO_3R^3$;
(r) —$CO_2R^3$;
(s) —$CONR^3R^4$;
(t) —CN; or
(u) phenyl optionally substituted by 1-3 substituents independently selected from fluoro, chloro, bromo, $C_1$-$C_6$ alkyl, —$OR^3$, —$NR^3R^4$, —$SO_3R^3$ or —$CONR^3R^4$, wherein, relative to the above-named $R^5$ substituents, the groups $R^3$ and $R^4$ are independently selected from hydrogen; alkyl, alkenyl and alkynyl, having 1-10 carbon atoms; cycloalkyl, cycloalkylalkyl and alkylcycloalkyl, having 3-6 carbon atoms in the cycloalkyl ring and 1-6 carbon atoms in the alkyl moieties; phenyl; aralkyl, aralkenyl and aralkynyl wherein the aryl moiety is phenyl and the aliphatic portion has 1-6 carbon atoms; and heteroaryl, heteroaralkyl, heterocyclyl and heterocyclylalkyl wherein the heteroaryl and heterocyclyl group or portion of a group is as defined above for $R^5$ and the alkyl moieties associated with said heterocyclic moieties have 1-6 carbon atoms; or $R^3$ and $R^4$ taken together with the nitrogen to which at least one is attached may form a 5- or 6-membered nitrogen-containing heterocyclic (as defined above for $R^5$) ring; and $R^9$ is as defined above for $R^3$ except that it may not be hydrogen. A most preferred $R^5$ substituent is $C_1$-$C_6$ alkyl, especially methyl.

In addition, the $R^5$ substituent, together with another ring atom of the

moiety, may form a fused heterocyclic or heteroaromatic ring, which ring may contain additional, preferably 1 or 2, hetero atoms selected from O, N and S. For example,

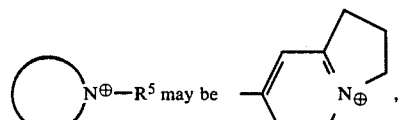

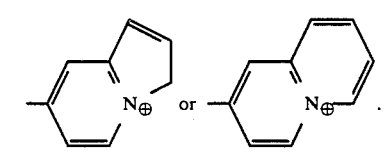

The group

preferably represents a substituted or unsubstituted mono-, bi- or polycyclic aromatic heterocycle containing at least one nitrogen in the ring and 0–5 additional ring hetero atoms selected from O, S and N, said heterocyclic ring being attached to A through a ring carbon atom and having a ring nitrogen atom quaternized by the group $R^5$.

The heteroaromatic

ring may be optionally substituted at available ring carbon atoms by preferably 1–5, most preferably 1–3, substituents independently selected from the group consisting of $C_1-C_4$ alkyl; $C_1-C_4$ alkyl substituted by, preferably 1–3, hydroxy, amino, $C_1-C_4$ alkylamino, di($C_1-C_4$)alkylamino, $C_1-C_4$ alkoxy, carboxy, halo (hereinafter intended to mean chloro, bromo, fluoro or iodo; preferably chloro, bromo or fluoro) or sulfo; $C_3-C_6$ cycloalkyl; $C_3-C_6$ cycloalkyl($C_1-C_4$)alkyl optionally substituted by 1–3 substituents mentioned above in connection with $C_1-C_4$ alkyl; $C_1-C_4$ alkoxy; $C_1-C_4$ alkylthio; amino; $C_1-C_4$ alkylamino; di($C_1-C_4$)alkylamino; halo; $C_1-C_4$ alkanoylamino; $C_1-C_4$ alkanoyloxy; carboxy; sulfo;

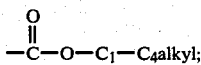

hydroxy; amidino; guanidino; phenyl; phenyl substituted by 1–3 substituents independently selected from amino, halo, hydroxy, trifluoromethyl, $C_1-C_4$ alkyl, $C_1-C_4$ alkoxy, $C_1-C_4$ alkylamino, di($C_1-C_4$)alkylamino, carboxy and sulfo; phenyl($C_1-C_4$)alkyl in which the phenyl portion may be optionally substituted by 1–3 substituents mentioned above in connection with phenyl and the alkyl portion may be optionally substituted by 1–3 substituents mentioned above in connection with $C_1-C_4$ alkyl; and heteroaryl or heteroaralkyl in which the hetero atom or atoms are selected from the group consisting of 1–4 O, S or N atoms and the alkyl moiety associated with heteroaralkyl has 1–6 carbon atoms, said heteroaryl and heteroaralkyl groups being optionally substituted in the heterocyclic ring moiety by 1–3 substituents independently selected from hydroxy, amino, halo, trifluoromethyl, $C_1-C_4$ alkyl, $C_1-C_4$ alkoxy, $C_1-C_4$ alkylamino, di($C_1-C_4$)alkylamino, carboxy and sulfo and in the alkyl moiety by 1–3 substituents selected from hydroxy, amino, $C_1-C_4$ alkylamino, di($C_1-C_4$)alkylamino, $C_1-C_4$ alkoxy, carboxy, halo and sulfo. In addition, available ring nitrogen atoms (other than the quaternized nitrogen) may be substituted by 1–3 substituents independently selected from the group consisting of $C_1-C_4$ alkyl; $C_1-C_4$ alkyl substituted by, preferably 1–3, hydroxy, amino, $C_1-C_4$ alkylamino, di($C_1-C_4$)alkylamino, $C_1-C_4$ alkoxy, carboxy, halo or sulfo groups; $C_3-C_6$ cycloalkyl; $C_3-C_6$ cycloalkyl ($C_1-C_4$) alkyl optionally substituted by 1–3 substituents mentioned above in connection with $C_1-C_4$ alkyl; phenyl; phenyl substituted by 1–3 substituents independently selected from amino, halo, hydroxy, trifluoromethyl, $C_1-C_4$ alkyl, $C_1-C_4$ alkoxy, $C_1-C_4$ alkylamino, di($C_1-C_4$)alkylamino, carboxy and sulfo; phenyl ($C_1-C_4$)alkyl in which phenyl portion may be optionally substituted by 1–3 substituents mentioned above in connection with phenyl and the alkyl portion may be optionally substituted by 1–3 substituents mentioned above in connection with $C_1-C_4$ alkyl; and heteroaryl or heteroaralkyl in which the hetero atom or atoms are selected from the group consisting of 1–4 O, S or N atoms and the alkyl moiety associated with heteroaralkyl has 1 to 6 carbon atoms, said heteroaryl and heteroaralkyl groups being optionally substituted in the heterocyclic ring moiety by 1–3 substituents independently selected from hydroxy, amino, halo, trifluoromethyl, $C_1-C_4$ alkyl, $C_1-C_4$ alkoxy, $C_1-C_4$ alkylamino, di($C_1-C_4$)alkylamino, carboxy and sulfo and in the alkyl moiety by 1–3 substituents selected from hydroxy, amino, $C_1-C_4$ alkylamino, di($C_1-C_4$)alkylamino, $C_1-C_4$ alkoxy, carboxy, halo and sulfo. The most preferred ring carbon and nitrogen substitutents are $C_1-C_6$ alkyl, especially methyl.

Within the above-described preferred embodiment, the preferred compounds are those in which A is $-(CH_2)_n-$ in which n is 1 or 2, most preferably those in which A is $-CH_2-$ and wherein (a) $R^1$ and $R^8$ taken together represent

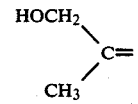

or (b) $R^8$ is hydrogen and $R^1$ represents hydrogen, $CH_3CH_2-$,

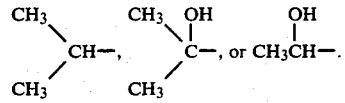

Particularly preferred are the compounds wherein $R^8$ is hydrogen and $R^1$ is

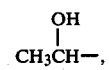

especially compounds having the absolute configuration 5R, 6S, 8R.

In a preferred embodiment the group

represents an aromatic 5- or 6-membered, N-containing heterocyclic ring containing 0–3 additional hetero atoms selected from O, S or N. Such aromatic heterocycle may, where possible, be fused to another ring which may be a saturated or unsaturated carbocyclic ring, preferably a $C_4-C_7$ carbocyclic ring, an aromatic carbocyclic ring preferably a phenyl ring, a 4–7 membered heterocyclic ring (saturated or unsaturated) containing 1–3 hetero atoms selected from O, S, N or $NR^{11}$ in which $R^{11}$ is hydrogen, $C_1$-$C_6$ alkyl optionally substituted by 1-2 substituents independently selected from —$OR^3$, —$NR^3R^4$, —$CO_2R^3$, oxo, phenyl, fluoro, chloro, bromo, —$SO_3R^3$ and —$CONR^3R^4$, or phenyl optionally substituted by 1-3 substituents independently selected from $C_1$-$C_6$ alkyl, —$OR^3$, —$NR^3R^4$, fluoro, chloro, bromo, —$SO_3R^3$, —$CO_2R^3$ and —$CONR^3R^4$, wherein $R^3$ and $R^4$ in such $R^{11}$ substituents are as defined above in connection with substituent $R^1$, or a 5-6 membered heteroaromatic ring containing 1-3 hetero atoms selected from O, S, N or $NR^{11}$ in which $R^{11}$ is as defined above. The 5- or 6-membered aromatic quaternized ring or, where appropriate, the carbocyclic, heterocyclic or heteroaromatic ring fused thereto, or both such rings, may be optionally substituted on available ring atoms by, preferably up to a total of five substituents for the total ring system, the substituents mentioned above in connection with the group

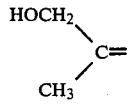

Within the above-described preferred embodiment, the preferred compounds are those in which A is —$(CH_2)_n$— in which n is 1 or 2, most preferbly those in which A is —$CH_2$— and wherein (a) $R^1$ and $R^8$ taken together represent

or (b) $R^8$ is hydrogen and $R^1$ represents hydrogen, $CH_3CH_2$—,

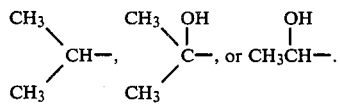

Particularly preferred are the compounds wherein $R^8$ is hydrogen and $R^1$ is

especially compounds having the absolute configuration 5R, 6S, 8R.

Still another preferred embodiment of the present invention comprises compounds of formula I wherein

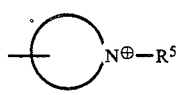

represents a radical selected from the group consisting of

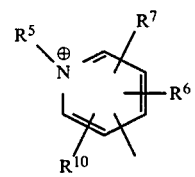

(a)

wherein $R^6$, $R^7$ and $R^{10}$ are independently selected from hydrogen; $C_1$-$C_4$ alkyl; $C_1$-$C_4$ alkyl substituted by, preferably 1-3, hydroxy, $C_1$-$C_4$ alkylamino, di($C_1$-$C_4$ alkyl)amino, $C_1$-$C_4$ alkoxy, amino, sulfo, carboxy or halo (chloro, bromo, fluoro or iodo; preferably chloro, fluoro or bromo); $C_3$-$C_6$ cycloalkyl; $C_1$-$C_4$ alkoxy; $C_1$-$C_4$ alkylthio; amino; $C_1$-$C_4$ alkylamino; di($C_1$-$C_4$ alkyl)amino; halo (chloro, bromo, fluoro or iodo; preferably chloro, fluoro or bromo); $C_1$-$C_4$ alkanoylamino; $C_1$-$C_4$ alkanoyloxy; carboxy;

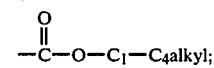

hydroxy; amidino; guanidino; phenyl; phenyl substituted by one, two or three amino, halo (chloro, bromo, fluoro or iodo; preferably chloro, fluoro or bromo), hydroxyl, trifluoromethyl, $C_1$-$C_4$ alkyl or $C_1$-$C_4$ alkoxy groups; phenyl ($C_1$-$C_4$)alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl and heteroaralkyl in which the hetero atom or atoms in the abovenamed heterocyclic moieties are selected from the group consisting of 1-4 oxygen, nitrogen or sulfur atoms and the alkyl moiety associated with said heteroaralkyl moiety has 1-6 carbon atoms; or wherein two of $R^6$, $R^7$ or $R^{10}$ taken together may be a fused saturated carbocyclic ring, a fused aromatic carbocyclic ring, a fused non-aromatic heterocyclic ring or a fused heteroaromatic ring, said fused rings being optionally substituted by 1 or 2 of the substituents defined above for $R^6$, $R^7$ and $R^{10}$;

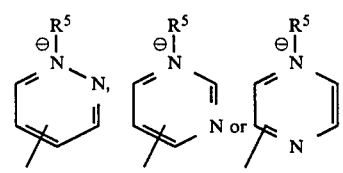

(b)

optionally substituted on a carbon atom by one to three substituents independently selected from $C_1$-$C_4$ alkyl; $C_1$-$C_4$ alkyl substituted by, preferably 1-3, hydroxy, $C_1$-$C_4$ alkylamino, sulfo, di($C_1$-$C_4$ alkyl)amino, $C_1$14 $C_4$ alkoxy, amino, carboxy or halo (chloro, bromo, fluoro or iodo; preferably chloro, fluoro or bromo); $C_3$-$C_6$ cycloalkyl; $C_1$-$C_4$ alkoxy; $C_1$-$C_4$ alkylthio; amino; $C_1$-$C_4$ alkylamino; di($C_1$-$C_4$ alkyl)amino; halo (chloro, bromo, fluoro or iodo; preferably chloro, fluoro or bromo); $C_1$-$C_4$ alkanoylamino; $C_1$-$C_4$ alkanoyloxy; carboxy;

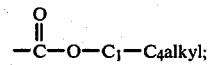

hydroxy; amidino; guanidino; phenyl; phenyl substituted by one, two or three amino, halo (chloro, bromo, fluoro or iodo; preferably chloro, fluoro or bromo), hydroxyl, trifluoromethyl, $C_1$–$C_4$ alkyl or $C_1$–$C_4$ alkoxy groups, phenyl($C_1$–$C_4$)alkyl in which the phenyl portion may be optionally substituted by 1–3 substituents mentioned above in connection with phenyl and the alkyl portion may be optionally substituted by 1–3 substituents mentioned above in connection with $C_1$–$C_4$ alkyl; and heteroaryl or heteroaralkyl in which the hetero atom or atoms in the above-named heterocyclic moieties are selected from the group consisting of 1–4 oxygen, nitrogen or sulfur atoms and the alkyl moiety associated with said heteroaralkyl moiety has 1–6 carbon atoms, or optionally substituted so as to form a fused carbocyclic, heterocyclic or heteroaromatic ring optionally substituted by 1 or 2 of the substituents defined above;.

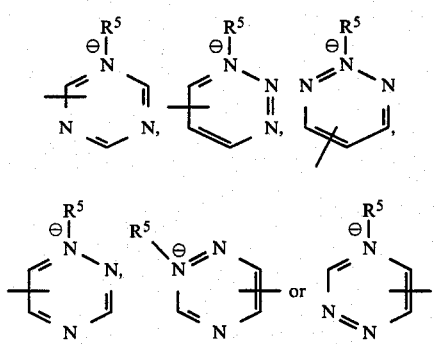

optionally substituted on a carbon atom by one or two substituents independently selected from $C_1$–$C_4$ alkyl; $C_1$–$C_4$ alkyl substituted by, preferably 1–3, hydroxy, $C_1$–$C_4$ alkylamino, sulfo, di($C_1$–$C_4$ alkyl)amino, $C_1$–$C_4$ alkoxy, amino, carboxy or halo (chloro, bromo, fluoro or iodo; preferably chloro, fluoro or bromo); $C_3$–$C_6$ cycloalkyl; $C_1$–$C_4$ alkoxy; $C_1$–$C_4$ alkylthio; amino; $C_1$–$C_4$ alkylamino; di($C_1$–$C_4$ alkyl)amino; halo (chloro, bromo, fluoro or iodo; preferably chloro, fluoro or bromo); $C_1$–$C_4$ alkanoylamino; $C_1$–$C_4$ alkanoyloxy; carboxy;

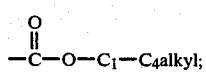

hydroxy, amidino; guanidino, phenyl; phenyl substituted by one, two or three amino, halo (chloro, bromo, fluoro or iodo; preferably chloro, fluoro or bromo), hydroxyl, trifluoromethyl, $C_1$–$C_4$ alkyl or $C_1$–$C_4$ alkoxy groups; phenyl($C_1$–$C_4$)alkyl in which the phenyl portion may be optionally substituted by 1–3 substituents mentioned above in connection with phenyl and the alkyl portion may be optionally substituted by 1–3 substituents mentioned above in connection with $C_1$–$C_4$ alkyl; and heteroaryl or heteroaralkyl in which the hetero atom or atoms in the above-named heterocyclic moieties are selected from the group consisting of 1–4 oxygen, nitrogen or sulfur atoms and the alkyl moiety associated with said heteroaralkyl moiety has 1–6 carbon atoms, or optionally substituted so as to form a fused carbocyclic, heterocyclic or heteroaromatic ring optionally substituted by 1 or 2 of the substituents defined above;

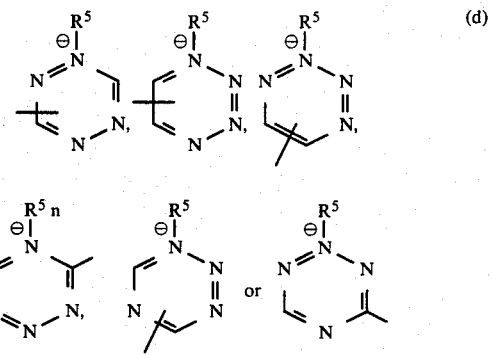

optionally substituted on a carbon atom by a substituent independently selected from $C_1$–$C_4$ alkyl; $C_1$–$C_4$ alkyl substituted by, preferably 1–3, hydroxy, $C_1$–$C_4$ alkylamino, di($C_1$–$C_4$ alkyl)amino, sulfo, $C_1$–$C_4$ alkoxy, amino, carboxy or halo (chloro, bromo, fluoro or iodo; preferably chloro, fluoro or bromo); $C_3$–$C_6$ cycloalkyl; $C_1$–$C_4$ alkoxy; $C_1$–$C_4$ alkylthio; amino; $C_1$–$C_4$ alkylamino; di($C_1$–$C_4$ alkyl)amino; halo (chloro, bromo, fluoro or iodo; preferably chloro, fluoro or bromo); $C_1$–$C_4$ alkanoylamino; $C_1$–$C_4$ alkanoyloxy; carboxy;

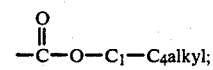

hydroxy; amidino; guanidino, phenyl; phenyl substituted by one, two or three amino, halo (chloro, bromo, fluoro or iodo; preferably chloro, fluoro or bromo), hydroxyl, trifluoromethyl, $C_1$–$C_4$ alkyl or $C_1$–$C_4$ alkoxy groups; phenyl($C_1$–$C_4$)alkyl in which the phenyl portion may be optionally substituted by 1–3 substituents mentioned above in connection with phenyl and the alkyl portion may be optionally substituted by 1–3 substituents mentioned above in connection with $C_1$–$C_4$ alkyl; and heteroaryl or heteroaralkyl in which the hetero atom or atoms in the above-named heterocyclic moieties are selected from the group consisting of 1-oxygen, nitrogen or sulfur atoms and the alkyl moiety associated with said heteroaralkyl moiety has 1–6 carbon atoms;

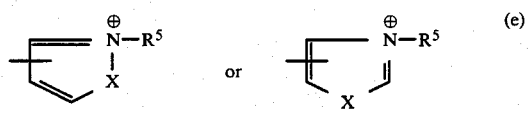

wherein X is O, S or NR in which R is $C_1$–$C_4$ alkyl; $C_1$–$C_4$ alkyl substituted by 1–3 hydroxy, amino, $C_1$–$C_4$ alkylamino, di($C_1$–$C_4$)alkylamino, $C_1$–$C_4$ alkoxy, carboxy, halo or sulfo groups; $C_3$–$C_6$ cycloalkyl; $C_3$–$C_6$ cycloalkyl($C_1$–$C_4$)alkyl optionally substituted by 1–3 substituents mentioned above in connection with $C_1$–$C_4$ alkyl; phenyl; phenyl substituted by 1–3 substituents independently selected from amino, halo, hydroxy, trifluoromethyl, $C_1$–$C_4$ alkyl, $C_1$–$C_4$ alkoxy, $C_1$–$C_4$ alkylamino, di($C_1$–$C_4$)alkylamino, carboxy and sulfo; phenyl($C_1$–$C_4$)alkyl in which the phenyl portion may be optionally substituted by 1–3 substituents mentioned above in connection with phenyl and the alkyl portion may be optionally substituted by 1-3 substituents mentioned above in connection with $C_1$-$C_4$ alkyl; and heteroaryl and heteroaralkyl in which the hetero atom or atoms are selected from the group consisting of 1-4 O, S or N atoms and the alkyl moiety associated with heteroaralkyl has 1-6 carbon atoms, said heteroaryl and heteroaralkyl groups being optionally substituted in the heterocyclic ring moiety by 1-3 substituents independently selected from hydroxy, amino, halo, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo and in the alkyl moiety by 1-3 substituents selected from hydroxy, amino, $C_1$-$C_4$ alkylamino, di($C_1$-$C_4$)alkylamino, $C_1$-$C_4$ alkoxy, carboxy, halo and sulfo; said heteroaromatic radical being optionally substituted on a carbon atom by one or more substituents independently selected from $C_1$-$C_4$ alkyl; $C_1$-$C_4$ alkyl substituted by, preferably 1-3, hydroxy, amino, $C_1$-$C_4$ alkylamino, di($C_1$-$C_4$ alkyl)amino, $C_1$-$C_4$ alkoxy, sulfo, carboxy or halo (chloro, bromo, fluoro or iodo; preferably chloro, fluoro or bromo); $C_3$-$C_6$ cycloalkyl; $C_1$-$C_4$ alkoxy; $C_1$-$C_4$ alkylthio; amino; $C_1$-$C_4$ alkylamino; di($C_1$-$C_4$ alkyl)amino; halo (chloro, bromo, fluoro or iodo; preferably chloro, fluoro or bromo); $C_1$-$C_4$ alkanoylamino; $C_1$-$C_4$ alkanoyloxy; carboxy;

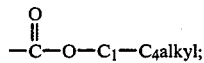

hydroxy; amidino; guanidino; phenyl; phenyl substituted by one, two or three amino, halo (chloro, bromo, fluoro or iodo; preferably chloro, fluoro or bromo), hydroxyl, trifluoromethyl, $C_1$-$C_4$ alkyl or $C_1$-$C_4$ alkoxy groups; phenyl($C_1$-$C_4$)alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl or heteroaralkyl in which the hetero atom or atoms in the above-named heterocyclic moieties are selected from the group consisting of 1-4 oxygen, nitrogen or sulfur atoms and the alkyl moiety associated with said heteroaralkyl moiety has 1-6 carbon atoms, or optionally substituted so as to form a fused carbocyclic, heterocyclic or heteroaromatic ring optionally substituted by 1 or 2 of the substituents defined above;

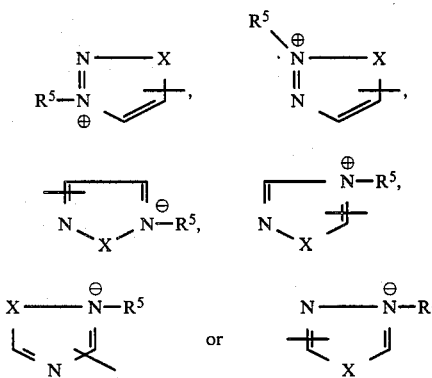

wherein X is O, S or NR in which R is $C_1$-$C_4$ alkyl; $C_1$-$C_4$ alkyl substituted by 1-3 hydroxy, amino, $C_1$-$C_4$ alkylamino, di($C_1$-$C_4$)alkylamino, $C_1$-$C_4$ alkoxy, carboxy, halo or sulfo groups; $C_3$-$C_6$ cycloalkyl; $C_3$-$C_6$ cycloalkyl($C_1$-$C_4$)alkyl optionally substituted by 1-3 substituents mentioned above in connection with $C_1$-$C_4$ alkyl; phenyl; phenyl substituted by 1-3 substituents independently selected from amino, halo, hydroxy, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo; phenyl($C_1$-$C_4$)alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl and heteroaralkyl in which the hetero atom or atoms are selected from the group consisting of 1-4 O, S or N atoms and the alkyl moiety associated with heteroaralkyl has 1-6 carbon atoms, said heteroaryl and heteroaralkyl groups being optionally substituted in the heterocyclic ring moiety by 1-3 substituents independently selected from hydroxy, amino, halo, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo and in the alkyl moiety by 1-3 substituents selected from hydroxy, amino, $C_1$-$C_4$ alkylamino, di($C_1$-$C_4$)alkylamino, $C_1$-$C_4$ alkoxy, carboxy, halo and sulfo; said heteroaromaic radical being optionally substituted on a carbon atom by a substituent selected from $C_1$-$C_4$ alkyl; $C_1$-$C_4$ alkyl substituted by, preferably 1-3, hydroxy, amino, $C_1$-$C_4$ alkylamino, di($C_1$-$C_4$ alkyl)amino, $C_1$-$C_4$ alkoxy, sulfo, carboxy or halo (chloro, bromo, fluoro or iodo; preferably chloro, fluoro or bromo); $C_3$-$C_6$ cycloalkyl; $C_1$-$C_4$ alkoxy; $C_1$-$C_4$ alkylthio; amino; $C_1$-$C_4$ alkylamino; d-($C_1$-$C_4$ alkyl)amino; halo (chloro, bromo, fluoro or iodo; preferably chloro, fluoro or bromo); $C_1$-$C_4$ alkanoylamino; $C_1$-$C_4$ alkanoyloxy; carboxy;

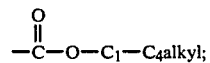

hydroxy; amidino; guanidino; phenyl; phenyl substituted by one, two or three amino, halo (chloro, brom, fluoro or iodo; preferably chloro, fluoro or bromo), hydroxyl, trifluoromethyl, $C_1$-$C_4$ alkyl or $C_1$-$C_4$ alkoxy groups; phenyl($C_1$-$C_4$)alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl or heteroaralkyl in which the hetero atom or atoms in the above-named heterocyclic moieties are selected from the group consisting of 1-4 oxygen, nitrogen or sulfur atoms and the alkyl moiety associated with said heteroaralkyl moiety has 1-6 carbon atoms; and

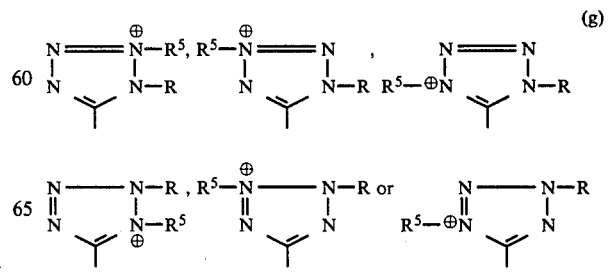

wherein R is $C_1$-$C_4$ alkyl; $C_1$-$C_4$ alkyl substituted by 1-3 hydroxy, amino, $C_1$-$C_4$ alkylamino, di($C_1$-$C_4$)alkylamino, $C_1$-$C_4$ alkoxy, carboxy, halo or sulfo groups; $C_3$-$C_6$ cycloalkyl; $C_3$-$C_6$ cycloalkyl($C_1$-$C_4$)alkyl optionally substituted by 1-3 substituents mentioned above in connection with $C_1$-$C_4$ alkyl; phenyl; phenyl substituted by 1-3 substituents independently selected from amino, halo, hydroxy, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo; phenyl($C_1$-$C_4$)alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl and heteroaralkyl in which the hetero atom or atoms are selected from the group consisting of 1-4 O, S or N atoms and the alkyl moiety associated with heteroaralkyl has 1-6 carbon atoms, said heteroaryl and heteroaralkyl groups being optionally substituted in the heterocylic ring moiety by 1-3 substituents independently selected from hydroxy, amino, halo, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo and in the alkyl moiety by 1-3 substituents selected from hydroxy, amino, $C_1$-$C_4$ alkylamino, di($C_1$-$C_4$)alkylamino, $C_1$-$C_4$ alkoxy, carboxy, halo and sulfo. The R and $R^5$ groups may also be taken together to form a fused heterocyclic or heteroaromatic ring.

Within the above-described preferred embodiment, the preferred compounds are those in which A is —$(CH_2)_n$— in which n is 1 or 2, most preferably those in which A is —$CH_2$— and wherein (a) $R^1$ and $R^8$ taken together represent

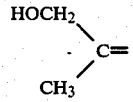

or (b) $R^8$ is hydrogen and $R^1$ represents hydrogen, $CH_3CH_2$—,

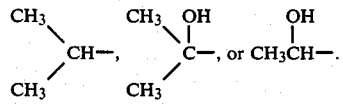

Particularly preferred are the compounds wherein $R^8$ is hydrogen and $R^1$ is

especially compounds having the absolute configuration 5R, 6S, 8R.

A particularly preferred embodiment of the present invention comprises compounds of formula I wherein

presents a radical of the formula

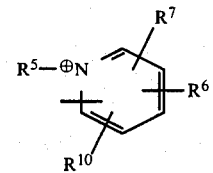

wherein $R^6$, $R^7$ and $R^{10}$ are independently selected from the group consisting of hydrogen, $C_1$-$C_4$ alkyl, $C_1$-$C_4$ alkoxy, carboxyl and carbamoyl and $R^5$ is as defined above, and is preferably $C_1$-$C_6$ alkyl, most preferably —$CH_3$.

Within the above-described preferred embodiment, the preferred compounds are those in which A is —$(CH_2)_n$— in which n is 1 or 2, most preferably those in which A is —$CH_2$— and wherein (a) $R^1$ and $R^8$ taken together represent

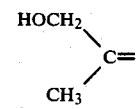

or (b) $R^8$ is hydrogen and $R^1$ represent hydrogen, $CH_3CH_2$—,

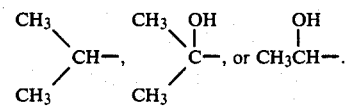

Particularly preferred are the compounds wherein $R^8$ is hydrogen and $R^1$ is

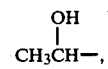

especially compounds having the absolute configuration 5R, 6S, 8R.

Another preferred embodiment comprises compounds of formula I wherein

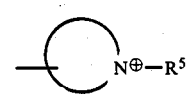

represents a radical of the formula

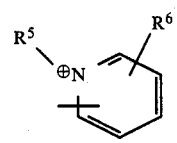

(a)

wherein $R^5$ is $C_1$-$C_4$ alkyl, most preferably methyl, and $R^6$ represents hydrogen or $C_1$-$C_4$ alkyl;

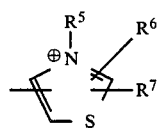 (b)

wherein $R^5$ is $C_1-C_4$ alkyl, most preferably methyl and $R^6$ and $R^7$ are hydrogen or $C_1-C_4$ alkyl;

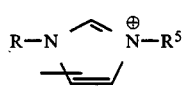 (c)

wherein $R^5$ is $C_1-C_4$ alkyl, most preferably methyl and R is $C_1-C_4$ alkyl or phenyl($C_1-C_4$)alkyl;

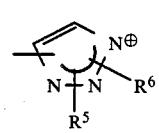 (d)

wherein $R^5$ is $C_1-C_4$ alkyl, most preferably methyl and $R^6$ is $C_1-C_4$ alkyl, most preferably methyl;

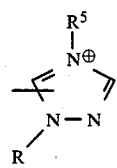 (e)

wherein $R^5$ is $C_1-C_4$ alkyl, most preferably methyl and R is $C_1-C_4$ alkyl, most preferably methyl; or

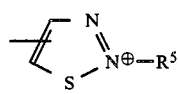 (f)

wherein $R^5$ is $C_1-C_4$ alkyl, most preferably methyl.

Within the above-described embodiment, the preferred compounds are those in which A is —(CH$_2$)$_n$— in which n is 1 or 2, most preferably those in which A is —CH$_2$— and wherein (a) $R^1$ and $R^8$ taken together represent

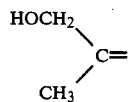

or (b) $R^8$ is hydrogen and $R^1$ represents hydrogen, CH$_3$CH$_2$—,

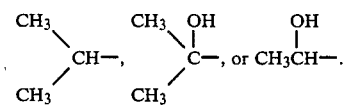

Particularly preferred are the compounds wherein $R^8$ is hydrogen and $R^1$ is

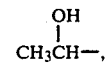

especially compounds having the absolute configuration 5R, 6S, 8R.

A most preferred embodiment of the present invention comprises compounds of formula I wherein

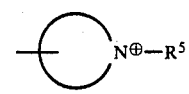

presents a radical of the formula

 (a)

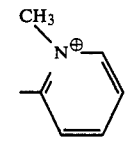 (b)

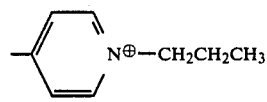 (c)

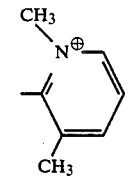 (d)

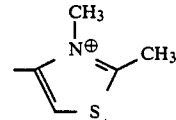 (e)

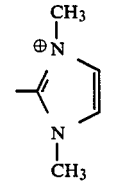 (f)

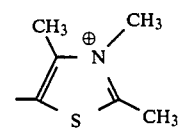 (g)

(h)

-continued (i) 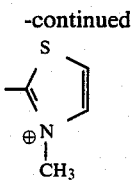

(j) 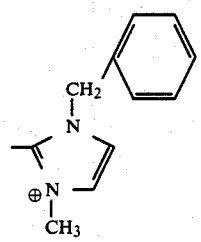

(k) 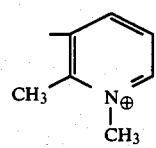

(l) 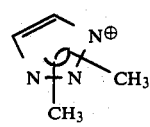

(m) 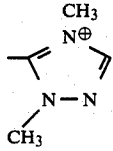

(n) 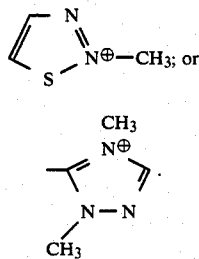

Within this above-described embodiment, the preferred compounds are those in which A is —(CH$_2$)$_n$— in which n is 1 or 2, most preferably those in which A is —(CH$_2$)— and wherein (a) R$^1$ and R$^8$ taken together represent

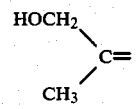

or (b) R$^8$ is hydrogen and R$^1$ represents hydrogen, CH$_3$CH$_2$—,

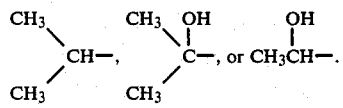

Particularly preferred are the compounds wherein R$^8$ is hydrogen and R$^1$ is

especially compounds having the absolute configuration 5R, 6S, 8R.

Specific preferred compounds of the present invention are those of the formula

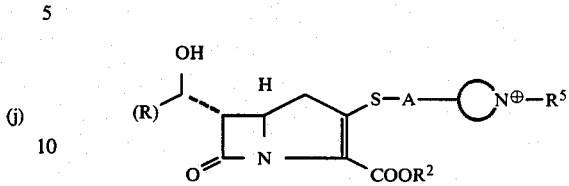

wherein R$^2$ is hydrogen, an anionic charge or a conventional readily removable carboxyl protecting group, providing that when R$^2$ is hydrogen or a protecting group, there is also present a counter ion and wherein

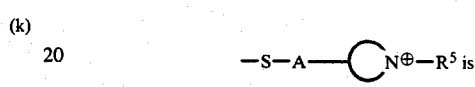 is (a) 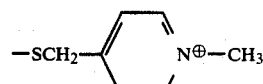

(b) 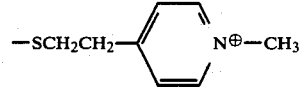

(c) 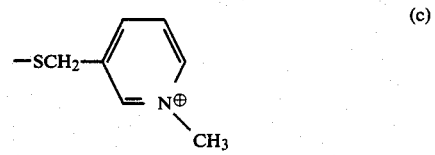

(d) 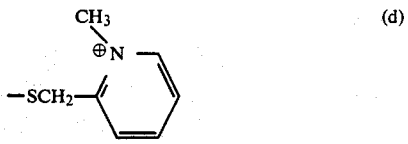

(e) 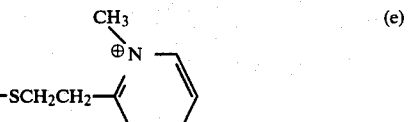

(f) 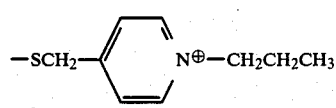

(g) 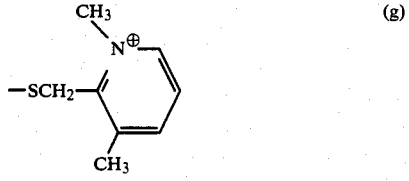

(h) 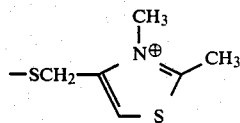

-continued $-S-A-$$N^{\oplus}-R^5$ is

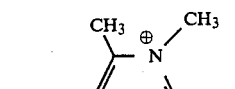 (i)

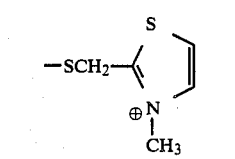 (j)

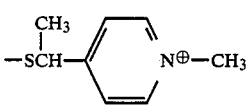 (k)

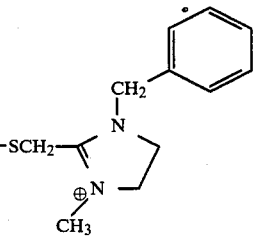 (l)

(m)

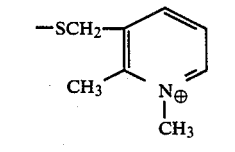 (n)

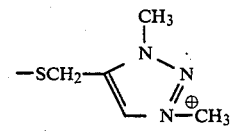 (o)

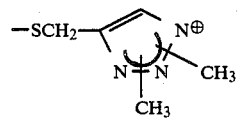 (p)

wherein the $^1$HNMR(D$_2$O) spectrum shows characteristic peaks at δ: 1.23 (3H, d, J=6.4 Hz), 3.12 (2H, q, J=1.4, 8.9 Hz), 3.39 (1H, q, J=2.7, 6.0 Hz), 4.07–4.68 (10H, m), 8.19 (1H, s);

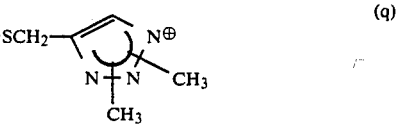 (q)

wherein the $^1$HNMR(D$_2$O) spectrum shows characteristic peaks at δ: 1.23 (3H, d, J=6.4 Hz), 3.15 (2H, q, J=3.7, 9.0 Hz), 3.37 (1H, q, J=2.6, 6.0 Hz), 3.95–4.65 (10H, m), 8.62 (1H, s);

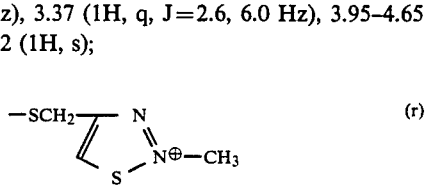 (r)

(s)

(t)

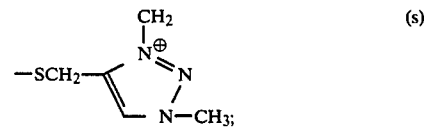 (u)

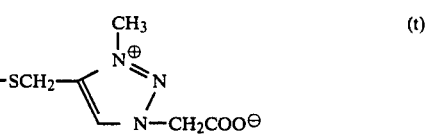 (v)

A most preferred embodiment of the present invention comprises compounds of formula I wherein

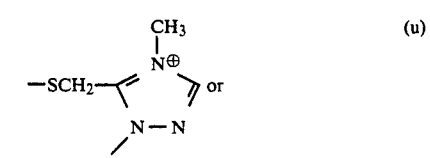

represents

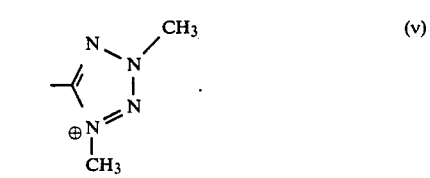

Within the above-described embodiment, the preferred compounds are those in which A is —(CH$_2$)$_n$— in which n is 1 or 2, most preferably those in which A is —CH$_2$— and wherein (a) R$^1$ and R$^8$ taken together represent

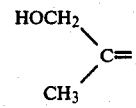

or (b) $R^8$ is hydrogen and $R^1$ represents hydrogen, $CH_3CH_2-$,

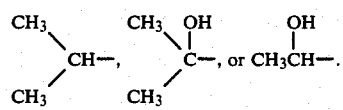

Particularly preferred are the compounds wherein $R^8$ is hydrogen and $R^1$ is

especially compounds having the absolute configuration 5R, 6S, 8R.

The carbapenem derivatives of general formula I are prepared from starting materials of the formula

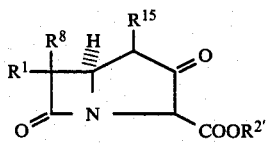

wherein $R^1$, $R^8$ and $R^{15}$ are defined above and wherein $R^{2'}$ represents a conventional readily removable carboxyl protecting group. Compounds of formula III have been disclosed, for example, in European Patent Application 38,869 (compound 7) and in European Patent Application No. 54,917, and may be prepared by the general methods described therein.

The process for preparing compounds I from starting materials III may be summarized by the following reaction scheme:

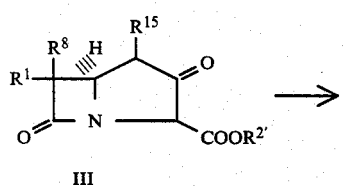

III

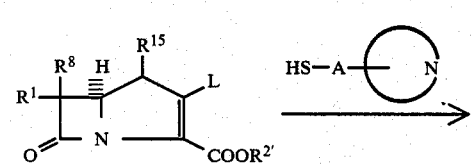

L = conventional leaving group

IV

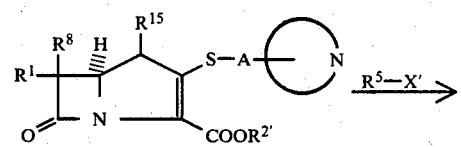

II

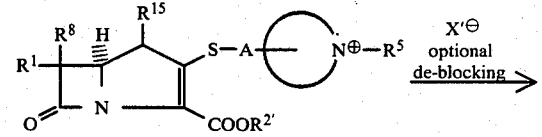

I'

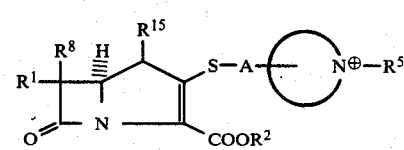

I

A variation of the above-described process is shown in the following reaction scheme:

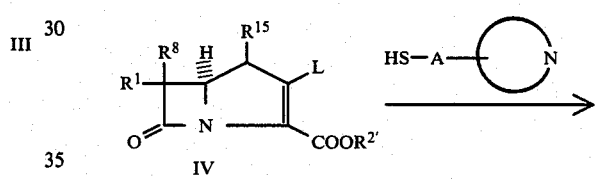

IV

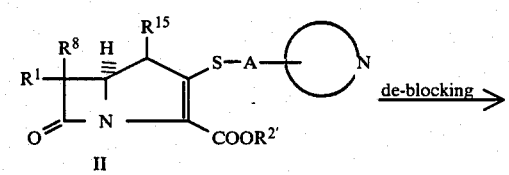

II

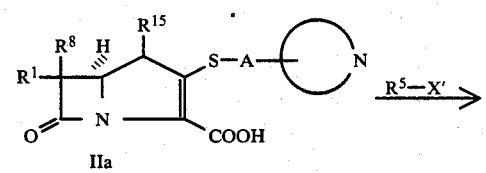

IIa

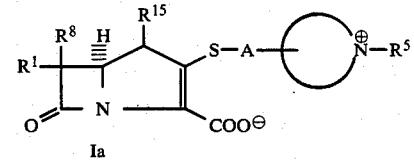

Ia

To elaborate on the above process, starting material III is reacted in an inert organic solvent such as methylene chloride, acetonitrile or dimethylformamide with about an equimolar amount of an agent $R^\circ$-L such as p-toluenesulfonic acid anhydride, p-nitrobenzenesulfonic acid anhydride, 2,4,6-triisopropylbenzenesulfonic acid anhydride, methanesulfonic acid anhydride, trifluoromethanesulfonic acid anhydride, diphenyl chlorophosphate, toluenesulfonyl chloride, p-bromobenzenesulfonyl chloride, or the like, wherein L is the corresponding leaving group such as toluenesulfonyloxy, p-nitrobenzenesulfonyloxy, diphenoxyphosphinyloxy, and other leaving groups which are established by conventional procedures and are well-known in the art. The reaction to establish the leaving group at the 2-position of intermediate III is advantageously carried out in the presence of a base such as diisopropylethylamine, triethylamine, 4-dimethylaminopyridine, or the like, at a temperature of from about −20° to +40° C., most preferably at about 0° C. The leaving group L of intermediate IV may also be halogen in which case such group is established by reacting intermediate III with a halogenating agent such as $\phi_3PCl_2$, $\phi_3PBr_2$, $(\phi O)_3PBr_2$, oxalylchloride or the like in a solvent such as $CH_2Cl_2$, $CH_3CN$, THF, or the like, in the presence of a base such as diisopropylethylamine, triethylamine, 4-dimethylaminopyridine, or the like. Intermediate IV may be isolated if desired, but is conveniently used for the next step without isolation or purification.

Intermediate IV is next converted to intermediate II by a conventional displacement reaction. Thus, intermediate IV may be reacted with approximately an equimolar amount of a heteroaralkyl mercaptan reagent of the formula

wherein A represents $C_1$-$C_6$ straight or branched chain alkylene and

represents a mono-, bi-or polycyclic aromatic heterocyclic radical containing a quaternizable nitrogen in the ring, said ring being attached to A through a ring carbon atom, in an inert organic solvent such as dioxane, dimethylformamide, dimethylsulfoxide or acetonitrile and in the presence of a base such as diisopropylethylamine, triethylamine, sodium hydrogen carbonate, potassium carbonate or 4-dimethylaminopyridine. The temperature for the displacement is not critical, but an advantageous temperature range is from about −40° C. to 25° C. Most conveniently, the reaction is carried out with cooling, e.g. at about 0° C. to −10° C.

Quaternization of the ring nitrogen in the heteroaralkyl group of intermediate II is carried out by reacting intermediate II in an inert organic solvent with at least an equivalent (up to about a 50% molar excess) of an alkylating agent of the formula $R^5$—X' wherein $R^5$ is as defined above and X' is a conventional leaving group such as halo (chloro, bromo or iodo most preferably iodo) or a sulfonate ester moiety such as a mesylate, tosylate or triflate. Examples of suitable nonreactive organic solvents are chloroform, methylene chloride, tetrahydrofuran, dioxane, acetone, dimethylsulfoxide and dimethylformamide. The temperature for the alkylation reaction is not critical and temperatures in the range of from about 0° C. to 40° C. are preferred. Most conveniently, the reaction step is carried out at room temperature.

Intermediate I' will have a counter ion X' (e.g. derived from the alkylating agent used) associated with it which at this stage or at a later stage, i.e. following the de-blocking step, may be substituted by a different counter ion, e.g. one which is more pharmaceutically acceptable, by conventional procedures. Alternatively, the counter ion may be subsequently removing during the de-blocking step.

The de-blocking step to remove the carboxyl protecting group $R^{2'}$ of intermediate I' is accomplished by conventional procedures such as solvolysis, chemical reduction or hydrogenation. When a protecting group such as p-nitrobenzyl, benzyl, benzhydryl or 2-naphthylmethyl is used which can be removed by catalytic hydrogenation, intermediate I' in a suitable solvent such as dioxane-water-ethanol, tetrahydrofuran-aqueous dipotassium hydrogen phosphate-isopropanol or the like may be treated under a hydrogen pressure of from 1 to 4 atmospheres in the presence of a hydrogenation catalyst such as palladium on charcoal, palladium hydroxide, platinum oxide or the like at a temperature of from 0° to 50° C. for from about 0.24 to 4 hours. When $R^{2'}$ is a group such as o-nitrobenzyl, photolysis may also be used for deblocking. Protecting groups such as 2,2,2-trichloroethyl may be removed by mild zinc reduction. The allyl protecting group may be removed with a catalyst comprising a mixture of a palladium compound and triphenylphosphine in an aprotic solvent such as tetrahydrofuran, diethyl ether or methylene chloride. Similarly, other conventional carboxyl protecting groups may be removed by methods known to those skilled in the art. Finally, as mentioned above, compounds of formula I' where $R^{2'}$ is a physiologically hydrolyzable ester such as acetoxymethyl, phthalidyl, indanyl, pivaloyloxymethyl, methoxymethyl, etc. may be administered directly to the host without de-blocking since such esters are hydrolyzed in vivo under physiological conditions.

It will be understood that where the $R^1$, $R^8$, $R^5$ or $R^{15}$ substituent or the heteroaromatic ring attached to substituent A contain a functional group which might interfere with the intended course of reaction, such group may be protected by a conventional blocking group and then subsequently de-blocked to regenerate the desired functional group. Suitable blocking groups and procedures for introducing and removing such groups are well known to those skilled in the art.

In a variant of the above process, the carboxyl protecting group of intermediate II may be removed prior to the quaternization step. Thus, the carboxyl protecting group is removed as described above to give the corresponding free carboxylic acid and the free acid is then quaternized with alkylating agent $R^5$-X' to give the desired quaternized product of formula I. When the de-protected intermediate IIa is quaternized, the solvent may be water or a non-reactive organic solvent, or mixtures thereof. Examples of suitable solvents include water, organic solvents such as chloroform, methylene chloride, tetrahydrofuran, dioxane, acetone, dimethylsulfoxide and dimethylformamide and water-organic solvent mixtures such as water-acetone or water-dimethylformamide. The temperature for the quaternization of intermediate IIa is not critical and temperatures in the range of from about −40° C. to about room temperature may be conveniently employed. Most advantageously, the reaction is carried out at about 0° C.

When deprotected intermediate IIa is obtained as a carboxylate salt, it is desirable to add a strong acid such as toluenesulfonic acid to generate the free carboxylic acid prior to quaternization. This is found to greatly facilitate the preferential quaternization of the ring nitrogen.

The above-described variant procedure is especially useful when the carboxyl protecting group is more easily removed from the unquaternized intermediate II than from quaternized intermediate I'. For example, in preparing the product of the formula

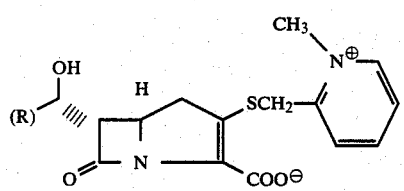

from the intermediate of the formula

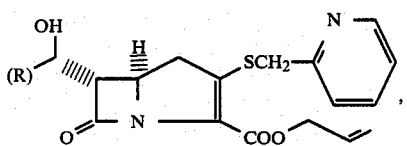

removal of the allyl protecting group prior to quaternization results in substantially improved yields of the desired end-product.

While the above-described process is suitable for preparing the compounds of the present invention, my colleague Pierre Dextraze has invented a new process which can be used to prepare compounds of formula I. This alternative process, which is disclosed and claimed in a co-pending U.S. patent application filed even date with the present continuation-in-part application, is described below and in the Examples which follow.

In the alternative process for preparation of compounds of formula I, an intermediate of the formula

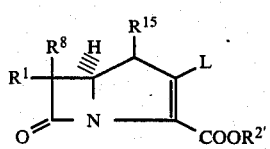

wherein $R^1$, $R^8$ and $R^{15}$ are as defined above, $R^{2'}$ is a conventional readily removable carboxyl protecting group and L is a conventional leaving group such as toluenesulfonyloxy, p-nitrobenzesulfonyloxy, diphenoxyphosphinyloxy or halo is reacted with a thiol compound of the formula

wherein A and

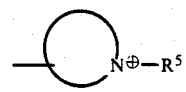

are as defined above and $X^\ominus$ is a counter anion in an inert solvent and in the presence of base to produce a carbapenem product of the formula

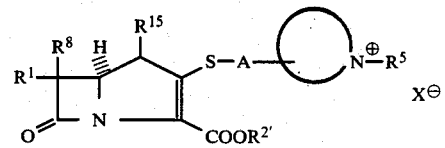

wherein $R^1$, $R^8$, $R^{2'}$, A, $R^{15}$,

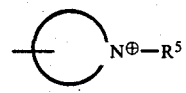

and $X^\ominus$ are as defined above and, if desired, the carboxyl protecting group $R^{2'}$ is removed to give the corresponding de-blocked compound of formula I, or a pharmaceutically acceptable salt thereof.

The alternative process utilizes the intermediate of the formula

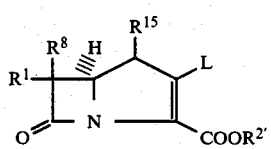

which, as mentioned before, has been disclosed, for example, in European Patent Applications Nos. 38,869 and 54,917 and which may be prepared by the general methods described therein. L represents a conventional leaving group (defined as "X" in European Patent Application No. 38,869) such as chloro, bromo, iodo, benzenesulfonyloxy, p-toluenesulfonyloxy, p-nitrobenzenesulfonyloxy, methanesulfonyloxy, trifluoromethanesulfonyloxy, diphenoxyphosphinyloxy or di(trichloroethoxy)phosphinyloxy. The preferred leaving group is diphenoxyphosphinyloxy.

Intermediates of Formula IV are generally formed in situ by reacting an intermediate of the formula

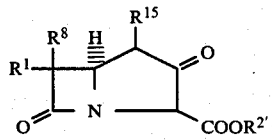

wherein $R^1$, $R^8$, $R^{15}$ and $R^{2'}$ are as defined above with a suitable acylating agent $R^0$-L. The preferred intermediate IV where L is diphenoxyphosphinyloxy may be prepared by reacting keto ester III in an inert organic solvent such as methylene chloride, acetonitrile or dimethylformamide with about an equimolar amount of diphenyl chlorophosphate in the presence of a base such as diisopropylethylamine, triethylamine, 4-dimethylaminopyridine or the like at a temperature of from about −20° C. to +40° C., most preferably at about 0° C. Intermediate IV may be isolated, if desired, but is conveniently used as the starting material for the alternative process without isolation or purification.

Carbapenem intermediate IV is reacted with a quaternary amine thiol compound of the formula

VII wherein

is as defined above and $X^\ominus$ is a counter anion. The reaction is carried out in an inert solvent such as acetonitrile, acetonitrile-dimethylformamide, tetrahydrofuran, tetrahydrofuran-H$_2$O, acetonitrile-H$_2$O or acetone in the presence of base. The nature of the base is not critical. Suitable bases include sodium hydroxide, diisopropylethylamine, 1,8-diazabicyclo[5.4.0]undec-7-ene, 1,5-diazabicyclo[4.3.0]non-5-ene and tri(C$_1$–C$_4$)alkylamines such as triethylamine, tributylamine or tripropylamine. Reaction of intermediate IV and thiol VII may be carried out over a wide temperature range, e.g. −15° C. up to room temperature, but is preferably done at a temperature in the range of from about −15° C. to +15° C., most preferably at around 0° C.

The carbapenem product produced by reaction of the quaternary amine thiol VII with intermediate IV will have a counter anion associated with it [e.g. (C$_6$H$_5$O)$_2$-PO$_2^\ominus$, Cl$^\ominus$ or the anion associated with the quaternary thiol] which may at this stage be substituted by a different counter anion, e.g. one which is more pharmaceutically acceptable, by conventional procedures. Alternatively, the counter anion may be removed during the subsequent de-blocking step. Where the quaternized cabapenem compound and counter anion form an insoluble product, the product may crystallize out as it is formed and be collected pure by filtration.

Following formation of the desired carbapenem product, the carboxyl protecting group R$^{2'}$ of Compound I' may be optionally removed by conventional procedures such as solvolysis, chemical reduction or hydrogenation. Where a protecting group such as p-nitrobenzyl, benzyl, benzhydryl or 2-naphthylmethyl is used which can be removed by catalytic hydrogenation, intermediate I' in a suitable solvent such as dioxane-water-ethanol, tetrahydrofuran-diethylether-buffer, tetrahydrofuran-aqueous dipotassium hydrogen phosphate-isopropanol or the like may be treated under a hydrogen pressure of from 1 to 4 atmospheres in the presence of a hydrogenation catalyst such as palladium on charcoal, palladium hydroxide, platinum oxide or the like at a temperature of from 0° to 50° C. for from about 0.24 to 4 hours. When R$^{2'}$ is a group such as o-nitrobenzyl, photolysis may also be used for deblocking. Protecting groups such as 2,2,2-trichloroethyl may be removed by mild zinc reduction. The allyl protecting group may be removed by using a catalyst comprising a mixture of a palladium compound and triphenyl phosphine in a suitable aprotic solvent such as tetrahydrofuran, methylene chloride or diethyl ether. Similarly, other conventional carboxyl protecting groups may be removed by methods known to those skilled in the art. Finally, as mentioned above, compounds of Formula I' where R$^{2'}$ is a physiologically hydrolyzable ester such as acetoxymethyl, phthalidyl, indanyl, pivaloyloxymethyl, methoxymethyl, etc., may be administered directly to the host without de-blocking since such esters are hydrolyzed in vivo under physiological conditions.

The thiol intermediates of Formula VII may be prepared, for example, from the corresponding thiolacetate compound of the formula

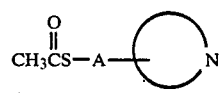

wherein A is as defined above and

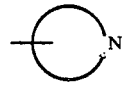

represents a mono-, bi- or polycyclic aromatic heterocyclic radical containing a quaternizable nitrogen in the ring, said ring being attached to A through a ring carbon atom. The thiolacetate compound is quaternized by reacting it in an inert organic solvent such as diethyl ether, dichloromethane, methylene chloride, dioxane, benzene, xylene, toluene or mixtures thereof with a suitable alkylating agent of the formula

wherein R$^5$ is as defined above and X' is a conventional leaving group such as halo (chloro, bromo or iodo, most preferably iodo) or a sulfonate ester moiety such as mesylate, tosylate or triflate. The temperature for the alkylation reaction is not critical, and temperatures in the range of from about 0° C. to 40° C. are preferred.

Prior to reaction with carbapenem intermediate IV, the quaternized thiolacetate compound is subjected to acidic or basic hydrolysis to generate quaternary thiol intermediate VII. This hydrolysis is preferably done immediately prior to coupling with IV so as to minimize decomposition of the relatively unstable quaternary thiol VII.

By proper selection of the solvents, the reaction from intermediate III to end product I may be carried out without isolation of the various intermediates, i.e. in a "one-pot" process. An example of such a process is illustrated below in Example 22.

As in the case of other β-lactam antibiotics, compounds of general formula I may be converted by known procedures to pharmaceutically acceptable salts which, for purposes of the present invention, are substantially equivalent to the non-salted compounds. Thus, for example, one may dissolve a compound of formula I wherein R$^2$ is an anionic charge in a suitable inert solvent and then add an equivalent of a pharmaceutically acceptable acid. The desired acid addition salt may be recovered by conventional procedures, e.g. solvent precipitation, lyophilization, etc. Where other basic or acidic functional groups are present in the compound of formula I, pharmaceutically acceptable base addition salts and acid addition salts may be similarly prepared by known methods.

It will be appreciated that certain products within the scope of formula I may be formed as optical isomers as well as epimeric mixtures thereof. It is intended that the present invention include within its scope all such optical isomers and epimeric mixtures. For example, when the 6-substituent is hydroxyethyl, such substituent may be in either the R or S configuration and the resulting isomers as well as epimeric mixtures thereof are encompassed by the present invention.

A compound of formula I where $R^2$ is hydrogen or an anionic charge, or a pharmaceutically acceptable salt thereof may also be converted by conventional procedures to a corresponding compound where $R^2$ is a physiologically hydrolyzable ester group, or a compound of formula I wherein $R^2$ is a conventional carboxyl protecting group may be converted to the corresponding compound where $R^2$ is hydrogen, an anionic charge or a physiologically hydrolyzable ester group, or a pharmaceutically acceptable salt thereof.

The novel carbapenem derivatives of general formula I wherein $R^2$ is hydrogen, an anionic charge or a physiologically hydrolyzable carboxyl protecting group, or the pharmaceutically acceptable salts thereof, are potent antibiotics active against various gram-positive and gram-negative bacteria and they may be used, for example, as animal feed additives for promotion of growth, as preservatives in food, as bactericides in industrial applications, for example in waterbased paint and in the white water of paper mills to inhibit the growth of harmful bacteria, and as disinfectants for destroying or inhibiting the growth of harmful bacteria on medical and dental equipment. They are especially useful, however, in the treatment of infectious disease in humans and other animals caused by gram-positive or gram-negative bacteria.

The pharmaceutically active compounds of this invention may be used alone or formulated as pharmaceutical compositions comprising, in addition to the active carbapenem ingredient, a pharmaceutically acceptable carrier or diluent. The compounds may be administered by a variety of means; those of principal interest include: orally, topically or parenterally (e.g. intravenous or intramuscular injection). The pharmaceutical compositions may be in solid form such as capsules, tablets, powders, etc. or in liquid form such as solutions, suspensions or emulsions.

Compositions for injection, the preferred route of delivery, may be prepared in unit dose form in ampules or in multidose containers and may contain formulatory agents such as suspending, stabilizing and dispersing agents. The compositions may be in ready to use form or in powder form for reconstitution at the time of delivery with a suitable vehicle such as sterile water.

The dosage to be administered depends to a large extent on the particular compound being used, the particular composition formulated, the route of administration, the nature and condition of the host and the particular situs and organism being treated. Selection of the particular preferred dosage and route of application, then, is left to the discretion of the therapist. In general, however, the compounds may be administered parenterally or orally to mammalian hosts in an amount of from about 5 to 200 mg/kg/day. Administration is generally carried out in divided doses, e.g. three to four times a day.

To illustrate the potent broad-spectrum antibacterial activity of the carbapenems of the present invention, both in vitro and in vivo, and the low toxicity of the compounds, biological data is provided below relating to the presently preferred carbapenem compounds of the present invention.

In Vitro Activity

Samples of the carbapenem compound prepared in Examples 1–2 after solution in water and dilution with Nutrient Broth were found to exhibit the following Minimum Inhibitory Concentrations (M.I.C.) in mcg/ml versus the indicated microorganisms as determined by overnight incubation at 37° C. by tube dilution. N-Formimidoyl thienamycin is included in the following tables as a comparison compound.

| | In Vitro Antibacterial Activity of Carbapenem Derivative of Example 1 | |
|---|---|---|
| | MIC (mcg/ml) | |
| Organism | New Compound | N—Formimidoyl Thienamycin |
| S. pneumoniae A-9585 | 0.25 | 0.004 |
| S. pyogenes A-9604 | 0.06 | 0.001 |
| S. aureus A-9537 | 0.13 | 0.004 |
| S. aureus A-9537 + 50% serum | 0.03 | 0.016 |
| S. aureus A-9606 (Pen-res.) | 0.06 | 0.008 |
| S. aureus A15097 (Meth-res.) | 4 | 0.5 |
| S. faecalis A20688 | 0.5 | 0.5 |
| E. coli A15119 ($10^{-4}$ dil.) | 0.06 | 0.016 |
| E. coli A15119 ($10^{-3}$) | — | 0.03 |
| E. coli A15119 ($10^{-2}$) | — | 0.06 |
| E. coli A20341-1 ($10^{-4}$) | 0.03 | 0.03 |
| E. coli A20341-1 ($10^{-3}$) | — | 0.03 |
| E. coli A20341-1 ($10^{-2}$) | — | 0.13 |
| K. pneumoniae A-9664 | 0.25 | 0.13 |
| K. pneumoniae A20468 | 0.25 | 0.06 |
| P. mirabilis A-9900 | 0.13 | 0.06 |
| P. vulgaris A21559 | 0.13 | 0.03 |
| P. morganii A15153 | 0.13 | 0.13 |
| P. rettgeri A22424 | 0.25 | 0.25 |
| S. marcescens A20019 | 0.13 | 0.03 |
| E. cloacae A-9569 | 0.13 | 0.06 |
| E. cloacae A-9656 | 0.13 | 0.06 |
| P. aeruginosa A-9843A | 4 | 1 |
| P. aeruginosa A21213 | 1 | 0.25 |
| H. influenzae A-9833 | 16 | 16 |
| H. influenzae A20178 | 32 | 32 |
| H. influenzae A21518 | 16 | 32 |
| H. influenzae A21522 | 8 | 32 |
| B. fragilis A22862 | 0.03 | 0.016 |
| B. fragilis A22053 | 0.03 | 0.06 |
| B. fragilis A22696 | 0.25 | 0.13 |
| B. fragilis A22863 | 0.03 | 1 |

| | In Vitro Antibacterial Activity of Carbapenem Derivative of Example 2 | |
|---|---|---|
| | MIC (mcg/ml) | |
| Organism | New Compound | N—Formimidoyl Thienamycin |
| S. pneumoniae A-9585 | 0.001 | 0.002 |
| S. pyogenes A-9604 | 0.001 | 0.002 |

In Vitro Antibacterial Activity of Carbapenem Derivative of Example 2

| | MIC (mcg/ml) | |
|---|---|---|
| Organism | New Compound | N—Formimidoyl Thienamycin |
| S. aureus A-9537 | 0.004 | 0.004 |
| S. aureus A-9537 + 50% serum | 0.016 | 0.016 |
| S. aureus A-9606 (Pen.-res.) | 0.008 | 0.008 |
| S. aureus A 15097 (Meth.-res.) | 8 | 4 |
| S. faecalis A 20688 | 0.25 | 0.5 |
| E. coli A 15119 | 0.016 | 0.016 |
| E. coli A 20341-1 | 0.016 | 0.03 |
| K. pneumoniae A9664 | 0.06 | 0.06 |
| K. pneumoniae A20468 | 0.13 | 0.13 |
| P. mirabilis A9900 | 0.03 | 0.06 |
| P. vulgaris A21559 | 0.016 | 0.03 |
| P. morganii A15153 | 0.06 | 0.13 |
| P. rettgeri A22424 | 0.13 | 0.13 |
| S. marcescens A20019 | 0.03 | 0.03 |
| E. cloacae A9659 | 0.13 | 0.06 |
| E. cloacae A9656 | 0.25 | 0.06 |
| P. aeruginosa A9843A | 8 | 1 |
| P. aeruginosa A21213 | 2 | 0.25 |

In Vivo Activity

The in vivo therapeutic efficacy of the compound of Example 1 and N-formimidoyl thienamycin after intramuscular administration to mice experimentally infected with various organisms are shown in the following Table. The $PD_{50}$ (dose in mg/kg required to give protection to 50% of the infected mice) is indicated.

| | Protective Effect in the Intramuscular Treatment of Infected Mice | | |
|---|---|---|---|
| | | $PD_{50}$/Treatment (mg/kg) | |
| Organism | Challenge (No. of organisms) | Compound of Example 1 | N—Formimidoyl Thienamycin |
| P. mirabilis A-9900 | $3.6 \times 10^6$ | 3.3 | 3*/15* |
| P. aeruginosa A-9843a | $5.5 \times 10^4$ | 0.3 | 0.5* |
| P. aeruginosa A-20481 | $5.4 \times 10^4$ | 0.63 | 0.4* |
| P. aeruginosa A-20599 | $1.4 \times 10^5$ | 0.7 | 0.18* |
| S. aureus A-9606 | $6.6 \times 10^8$ | 0.09 | 0.07* |
| S. faecalis A-20688 | $2.3 \times 10^8$ | 3.3 | 2.8* |
| E. coli A-15119 | $6.2 \times 10^6$ | 0.6 | 2.5* |
| K. pneumoniae A-9964 | $5.1 \times 10^6$ | 2.5 | 2.2* |

*Historical data
Treatment Schedule:
Except for E. coli A15119 and K. pneumoniae A9964, mice were treated i.m. with drugs 0 and 2 hours post-infection. For E. coli and K. pneumoniae the treatment schedule was 1 and 3.5 hours post-infection. 5 mice per dose were used for each test

Toxicity

The toxicity of the compound of Example 1 after intracranial administration to mice was determined and is shown in the following Table.

| | Toxicity After Intracranial Administration to Mice | |
|---|---|---|
| Compound | *$LD_{50}$ (mg/kg) | Highest Dose (mg/kg) Without Clinical Signs of Toxicity |
| Compound of Example 1 | 14 | 5 |
| N—Formimidoyl Thienamycin | 32 | ~5 |

*Average of 25/mice/compound

Blood Levels in Mice After Intramuscular Administration

Blood levels and the half-life of the compound of Example 1 after intramuscular administration of 20 mg/kg in mice are shown in the Table below.

| | Blood Level (μg/ml) | | | | | | **$t_{\frac{1}{2}}$ | **AUC |
|---|---|---|---|---|---|---|---|---|
| | 10 | 20 | 30 | 45 | 60 | 90 | | (μg · h/ |
| Compound | Minutes after Administration | | | | | | (min) | ml) |
| Compound of Example 1 | 14 | 10.8 | 6.8 | 2.6 | 0.8 | <0.6 | 10 | 6.3 |
| N—Formimidoyl Thieramycin | 12.6 | 9.9 | 7.3 | 2.6 | 0.7 | <0.3 | 9 | 6 |

Compounds were solubilized in 0.1 M phosphate buffer pH 7.
Values are from a single test; 4 mice used per compound.
*$t_{\frac{1}{2}}$ refers to half-life in minutes
**AUC refers to the area under the curve

Urinary Recovery

The urinary recovery of the compound of Example 1 after intramuscular administration (20 mg/kg) to mice is shown in the following Table.

| | Urinary Recovery Intramuscular Administration of 20 mg/kg to Mice | | | |
|---|---|---|---|---|
| | Percentage of Dose Recovered | | | |
| | 0-3 | 3-6 | 6-24 | 0-24 |
| Compound | Hours After Administration | | | |
| Compound of Example 1 | 26.1 | 0.5 | 0.1 | 26.7 ± 6.7 |
| N—Formimidoyl Thienamycin | 12.1 | 0.1 | <0.1 | 12.2 ± 3.6 |

Compounds were solubilized in 0.1 M phosphate buffer pH 7. Values are from a single test; 4 mice per compound.

Additional Biological Data

In Vitro Activity

Samples of the carbapenem compounds indicated below (identified by example number) after solution in water and dilution with Nutrient Broth were found to exhibit the following Minimum Inhibitory Concentration (M.I.C.) in mcg/ml versus the indicated microorganisms as determined by overnight incubation at 37° C. by tube dilution. N-Formimidoyl thienamycin is included in the following tables as a comparision compound.

| | MIC (μg/ml) | | | | | |
|---|---|---|---|---|---|---|
| Organism | Ex. 3 | Ex. 4 | Ex. 5 | Ex. 6 | Ex. 7 | MK 0787* |
| S. pneumoniae A-9585 | 0.002 | 0.002 | 0.004 | 0.004 | 0.004 | 0.002 |
| S. pyogenes A-9604 | 0.002 | 0.001 | 0.004 | 0.004 | 0.004 | 0.002 |
| S. faecalis A20688 | 0.5 | 0.5 | 0.25 | 0.5 | 0.13 | 0.5 |
| S. aureus A-9537 | 0.016 | 0.008 | 0.004 | 0.03 | 0.008 | 0.004 |

-continued

| | | | | | | |
|---|---|---|---|---|---|---|
| S. aureus A-9537 + 50% serum | 0.016 | 0.03 | 0.016 | 0.06 | 0.03 | 0.016 |
| S. aureus A-9606 (Pen-res) | 0.016 | 0.016 | 0.008 | 0.03 | 0.016 | 0.008 |
| S. aureus A15097 (Meth-res) | 4 | 4 | 8 | 4 | 2 | 4 |
| E. coli A15119 | 0.03 | 0.016 | 0.016 | 0.06 | 0.004 | 0.016 |
| E. coli A20341-1 | 0.016 | 0.016 | 0.016 | 0.06 | 0.004 | 0.03 |
| K. pneumoniae A-9664 | 0.06 | 0.03 | 0.03 | 0.13 | 0.016 | 0.06 |
| K. pneumoniae A20468 | 0.06 | 0.03 | 0.06 | 0.25 | 0.016 | 0.13 |
| E. cloacae A-9659 | 0.13 | 0.03 | 0.06 | 0.25 | 0.016 | 0.06 |
| E. cloacae A-9656 | 0.13 | 0.06 | 0.13 | 0.25 | 0.016 | 0.06 |
| P. mirabilis A-9900 | 0.13 | 0.06 | 0.03 | 0.025 | 0.016 | 0.06 |
| P. vulgaris A21559 | 0.016 | 0.016 | 0.016 | 0.06 | 0.008 | 0.03 |
| M. morganii A15153 | 0.13 | 0.016 | 0.06 | 0.13 | 0.016 | 0.13 |
| P. rettgeri A22424 | 0.25 | 0.13 | 0.13 | 0.25 | 0.06 | 0.13 |
| S. marcescens A20019 | 0.016 | 0.03 | 0.06 | 0.13 | 0.008 | 0.03 |
| P. aeruginosa A-9843a | 2 | 2 | 4 | 8 | 1 | 0.25 |
| P. aeruginosa A21213 | 0.5 | 0.13 | 2 | 1 | 0.25 | 0.25 |
| H. influenzae A-9833 | 2 | 2 | 4 | >32 | >32 | 16 |
| H. influenzae A21518 | 2 | 2 | 4 | >32 | >32 | 16 |
| B. fragilis A22862 | 0.25 | 0.06 | 0.03 | 0.03 | 0.016 | 0.06 |
| B. fragilis A22696 | 0.5 | 0.5 | 0.25 | 0.25 | 0.25 | 0.13 |

| | MIC (μg/ml) | | | | |
|---|---|---|---|---|---|
| Organism | Ex. 8 | Ex. 9 | Ex. 10 | Ex. 11 | MK 0787* |
| S. pneumoniae A-9585 | 0.002 | 0.001 | 0.001 | 0.002 | 0.002 |
| S. pyogenes A-9604 | 0.002 | 0.001 | 0.001 | 0.002 | 0.002 |
| S. faecalis A20688 | 0.5 | 0.13 | 0.25 | 0.5 | 0.25 |
| S. aureus A-9537 | 0.008 | 0.004 | 0.008 | 0.004 | 0.002 |
| S. aureus A-9537 + 50% serum | 0.03 | 0.008 | 0.06 | 0.016 | 0.016 |
| S. aureus A-9606 (Pen-res) | 0.03 | 0.008 | 0.008 | 0.016 | 0.008 |
| S. aureus A15097 (Meth-res) | — | — | | | — |
| E. coli A15119 | 0.016 | 0.008 | 0.016 | 0.016 | 0.016 |
| E. coli A20341-1 | 0.03 | 0.004 | 0.008 | 0.03 | 0.016 |
| K. pneumoniae A-9664 | 0.03 | 0.016 | 0.06 | 0.03 | 0.03 |
| K. pneumoniae A20468 | 0.13 | 0.03 | 0.13 | 0.13 | 0.13 |
| E. cloacae A-9659 | 0.13 | 0.03 | 0.13 | 0.06 | 0.13 |
| E. cloacae A-9656 | 0.06 | 0.03 | 0.13 | 0.13 | 0.06 |
| P. mirabilis A-9900 | 0.13 | 0.016 | 0.13 | 0.03 | 0.03 |
| P. vulgaris A21559 | 0.03 | 0.008 | 0.016 | 0.03 | 0.016 |
| M. morganii A15153 | 0.13 | 0.03 | 0.13 | 0.06 | 0.06 |
| P. rettgeri A22424 | 0.13 | 0.06 | 0.13 | 0.13 | 0.13 |
| S. marcescens A20019 | 0.06 | 0.016 | 0.06 | 0.06 | 0.03 |
| P. aeruginosa A-9843A | 1 | 2 | 32 | 0.5 | 1 |
| P. aeruginosa A21213 | 0.25 | 0.13 | 2 | 0.13 | 0.13 |

| | MIC (μg/ml) | | | |
|---|---|---|---|---|
| Organism | Ex. 12 | Ex. 13 | Ex. 14 | MK 0787* |
| S. pneumoniae A-9585 | 0.002 | 0.0005 | 0.0005 | 0.002 |
| S. pyogenes A-9604 | 0.004 | 0.0005 | 0.0005 | 0.002 |
| S. faecalis A20688 | 0.5 | 0.13 | 0.13 | 0.25 |
| S. aureus A-9537 | 0.008 | 0.008 | 0.008 | 0.002 |
| S. aureus A-9537 + 50% serum | 0.016 | 0.016 | 0.03 | 0.008 |
| S. aureus A-9606 (Pen-res) | 0.03 | 0.008 | 0.016 | 0.008 |
| S. aureus A15097 (Meth-res) | — | — | — | — |
| E. coli A15119 | 0.016 | 0.004 | 0.008 | 0.016 |
| E. coli A20341-1 | 0.008 | 0.008 | 0.008 | 0.016 |
| K. pneumoniae A-9664 | 0.03 | 0.03 | 0.03 | 0.03 |
| K. pneumoniae A20468 | 0.06 | 0.13 | 0.03 | 0.06 |
| E. cloacae A-9659 | 0.06 | 0.06 | 0.03 | 0.06 |
| E. cloacae A-9656 | 0.03 | 0.03 | 0.03 | 0.06 |
| P. mirabilis A-9900 | 0.03 | 0.016 | 0.016 | 0.016 |
| P. vulgaris A21559 | 0.016 | 0.008 | 0.016 | 0.016 |
| M. morganii A15153 | 0.06 | 0.016 | 0.03 | 0.06 |
| P. rettgeri A22424 | 0.13 | 0.25 | 0.06 | 0.13 |
| S. marcescens A20019 | 0.03 | 0.016 | 0.016 | 0.03 |
| P. aeruginosa A-9843A | 16 | 32 | 8 | 1 |
| P. aeruginosa A21213 | 2 | 2 | 0.5 | 0.13 |

| | MIC (μg/ml) | | | |
|---|---|---|---|---|
| Organism | Ex. 15 "A" | Ex. 15 "B" | Ex. 15 "C" | MK 0787* |
| S. pneumoniae A-9585 | 0.0005 | 0.0005 | 0.0005 | 0.002 |
| S. pyogenes A-9604 | 0.0005 | 0.001 | 0.0003 | 0.002 |
| S. faecalis A20688 | 0.13 | 0.5 | 0.5 | 0.25 |
| S. aureus A-9537 | 0.03 | 0.004 | 0.016 | 0.004 |
| S. aureus A-9537 + 50% serum | 0.03 | 0.016 | 0.06 | 0.008 |
| S. aureus A-9606 (Pen-res) | 0.004 | 0.008 | 0.03 | 0.008 |
| S. aureus A15097 (Meth-res) | — | — | — | — |
| E. coli A15119 | 0.004 | 0.008 | 0.06 | 0.008 |
| E. coli A20341-1 | 0.004 | 0.008 | 0.03 | 0.016 |
| K. pneumoniae A-9664 | 0.008 | 0.03 | 0.06 | 0.03 |
| K. pneumoniae A20468 | 0.008 | 0.016 | 0.13 | 0.06 |
| E. cloacae A-9659 | 0.016 | 0.016 | 0.13 | 0.13 |
| E. cloacae A-9656 | 0.016 | 0.03 | 0.13 | 0.13 |
| P. mirabilis A-9900 | 0.008 | 0.03 | 0.06 | 0.06 |
| P. vulgaris A21559 | 0.008 | 0.008 | 0.06 | 0.016 |
| M. morganii A15153 | 0.03 | 0.06 | 0.25 | 0.13 |
| P. rettgeri A22424 | 0.03 | 0.13 | 0.25 | 0.13 |
| S. marcescens A20019 | 0.008 | 0.016 | 0.13 | 0.016 |
| P. aeruginosa A-9843A | 0.5 | 2 | 8 | 0.5 |
| P. aeruginosa A21213 | 0.03 | 0.13 | 0.5 | 0.13 |

| Organism | Ex. 16 | Ex. 17 | *MK 0787 |
|---|---|---|---|
| S. pneumoniae A-9585 | 0.002 | 0.016 | 0.001 |
| S. pyogenes A-9604 | 0.002 | 0.016 | 0.001 |
| S. faecalis A20688 | 1 | 4 | 0.25 |
| S. aureus A-9537 | 0.008 | 0.25 | 0.001 |
| S. aureus A-9537 + 50% serum | 0.03 | 1 | 0.008 |
| S. aureus A-9606 (Pen-res) | 0.016 | 0.5 | 0.002 |
| S. aureus A15097 (Meth-res) | — | — | — |
| E. coli A15119 | 0.016 | 0.6 | 0.008 |
| E. coli A20341-1 | 0.016 | 0.6 | 0.008 |
| K. pneumoniae A-9664 | 0.06 | 0.13 | 0.03 |
| K. pneumoniae A20468 | 0.06 | 0.5 | 0.06 |
| E. cloacae A9659 | 0.06 | 2 | 0.06 |
| E. cloacae A-9656 | 0.06 | 2 | 0.06 |
| P. mirabilis A-9900 | 0.06 | 0.13 | 0.016 |
| P. vulgaris A21559 | 0.03 | 0.13 | 0.008 |
| M. morganii A15153 | 0.13 | 0.5 | 0.06 |
| P. rettgeri A22424 | 0.25 | 2 | 0.06 |
| S. marcescens A20019 | 0.06 | 0.13 | 0.016 |
| P. aeruginosa A-9843A | 0.25 | >63 | 0.5 |
| P. aeruginosa A21213 | 0.13 | 16 | 0.13 |

| Organism | Ex. 18 | Ex. 19 | Ex. 20 | *MK 0787 |
|---|---|---|---|---|
| S. pneumoniae A-9585 | 1 | 0.002 | 0.06 | 0.001 |
| S. pyogenes A-9604 | 2 | 0.002 | 0.13 | 0.002 |
| S. faecalis A20688 | 63 | 0.5 | 16 | 0.25 |
| S. aureus A-9537 | 32 | 0.004 | 0.5 | 0.002 |
| S. aureus A-9537 + 50% serum | >63 | 0.008 | 2 | 0.004 |
| S. aureus A-9606 (Pen-res) | >125 | 0.016 | >125 | 0.004 |
| S. aureus A15097 (Meth-res) | — | — | — | — |
| E. coli A15119 | 16 | 0.008 | 1 | 0.016 |
| E. coli A20341-1 | 16 | 0.008 | 2 | 0.016 |
| K. pneumoniae A-9664 | 32 | 0.03 | 4 | 0.03 |
| K. pneumoniae A20468 | 63 | 0.06 | 4 | 0.06 |
| E. cloacae A-9659 | 63 | 0.03 | 8 | 0.06 |
| E. cloacae A-9656 | 125 | 0.03 | 16 | 0.06 |
| P. mirabilis A-9900 | 32 | 0.03 | 4 | 0.016 |
| P. vulgaris A21559 | 32 | 0.016 | 4 | 0.016 |
| M. morganii A15153 | 32 | 0.06 | 8 | 0.06 |
| P. rettgeri A22424 | 32 | 0.13 | 8 | 0.13 |
| S. marcescens A20019 | 32 | 0.03 | 4 | 0.03 |
| P. aeruginosa A-9843A | 63 | 0.5 | 32 | 0.5 |
| P. aeruginosa A21213 | 63 | 0.06 | 16 | 0.13 |

*N—Formimidoyl Thienamycin

In Vivo Activity

The in vivo therapeutic efficacy of certain compounds of the present invention and N-formimidoyl thienamycin (MK 0787) after intramuscular administration to mice experimentally infected with various organisms is shown below. The PD$_{50}$ (dose in mg/kg) required to give protection to 50% of the infected mice is indicated.

Protective Effect in the Intramuscular Treatment of Infected Mice

| | PD$_{50}$/treatment (mg/kg) | | | | | | |
|---|---|---|---|---|---|---|---|
| | Ex. 6 | Ex. 8 | Ex. 9 | Ex. 12 | Ex. 14 | Ex. 15 ("A") | Ex. 15 ("B") | MK 0787 |
| S. aureus A9606 | — | 0.21 | — | 0.89 | 0.07 | — | — | 0.07 |
| E. coli A15119 | — | 0.86 | 1.2 | — | — | — | — | 3 |
| K. pneumoniae A9664 | — | 1.8 | 1.8 | — | — | — | — | 3 |
| P. mirabilis A9900 | — | 1.4 | 7.1 | — | — | — | — | 9 |
| P. aeruginosa A9843A | 0.4 | 0.19 | 0.19 | 1.8 | 0.45 | 0.39 | 0.89 | 1 |
| P. aeruginosa A24081 | — | 0.33 | 0.19 | — | — | — | — | 0.4 |

| | Ex. 3 | Ex. 4 | Ex. 7 | MK 0787 |
|---|---|---|---|---|
| S. aureus A9606 | 0.07 | 0.1 | 0.2 | 0.07 |
| E. coli A15119 | 1 | 0.4 | 0.2 | 3 |
| K. pneumoniae A9664 | 3 | 3 | 1 | 3 |
| P. mirabilis A9900 | 2 | 4 | 2.4 | 9 |
| P. aeruginosa A9843A | 0.5 | 0.2 | 0.2 | 0.5 |
| P. aeruginosa A24081 | 0.8 | 0.2 | 0.1 | 0.4 |

| | Ex. 5 | MK 0787 |
|---|---|---|
| S. aureus | 0.2 | 0.07 |
| E. coli | 4 | 2.2 |
| K. pneumoniae | 3 | 2.3 |
| P. mirabilis | 10 | 9 |
| P. aeruginosa A9843A | 1.6 | 0.5 |

Blood Levels in Mice After Intramuscular Administration

Blood levels and the half-life of certain compounds of the present invention after intramuscular administration of 20 mg/kg in mice are shown below.

| Compound | C$_{max}$ (μg/ml) | *T$_{\frac{1}{2}}$ (min) | **AUC (μg · h/ml) |
|---|---|---|---|
| Example 1 | 14 | 10 | 6.3 |
| Example 2 | 13.9 | 9 | 5.3 |
| Example 3 | 14.5 | 10 | 6.9 |
| Example 4 | 15.5 | 11 | 7.7 |
| Example 5 | — | — | — |
| Example 6 | 17.7 | 9 | 8.5 |
| Example 7 | 19.2 | 11 | 11.8 |
| Example 8 | 18.8 | 11 | 10.5 |
| Example 9 | 16.7 | 12 | 8.5 |
| Example 10 | 20.1 | 11 | 9.5 |
| Example 11 | 14.9 | 11 | 7.4 |
| Example 13 | 14.8 | 11 | 6.4 |
| Example 14 | 15.8 | 13 | 7.6 |
| Example 15 "A" | 16.7 | 12 | 9.5 |
| Example 15 "B" | 15.9 | 10 | 7.4 |
| Example 15 "C" | 15.1 | 10 | 7.3 |
| MK 0787 | 14.6 | 10 | 6 |
| Example 17 | 11 | 8 | 3.4 |
| Example 18 | 14.9 | 6 | 3.9 |
| Example 19 | 27 | 16.7 | 15.1 |
| Example 20 | 28.4 | 14 | 15.6 |

Compounds were solubilized in 0.1 M phosphate buffer, pH 7.
Valves based on a single test; 4 mice per compound.
*T$_{\frac{1}{2}}$ refers to half-life in minutes
**AUC refers to the area under the blood concentration-time curve The following examples illustrated but do not limit the scope of the present invention. As used below the abbreviations "TMF" and "TEA" refer to tetrahydrofuran and triethylamine, respectively.

EXAMPLE 1

Preparation of 1-Methyl-4-[2-carboxy-6α-[1(R)-hydroxyethyl]-7-oxo-1-azabicyclo[3.2.0]hept-2-en-3-thiomethyl]pyridinium hydroxide inner salt

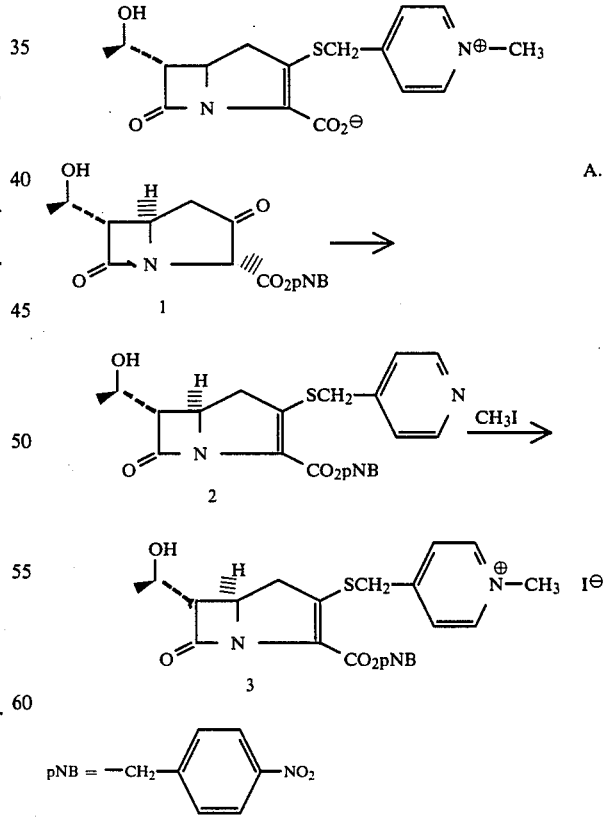

A solution of 673 mg (1.86 mmol) of p-nitrobenzyl 6α-[1-(R)-hydroxyethyl]-3,7-dioxo-1-azabicyclo[3.2.0-]hept-2-ene-2-carboxylate (1) in 10 ml of acetonitrile was cooled to −10° C. under a nitrogen atmosphere. A solution of 245 mg (1.90 mmol) of diisopropylethylamine in 1 ml of acetonitrile was added followed by a dropwise addition of 510 mg (1.90 mmol) of diphenyl chlorophosphate in 1 ml of acetonitrile over a period of 2 minutes. The resulting solution was stirred at −10° C. for 15 minutes to provide a p-nitrobenzyl 3-(diphenylphosphoryloxy)-6α-[1-(R)-hydroxyethyl]-7-oxo-1-azabicyclo[3.2.0]hept-2-ene-2-carboxylate. To this solution was added a solution of 245 mg (1.90 mmol) of diisopropylethylamine in 0.5 ml of acetonitrile followed by a solution of 270 mg (2.16 mmol) of 4-mercaptomethylpyridine in 0.5 ml of acetonitrile. The reaction mixture was stirred at −10° C. for 60 minutes and the white precipitate which formed was collected by filtration and washed with 5 ml of ice-cold acetonitrile to give 660 mg (76% yield) of compound 2 as white crystals, m.p. 145° C.

NMR(DMSO-d6) δ: 1.20(3H, d, J=6.0 Hz), 3.2–3.4 (3H, m), 3.7–4.1 (2H, m), 4.25 (2H, s), 5.05 (1H, d, J=4.0 Hz), 5.25 (1H, d, J=14.0 Hz), 5.48 (1H, d, J=14.0 Hz), 7.40 (2H, d, J=5.5 Hz), 7.70 (2H, d, J=8.5 Hz), 8.23 (2H, d, J=8.5 Hz) and 8.58 (2H, d, J=5.5 Hz).

IR (KBr) γ max: 3400, 1790, 1695 and 1600 cm$^{-1}$.

Anal. Calc'd for $C_{22}H_{21}N_3O_6S$: C, 58.01; H, 4.56; N, 9.23; S, 7.04. Found: C, 57.74; H, 4.56; N, 9.58; S, 7.21.

To a solution of 660 mg (1.41 mmol) of intermediate 2 in 140 ml of acetone there was added 5 ml of methyl iodide. The reaction solution was stirred for 8 hours at 25° C. The solvent was evaporated in vacuo affording a slightly yellow solid which was triturated with diethyl ether to give 779 mg (90% yield) of the title compound 3 as a white amorphous solid, m.p. 130° C. (decomp.).

NMR (DMSO-d6) δ: 1.15 (3H, d, J=6.0 Hz), 3.2–3.4 (3H, m), 3.7–4.1 (2H, m), 4.25 (3H, s), 4.30 (2H, s), 5.25 (1H, d, J=14.0 Hz), 5.50 (1H, d, J=14.0 Hz), 7.70 (2H, d, J=9.0 Hz), 8.10 (2H, d, J=7.0 Hz), 8.25 (2H, d, J=9.0 Hz) and 8.90 (2H, d, J=7.0 Hz).

IR (KBr) γ max: 3400, 1770, 1690 and 1640 cm$^{-1}$.

Anal. Calc'd for $C_{23}H_{24}N_3O_6SI \cdot H_2O$: C, 44.39; H, 4.22; N, 6.82; S, 5.20. Found: C, 44.66; H, 4.01; N, 6.84; S, 5.64.

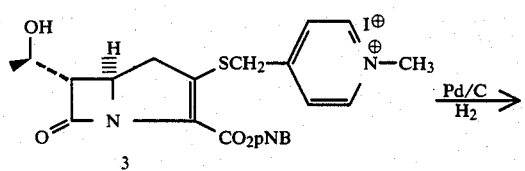

B.

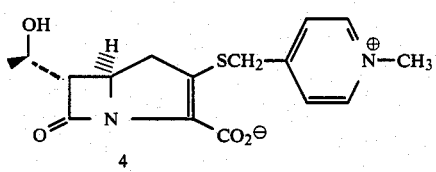

4

To a solution of 779 mg (1.27 mmol) of compound 3 in tetrahydrofuran-water-diethyl ether (80 ml-80 ml-100 ml), there was added 140 mg (1.4 mmol) of potassium bicarbonate and 125 mg (0.7 mmol) of dibasic potassium phosphate. Then, 700 mg of 10% palladium on charcoal was added and the mixture was hydrogenated at 40 psi for 45 min on the Parr Shaker. The mixture was then filtered and the catalyst was washed with water (2×10 ml). The combined filtrate and washings were extracted with diethyl ether (150 ml) and then lyophilized to give a brown powder. This crude material was purified on a $C_{18}$ BONDAPAK reverse phase column (30 g) (Waters Associates), eluting with water under a 8 psi pressure. Each fraction (20 ml) was screened by high pressure liquid chromatography, and fractions having an ultraviolet absorption at λ max=300 nm were collected and lyophilized to give 135 mg (32% yield) of the title compound 4 as a slightly yellow solid.

NMR ($D_2O$) δ: 1.25 (3H, d, J=6.0 Hz), 2.7–3.2 (2H, m), 3.40 (1H, q, J=9.0 and 2.5 Hz), 3.9–4.2 (2H, m), 4.40 (3H, s), 4.72 (2H, s), 8.10 (2H, d, J=6.0 Hz), 8.72 (2H, d, J=6.0 Hz).

IR (KBr) γ max: 3400, 1755, 1640 and 1590 cm$^{-1}$.

UV λ max ($H_2O$): 296 nm (ε=7782), 258 nm (ε=6913).

EXAMPLE 2

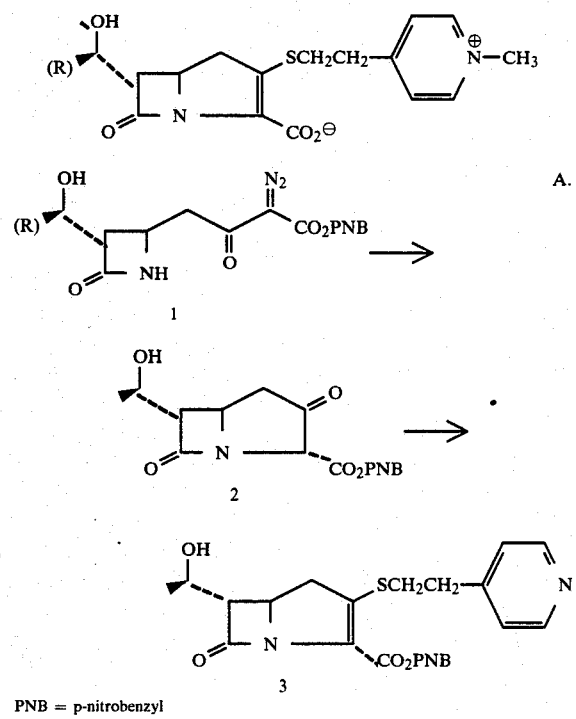

PNB = p-nitrobenzyl

A suspension of 1.1 g (2.93 m moles) of diazo compound 1 was purged at room temperature with nitrogen for 5 minutes in 30 ml dry benzene. It was treated with 25 mg of rhodium acetate dimer and the mixture was heated to reflux for 45 minutes. The warm solution was diluted with ethyl acetate (25 ml), filtered to remove the catalyst and evaporated to dryness to give the keto compound 2 as a white solid. This was dissolved in dry acetonitrile (20 ml) and cooled to −10° C. To this solution was added, under nitrogen, diisopropylethylamine (417 mg, 3.2 m moles) followed by 810 mg (3.0 m moles) of diphenyl chlorophosphate and the reaction mixture was stirred at −10° C. for 20 minutes. The reaction mixture was then treated with diisopropylethylamine (420 mg, 3.2 m moles) and 2-(4-pyridyl)ethane thiol (560 mg; 4.03 m moles) in 2 ml acetonitrile [J. Org. Chem. 26: 82 (1961) Ludwig Bauer and Libero A. Gardella Jr.]. The reaction mixture was stirred at −5° C. to −10° C. for 1 hour, then diluted with methylene chloride (100 ml) and washed successively with brine-$H_2O$ (1:1), 4% $H_3PO_4$, 5% $NaHCO_3$, $H_2O$ and brine. The organic phase was dried (MgSO4) and evaporated to give a white solid. This solid was washed with diethyl ether:-hexane (1:1) and dried under high vacuum to give 901 mg (63.9%) of compound 3.

IR(KBr) 1790, 1690 cm$^{-1}$.

NMR (CDCl3/DMSO) δ1.20 (3H, d, J=3.0 Hz, CH3), 2.8 to 3.2 (7H, m), 3.9 to 4.4 (2H, m), 5.1 (1H, d), 5.4 (2H, q), 7.3 (2H, d), 8.5 (2H, q), 7.76 (2H, d), 8.3 (2H, q).

B.

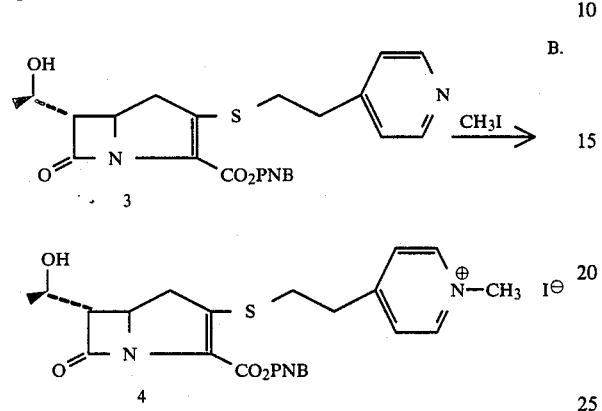

A suspension of carbapenem 3 (890 mg, 1.85 m moles) and 7 ml of iodomethane in 200 ml dry acetone and 12 ml methylene chloride was stirred at 25° C. for 24 hours. The reaction mixture became a clear solution in 18 hours. The solvent was removed under reduced pressure, then the residue was washed with diethyl ether to give 920 mg (1.48 m moles) (79.8%) of 4 as a foamy solid.

IR(KBr) 1765, 1690 cm$^{-1}$.

NMR (DMSO) δ1.3 (3H, d, J=3.0 Hz), 3.1 to 3.7 (7H, m), 4.1 (3H, m), 4.3 (3H, s), 5.38 (2H, q, J=7.0 Hz), 8.1 (2H, d, J=3.0 Hz), 8.9 (2H, d, J=3.0 Hz), 7.6 (2H, d, J=4.0 Hz), 8.2 (2H, d, J=4.0 Hz).

C.

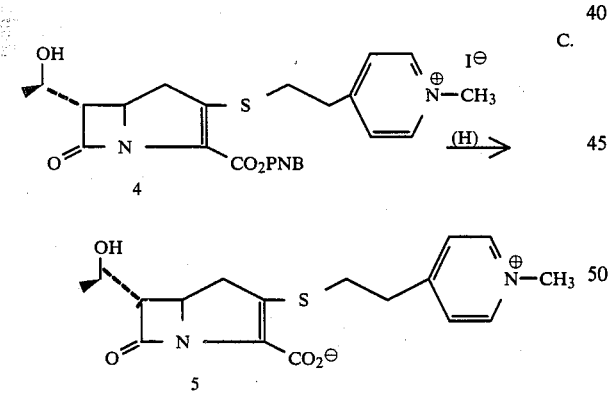

The carbapenem 4 (920 mg, 1.47 m moles), dissolved in 90 ml tetrahydrofuran, 90 ml diethyl ether and 90 ml water, was treated with 265 mg (1.51 m moles) dibasic potassium phosphate, 190 mg (1.9 m moles) potassium hydrogen carbonate and 800 mg 10% palladium on carbon. It was hydrogenated at 45 psi for 1 hour. The catalyst was filtered off through CELITE and the filtrate was washed with diethyl ether (3×25 ml). The aqueous layer was lyophilized to give a brownish material which was then purified twice by chromatography through a 12 g*C18 column (H2O) to give 55 mg of 5.
*C18 BONDAPAK reverse phase column (Waters Associates)

IR(KBr) 1750, 1640 cm$^-$.

NMR (D2O) δ1.30 (3H, d, J=3.0 Hz), 3.0 to 3.5 (7H, m), 4.3 (3H, s), 4.0 to 4.5 (3H, m), 7.90 (2H, d), 8.70 (2H, d).

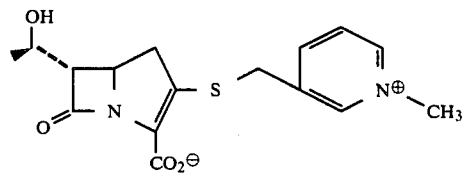

EXAMPLE 3

Preparation of 3-(N-Methylpyridine-3-yl-methanethio)-6α-[1-(R)-hydroxyethyl]-7-oxo-1-azabicyclo(3.2.0)hept-2-ene-2-carboxylate

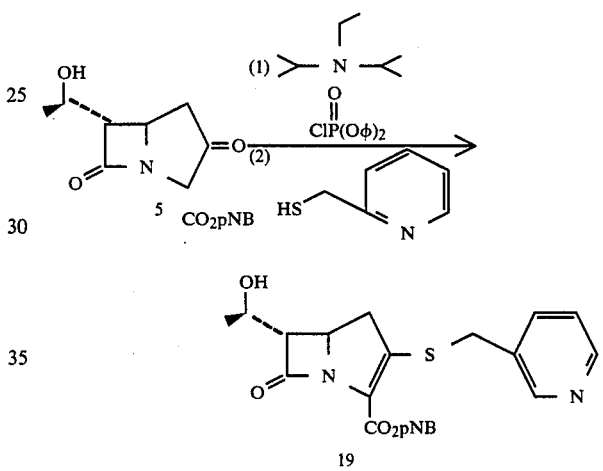

p-Nitrobenzyl 3-(pyridine-3-yl-methane thio)-6α-[1-(R)-hydroxy ethyl]-7-oxo-1-azabicyclo(3.2.0)hept-2-ene-2-carboxylate To a cooled (0°) solution of 925 mg (2.66 mmole) of the keto intermediate 5 in 14 ml of acetonitrile was added a solution of 377 mg (2.9 mmole) of diisopropyl ethylamine in 1 ml of acetonitrile followed by 786 mg (2.9 mmole) of diphenyl chlorophosphonate in 1 ml of acetonitrile under a nitrogen atmosphere. The resulting solution was stirred for 15 min at 0° C., and there was then added a solution of 377 mg (2.9 mmole) of 3-mercaptomethyl pyridine[prepared by the procedure described in Can. J. Chem., 56, 3068 (1978)] in 2 ml of acetonitrile. The reaction solution was stirred for 90 minutes at 0°. The precipitate was collected by filtration and washed with 20 ml of ethylacetate to give 950 mg (60% yield) of the title product as white crystals.

NMR(DMSO-d6) δ: 1.30(3H, d, J=6.0 Hz), 3.4–4.2(5H, m) 4.25(2H, s), 5.1(1H, d, J=4.5 Hz), 5.40(2H, ABq, J=14.4 Hz), 7.2–8.5(8H, m).

IR (KBr) γ max 3500, 1775, and 1580 cm$^{-1}$. Anal Calc'd. for C22H21J3O6S1: C, 58.01; H, 4.65; N, 9.23; S, 7.04. Found: C, 57.19; H, 5.19; N, 8.76; S, 7.08.

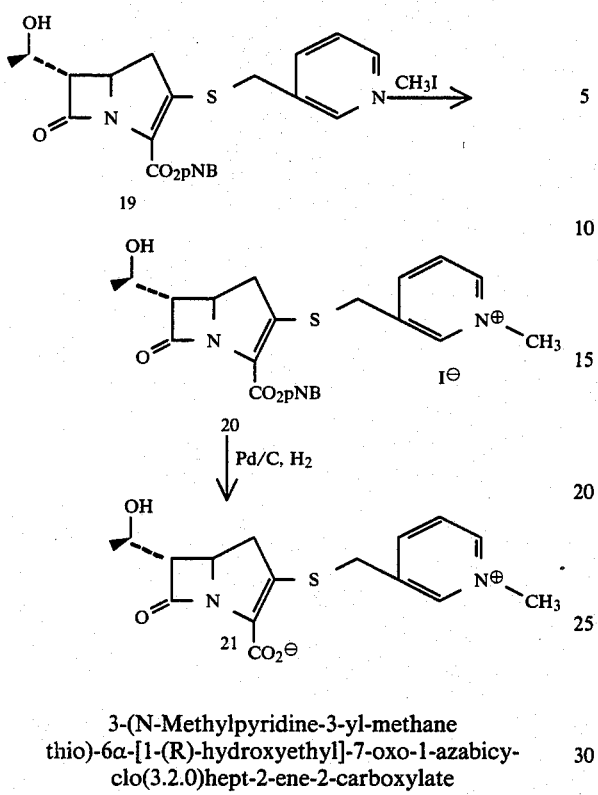

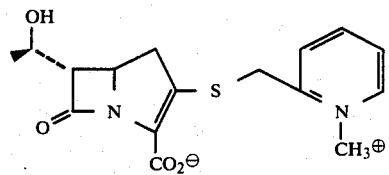

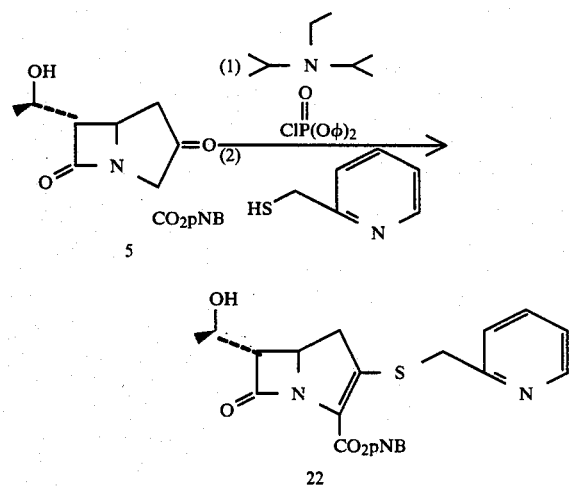

3-(N-Methylpyridine-3-yl-methane thio)-6α-[1-(R)-hydroxyethyl]-7-oxo-1-azabicyclo(3.2.0)hept-2-ene-2-carboxylate To a solution of 730 mg (1.56 mmole) of compound 19 in 120 ml of acetone was added 5 ml of methyl iodide and the reaction mixture was stirred for 18 hours at room temperature. The precipitate was collected by filtration and washed with acetone (10 ml) to give 940 mg (100% yield) of the quaternized pyridine 20 as a slightly yellow powder.

NMR (DMSO-d6) δ: 1.25(3H, d, J=5.8 Hz), 3.6–4.3(5H, m), 4.20(3H, s), 4.25(2H, s), 5.25(1H, d, J=7.2 Hz), 5.40(2H, ABq, J=12,16 Hz), and 7.6–9.2 (9H, m). IR(KBr) λ max: 3300, 1765 and 1690 cm$^{-1}$. Anal Calc'd. for $C_{23}H_{24}N_3O_6S_1I_1$: C, 46.24; H, 4.05; N, 7.03; S, 5.37. Found: C, 45.82; H, 4.11; N, 6.87; S, 6.10.

To a solution of 933 mg (1.6 mmole) of compound 20 in 90 ml of tetrahydrofuran and 90 ml of ether was added 200 mg of $KHCO_3$ and 349 mg of $K_2HPO_4$ in 90 ml of water followed by 1.0 g of palladium on charcoal. The mixture was hydrogenated at 45 psi on the Parr shaker for 45 minutes. The mixture was filtered through a Celite pad and the catalyst was washed with water. (2×10 ml). The combined filtrate and washing were extracted with ether (2×100 ml) and lyophilized to give a yellow solid which was purified on a $C_{18}$ BON-DAPAK (Waters Associates) reverse phase column (8 g), eluting with 5% acetonitrile in water under 8 psi pressure. Each 15 ml fraction was assayed by high pressure liquid chromatography and fractions having an ultraviolet absorption at λ max 300 nm were collected and lyophilized to give 230 mg (43% yield) of the title product as slightly yellow crystals. m.p. 130° C. (decomp)

NMR ($D_2O$) δ: 1.25(3H, d, J=7.0 Hz), 3.12(2H, d.d, J=7.9 Hz, 1.6 Hz), 3.42(1H, q, J=7.2 Hz, 1.6 Hz), 3.9–4.6(3H, m), 4.25(2H, s), 4.42(3H, s) and 8.0–9.0(4H,m). IR(KBr) γ max: 3400, 1750 and 1580 cm$^{-1}$.

UVλ max ($H_2O$): 298 nm (ε=8058). Anal. Calc'd. for $C_{16}H_{18}N_2O_4S_1\cdot 2H_2O$: C, 51.87; H, 5.44; N, 7.56. Found: C, 51.95; H, 5.66; N, 7.56.

EXAMPLE 4

Preparation of 3-(N-Methylpyridine-2-yl-methane thio)-6α-[1-(R)-hydroxyethyl]-7-oxo-1-azabicyclo(3.2.0)hept-2-ene-2-carboxylate p-Nitrobenzyl-3-(pyridine-2-yl-methane thio)-6α-[1-(R)-hydroxyethyl]-7-oxo-1-azabicyclo(3.2.0)hept-2-ene-2-carboxylate To a cooled (0°) solution of 925 mg (2.65 mmole) of the keto intermediate 5 in 14 ml of acetonitrile was added a solution of 377 mg (2.92 mmole) of diisopropyl ethylamine in 1 ml of acetonitrile followed by 786 mg (2.90 mmole) of diphenyl chlorophosphate in 1 ml of acetonitrile under a nitrogen atmosphere. The resulting solution was stirred for 15 minutes at 0°, and there was then added a solution of 377 mg (2.92 m mole) of diisopropyl ethylamine in 1 ml of acetonitrile followed by 350 mg (3.0 mmole) of 2-mercaptomethyl pyridine [prepared by the procedure described in Can. J. Chem., 56, 3068 (1978)] in 1 ml of acetonitrile. The reaction solution was stirred for 2 hours at −10° C. The precipitate was collected by filtration and washed with 20 ml of methylene chloride to give 650 mg (54% yield) of the title product as a yellow powder. NMR(DMSO-d6) δ: 1.26(3H, d, J=7.0 Hz), 2.7–3.5 (4H, m), 3.9–4.3(2H, m), 4.2(2H, s), 5.42(2H, ABq, J=14.4 Hz) and 7.2–8.8 (8H,m). IR(KBr) γ max: 3400, 1775 and 1690 cm$^{-1}$.

Anal. Calc'd for $C_{22}H_{21}N_3O_6S_1$: C, 58.01; H, 4.65; N, 9.23; S, 7.04. Found: C, 57,56, H, 4,92, N, 8.94; S, 7.03.

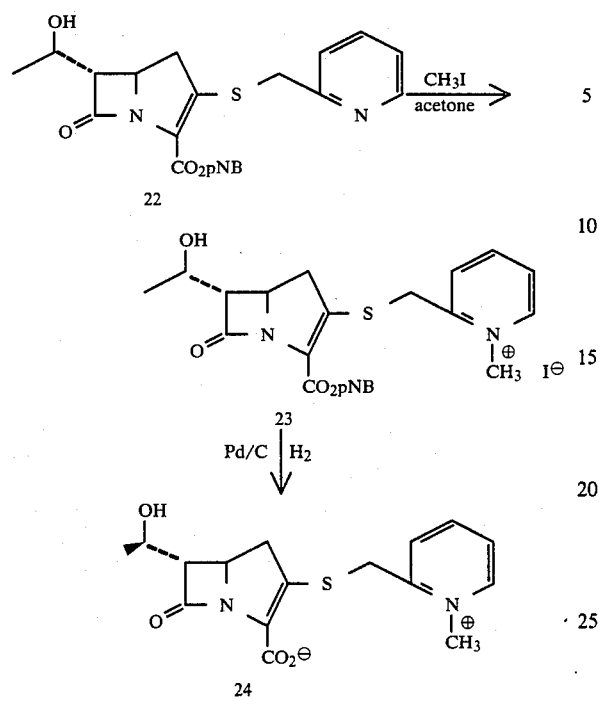

3-(N-Methyl pyridine-2-yl-methane thio)-6α-[1-(R)-hydroxyethyl]-7-oxo-1-azabicyclo(3.2.0)hept-2-ene-2-carboxylate To a solution of 650 mg (1.39 mmole) of compound 22 in 100 ml of acetone was added 4 ml of methyl iodide. The reaction mixture was stirred for 3 days at room temperature. The precipitate was collected by filtration and washed with acetone (10 ml) to give 500 mg (60% yield) of the quaternized pyridine 23 as a slightly yellow solid.

NMR (DMSO-d6) δ: 1.26(3H, d, J=7.0 Hz) 3.9–4.2(2H, m), 4.4(3H, s), 4.78(2H,s), 5.2(1H, d, J=3.9 Hz), 5.50(2H, ABq, J=14 Hz) and 7.8–9.4 (8H, m). IR (KBr) γ max: 3400,1765, and 1690 cm$^{-1}$.

Anal. Calc'd for C$_{23}$H$_{24}$N$_{3}$O$_{6}$S$_{1}$I$_{1}$: C, 46.24; H, 4.05; N, 7.03; S, 5.37. Found: C, 45.62; H, 4.27; N, 6.80; S, 5.30.

To a solution of 1.0 g (1.167 mmole) of compound 23 in 90 ml of tetrahydrofuran and 90 ml of ether was added 215 mg (2.15 m mole) of KHCO$_3$ and 374 mg (2.1 mmole) of K$_2$HPO$_4$ in 90 ml of water followed by 1.0 g of 10% palladium on charcoal. The mixture was hydrogenated at 45 psi on the Parr shaker for 45 minutes. The mixture was filtered through a Celite pad and the catalyst was washed with water (2×10 ml). The combined filtrate and washing were extracted with ether (2×200 ml) and lyophilized to give a yellow solid which was purified on a C$_{18}$ BONDAPAK (Waters Associates) reverse phase column (10 g), eluting with 5% acetonitrile in water under 8 psi pressure. Each 15 ml fraction was assayed by high pressure liquid chromatography and fractions having an ultraviolet absorption at λ max 300 nm were collected and lyophilized to give 390 mg (44% yield) of the title product. Recrystallization of this material from water-acetone-ethanol produced fine needles. m.p. 194°–196° C. (decomp). NMR (D$_2$O) δ: 1.30(3H, d, J=6.2 Hz), 3.2(2H, q, J=9.0 Hz, 3.6 Hz) 3.46(1H, q, J=6.0 Hz, 2.7 Hz), 4.1–4.6 (3H, m), 4.60 (3H, s) and 7.9–8.9(4H, m). IR (KBr) γ max: 3400, 1755, and 1590 cm$^{-1}$. UV λ max (H$_2$O): 292 nm (ε=8092). Anal Calc'd for C$_{16}$H$_{28}$N$_2$O$_4$S$_1$.2H$_2$O: C, 51.87; H, 5.44; N, 7.56. Found: C, 51.37; H, 5.69; N, 7.37.

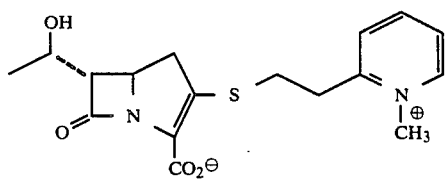

EXAMPLE 5

Preparation of 3-[N-Methylpyridine-2-yl-ethane thio]-6α-[1-(R)-hydroxyethyl]-7-oxo-1-azabicyclo(3.2.0)hept-2-ene-2-carboxylate

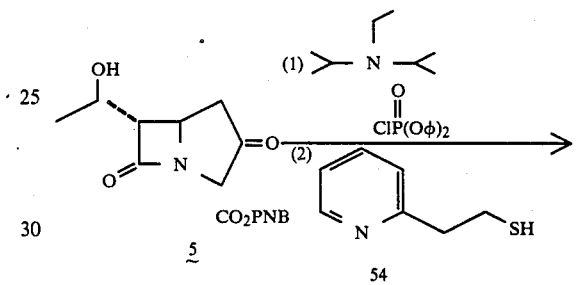

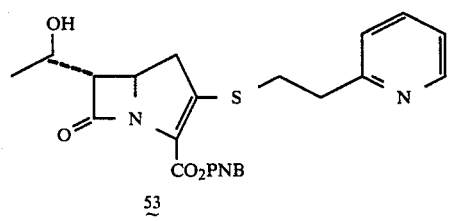

P-Nitrobenzyl-3-(pyridine-2-yl-ethane thio)-6α-[1-(R)-hydroxyethyl]-7-oxo-1-azabicyclo(3.2.0)hept-2-ene-2-carboxylate To a cooled solution of 1.78 g (5.0 mmole) of the keto intermediate 5 in 25 ml of acetonitrile was added 710 mg (5.5 mmole) of diisopropyl ethylamine in 1 ml of acetonitrile followed by 1.4 g (5.0 mmole) of diphenylchlorophosphate in 1 ml of acetonitrile under a nitrogen atmosphere. The resulting solution was stirred for 20 minutes at 0° C., and there was then added a solution of 710 mg (5.5 mmole) of diisopropyl ethylamine in 1 ml of acetonitrile followed by a solution of 850 mg (6.1 mmole) of the thiol 54 [prepared by the procedure described in J. Org. Chem., 26, 82 (1961)] in 2 ml of acetonitrile. The reaction mixture was stirred for 60 minutes at 0° C. The precipitate was collected by filtration and washed with methylene chloride (20 ml) to give 1.3 g (57%) of the title product as a yellow solid. NMR(CDCl$_3$) δ: 1.25 (3H, d, J=6.5 Hz), 2.6–3.4 (7H, m), 4.2–4.6 (2H, m), 5.30 and 5.65 (1H each, ABq, J=14 Hz) and 7.2–8.5 (8H, m). IR(KBr) γ max: 3400, 1780 and 1680 cm$^{-1}$.

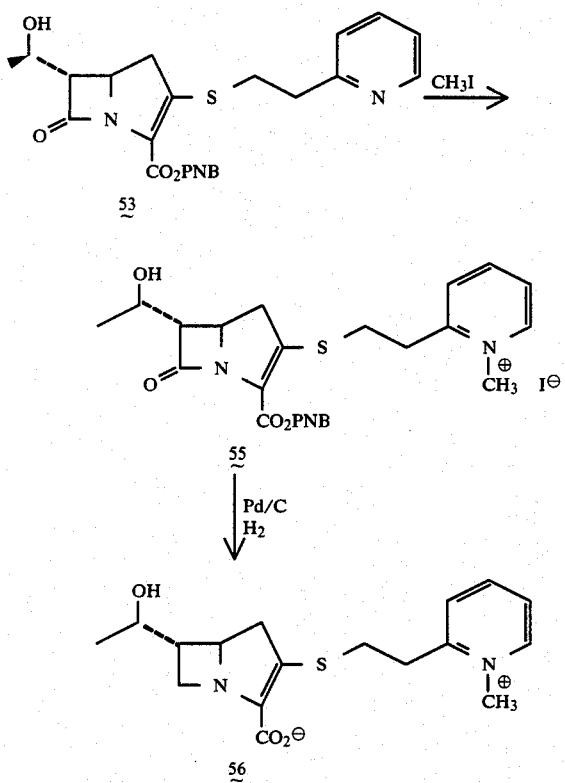

3-(N-Methyl pyridine-2-yl-ethane thio)-6α-[1-(R)-hydroxyethyl]-7-oxo-1-azabicyclo(3.2.0)hept-2-ene-2-carboxylate To a suspended solution of 800 mg (1.7 mmole) of compound 53 in 50 ml of acetone was added 5 ml of methyl iodide. The reaction mixture was stirred for 48 hours at room temperature. The precipitate was collected by filtration and washed with acetonitrile (15 ml) to give 810 mg (76% yield) of the quaternized pyridine 55 as a slightly yellow powder. NMR (DMSO-d6) δ: 1.20 (3H, d, J=5.6 Hz), 3.2–4.3 (9H, m), 4.20 (3H, s), 5.26 and 5.55 (1H each, ABq, J=15 Hz) and 7.8–9.2 (8H, m). IR(KBr) γ max: 3400, 1770 and 1690 cm$^{-1}$.

To a solution of 790 mg (1.27 mmole) of compound 55 in 100 ml of tetrahydrofuran and 100 ml of ether was added 100 ml of pH=7.0 buffer solution followed by 1.0 g of 10% palladium on charcoal. The mixture was hydrogenated at 40 psi on the Parr shaker for 40 minutes. The mixture was filtered through a Celite pad and the catalyst was washed with water (2×10 ml).

The combined filtrate and washing were extracted with ether (3×100 ml) and lyophilized to give a yellow powder which was purified on a $C_{18}$ BONDAPAK (Waters Associates) column (30 g), eluting with 10% acetonitrile in water under 8 psi pressure.

Each 15 ml fraction was assayed by high pressure liquid chromatography and fractions having an ultraviolet absorption at λmax 300 nm were collected and lyophilized to give 65 mg (15% yield) of the title product as a yellow powder.

NMR (D$_2$O) δ: 1.25 (3H, d, J=6.2 Hz), 3.1–3.6 (7H, m), 4.0–4.3 (2H, m), 4.32 (3H, s) and 7.8–8.9 (4H, m). IR(KBr) γmax: 3400, 1750 and 1590 cm$^{-1}$. UV λmax (H$_2$O): 300 nm (ε=8108).

EXAMPLE 6

Preparation of 3-(1-Propylpyridine-4-yl-methane thio)-6α-[1-(R)-hydroethyl]-7-oxo-1-azabicyclo(3.2.0-)hept-2-ene-2-carboxylate

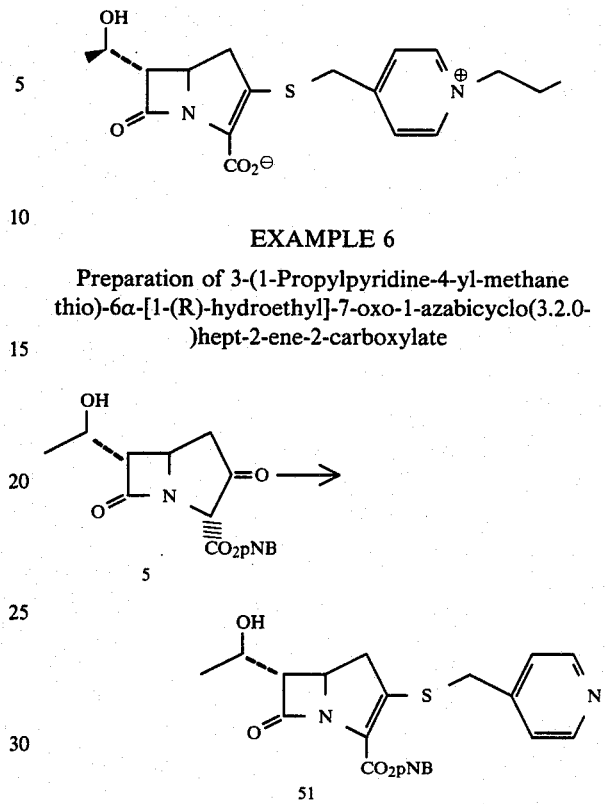

P-Nitrobenzyl-3-(pyridine-4-yl-methane thio)-6α-[1-(R)-hydroxyethyl]-7-oxo-1-azabicyclo(3.2.0)-hept-2-ene-2-carboxylate A solution of 673 mg (1.86 m mole) of p-nitrobenzyl 6α-[-(R)-hydroxyethyl]-3,7-dioxo-1-azabicyclo[3.2.0-]hept-2-ene-2-carboxylate (5) in 10 ml of acetonitrile was cooled to −10° C. under a nitrogen atmosphere. A solution of 245 mg (1.90 m mole) of diisopropylethylamine in 1 ml of acetonitrile was added followed by a dropwise addition of 510 mg (1.90 m mole) of diphenyl chlorophosphate in 1 ml of acetonitrile over a period of 2 minutes. The resulting solution was stirred at −10° C. for 15 minutes to provide a p-nitrobenzyl 3-(diphenyl-phosphoryloxy)-6α-[1-(R)-hydroxyethyl]-7-oxo-1-azabicyclo-(3.2.0)hept-2-ene-2-carboxylate. To this solution was added a solution of 245 mg (1.90 m mole) of diisopropylethylamine in 0.5 ml of acetonitrile followed by a solution of 270 mg (2.16 m mole) of 4-mercaptomethylpyridine in 0.5 ml of acetonitrile. The reaction mixture was stirred at −10° C. for 60 minutes and the white precipitate which formed was collected by filtration and washed with 5 ml of ice-cold acetonitrile to give 660 mg (76% yield) of compound 51 as white crystals, m.p. 145° C. NMR (DMSO-d6) δ: 1.20 (3H, d, J=6.0 Hz), 3.2–3.4 (3H, m), 3.7–4.1 (2H, m), 4.25 (2H, s), 5.05 (1H, d, J=4.0 Hz), 5.35 (1H, d, J=14.0 Hz), 5.48 (1H, d, J=14.0 Hz), 7.40 (2H, d, J=5.5 Hz), 7.70 (2H, d, J=8.5 Hz), 8.23 (2H, d, J=8.5 Hz) and 8.58 (2H, d, J=5.5 Hz). IR(KBr) γmax: 3400, 1790 and 1695 cm$^{-1}$. Anal. Calc'd for $C_{22}H_{21}N_3O_6S$: C, 58.01; H, 4.56; N, 9.23; S, 7.04. Found: C, 57.74; H, 4.56; N, 9.58; S, 7.21.

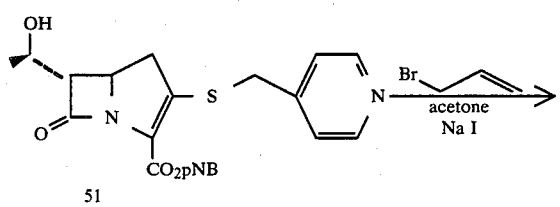

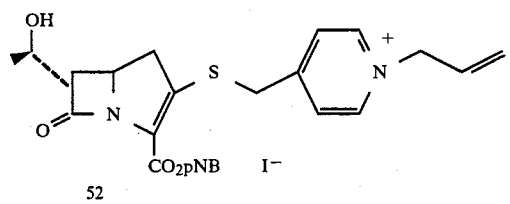

3-(1-Allyl pyridine-4-yl-methane thio)-6α-[1-(R)-hydroxyethyl]-7-oxo-1-azabicyclo(3.2.0)-hept-2-en3-2-carboxylate To a solution of 900 mg (2.13 m mole) of compound 51 in 150 ml of acetone was added 2 ml of allyl bromide and 380 mg of sodium iodide. The mixture was stirred for 48 hours at room temperature and the solvent was evaporated in vacuo to give a yellow solid. This material was suspended into 120 ml of acetonitrile, filtered and evaporated in vacuo to give 1.0 g (87% yield) of the title product as a yellow solid. NMR (CD$_3$CN)δ: 1.20 (3H, d, J=6.2 Hz), 3.0–3.4 (4H, m), 4.0–4.4 (4H, m), 5.1–5.6 (4H, m) and 7.4–7.9 (8H, m). IR(KBr) γmax: 3400, 1770 and 1690 cm$^{-1}$. Anal. Calc'd for C$_{25}$H$_{26}$N$_3$O$_6$S$_1$I$_1$: C, 48.16; H 4,21; N, 6.74; S, 5.15. Found: C, 48.55; H, 4.46; N, 6.69; S, 5.15.

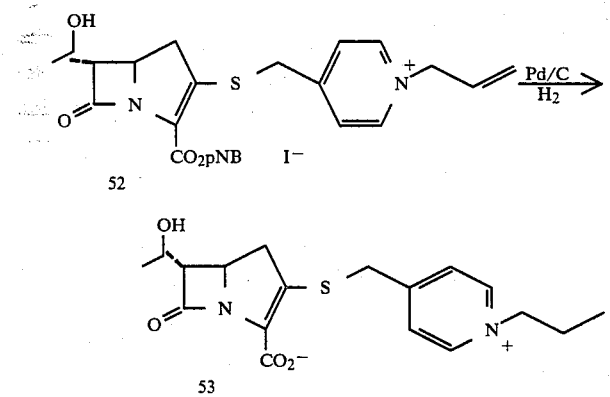

3-(1-Propyl pyridine-4-yl-methane thio)-6α-[1-(R)-hydroxyethyl]-7-oxo-1-azabicyclo(3.2.0)hept-2-ene-2-carboxylate To a solution of 1.27 g (2.15 m mole) of compound 52 in 100 ml of tetrahydrofuran and 100 ml of ether was added 100 ml of pH=7.0 buffer solution followed by 1.0 g of 10% palladium on charcoal. The mixture was hydrogenated at 40 psi on the Parr shaker for 40 minutes. The mixture was filtered through a Celite pad and the catalyst was washed with water (2×10 ml). The combined filtrate and washing were extracted with ether (3×100 ml) and lyophilized to give a yellow powder which was purified on a C$_{18}$ BONDAPAK (Waters Associates) column (40 g), eluting with 10% acetonitrile in water under 8 psi pressure. Each 15 ml fraction was assayed by high pressure liquid chromatography and fractions having an ultraviolet absorption at λmax 300 nm were collected and lyophilized to give 48 mg (6% yield) of the title product as a yellow powder. NMR(D$_2$O)δ: 0.95 (3H, t, J=7.5 Hz), 1.25 (3H, d, 7.0 Hz), 2.05 (2H, sextet, J=7.5 Hz) 3.10 (2H, dd, J=10 Hz, 2.5 Hz) 3.35 (1H, dd, J=6.5 Hz, 2.5 Hz), 4.0–4.8 (6H, m), 7.1 (2H, d, J=6.0 Hz) and 7.80 (2H, d, J=6.0 Hz). IR(KBr) γmax: 3400, 1750, and 1590 cm$^{-1}$. Anal. Calc'd for C$_{18}$H$_{22}$N$_2$O$_4$S.2H$_2$O: C, 54.52; H, 6.10; N, 7.07. Found: C, 54.32; H, 603; N, 6.99.

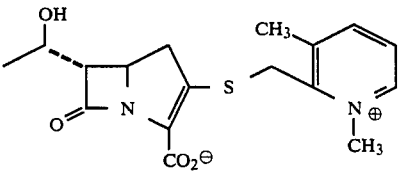

EXAMPLE 7

Preparation of 3-(N-Methyl-3-methylpyridine-2-methane thio)-6α-[1-(R)-hydroxyethyl]-7-oxo-1-azabicyclo(3.2.0)hept-2-ene-2-carboxylate

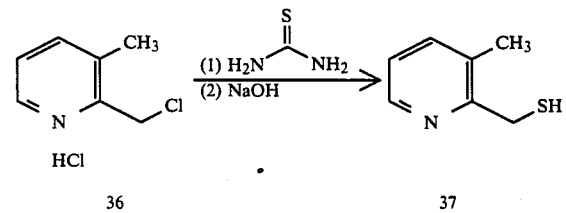

3-Methyl-2-mercaptomethyl pyridine

A solution of 2.45 g (17.0 mmole) of the chloro compound 36 and 1.37 g (18.0 m mole) of thiourea in 60 ml of absolute ethanol was heated at reflux for 5 hours. Evaporation of ethanol followed by addition of ether give 3.08 g (72% yield) of the isothiouronium salt which was dissolved in 10 ml of water containing 1.44 g (26 m mole) of sodium hydroxide. The solution was then heated at 100° C. for 5 minutes under a nitrogen atmosphere. The reaction mixture was cooled to 5° C., adjusted to pH 6.4 by addition of acetic acid and extracted with ether (4×50 ml). The combined ether extracts were washed with 5% aqueous sodium bicarbonate and brine. Evaporation of dried (MgSO$_4$) solvent gave 1.4 g (83% Yield) of the thiol 37 as a yellow oil which was used for the next step without further purification. NMR (CDCl$_3$)δ: 2.20 (3H, s), 2.5–2.7 (1H, broad s), 3.8 (2H, t, J=6.5 Hz) and 6.9–8.2 (3H, m).

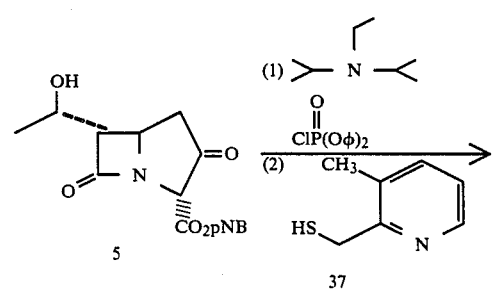

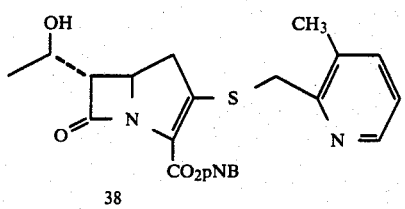

38

P-Nitrobenzyl-3-[3-methyl pyridine-2-yl-methane thio]-6α-[1-(R)-hydroxyethyl]-7-oxo-1-azabicyclo(3.2.0)hept-2-ene-2-carboxylate To a cooled (0° C.) solution of 1.74 g (5.0 mmole) of the keto intermediate 5 in 25 ml of acetonitrile was added 960 mg (5.8 m mole) of diisopropyl ethylamine in 2 ml of acetonitrile followed by 1.4 g (5.8 mmole) of diphenyl chlorophosphate in 2 ml of acetonitrile under a nitrogen atmopshere. The resulting solution was stirred for 20 minutes at 0° C., and there was then added a solution of 760 mg (5.8 m mole) of diisopropyl ethylamine in 2 ml of acetonitrile followed by 810 mg of the mercaptomethyl pyridine 37 in 3 ml of acetonitrile. The reaction mixture was allowed to stir for 2 hours at 0° C. The precipitate was collected by filtration and washed with acetonitrile to give 1.56 g (66% yield) of the title product as a white solid. m.p. 145° C. NMR (DMSO-d6) δ: 1.23 (3H, d, J=6.5 Hz), 2.30 (3H, s), 3.1–4.3 (6H, m), 4.35 (2H, s), 5.20 and 4.45 (1H each, ABq, J=15.0 Hz) and 7.3–8.4 (7H, m). IR(KBr) γmax: 3400, 1767 and 1695 cm$^{-1}$. Anal. Calc'd for $C_{24}H_{26}N_3O_9S_2F$: C, 47.91; H, 4.69; N, 6.98; S, 10.66. Found: C, 47.72; H, 4.34; N, 6.72; S, 11.22.

3-(N-Methyl-3-methyl pyridine-2-yl-methane thio)-6α-[1-(R)-hydrroxy ethyl]-7-oxo-1-azabicyclo(3.2.0)hept-2-ene-2-carboxylate To a solution of 680 mg (1.45 mmole) of compound 38 in 120 ml of methylene chloride was added 270 mg (2.33 mmole) of methyl fluorosulfonate. The reaction mixture was stirred for 3 hours at room temperature. The precipitate was collected by filtration and washed with methylene chloride (5 ml) to give 840 mg (99% yield) of the quaternized pyridine 39 as white crystals. NMR (DMSO-d6)δ: 1.15 (3H, d, J=5.8 Hz), 2.62 (3H, s), 3.2–4.4 (5H, m), 4.45 (3H, s), 4.60 and 4.82 (1H each, ABq, J=9.2 Hz), 5.30 and 5.46(1H each, ABq, J=12.8 Hz), and 7.6–8.9 (7H, m). IR (KBr) γmax: 3400, 1750 and 1590 cm$^{-1}$. Anal. Calc'd for $C_{24}H_{24}N_3O_9S_2F$: C, 49.14; H, 4.47; N, 7.13; S, 11.43. Found: C, 49.56; H, 4.16; N, 7.26; S, 11.03.

To a solution of 810 mg (1.39 mmole) of compound 39 in 100 ml of tetrahydrofuran and 100 ml of ether was added 100 ml of pH=7.0 buffer solution followed by 750 mg of 10% palladium on charcoal. The mixture was hydrogenated at 45 psi on the Parr shaker for 60 min. in the cold room (4°–6° C.). The mixture was filtered through a Celite pad and the catalyst was washed with ether (2×10 ml). The combined filtrate and washing were extracted with ether (2×40 ml) and lyophilized to give a yellow solid which was purified on the $C_{18}$ BONDAPAK (Waters Associates) column (20 g), eluting with 5% acetonitrile in water under 8 psi pressure. Eash 15 ml fraction was assayed by high pressure liquid chromatography and fractions having an ultraviolet absorption at λmax 300 nm were collected and lyophilized to give 141 mg (30% yield) of the title product as a yellow solid. NMR (D2O)δ: 1.24 (3H, d, J=7.0 Hz), 2.62 (3H, s),3.2–3.5 (3H, m), 4.2–4.4 (2H, m), 4.45 (3H, s), 4.50 and 4.59 (1H each, ABq, J=12.6 Hz), 7.82 (1H, q, J=7.0 Hz, 6.5 Hz), 8.35 (1H, d, J=7.0 Hz) and 8.65 (1H, d, J=6.5 Hz). IR(KBr) γmax: 3400, 1750 and 1580 cm$^{-1}$. UV λmax (H2O): 296 nm (δ=8014). Anal. Calc'd for $C_{17}H_{20}N_2O_4S_1.\frac{1}{4}H_2O$: C, 57.85; H, 5.85; N, 7.94. Found: C, 58.60; H, 5.86; N, 7.87.

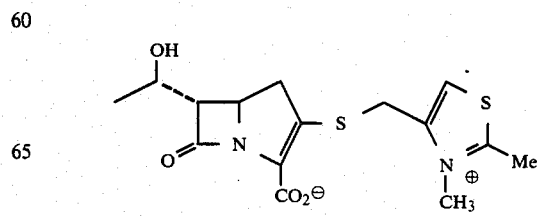

EXAMPLE 8

Preparation of 3-(2-Methyl-N-methylthiazole-4-yl-methane thio)-6α-[1-(R)-hydroxyethyl]-7-oxo-1-azabicyclo(3.2.0)hept-ene-2-carboxylate

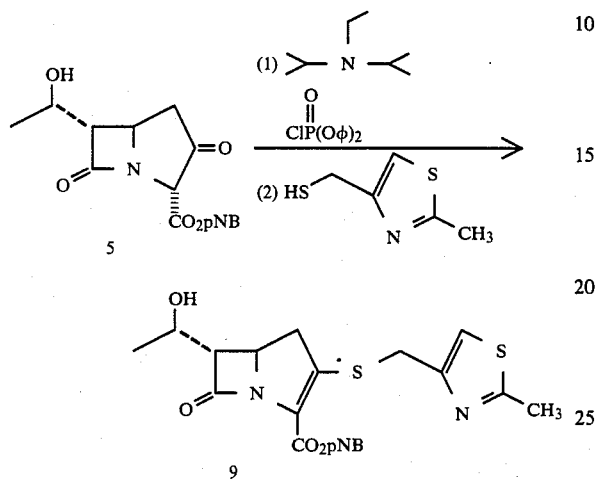

p-Nitrobenzyl 3-[2-methyl thiazole-4-yl-methane thio]-6α-[1-(R)-hydroxyethyl]-7-oxo-1-azabicyclo(3.2.0)hept-2-ene-2-carboxylate To a cooled (0°) solution of 1.4 g (4.0 mmole) of the keto intermediate 5 in 12 ml of acetonitrile was added 0.83 ml (4.6 mmole) of diisopropylethylamine followed by 1.16 g (4.3 mmole) of diphenylchlorophosphate in 2 ml of acetonitrile under a nitrogen atmospere. The resulting solution was stirred at 0° for 30 minutes to provide p-nitrobenzyl 3-(diphenylphosphoryloxy)-6α-[1-(R)-hydroxyethyl]-7-oxo-1-azabicyclo(3.2.0)hept-2-ene-2-carboxylate. To this solution was added a solution of 0.83 ml (4.6 mmole) of diisopropylethylamine in 2 ml of acetonitrile followed by a solution of 0.62 g (4.2 mmole) of 2-methyl-4-mercaptomethyl thiazole [prepared by the procedure described in J. Amer. Chem Soc., 71, 3570 (1949)] in 3 ml of acetonitrile. The reaction solution was stirred for 40 minutes at 0°. The precipitate was collected and washed with ether (30 ml) to give 943 mg of the title product as a white solid.

NMR (CDCl₃) δ: 1.32 (3H, d, J=7 Hz), 2.68 (3H, S), 3.20 (2H, m) 3.76 (1H, d, J=5.5 Hz), 4.16 (2H, S), 4.20 (1H, m), 5.40 (2H, q, J=14 Hz), 7.06 (1H, S), 7.68 (2H, d, J=8 Hz) and 8.24 (2H, d, J=8 Hz), IR(KBr) γmax: 3500, 1770, and 1700 cm⁻¹.

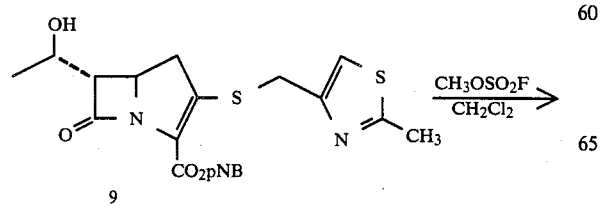

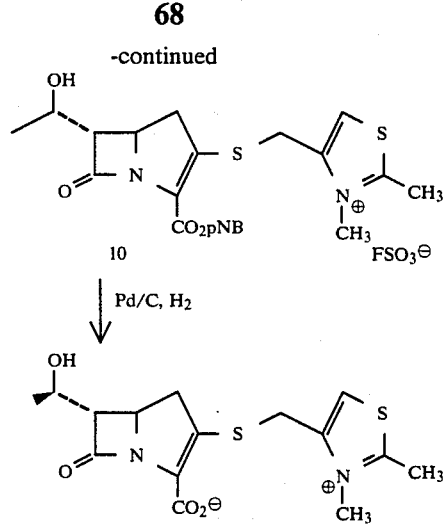

3-(2-Methyl-N-methyl-thiazole-4-yl-methane thio)-6-α-[1-(R)-hydroxyethyl]-7-oxo-1-azabicyclo(3.2.0)hept-2-ene-2-carboxylate To a solution of 525 mg (1.1 mmole) of compound 9 in 20 ml of methylene chloride was added 0.27 ml (3.3 mmole) of methyl fluorosulfonate. The reaction mixture was stirred for 90 minutes at room temperature. The precipitate was collected by filtration and washed with methylene chloride (50 ml) to give 650 mg (100% yield) of the quaternized thiazole 10 which was used for the next step without further purification.

Thus, to a solution of compound 10 in 100 ml of tetrahydrofuran and 100 ml of ether was added 100 ml of pH=7.0 buffer solution followed by 500 mg of 10% palladium on charcoal. The mixture was hydrogenated at 35 psi on the Parr shaker for 45 minutes. The mixture was filtered through a Celite pad and the catalyst was washed with water (2×10 ml). The combined filtrate and washings were extracted with ether (2×100 ml) and lyophilized to give a yellow powder which was purified on a C₁₈ BONDAPAK reverse phase column (8 g) (Water Associates), eluting with 5% acetonitrile in water under 8 psi pressure. Each 15 ml fraction was assayed by high pressure liquid chromatography and fractions having an ultraviolet absorption at λmax 300 nm were collected and lyophilized to give 145 mg (48% yield) of the title compound as a pale yellow powder.

NMR (CDCl₃) δ: 1.20 (3H, d, J=7 Hz), 2.92 (3H, S), 3.08 (1H, d, J=3.5 Hz), 3.20 (1H, d, H=3 Hz), 3.44 (1H, dd, J=1 Hz, J=3.5 Hz), 4.00 (3H, 5), 4.20 (3H, m), 4.36 (2H, m) and 7.88 (1H, s). IR (KBr) γmax: 3400, 1750 and 1585 cm¹. UV λmax (H₂O): 296 nm (ε=7500). Anal. Calc'd. for C₁₅H₁₈N₂O₄S₂.2H₂O: C, 46.15; H, 5.64; N, 7.17; S, 16.41. Found: C, 46.50; H, 5.26; N, 7.13; S, 16.20.

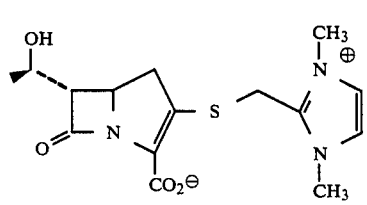

EXAMPLE 9

Preparation of 3-(N,N'-Dimethyl imidazole-2-yl-methane thio)-6α-[1-(R)-hydroxyethyl]-7-oxo-1-azabicyclo(3.2.0)hept-2-ene-2-carboxylate

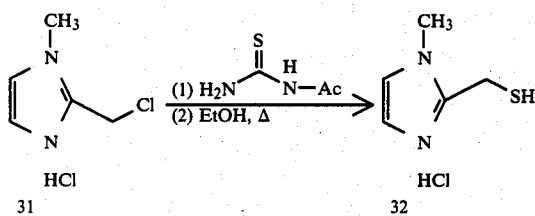

2-Merceptomethyl N-methylimidazole

To a solution of 10.4 g (58 m mole) of 2-chloromethyl-N-methylimidazole 31 [prepared by the procedure described in J. Amer. Chem. Soc., 71, 383 (1949)] in 200 ml of acetonitrile was added 7.1 g (60 m mole) of N-acetyl thiourea and, the reaction mixture was heated at reflux for 90 minutes. The precipitate was filtered and washed with acetonitrile (20 ml) to give the isothiouronium salt which was then dissolved into 120 ml of ethanol and heated at reflux for 18 hours under a nitrogen atmosphere. The reaction mixture was cooled to room temperature, condensed in vacuo to about 60 ml of volume and the precipitate was removed by filtration. Evaporation of the filtrate in vacuo gave 2-mercaptomethyl-N-methylimidazole 32 as a yellow oil which was used for the next step without further purification. NMR (D$_2$O) δ: 3.90 (3H, s), 4.10 (2H, s) and 7.25 (2H, S).

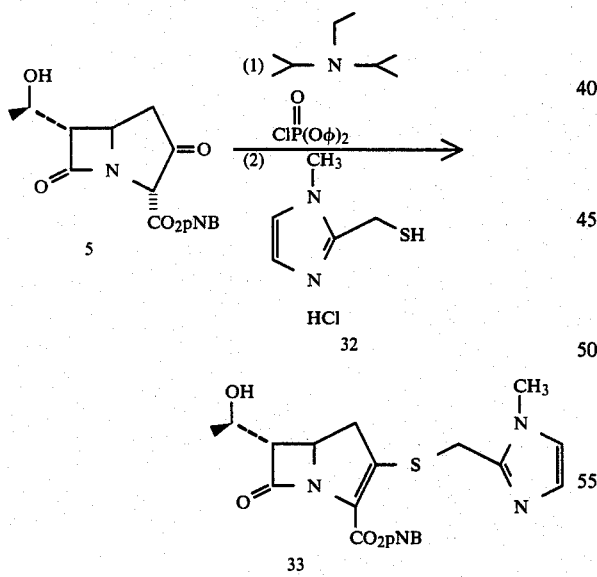

p-Nitrobenzyl-3-[N-methyl imidazole-2-yl-methane thio]6α-[1-(R)-hydroxyethyl]-7-oxo-1-azabicyclo(3.2.0-)hept-2-ene-2-carboxylate To a cooled (0° C.) solution of 7.24 g (20.3 m mole) of the keto intermediate 5 in 35 ml of acetonitrile was added 2.8 g (21.3 m mole) of diisopropyl ethylamine in 2 ml of acetonitrile followed by 5.5 g (20.4 m mole) of diphenyl chlorophosphate in 2 ml of acetonitrile under a nitrogen atmosphere. The resulting solution was stirred at 0° C. for 15 minutes and there was then added a solution of 4.1 g (3.0 m mole) of diisopropyl ethylamine in 2 ml of acetonitrile followed by 4.6 g (31.0 m mole) of the thiol 32. The reaction mixture was allowed to stir for 60 minutes at 0° C. The white precipitate was collected by filtration and washed with methylene chloride (20 ml) to give 6.6 g (71% yield) of the title product as a white solid. M.p. 142°. NMR (DMSO-d6) δ: 1.32 (3H, d, J=7.0 Hz), 3.2–4.5 (5H, m), 3.2 (2H, s), 3.9 (3H, s), 5.50 (2H, Abq, J=14.0 Hz), 7.65 (2H, d, J=6.5 Hz), 7.70 (2H, s) and 8.24 (2H, d, J=6.6 Hz). IR(KBr) γmax: 3450, 1770 and 1690 cm$^{-1}$. Anal. Calc'd for C$_{21}$H$_{20}$N$_4$O$_6$S$_1$·1½H$_2$O; C, 52.18; H, 4.79; N, 11.59. Found: C, 52.22; H, 4.91; N, 12.16.

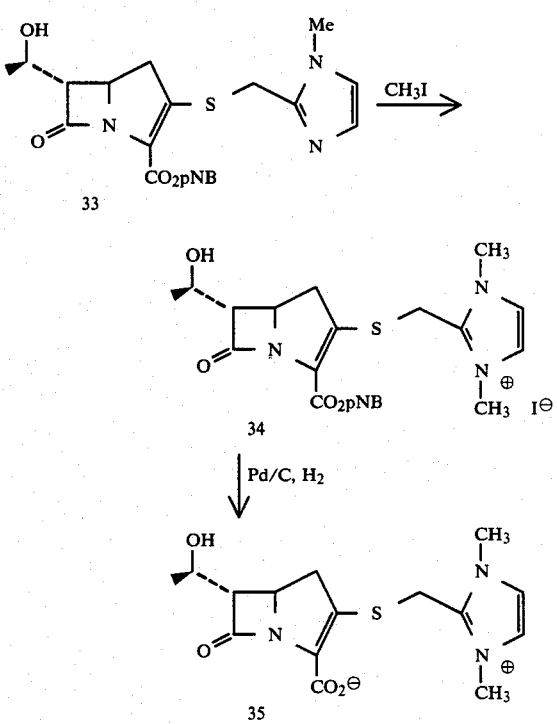

3-(N,N'-Dimethyl imidazole-2-yl-methane thio)-6α-[1-(R)-hydroxyethyl]-7-oxo-1-azabicyclo(3.2.0)hept-2-ene-2-carboxylate To a suspended solution of 1.34 g (3.0 m mole) of compound 33 in 270 ml of acetone was added 20 ml of methyl iodide. The reaction mixture was stirred for 4 days at room temperature. The precipitate was collected by filtration and washed with acetone (20 ml) to give 1.70 g (96% yield) of the quaternized imidazole 34 as yellow crystals. m.p. 175°–177° C. NMR (DMSO-d6) δ: 1.10 (3H, d, H=6.2 Hz), 3.30 (2H, s), 3.2–4.3 (6H, m), 3.95 (6H, s), 5.45 (2H, ABq, J=14 Hz), 7.65 (2H, d, J=6.0 Hz). IR (KBr) νmax: 3400, 1750 and 1600 cm$^1$. Anal. Calc'd for C$_{21}$H$_{22}$N$_4$O$_6$S$_1$: C, 43.08; H, 9.60; N, 5.48. Found: C, 43.02; H, 9.02; N, 5.44.

To a solution of 1.30 g (1.86 m mole) of compound 34 in 120 ml of tetrahydrofuran and 120 ml of ether was added 120 ml of pH=7.0 buffer solution followed by 900 mg of 30% palladium on Celite. The mixture was hydrogenated at 40 psi on the Parr shaker for 40 minutes. The mixture was filtered through a Celite pad and the catalyst was washed with water (2×15 ml). The combined filtrate and washing were extracted with ether (3×100 ml) and lyophilized to give a yellow amorphous powder which was purified on a C$_{18}$ BONDPAK (Waters Associates) column (30 g), eluting with 10% acetonitrile in water under 8 psi pressure. Each 20 ml fraction was assayed by high pressure liquid chromatography and fractions having an ultraviolet absorption at λmax 300 nm were collected and lyophilized to give 220 mg (35% yield) of the title product as a yellow powder. NMR(D$_2$O)δ: 1.12 (3H; d, J=7.0 Hz), 3.08 (1H, dd, J=13.0 Hz, 6.4 Hz), 3.15 (1H, dd, J=13.0 Hz, 6.4 Hz), 3.45 (1H, dd, J=3.2 Hz, 4.5 Hz) 3.85 (6H, s,) 4.1–4.3 (2H, m), 4.40 (1H, d, J=13.5 Hz), 4.52 (1H, d, J=13.5 Hz) and 7.40 (2H, s). IR(KBr) λmax: 3500, 1750 and 1590 cm$^{-1}$. UV λmax (H$_2$O): 296 nm (ε=8411). Anal. Calc'd for C$_{15}$H$_{19}$N$_3$O$_4$S.H$_2$O: C, 51.68; H, 5.67; N, 12.06; S, 9.50. Found: C, 49.93; H, 5.94; N, 11.46; S, 9.03.

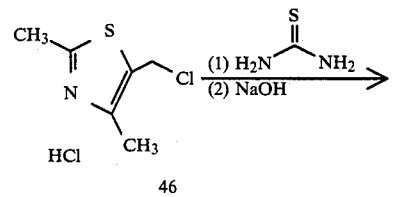

EXAMPLE 10

Preparation of 3-(2,3,4-Trimethyl thiazole-5-yl-methane thio)-6α[1-(R)-hydroxyethyl]-7-oxo-1-azabicyclo(3.2.0-)hept-2-ene-2-carboxylate

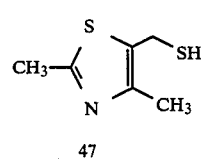

2,-4-Dimethyl-5-mercaptomethyl thiazole

To a solution of 4.8 g (26.0 mmole) of the chloro compound 46 [prepared by the procedure described in J. Amer. Chem. Soc., 104, 4461 (1982)] in 50 ml of absolute ethanol was added 2.4 g (30 mmole) of thiourea. The reaction mixture was heated at reflux for 18 hours. The precipitate was collected by filtration and washed with ether (20 ml) to give the isothiouronium salt which was dissolved into 22 ml of 1N-sodium hydroxide and heated at 100° C. for 4 minutes under a nitrogen atmosphere. The reaction mixture was then cooled to room temperature, adjusted to pH 7.0 with 1N hydrochloric acid and extracted with ether (3×50 ml). The combined ether phases were washed with water, brine and dried over MgSO$_4$.

Evaporation of dried solvent gave 780 mg (49% yield) of the thiol 47 as a colorless oil which was used for the next step without further purification.

NMR(DCl$_3$)δ: 2.05 (3H, s), 2.35 (3H, s) and 3.60 (2H, d, J=6.5 Hz).

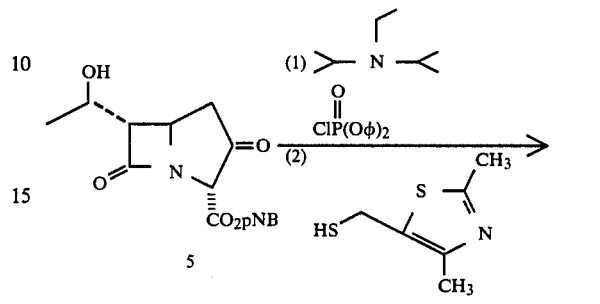

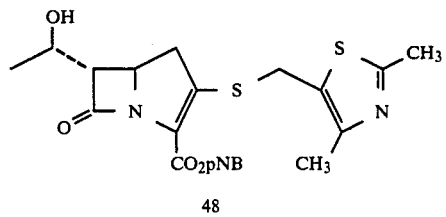

P-Nitrobenzyl-3-[2,4-dimethyl thiazole-5-yl-methane thio]6α-[1-(R)-hydroxy ethyl]-7-oxo-1-azabicyclo(3.2.0)hept-2-ene-2-carboxylate To a cooled (0°C.) solution of 1.4 g (4.0 mmole) of the keto intermediate 5 in 25 ml of acetontrile was added 610 mg (4.7 mmole) of diisopropyl ethylamine in 1 ml of acetonitrile followed by 1.15 g (4.3 mmole) of diphenylchlorophosphate in 1 ml of acetonitrile under a nitrogen atmosphere. The resulting solution was stirred for 20 minutes at 0° C., and there was then added a solution of 610 mg (4.7 mmole) of diisopropyl ethylamine in 1 ml of acetonitrile followed by 750 mg (4.7 mmole) of the thiol 47 in 2 ml of acetonitrile. The reaction mixture was allowed to stir for 3 hours at 0° C. The precipitate was collected by filtration and washed with methylene chloride (20 ml) to give 1.14 g (61% yield) of the title product as a white solid. NMR (DMSO-d6) δ: 1.25(3H, d, J=6.4 Hz), 2.30(3H, s), 2.65(3H, s), 3.1–3.4(3H, m), 4.10(1H, broad s), 4.0–4.5 (3H, m), 5.25 and 5.50(1H each, ABq, J=4 Hz), 7.68 (2 H, d, J=8.5 Hz) and 8.25 (2H, d, J=8.5 Hz). IR(KBr) γmax: 3500, 1770 and 1690 cm$^{-1}$. Anal. Calc'd for C$_{22}$H$_{23}$N$_3$O$_6$S$_2$: C, 53.73; H, 4.71; N, 8.57; S, 13.44. Found: C, 53.97; H, 4.74; N, 8.58; S, 13.10.

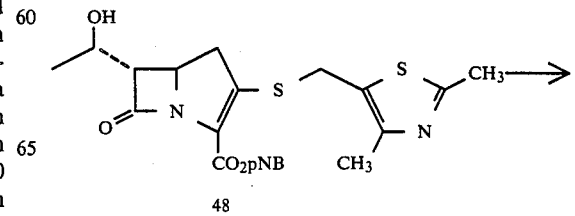

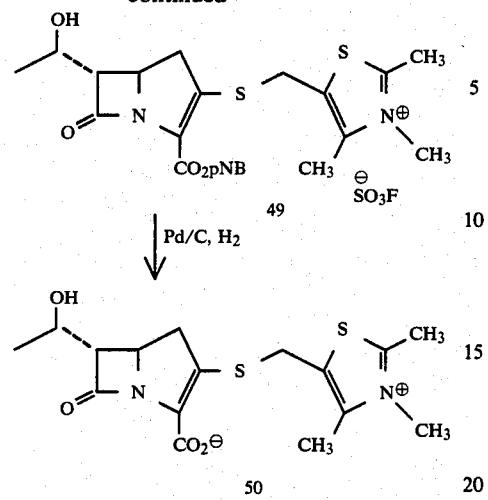

3-(2,3,4-Trimethyl thiazole-5-yl-methane thio)-6α-[1-(R)-hydroxyethyl]-7-oxo-1-azabicyclo(3.2.0)hept-2-ene-2-carboxylate To a solution of 1.97 g (4.0 mmole) of compound 48 in 180 ml of methylene chloride was added a solution of 0.98 ml (13 mmole) of methyl fluorosulfonate in 2 ml of methylene chloride. The reaction mixture was stirred for 70 minutes at room temperature. The reaction mixture was poured into a solution of ether (400 ml) and n-pentane (100 ml). The precipitate was collected by filtration and washed with ether (20 ml) to give 1.6 g (65.5% yield) of the quaternized thiazole 49 as a white amorphous powder. NMR (DMSO-d6)δ. 1.25(3H, s, J=6.5 Hz), 2.45(3H, s), 2.80(3H, s), 3.2–4.5(6H, m), 3.90(3H, s), 5.30(2H, broad s), 7.60 and 8.2(1H, each, d, J=8.5 Hz). IR(KBr) γmax: 3400, 1770 and 1690 cm$^{-1}$. Anal. Calc'd for $C_{23}H_{26}N_3O_9S_3F \cdot \frac{1}{2}H_2O$: C, 45.09; H, 4.44; N, 6.86. Found: C, 44.50; H, 4.38; N, 6.58.

To a solution of 1.0 g (1.72 mmole) of compound 49 in 100 ml of tetrahydrofuran and 100 ml of ether was added 100 ml of pH=7.0 buffer solution followed by 1.0 g of 10% palladium on charcoal. The mixture was hydrogenated at 40 psi on the Parr shaker for 40 minutes. The mixture was filtered through a Celite pad and the catalyst was washed with water (2×10 ml). The combined filtrate and washing were extracted with ether (3×100 ml) and lyophilized to give a yellow powder which was purified on a $C_{18}$ BONDAPAK (Waters Associates) column (40 g), eluting with 10% acetonitrile in water under 8 psi pressure.

Each 15 ml fraction was assayed by high pressure liquid chromatography and fractions having an ultraviolet absorption at λmax 300 nm were collected and lyophilized to give 315 mg (50% yield) of the title produce as a yellow solid. NMR (D$_2$O) δ: 1.25 (3H, d, J=7.0 Hz), 2.25 (3H, s), 2.90 (3H, s), 3.0–3.30 (3H, m), 3.90 (3H, s) and 4.1–4.4 (4H, m). IR(KBr) γmax 3400, 1750 and 1580 cm$^{-1}$. UV λmax: (H$_2$O): 2.97 nm (ε=8994). Anal. Calc'd for $C_{15}H_{19}N_3O_4S \cdot 2H_2O$: C, 48.25; H, 6.09; N, 7.79. Found: C, 47.96; H, 5.83; N, 7.89.

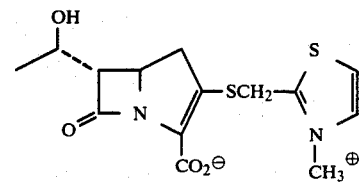

EXAMPLE 11

Preparation of 3-[2-(N-Methylthiazolium)methyl thio]-6α-[1-(R)-hydroxyethyl]-7-oxo-1-azabicyclo(3.2.0)hept-2-ene-2-carboxylate

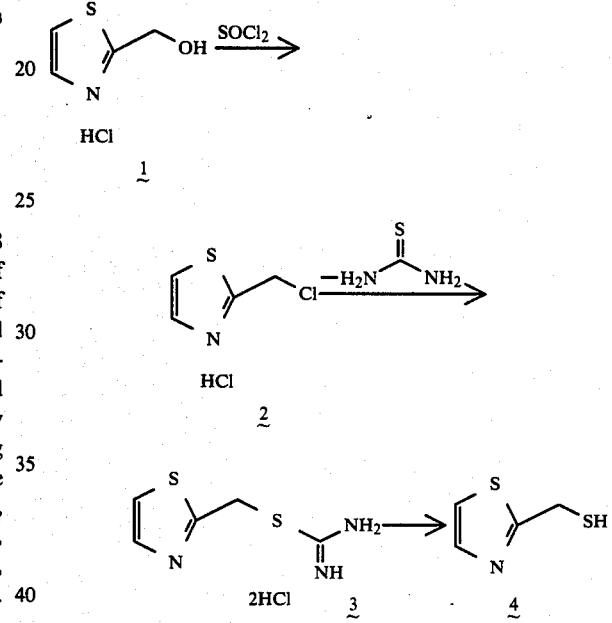

2-Mercaptomethyl thiazole

To a chloroform solution (30 ml) of thionyl chloride (3.81 ml, 0.052M) was added at room temperature 3.60 g (0.026M) of the hydroxymethyl thiazole 1 followed by heating at 50° for 2 hours. Chloroform was evaporated in vacuo leaving a brown solid which was dissolved in 30 ml of absolute ethanol. There was then added 2.04 g (0.026M) of thiourea. The mixture was then heated at reflux for 18 hours. The precipitate was collected by filtration, washed with ethanol and ether to give 3.4 g (55% yield) of the isothiouronium salt 3. The isothiouronium salt 3 was dissolved in 30 ml of water and purged with N$_2$ for 20 minutes. There was added 1.10 g (0.027M) of sodium hydroxide and the mixture was heated at 100° for two minutes. The cooled (0°) solution's pH was adjusted to 6.0 with acetic acid followed by ethylacetate (35 ml×2) extraction. The organic layer was dried MgSO$_4$) and evaporated in vacuo to give 0.75 g (42% yield) of the thiol 4 as a yellow oil which was used without further purification; NMR (CDCl$_3$) δ: 2.1(1H, t), 4.0(2H, d, J=10 Hz), 7.27(1H, d, J=3.0 Hz) and 8.85(1H, d, J=3.0 Hz).

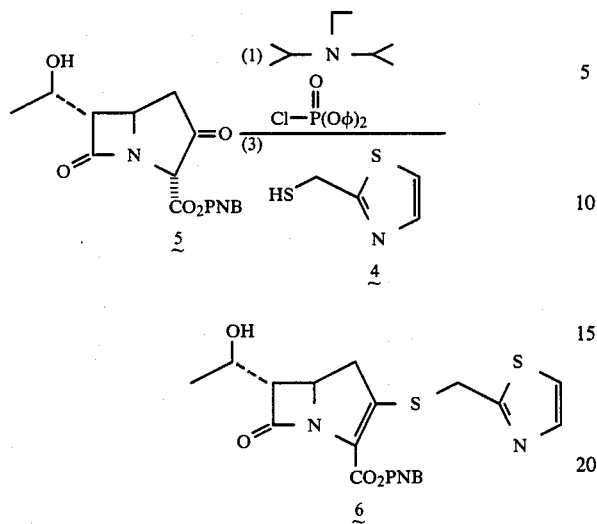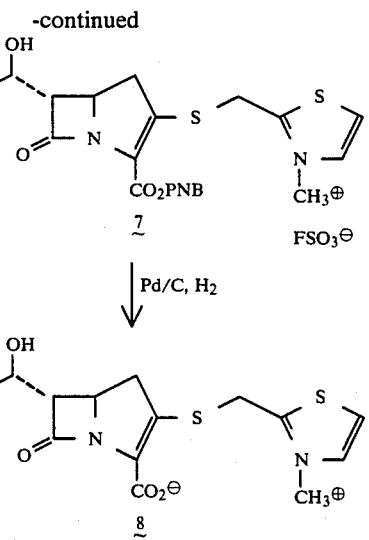

p-Nitrobenzyl 3-[(2-thiazole)methyl thio]-6α-[1-(R)-hydroxyethyl]-7-oxo-1-azabicyclo(3.2.0)hept-2-ene-2-carboxylate To a cooled (0°) solution of 1.4 g (4.0 mmole) of the keto intermediate 5 in 8 ml of acetonitrile was added 0.79 ml (4.4 mmole) of diisopropyl ethylamine followed by 1.17 g (4.4 mmole) of diphenyl chlorophosphate under a nitrogen atmosphere. The resulting solution was stirred at 0° for 30 minutes to provide p-nitrobenzyl 3-(diphenyl phosphoryloxy)-6-[1-(R)-hydroxethyl]-7-oxo-1-azabicyclo(3.2.0)hept-2-ene-2-carboxylate. To this solution was added a solution of 0.79 ml (4.4 mmole) of diisopropyl ethylamine in 2 ml of acetonitrile followed by a solution of 0.72 g of the thiol 4 in 2 ml of acetonitrile. The reaction solution was stirred for 60 minutes at 0° and then diluted with 50 ml of ethylacetate and washed with 30 ml of water, 20 ml of 10% aqueous $H_3PO_4$ and 30 ml of brine. Evaporation of dried ($MgSO_4$) solvent gave a crystalline solid which was triturated with ether to yield 782 mg (42% yield) of the title product 6 as a white crystalline material. m.p. 158°–160° C. NMR (CDCl$_3$) δ: 1.32(3H, d, J=7.0 Hz), 3.28(3H, m), 4.20(2H, m), 4.36(2H, s), 5.40(2H, q), 7.40(1H, d, J=4.0 Hz), 7.64(2H, d, J=8 Hz), 7.76(1H, d, J=4.0 Hz) and 8.24(2H, d, J=8 Hz)

IR(KBr) γmax: 3500, 1770 and 1700 cm$^{-1}$.

Anal. Calc'd. for $C_{20}H_{19}N_3O_6S_2$: C, 52.05; H, 4.15; N, 9.10; S, 13.89. Found: C, 52.35; H, 4.40; N, 8.72; S, 13.90.

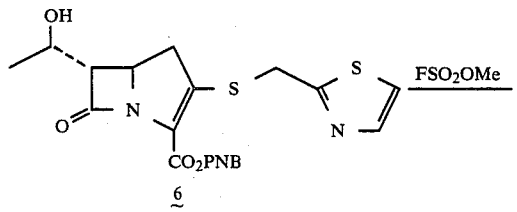

3-[2-(N-Methyl thiazolium) methylthio]-6α-[1-(R)-hydroxyethyl]-7-oxo-1-azabicyclo(3.2.0)hept-2-ene-2-carboxylate To a solution of 782 mg (1.36 mmole) of compound 6 in 55 ml of methylene chloride was added 0.5 ml of methyl fluorosulfonate and stirred for 90 minutes at room temperature. The precipitate was collected by filtration and washed with methylene chloride (30 ml) and ether (20 ml) to give 630 mg of a crude guaternized thiazole 7 which was used for next the step without further purification.

Thus, to a solution of compound 7 in 140 ml of tetrahydrofuran and 120 ml of ether was added 140 ml of pH=7.0 buffer solution followed by 650 mg of 10% palladium on charcoal. The mixture was hydrogenated at 30 psi on the Parr shaker for 35 minutes. The mixture was then filtered and the catalyst was washed with water (2×10 ml). The combined filtrate and washing were extracted with ether (2×150 ml) and lyophilized to give a yellow powder. The crude yellow powder was purified on a C$_{18}$ BONDAPAK reverse phase column (7 g) (Waters Associates), eluting with 5% acetonitrile in water under 8 psi pressure. Each 15 ml fraction was assayed by high pressure liquid chromotography, and fractions having an ultraviolet absorption at λmax 300 nm were collected and lyophilized to give 23 mg (5yield) of the title compound as a yellow amorphous solid.

NMR (D$_2$O) δ: 1.28(3H, d, J=7.0 Hz), 3.12(2H, d, J=7.0 Hz), 3.44(1H, dd, J=1.0 Hz and 3.0 Hz), 4.20(3H, s), 4.24(2H, m), 4.76(3H, m), 8.12(1H, d, J=4 Hz) and 8.24(1H, d, J=Hz): IR(KBr) γmax: 3400, 1740 and 1580 cm$^{-1}$. uv λmax (H$_2$O) 292 nm (ε=7285).

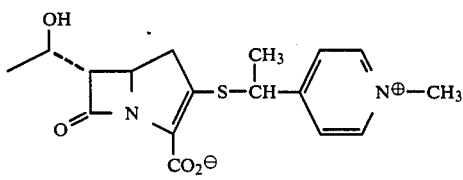

EXAMPLE 12

Preparation of 3-[1-(RS)-Methyl-N-methyl-pyridine-3-yl-methane thio]6α-]1-(R)-hydroxyethyl]-7-oxo-1-azabicyclo(3.2.0) hept-2-ene-2-carboxylate

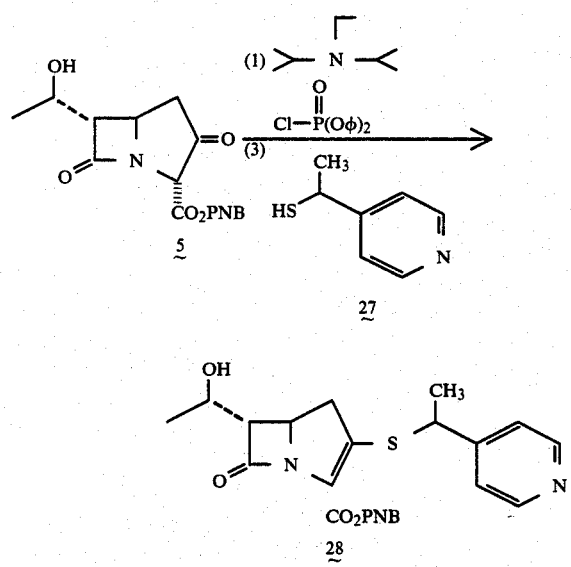

P-Nitrobenzyl-3-[1-(R,S)methyl-pyridine-3-yl-methane thio]6α-[1-(R)-hydroxyethyl]-7-oxo-1-azabicyclo(3.2.0-)hept-2-ene-2-carboxylate To a cooled (0° C.) solution of 1.85 g (5.3 mmole) of the keto intermediate 5 in 20 ml of acetonitrile was added 754 mg (5.8 mmole) of diisopropyl ethylamine in 1 ml of acetonitrile followed by a solution of 1.57 g (5.84 mmole) of diphenyl chlorophosphate in 2 ml of acetonitrile under a nitrogen atmosphere. The resulting solution was stirred for 15 minutes at 0° C., and there was then added a solution of 754 mg (5.8 mmole) of diisopropyl ethylamine in 1 ml of acetonitrile followed by 814 mg (5.8 mmole) of the thiol 27 in 2 ml of acetonitrile. The mixture was stirred at 0° for 3 hours, and then the reaction mixture was diluted with 200 ml of ethylacetate, and washed with ice-cold brine (200 ml), water (200 ml), aqueous bicarbonate (100 ml) and brine (100 ml). Evaporation of dried (MgSO4) solvent gave a yellow oil which was purified by silica gel column chromatography, eluting with 50% acetone-50% methylene chloride to give 1.65 g of the title product as a yellow solid.

NMR (CDCl$_3$) δ: 1.22 and 1.25(3H each d, J=7.0 Hz), 1.46 and 1.50(3H each d, J=7.2 Hz), 2.4–3.3(3H, m), 3.8–4.2(3H, m), 5.35(2H, ABq, J=14.5 Hz) and 7.2–8.6(8H, m). IR(KBr) νmax: 3400, 1765 and 1690 cm$^{-1}$. Anal. Calc'd. for $C_{23}H_{23}N_3O_3S_1$: C, 58.83; H, 4.94; N, 8.95; S, 6.83. Found: C. 57.15; H, 5.04; N, 8.28; S, 6.78.

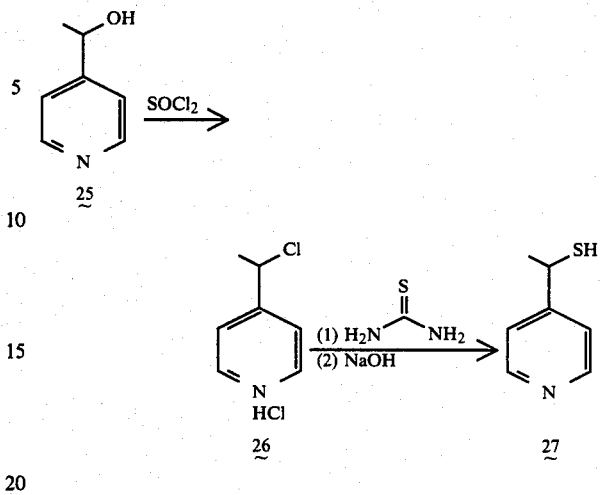

4-(1'-mercaptoethyl)-pyridine

To a solution of 25 g of 1-(4-pyridyl)-ethanol 25 [prepared by the procedure described in J. Chem. Soc., Perkin II, 1462 (1974)] in 100 ml of chloroform was added 50 g of thionyl chloride. The mixture was refluxed for 2 hours. Evaporation of solvents in vacuo gave the chloro compound 26 as a semi solid which was used for the next step without further purification. Thus, to a solution of 26 in 160 ml of ethanol was added a hot solution of 14.4 g of thiourea in 75 ml of ethanol. The reaction mixture was heated at reflux for 18 hours. Ethanol was evaporated and residue was dissolved in 100 ml of water and adjusted to pH 10 by addition of 2NNaOH. The mixture was stirred at room temperature for 90 minutes, adjusted to pH 6.0 by addition of 6NHCl and extracted with ether (2×200 ml). Evaporation of dried (MgSO4) solvent gave a yellow oil which was distilled at 5 mmHg and collected at the boiling range 60°–65° C. to give 11.0 g (38% yield) of the pure thiol 27 as a colorless oil.

NMR (CDCl$_3$) δ: 1.70(3H, d, J=6.0 Hz), 2.05(1H, d, J=5.8 H), 4.20(1H, t, J=6.0 Hz, 5.8 Hz), 7.20(2H, d, J=6.2 Hz) and 8.5(2H, d, J=6.2 Hz).

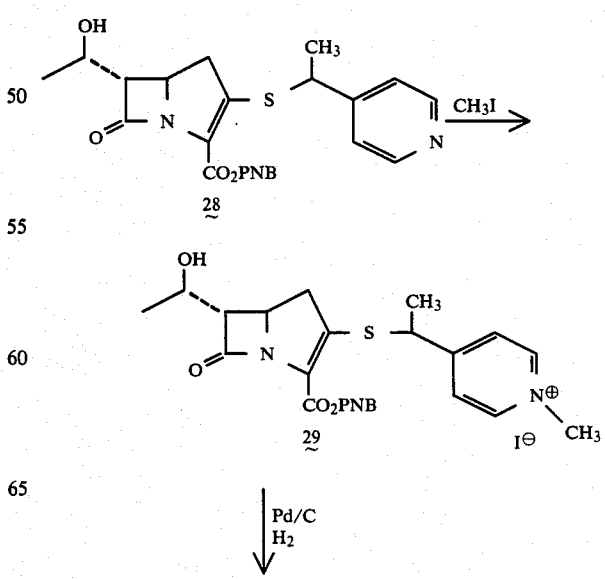

-continued

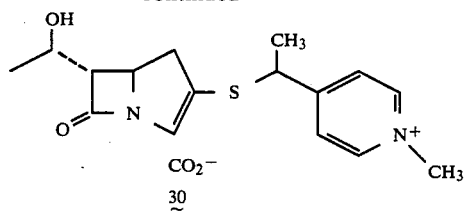

3-[1-(RS)-methyl-N-methyl-pyridine-3-yl-methane thio]-6α-[1-(R)-hydroxyethyl]-7-oxo-1-azabicyclo(3.2.0)hept-2-ene-2-carboxylate To a solution of 1.1 g (2.34 mmole) of compound 28 in 100 ml of acetone was added 10 ml of methyl iodide. The reaction mixture was stirred for 18 hours at room temperature. The precipitate was collected by filtration and washed with methylene chloride (10 ml) to give 1.4 g (100% yield) of the quaternized pyridine 29 as a yellow powder.

NMR (DMSO-d6) δ: 1.10 (3H, d, J=6.5 Hz), 1.62 (3H, d, J=7.5 Hz), 2.6–4.2 (6H, m), 4.39 (3H, s), 5.42 (2H, ABq, J=13.6 Hz) and 7.9–9.2 (8H, m). IR(KBr) νmax: 3400, 1770 and 1190 cm$^{-1}$.

Anal. Calc'd. for $C_{24}H_{26}N_3O_6S_1I_1$: C, 47.14; H, 4.29; N, 6.87; S, 5.24. Found: C, 47.19; H, 4.78; N, 6.11; S, 5.41.

To a solution of 1.45 g (2.37 mmole) of compound 29 in 120 ml of tetrahydrofuran and 120 ml of ether was added 120 ml of pH=7.0 buffer solution followed by 1.5 g of 10% palladium on charcoal. The mixture was hydrogenated at 45 psi on the Parr shaker for 60 minutes. The mixture was filtered through a Celite pad and the catalyst was washed with water (2×15 ml). The combined filtrate and washing were extracted with ether (2×200 ml) and lyophilized to give a yellow solid which was purified on a C18 BONDAPAK (Waters Associates) reverse phase column (50 g), eluting with 5% acetonitrile in water under 8 psi pressure.

Each 20 ml fraction was assayed for high pressure liquid chromatography and fractions having an ultraviolet absorption at λmax 300 nm were collected and lyophilized to give 200 mg (24% yield) of the title product as a yellow amoprhous solid.

NMR (D2O) δ: 1.32 (3H, d, J=7.0 Hz), 1.63 (3H, d, J=7.2 Hz), 2.5–4.6 (6H, m), 4.32 (3H, s) and 8.2–8.9 (4H, m). IR(KBr) νmax: 3400, 1750 and 1590 cm$^{-1}$. UV λmax (H2O): 296 nm (ε=7573).

Anal. Calc'd. for $C_{17}H_{20}N_2O_4S_1 \cdot \frac{1}{2}H_2O$: C, 54.38; H, 5.77; N, 7.46 Found: C, 54.39; H, 5.98; N, 7.68.

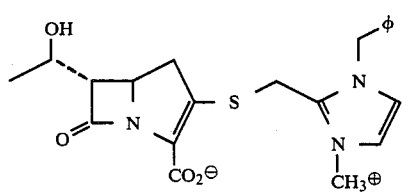

EXAMPLE 13

Preparation of 3-(N-Methyl-N'-benzyl imidazole-2-yl-methane thio)-6α-[1-(R)-hydroxyethyl]-7-oxo-1-azabicyclo(3.2.0)hept-2-ene-2-carboxylate

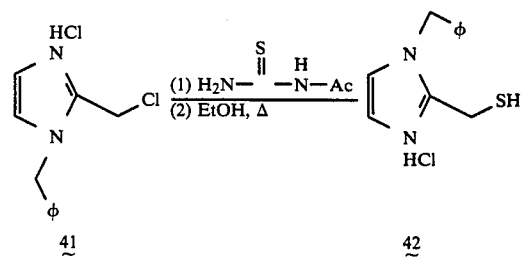

N-Benzyl-2-mercaptomethyl imidazole

To a solution of 3.23 g (13.0 mmole) of the chloro compound 41 [prepared by the procedure described in J. Amer. Chem. Soc., 71, 383 (1949)] in 80 ml of acetonitrile was added 1.72 g (14.5 mmole) of N-acetylthiourea. The reaction mixture was heated at reflux for 3 hours. The precititate was collected by filtration and washed with acetonitrile (10 ml) to give the isothiouronium salt which was then dissolved into 80 ml of absolute ethanol and heated at reflux for 18 hours under a nitrogen atmosphere. The reaction was cooled to room temperature, condensed in vacuo to about 30 ml of volume and the precipitate was removed by filtration. Evaporation of the filtrate in vacuo gave 3.5 g (97% yield) of the thiol 42 as a yellow thick syrup.

NMR (CDCl3) δ: 2.1 (1H, t, J=4.5 Hz), 3.80(2H, s), 5.20(2H, s) and 6.8–7.5(7H, m).

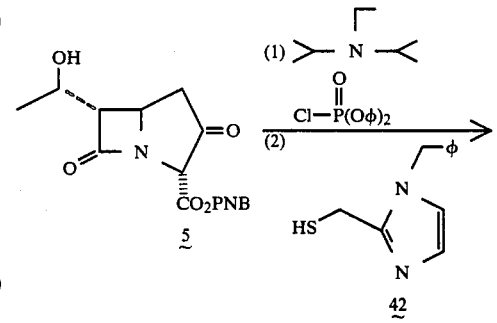

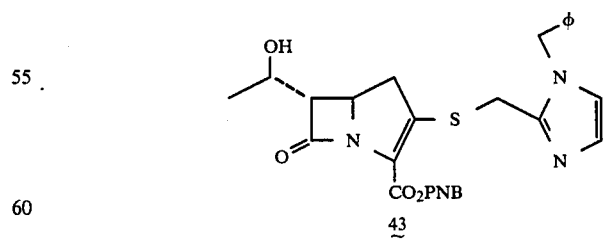

P-Nitrobenzyl-3-[N-benzylimidazole-2-yl-methane thio]6α-[1-(R)-hydroxyethyl]-7-oxo-1-azabicyclo(3.2.0)hept-2-ene-2-carboxylate To a cooled (0°) solution of 3.03 g (8.5 mmole) of the keto intermediate 5 in 70 ml of acetonitrile was added 1.17 g (9.0 mmole) of diisopropyl ethylamine in 2 ml of acetonitrile followed by 2.4 g (9.0 mmole) of diphenyl chlorophosphate in 2 ml of acetonitrile under a nitrogen atmosphere. The resulting solution was stirred for 20 minutes at 0° C., and there was then added a solution of 1.17 g (9.0 mmole) of diisopropyl ethylamine in 2 ml of acetonitrile followed by 4.8 g (15 mmole) of the thiol 42. An additional 1.93 g (15 m ml) of diisopropyl ethylamine was added and the reaction mixture was allowed to stir for 2 hours at 0° C. The precipitate was collected by filtration and washed with cold methylene chloride (20 ml) to give 2.5 g (55% yield) of the title product as a white solid. NMR (DMSO-d6) δ: 1.23 (3H, d, J=7.2 Hz), 2.5–4.1 (6H, m), 4.25 (2H, s), 5.20 (2H, s), 5.20 and 5.45 (1H each, d, J=14.5 Hz) and 6.9–8.3 (11H, m). IR(KBr) γmax: 3400, 1775 and 1690 cm$^{-1}$.

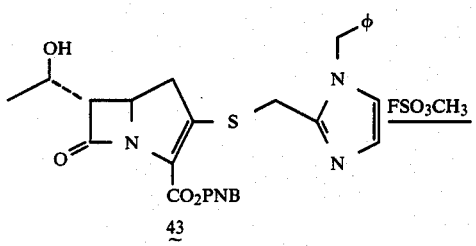

43

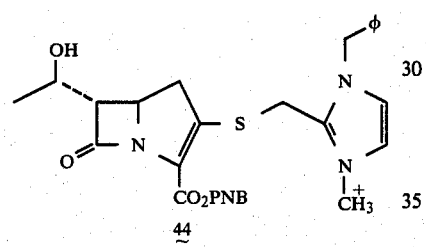

44

Pd/C
H$_2$

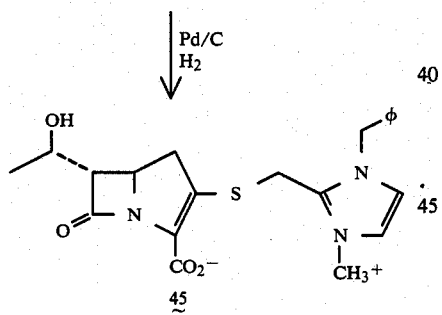

45

3-(N Methyl-N'-benzyl imidazole-2-yl-methane thio)-6α-[1-(R)-hydroxy ethyl]-7-oxo-1-azabicyclo(3.2.0)hept-2-ene-2-carboxylate To a solution of 1.76 g (3.3 mmole) of compound 43 in 1.1 l of methylene chloride was added 1.15 ml (13.4 mmole) of methyl fluorosulfonate. The reaction mixture was stirred for 2 hours at room temperature. The reaction was concentrated in vacuo to about 15 ml of volume. The precipitate was collected by filtration and washed with methylene chloride (10 ml) to give 1.58 g (74% yield) of the quaternized imidazole 44 as a white solid. NMR (DMSO-d6) δ: 1.15 (3H, d, J=7.0 Hz), 3.2–4.4 (6H, m), 4.70 and 5.0 (1H each, ABq, J=10.8 Hz), 5.24 and 5.46 (1H each, ABq, J=14 Hz), 5.50 (2H, s) and 7.4–8.4 (11H, m). IR(KBr) γmax: 3500, 1770 and 1700 cm$^{-1}$. Anal. Cald'd for C$_{28}$H$_{29}$N$_4$O$_9$S$_2$F: C, 51.48; H, 4.47; N, 8.67; S, 10.20. Found: C, 51.84; H, 4.52; N, 8.65; S, 9.87.

To a solution of 1.11 g (1.71 m mole) of compound 44 in 100 ml of tetrahydrofuran and 100 ml of ether was added 120 ml of pH=7.0 buffer solution followed by 1.0 g of 10% palladium on charcoal. The mixture was hydrogenated at 45 psi on the Parr shaker for 45 minutes. The mixture was filtered through a Celite pad and the catalyst was washed with water (2×10 ml). The combined filtrate and washing were extracted with ether (2×70 ml) and lyophilized to give a yellow powder which was purified on a C$_{18}$ BONDAPAK (Waters Associates) column (40 g), eluting with 10% acetonitrile in water under 8 psi pressure.

Each 15 ml fraction was assayed by high pressure liquid chromatography and fractions having an ultraviolet absorption at λmax 300 nm were collected and lyophilized to give 305 mg (43%) of the title product as a slightly yellow amorphous solid. NMR (DMSO) δ: 1.40 (3H, d, J=7.0 Hz), 2.9–3.4 (3H, m), 3.98 (3H, s), 4.0–4.2 (2H, m), 4.23 (2H, broad s), 5.57 (2H, s) and 7.2–7.65 (7H, m). IR(KBr) γmax: 3400, 1760 and 1590 cm$^{-1}$. UV λmax (H$_2$O): 299 nm (ε=8807). Anal. Calc'd for C$_{21}$H$_{23}$N$_3$O$_4$S$_1$.1½H$_2$O: C, 57.25; H, 5.94; N, 9.54; S, 7.28. Found: C, 56.66; H, 5.70; N, 9.49; S, 8.30.

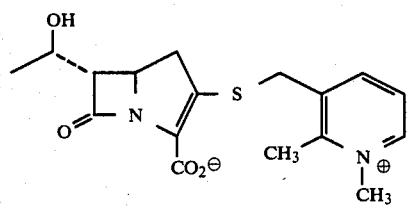

EXAMPLE 14

Preparation of 3-(2-Methyl-N-methylpyridine-3-yl-methane thio)-6α-[1-(R)-hydroxyethyl]-7-oxo-1-azabicyclo(3.2.0)hept-2-ene-2-carboxylate

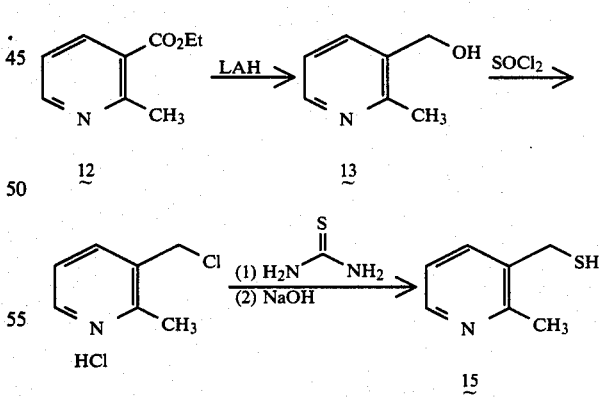

2-Methyl-3-mercaptomethyl pyridine

The ester 12 was prepared by the procedure described in J. Org. Chem., 21 800 (1956). To a cooled (0°) suspended solution of 2.86 g of lithium aluminum hydride in 50 ml of dry tetrahydrofuran was added dropwise a solution of 6.23 g (0.038M) of the ester 12 in 15 ml of tetrahydrofuran over a 15 minute period. The mixture was stirred for 60 minutes at 0°, and there was then added 50 ml of ethylacetate. The precipitate was filtered, and washed with aqueous saturated ammonium chloride. The organic layer was dried over MgSO$_4$, filtered and evaporated in vacuo affording 3.2 g (70% yield) of the hydroxymethyl pyridine 13 as a yellow oil. NMR (CDCl$_3$) of compound 13 δ: 2.46 (3H, S), 4.73 (2H, S), 5.1 (1H, broad), 7.2 (1H, dd, J=8 Hz), 7.8 (1H, dd, J=8 Hz, J=1 Hz) and 8.3 (1H, dd, J=7 Hz, J=1 Hz) and 8.3 (1H, dd J=7 Hz, J=1 Hz).

To a cooled (0°) solution of 4 ml of thionyl chloride in 10 ml of methlene chloride was added dropwise a solution of 3.2 g (0.026M) of the alcohol 13 in 10 ml of methylene chloride over a 15 minute period under a nitrogen atmosphere. Cooling bath was removed and the reaction was allowed to stir for 3 hours at room temperature. All solvents were evaporated in vacuo leaving compound 14 as a brown solid which was used for the next step without purification. The crude brown solid was dissolved in 30 ml of absolute methanol. There was then added 2.5 g (0.032M) of thio urea and the mixture was heated at 65°-70° C. for 18 hours. The mixture was cooled to room temperature. The precipitate was collected by filtration and washed with ethanol (20 ml) and ether (50 ml) to yield 30 g of the isothiouronium salt. This salt was dissolved in 10 ml of water and a solution of 640 mg (0.016M) of sodium hydroxide in 10 ml water was added under nitrogen. The reaction mixture was heated at 100° for 2 minutes and then cooled to 0°, adjusted to pH=6.0 with acetic acid and extracted with chloroform (2×35 ml). Evaporation of dried (MgSO$_4$) chloroform gave 941 mg (46% yield) of the thiol 15 as a yellow oil.

NMR (CDCl$_3$) of the thiol 15 δ: 1.8 (1H, t), 2.60 (3H, S), 3.73 (2H, d, J=10 Hz), 7.13 (1H, dd, J=8 Hz), 7.57 (1H, dd, J=8 Hz), and 8.43 (1H, dd, J=8 Hz, 3 Hz).

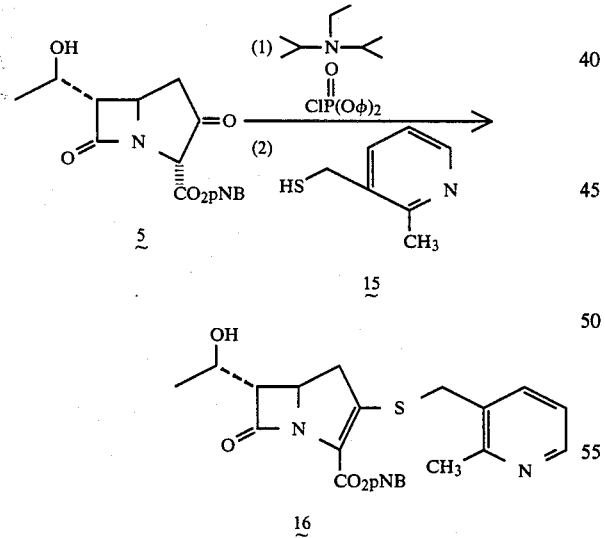

P-Nitrobenzyl-3-(2-methylpyridine-3-yl-methanethio)-6α-[1-(R)-hydroxyethyl]-7-oxo-1-azabicyclo(3.2.0)hept-2-ene-2-carboxylate To a cooled (0°) solution of 1.52 g (4.37 mmole) of the keto intermediate 5 in 5 ml of acetonitrile was added 0.86 ml (4.80 mmole) of diisopropyl ethylamine followed by a solution of 1.17 g (4.37 mmole) of diphenylchlorophosphate in 3 ml of acetonitrile under a nitrogen atmosphere. The resulting solution was stirred for 30 minutes at 0° C. to provide p-nitrobenzyl-3-(diphenylphosphoryloxy)-6α-[1-(R)-hydroxy ethyl]-7-oxo-1-azabicyclo(3.2.0)hept-2-ene-2-carboxylate. To this solution was added a solution of 0.86 ml (4.80 mmole) of diisopropyl ethyl amine in 2 ml of acetonitrile followed by a solution of 940 mg (6.76 mmole) of the thiol 15 in 2 ml of acetonitrile. The reaction mixture was stirred for 60 minutes at 0° C. The precipitate was collected by filtration and washed with ether (30 ml) to give 1.12 g (55% yield) of the title product as a pale yellow solid. M.P. 186°–188° C. (decomp).

NMR (DMSO-d6) δ: 1.20 (3H, d, J=7 Hz), 2.60 (3H, S), 3.40 (m, 2H), 4.16 (m, 2H), 4.32 (2H, S), 5.16 (1H, d, J=5 Hz), 5.44 (2H, q, J=14 Hz), 7.32 (2H, m), 7.8 (2H, d, J=8 Hz), 8.36 (2H, d, J=8 Hz) and 8.48 (1H, dd, J=5.5 Hz, 1.5 Hz). IR (KBr)γmax: 3500, 1770 and 1750 cm$^{-1}$.

Anal. Calc'd. for $C_{23}H_{24}N_3O_6S$: C, 58.83; H, 4.94; N, 8.94; S, 6.83. Found: C, 58.63; H, 4.99; N, 9.06; S, 6.58.

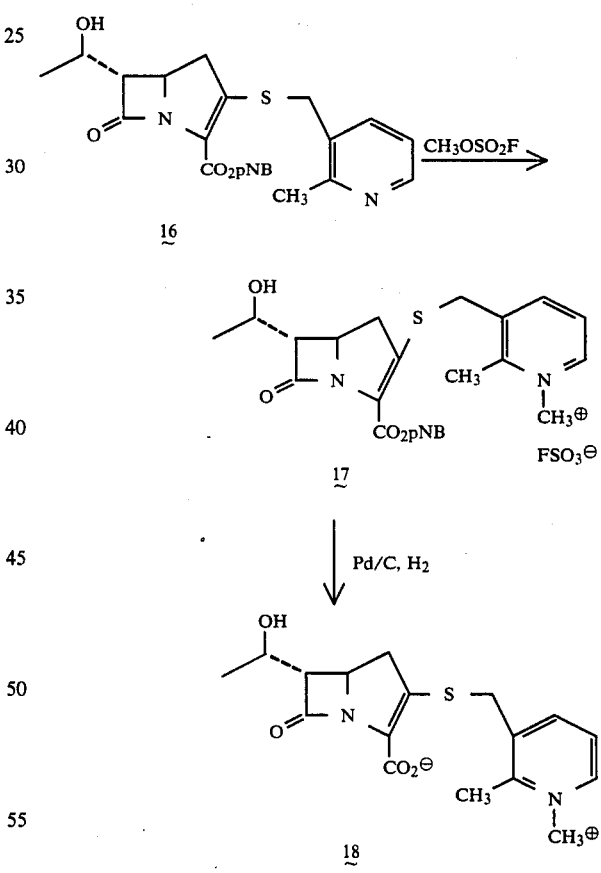

3-(2-Methyl-N-methylpyridine-3-yl-methanethio)-6α[1-(R)-hydroxyethyl]-7-oxo-1-azabicyclo(3.2.0)hept-2-ene-2-carboxylate To a solution of 697 mg (1.19 mmole) of compound 16 in 100 ml of methylene chloride was added dropwise at 10° C. 0.5 ml (6.18 mmole) of methyl fluorosulfonate over a 10 minute period. The mixture was stirred for 2.5 hours at room temperature. The precipitate was collected by filtration and washed with 30 ml of methylene chloride to give 777 mg (90%) of the quaternized pyridine 17 as a yellow solid.

NMR (COCl₃) of compound 17 δ: 1.20 (3H, d, J=7 Hz), 2.82 (3H, s), 4.36 (3H, s), 4.16 (2H, m), 4.60 (2H, s), 5.20 (1H, m), 5.42 (2H, q, J=14 Hz), 7.80 (2H, d, J=8 Hz), 8.04 (1H, dd, J=7 Hz, 6.5 Hz), 8.32 (2H, d, J=8 Hz) 8.64 (1H, d, J=7.5 Hz) and 9.08 (1H, d, J=7.5 Hz). IR (KBr) νmax: 3500 and 1765 cm⁻¹.

Anal. Calc'd. for C₂₄H₂₆FN₃O₉S: C, 48.91; H, 4.55; N, 7.23; S, 11.04. Found: C, 49.39; H, 3.97; N, 7.20; S, 10.98.

To a solution of 1.10 g (1.88 mmole) of compound 17 in 80 ml of tetrahydrofuran and 80 ml of ether was added 80 ml of pH 7.0 buffer solution followed by 800 mg of 10% palladium on charcoal. The mixture was hydrogenated at 30 psi on the Parr shaker for 40 minutes. The mixture was filtered through a Celite pad and the catalyst was washed with water (2×10 ml). The combined filtrate and washing were extracted with ether (2×100 ml) and lyophilized to give a yellow powder which was purified by HP-20 column chromatography, eluting with water followed by 5% acetonitrile in water. Each 15 ml fraction was assayed by high pressure liquid chromatography and fractions having an ultraviolet absorption at λmax 300 nm were collected and lyophilized to give 614 mg (42% yield) of the title product as a slightly yellow powder.

NMR (D₂O) δ: 1.28 (d, 3H, J=7 Hz), 2.86 (3H, s), 3.20 (2H, dd, J=10 Hz, 3.5 Hz), 3.42 (1H, dd, J=5.4 Hz, 3.5 Hz), 4.20 (3H, m), 4.32 (3H, s), 4.35 (2H, S), 9.88 (1H, dd, J=7.2 Hz, 6.5 Hz), 8.5 (1H, d, J=8 Hz) and 8.70 (1H, d, J=8 Hz). IR(KBr) γmax: 3400, 1760, and 1590 cm⁻¹. UV λmax (H₂O): 298 nm (ε=8391).

Anal. Calc'd. for C₁₇H₂₀N₂O₃S.H₂O: C, 5.46; N, 7.65; S, 8.74. Found: C, 55.50; H, 6.05; N, 7.74; S, 8.68.

EXAMPLE 15

Preparation of 3-[4-(N,N-dimethyl-1,2,3-triazolium)methylthio]-6α-[1-(R)-hydroxyethyl]-7-oxo-1-azabicyclo(3.2.0)hept-2-ene-2-carboxylate

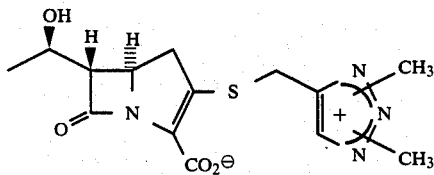

A. Preparation of isomer A

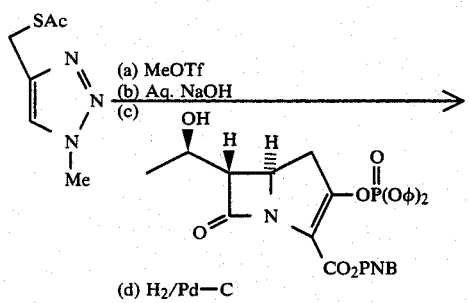

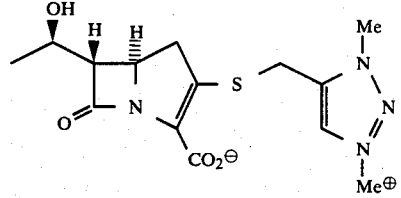

Methyltrifluoromethane sulfonate (0.58 mL, 5.16 mmol) was added dropwise to an ice-cooled, stirred, solution of 4-(methanethiolacetate)-1-methyl-1,2,3-triazole (590 mg, 3.52 mmol) in dry methylene chloride (2 mL) under nitrogen. After 0.5 h, the bath was removed and after 1 h, the solvent was removed with an aspirator. The residual oil was dissolved in a few mL of water and this solution was cooled in an icebath. A cold solution of sodium hydroxide (305 mg, 7.59 mmol) in a few mL of water was then added and the reaction was left stirring for 0.75 h. The solution was diluted to 25 mL with water and the pH was adjusted to 7.5 by the addition of solid sodium dihydrogen phosphate monohydrate. Then, 14 mL of this solution (ca. 1.9 mmol of the triazolium thiol) was added to an ice-cooled, stirred, solution of the enol phosphate (1.0 g, 1.72 mmol) in tetrahydrofuran (THF) (10 mL). This was left stirring for 0.75 h (some crystalline material, presumably Na₂HPO₄ is deposited during the course of this reaction). The suspension was transferred to a pressure bottle with the aid of some THF (20 mL) and water (20 mL). Ether (30 mL) and 10% palladium on charcoal (1.0 g) were added and the mixture hydrogenated (40 P.S.I.) for 1 h. The organic phase was separated and washed with water (2×5 mL). The combined aqueous phases were filtered and the filtrate was concentrated under high vacuum (ca. 0.5 mm, 1.5 h). The yellow solution was then chromatographed (medium pressure reverse phase column, 35×90 mm, H₂O as eluent) to afford, after lyophilization, 395 mg of the carbapenem slightly contaminated with some inorganic material. It was purified by HPLC (10×30 mm Waters Microbondapack C-18 column, multiple injections, H₂O as eluent) to give 130 mg (57%) of isomer A as a tan-colored powder: ¹HNMR (D₂O) δ: 1.23 (3H, d, J=6.4 Hz), 3.10 (2H, d, J=9.1 Hz), 3.24 (1H, q, J=2.7, 6.1 Hz), 4.03–4.71 (10H, m), 8.46 (1H, s); IR (nujol) 1760 cm⁻¹; uv (phosphate buffer, pH 7.4, M=0.05)λmax: 296 (ε=7,500).

B. Preparation of isomer B and isomer C

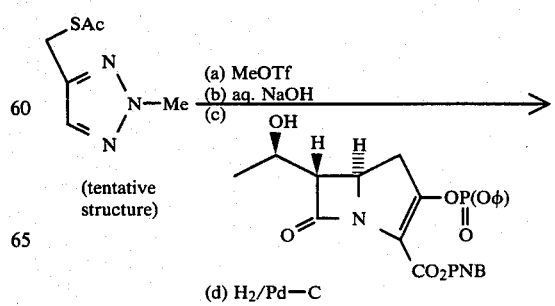

-continued

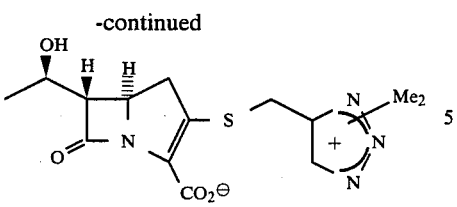

Methyltrifluoromethane sulfonate (1.60 mL, 14.0 mmol) was added dropwise to an ice-cooled solution of 4-(methanethiolacetate)-2-methyl-1,2,3-triazole (1.20 g, 7.02 mmol) in dry methylene chloride (6 mL) under nitrogen. This was allowed to warm to room temperature and left stirring for 16 h. Additional methyltrifluoromethane sulfonate (0.40 mL, 3.56 mmol) was added and after 3 h at room temperature, the solvent was removed with an aspirator. The residual oil was triturated with ether and the resulting gum was dissolved in water (5 mL). This was cooled in an icebath and a solution of sodium hydroxide (844 mg, 21.1 mmol) in water (5 mL) was added. After stirring for 0.75 h, this solution was diluted to 60 mL with water and the pH adjusted to 8 by the addition of solid potassium dihydrogen phosphate. Then, 40 mL of this solution (ca. 4.7 mmol of a mixture of isomeric triazolium thiols) was added to an ice-cooled, stirred, solution of the enol phosphate (2.00 g, 3.45 mmol) in THF (60 mL). This mixture was left stirring in the icebath for 0.5 h after which it was transferred to a pressure bottle containing a suspension of 10% palladium on charcoal (2.00 g) and ether (60 mL). The mixture was hydrogenated (40 P.S.I.) for 1 h. The organic phase was separated and washed with water (2×10 mL). The combined aqueous phases were filtered and the filtrate was concentrated under high vacuum (ca. 0.5 mm, 1.5 h). The remaining solution was then chromatographed (medium pressure reverse phase column, 45×130 mm, H$_2$O as eluent) to afford, after lyophilization, 595 mg of a mixture of isomeric carbapenems which were contaminated with a little inorganic material. These were separated and purified by HPLC (10×300 mm Waters Microbondapack C-18 column, multiple injections, H$_2$O as eluent) to afford, in order of elution: isomer B; 153 mg (13%); $^1$HNMR (D$_2$O) δ: 1.23 (3H, d, J=6.4 Hz), 3.12 (2H, q, J=1.4, 8.9 Hz), 3.39 (1H, q, J=2.7, 6.0 Hz), 4.07–4.68 (10H, m), 8.19 (1H, s); IR (nujol) 1755 cm$^{-1}$; uv (phosphate buffer, pH=7.4, M=0.05) λ$_{max}$: 296 nm (ε=6,700); and isomer C; 284 mg (24%); $^1$HNMR (D$_2$O) δ: 1.23 (3H, d, H=6.4 Hz), 3.15 (2H, q, J=3.7, 9.0 Hz), 3.37 (1H, q, J=2.6, 6.0 Hz), 3.95–4.65 (10H, m), 8.62 (1H, s); IR (nujol) 1750 cm$^{-1}$; uv (phosphate buffer, pH 7.4, M=0.05) λ$_{max}$: 298 nm (ε=7,600).

EXAMPLE 16

(5R,6S) 6-(1R-hydroxyethyl)-3-(2-methyl-1,2,3-thiadiazolium-4-ylmethylthio)-7-oxo-1-azabicyclo[3.2.0]hept-2-ene-2-carboxylate

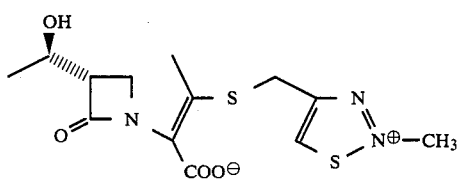

A. Ethyl 1,2,3-thiadiazol-4-ylcarboxylate[1]

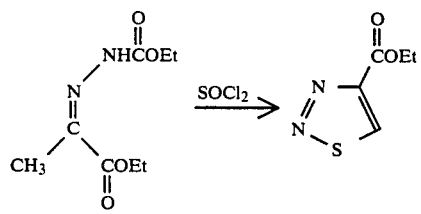

[1] C. D. Hurd and R. I. Mori, *J. Am. Chem. Soc.*, 77, 5359 (1955).

A solution of ethyl α-N-carbethoxyhydrazonopropionate (31.2 g, 0.154 mol) in thionyl chloride (80 mL) was stirred at 23° C. for 3 h and heated at 70° C. for 20 min. Thionyl chloride was evaporated and the residue was triturated in hexane (4×30 mL). The red solid was dissolved in dichloromethane (150 mL) and the solution was washed with saturated sodium bicarbonate solution and water. After drying over Na$_2$SO$_4$ the solution was concentrated until the compound crystallized. After standing at 23° C. for a while, the crystals were filtered; 16.8 g, mp 86° C., 69%. The filtrate was concentrated and purified by chromatography on a silica gel column with dichloromethane as eluting solvent to give 3.17 1 g, mp 86° C., 13%, ir (KBr)ν$_{max}$: 1720 (ester) cm$^{-1}$; $^1$Hmr (CDCl$_3$) δ: 1.52 (3H, t, J=7.1 Hz, CH$_3$CH$_2$O), 4.57 1 (2H, q, J=7.1 Hz, CH$_3$CHHd 2O), 9.47 (1H, s, H of thiadiazole).

B. 1,2,3-thiadiazol-4-ylmethanol[1]

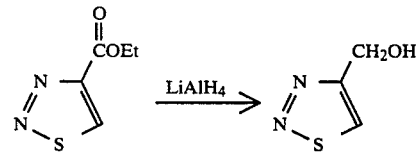

[1] S. I. Rämbsby, S. O. Ögren, S. B. Ross and N. E. Stjernström, *Acta Pharm. Succica.*, 10, 285–96 (1973); C.A., 79, 137052W (1973).

To a suspension of ethyl 1,2,3-thiadiazol-4-ylcarboxylate (18.35 g, 0.116 mol) in ether (400 mL) was added portionwise lithium aluminum hydride (2.47 g, 0.065 mol) over 1 h period. The reaction mixture was stirred at 23° C. for 7 h and treated with lithium aluminum hydride (2.47 g, 0.065 mL). The stirring was continued for 24 h before adding successively water (7 mL), 15% sodium hydroxide solution (7 mL) and water (21 mL). After stirring for 15 min, the ether solution was decanted and the gum was extracted with ether (5×100 mL). The ether extracts were combined, dried (MgSO$_4$) and concentrated (5.4 g). The crude material was purified on silica gel column (120 g, 4×16 cm), with ether as eluting solvent to give 1.3 g (7%) of ethyl 1,2,3-thiadiazol-4-ylcarboxylate and 2.45 g (18%) of 1,2,3-thiadiazol-4-ylmethanol; ir (film)ν$_{max}$: 3380 (OH) cm$^{-1}$; $^1$Hmr (CDCl$_3$)δ: 2.31 (1H, s, OH), 5.22 (2H, s, CH$_2$O), 8.50 (1H, s, H of thiadiazole).

C. 1,2,3-thiadiazol-4-ylmethanol methanesulfonate

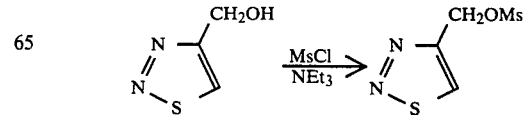

A solution of 1,2,3-thiadiazol-4-ylmethanol (0.75 g, 6.5 mmol) in dichloromethane (20 mL) was cooled to 5° C. under a nitrogen atmosphere and treated with triethylamine (1.018 mL, 7.3 mmol) and methanesulfonyl chloride (0.565 mL, 7.3 mmol). After 15 min, the ice-bath was removed and the reaction mixture was stirred for 2 h. The solution was washed with 1N hydrochloric acid solution (2×2 mL) and water, dried (MgSO$_4$+MgO) and concentrated. The residue was purified by chromatography (silica gel column 1.5×21 cm) with ether as eluting solvent to give 0.90 g (71%) of 1,2,3-thiadiazol-4-ylmethanol methanesulfonate; ir (film)$\nu_{max}$: 1350 (SO$_2$) cm$^{-1}$, 1172 (SO$_2$) cm$^{-1}$; $^1$Hmr (CDCl$_3$)δ: 3.09 (3H, s, CH$_3$), 5.75 (2H, s, CH$_2$), 8.72 (1H, s, H of thiadiazole); uv (CH$_2$Cl$_2$)λ$_{max}$: 251 (ε1990). Anal. calcd for C$_6$H$_6$N$_2$O$_3$S: C 24.73, H 3.11, N 14.42, S 33.02; found: C 24.78 H 3.09, N 14.66, S 31.94 and 0.13 g (19%) of di-(1,2,3-thiadiazol-4-ylmethyl)ether; ir (film)$\nu_{max}$: 1272, 1242, 1200, 986, 805, 728 cm$^{-1}$; $^1$Hmr (CDCl$_3$)δ: 5.16 (s, 4H, CH$_2$), 8.42 (s, 2H, H's of thiadiazole).

D. 4-acetylthiomethyl-1,2,3-thiadiazole

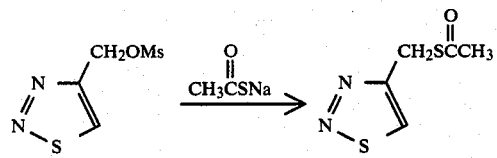

To a solution of 1,2,3-thiadiazol-4-ylmethanol methanesulfonate (0.90 g, 4.6 mmol) in tetrahydrofuran (9 mL) was added an aqueous solution (2 mL) of sodium thiolacetate [prepared from thiolacetic acid (0.38 mL, 5.3 mmol) and sodium bicarbonate (0.445 g, 5.3 mmol)]. The resulting mixture was stirred at 23° C. for 1 h and diluted with ether (75 mL). The organic solution was washed with water (3×3 mL), dried (MgSO$_4$) and concentrated. The crude mixture was purified by chromatography (silica gel column: 1.4×19 cm) with 50% ether in hexane as eluting solvent to give 0.60 g (75%); ir (film)$\nu_{max}$: 1675 (C=O) cm$^{-1}$; $^1$Hmr (CDCl$_3$)δ: 2.37 (3H, s, CH$_3$), 4.58 (2H, s, CH$_2$), 8.44 (1H, s, H of thiadiazole). Anal. calcd for C$_5$H$_6$N$_2$OS$_2$: C 34.47, H 3.47, N 16.08, S 36.80; found: C 34.48, H 3.83, N 16.28, S 36.80.

E. 4-acetylthiomethyl-2-methyl-1,2,3-thiadiazolium trifluoromethanesulfonate and 4-acetylthiomethyl-3-methyl-1,2,3-thiadiazolium trifluromethane sulfonate

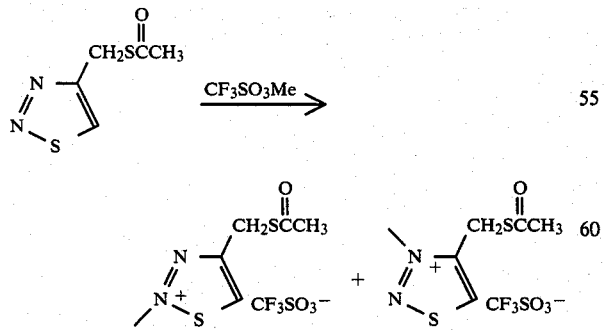

To a solution of 4-acetylthiomethyl-1,2,3-thiadiazole (0.60 g, 3.44 mmol) in a mixture of ether (4 mL) and dichloromethane (0.4 mL) were added a few crystals of the title compounds and trifluoromethanesulfonate (0.407 mL, 3.6 mmol) over 5 min period. The reaction mixture was stirred at 23° C. under a nitrogen atmosphere for 6 h. The white solid that was a mixture of the two title compounds was filtered and washed with ether, 1.05 g, 90%; ir (KBr)$\nu_{max}$: 1675 (C=O) cm$^{-1}$; $^1$Hmr (DMSO, d-6)δ: 2.43 (3H, s, CH$_3$COS), 3,33 (s, CH$_3$ on N-3), 4.57 (s, CH$_3$ on N-2), 4.66 (2H, s, CH$_2$), 9.55 (H on thiadiazolium N-2), 9.66 (H on thiadiazolium N-3). Anal. calcd for C$_7$H$_9$N$_2$O$_4$S$_3$F$_3$: C 20.27, H 2.38, N 9.45, S 32.46; found: C 24.61, H 2.57, N 8.47, S 28.21.

F. 4-mercaptomethyl-2-methyl-1,2,3-thiadiazolium trifluoromethanesulfonate and 4-mercaptomethyl-3-methyl-1,2,3-thiadiazolium trifluoromethanesulfonate

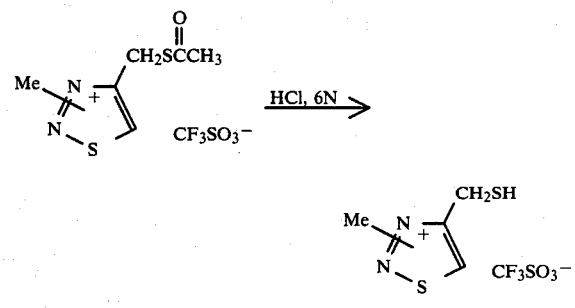

A solution of a mixture of 4-acetylthiomethyl-2-methyl-1,2,3-thiadiazolium trifluoromethanesulfonate and 4-acetylthiomethyl-3-methyl-1,2,3-thiadiazolium trifluoromethanesulfonate (1.05 g, 3.1 mmol) in 6N hydrochloric acid (10 mL) was heated at 65° C. under a nitrogen atmosphere for 1.75 h. The solvent was evaporated under reduced pressure leaving a yellow syrup 0.91 g. This compound was used in the next step without purification.

G. (5R,6S) 6-(1R-hydroxyethyl)-3-(2-methyl-1,2,3-thiadiazolium-4-ylmethylthio)-7-oxo-1-azabicyclo[3.2.0]hept-2-ene-2-carboxylate

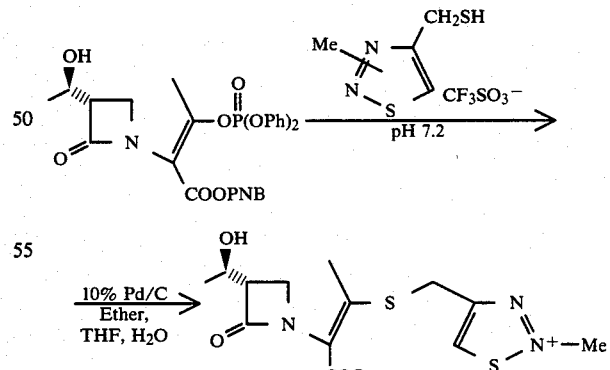

A cold (5° C.) solution of (5R,6S) paranitrobenzyl 6-(1R-hydroxyethyl)-3-(diphenylphosphono)-7-oxo-1-azabicyclo(3.2.0)hept-2-ene-2-carboxylate (1.7 g, 2.92 mmol) in tetrahydrofuran (10 mL) was treated with a solution of a crude mixture of 4-mercaptomethyl-2-methyl-1,2,3-thiadiazolium trifluoromethanesulfonate and 4-mercaptomethyl-3-methyl-1,2,3-thiadiazolium trifluoromethanesulfonate (0.9 g) in a mixture of phosphate buffer (pH 7.2, 0.3M, 15 mL) and tetrahydrofuran (5 mL). The reaction mixture was stirred for 1 h and the pH was kept at 7.2 with 2N sodium hydroxide solution. The stirring was continued for one more hour before adding ether (50 mL) and 10% palladium on charcoal (1 g). The resulting mixture was hydrogenated at 23° C. under 45 psi for 2 h and filtered through a Celite pad. The organic phase was separated, diluted with ether (50 mL) and phosphate buffer (pH 7.2, 0.3M, 20 mL) and hydrogenated (2 g of 10% palladium on charcoal) for 2 h under 50 psi. The aqueous phases were combined (from the first and second hydrogenolysis), washed with ether and purified by chromatography on PrepPak 500-C/18 with water as eluting solvent to give 0.22 g of crude material. It was repurified by hplc with water as eluting solvent to give 0.040 g (4%) of the title compound after lyophilization, ir (KBr)$\nu_{max}$: 3400 (br, OH), 1745 (C=O of β-lactam), 1580 (carboxylate) cm$^{-1}$; $^1$Hmr (D$_2$O) δ: 1.23 (3H, d, J=6.3 Hz, C$\underline{H}_3$CHOH), 3.04, 3.05, 3.16 (2H, m, H-4), 3.38 (1H, dd, J=2.8 Hz, J=6.0 Hz, H-6), 3.9–4.6 (2H, m, H-5,CH$_3$C$\underline{H}$OH), 4.51, 4.53(2"s", SCH$_2$), 4.61 (s, N+CH$_3$); uv (H$_2$O) $\lambda_{max}$: 224 (ε4345), 262 (ε4980), 296 (ε6885), [α]$_D^{23}$ 18° (c 0.18, H$_2$O); T$_{\frac{1}{2}}$=9.8 h (measured at a concentration of 10$^{-4}$ M in phosphate buffer pH 7.4 at 36.8° C.).

EXAMPLE 17

Potassium 3-[5-(1-carboxylatomethyl-3-methyl-1,2,3-triazolium)-methanethio]-6α-[1-(R)-hydroxyethyl]-7-oxo-1-azabicyclo[3.2.0]hept-2-ene-2-carboxylate

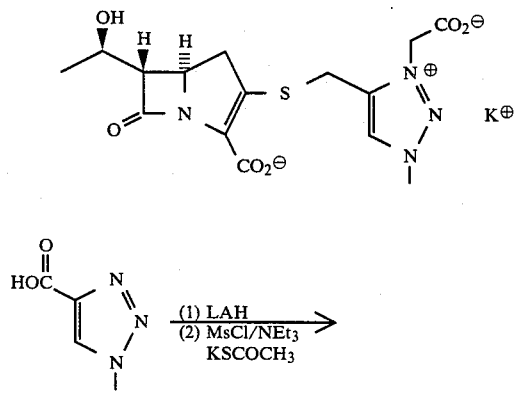

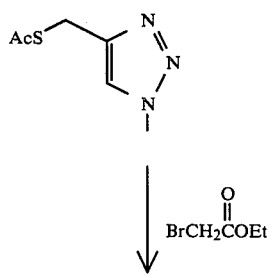

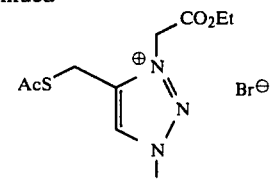

(a) KOH
(b)
(c) H$_2$/Pd—C

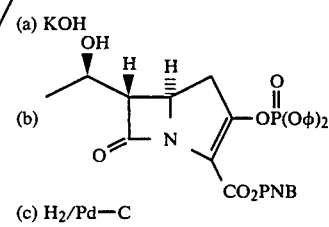

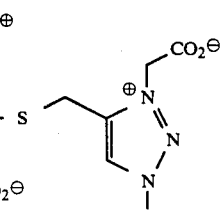

Lithium aluminum hydride (2.83 g, 70.9 mmol) was added in small portions to a stirred suspension of 1-methyl-1,2,3-triazole-4-carboxylic acid[1] (900 g, 70.9 mmol) in dry THF (200 mL). The mixture was left stirring at room temperature for 15 h after which a 20% aqueous solution of sodium hydroxide (20 mL) was carefully added in ca. 1 mL aliquots. The resulting granular suspension was filtered and the solid washed with additional THF (5×75 mL). The combined THF solutions were dried (MgSO$_4$) and the solvent removed. The residual yellow oil was flash chromatographed on a silica gel column (90×35 mm) [100 mL portions of hexane, mixtures of ethyl acetate-hexane (1:1) and (1:3), and lastly ethyl acetate-methanol (9:1) as eluent]. This afforded 4-hydroxymethyl-1-methyl-1,2,3-triazole (3.18 g, 40%) as a colourless oil: $^1$HNMR (CDCl$_3$) δ 4.07 (3H, s), 4.73 (2H, d), 7.52 (1H, s); IR (neat) 3320 cm$^{-1}$.
[1]C. Pederson, Acta. Chem. Scand., 1959, 13, 888

Methanesulfonyl chloride (3.82 mL, 49.6 mmol) was added dropwise to an ice-cooled, stirred, solution of the alcohol (4.67 mL, 41.3 mmol) and triethylamine (7.47 mL, 53.7 mmol) in methylene chloride (20 mL). After 0.5 h, the solvent was removed and the residual solid was taken up in actonitrile (30 mL). Potassium thiolacetate (7.06 g, 62.0 mmol) was then added and the suspension was left stirring at room temperature for 3 h. An additional quantity of potassium thiolacetate (3.0 g, 26.3 mmol) was added and the suspension was left stirring for a further 16 h. The dark-coloured suspension was then concentrated and water (10 mL) was added. This mixture was extracted with methylene chloride (5×40 mL). The combined extracts were dried (MgSO$_4$) and the solvent removed. The residual oil was flash chromatographed on a silica gel column (90×36 mm) [hexane followed by a mixture of hexane-ethyl acetate (1:1) being used as eluent]. This afforded 4-(methanethiolacetate)-1-methyl-1,2,3-triazole (5.95 g, 84%) as a faint pink coloured solid: $^1$HNMR (CDCl$_3$) δ 2.40 (3H, s), 41.0 (3H, s), 4.20 (2H, s), 7.53 (1H, s); IR (nujol mulll) 1675 cm$^{-1}$.

A solution of the triazole (1.00 g, 5.85 mmol) and ethyl bromoacetate (1.48 mL, 13.3 mmol) in dry acetonitrile (10 mL) was heated at 60° for 90 h under nitrogen. The solvent was removed and the residual oil was triturated with ether (4×25 mL) to leave 1-methyl-3-(ethyl carboxymethyl)-4-methanethiolacetate-1,2,3-triazolium bromide as a brownish gum which was used directly.

A cold solution of KOH (0.66 g, 12 mmol) in water (5 mL) was added to an ice-cooled, stirred, solution of the triazolium bromide in water (20 mL). After 20 min, this was diluted to 35 mL and sufficient solid potassium dihydrogen phosphate was added to bring the pH of this solution to 8.0. This was then added to a stirred, ice-cooled, solution of the enol phosphate in THF (35 mL). After 0.5 h, this mixture was transferred to a pressure bottle containing ether (35 mL) and 10% palladium on charcoal (1.5 g). It was hydrogenated at 40 p.s.i. for 55 min. The organic phase was then separated and washed with water (2×5 mL). The combined aqueous phases were filtered and the filtrate concentrated under high vacuum. The residual material was chromatographed on a reverse phase column (35×120 mm) with water as eluent. Lyophilization of the carbapenem containing fractions left 1.20 g of a greencoloured solid. This was rechromatographed on a Waters Prep. 500 HPLC (PrepPAK-500/$C_{18}$ column) with 2% acetonitrile-water as eluent. The fractions containing the carbapenem were combined and lyophilized. This material was again rechromatographed by HPLC (10×300 mm Waters Microbondapack C-18 column) with water as eluent to afford, after lyophilization, pure title compound (190 mg, 17%) as a pale yellow solid: $^1$HNMR ($D_2O$) δ1.24 (3H, d, J=6.4 Hz), 3.07 (2H, d, J=9 Hz), 3.38 (1H, q, J=2.7, 6.0 Hz), 4.02–4.30 (3H, m), 4.29 (3H, s), 5.23 (2H, s), 8.52 (1H, s); IR (nujol mull) 1750 cm$^{-1}$; UV (phosphate buffer, pH 7.4)$\lambda_{max}$ 296 nm (ε=7,520).

EXAMPLE 18

Potassium 3-[4-(1-carboxylatomethyl-3-methyl-1,2,3-triazolium)-methanethio]-6α-[1-(R)-hydroxyethyl]-7-oxo-1-azabicyclo[3.2.0]hept-2-ene-2-carboxylate

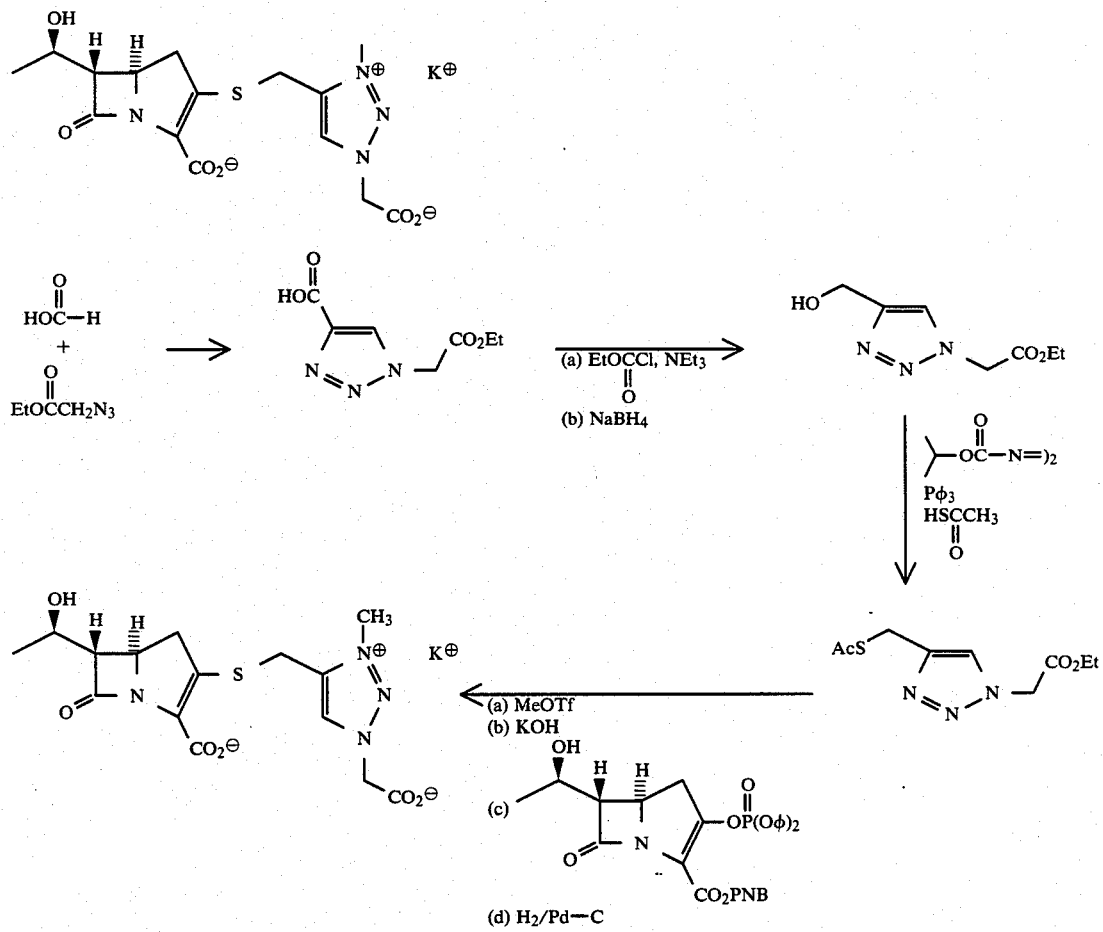

A mixture of ethyl azidoacetate (30.0 g, 0.23 mol) and propiolic acid (14.3 mL, 0.23 mol) in toluene (75 mL) was stirred at room temperature. The reaction remained mildly exothermic for 1.5 h after which it quickly became vigorously exothermic and cooling with an ice bath was necessary. After this exothermic phase had passed, the reaction was heated at reflux for 0.5 h. After being cooled in an ice bath, the crystalline material was collected by filtration and washed with a little toluene. The crude material obtained in this manner (33.3 g, 72%) consisted of a single isomer [$^1$HNMR (DMSO-$d_6$) δ1.20 (3H, t, J=7 Hz), 4.15 (2H, q, J=7 Hz), 5.42 (2H, s), 8.67 (1H, 3)], presumably 1-(ethyl carboxymethyl)-1,2,3-triazole-4-carboxylic acid by analogy with earlier work[1].

[1] C. Pederson, *Acta. Chem. Scand.*, 1959, 13, 888

A solution of the carboxylic acid (5.00 g, 25.1 mmol) and triethylamine (3.68 mL, 26.4 mmol) in dry methylene chloride (50 mL) was added to an ice-cooled, stirred, solution of ethylchloroformate (2.52 mL, 26.4 mmol) in dry methylene chloride (50 mL). The purple coloured solution was left stirring for 0.5 h afterwhich it was washed with water (10 mL), dried (MgSO$_4$) and the solvent removed. The crude mixed anhydride was dissolved in THF (50 mL) and added slowly to an ice-cooled suspension of sodium borohydride (0.72 g, 18.9 mmol) in THF (50 mL). After stirring for 0.5 h, additional sodium borohydride (0.30 g, 7.9 mmol) was added and the reaction was left in the ice bath for 1 h. Water (5 mL) was then added and after 10 min, this was followed by 10% aqueous HCl (3 mL). After gas evolution had ceased, solid potassium carbonate (2 g) was added with stirring. The organic phase was then removed and the residual white paste was extracted with additional THF. The combined organic phases were dried (MgSO$_4$) and the solvent removed. Flash column chromatography on silica gel, eluting with hexane, mixtures of ethyl acetate-hexane, and finally ethyl acetate afforded 1-(ethyl carboxymethyl)-4-hydroxymethyl-1,2,3-triazole (2.04 g, 44%) as a crystalline solid: $^1$HNMR (CDCl$_3$) δ1.28 (3H, t, J=7 Hz), 4.23 (2H, q, J=7 Hz), 4.75 (2H, s), 4.85 (2H, s), 7.73 (1H, s).

Diisopropylazodicarboxylate (4.11 mL, 20.8 mmol) was added dropwise to an ice-cooled solution of triphenylphosphine (5.47 g, 20.8 mmol) in dry THF (100 mL) under nitrogen. After 0.5 h, an ice-cooled solution of the alcohol (1.93 g, 10.4 mmol) and thiolacetic acid (1.49 mL, 20.8 mmol) in dry THF (50 mL) under nitrogen was added to this mixture. This was left for 2 h in the ice bath and then for an additional 12 h at room temperature; afterwhich the solvent was removed. The reaction mixture was flash chromatographed on silica gel (40 g; eluting with 100 mL portions of hexane, 5%, 10%, 15%... 50% ethyl acetatehexane). Fractions containing the thiolacetate were combined and rechromatographed on silica gel (60 g) [elution with 200 mL portions of: hexane, 5%, 10%, 15%, 20% ethyl acetate-hexane and 22.5, 25, 27.5... 35% ethyl acetatehexane]. This afforded 1.24 g (49%) of 1-(ethyl carboxymethyl)-4-methanethiolacetate-1,2,3-triazole as a crystalline solid [$^1$HNMR δ1.28 (3H, t, J=7 Hz), 2.37 (3H, s), 3.87 (2H, s), 3.90 (2H, q, J=7 Hz), 5.12 (2H, s), 7.63 (1H, s); IR (nujol mull), 1735, 1780 cm$^{-1}$] and an additional 1.40 g of material contaminated with triphenylphosphine oxide.

Methyl trifluoromethane sulfonate (0.51 mL, 4.53 mmol) was added dropwise to an ice-cooled, stirred, solution of the triazole (1.00 g, 4.12 mmol) in dry methylene chloride (5 mL). The bath was removed after 0.5 h and after an additional 0.5 h, the solvent was removed with an aspirator vacuum. This left a white solid which was suspended in water (15 mL) and this stirred mixture was cooled in an icebath. A solution of KOH (0.69 g, 12.4 mmol) in water (5 mL) was added and the reaction was left stirring for 1 h. It was then diluted to 30 mL with water and solid potassium dihydrogen phosphate was added to bring the pH to 8.0. A portion of this solution (22 mL, ca. 3.0 mmol of the thiolcarboxylate) was added to an ice-cooled, stirred solution of the enol phosphate (1.60 g, 2.76 mmol) in THF (30 mL). After 0.5 h, the reaction was taken and put under high vacuum to remove the THF. The yellow solution was then chromatographed on a reverse phase column (35×120 mm) eluting with water (300 mL) followed by 100 mL portions of 5, 10, 15... 30% acetonitrile-water. Lyophilization of the desired fractions afforded the p-nitrobenzyl ester as a yellow solid (930 mg). This was transferred to a pressure bottle containing ether (25 mL), THF (25 mL), and phosphate buffer [25 mL, prepared by dissolving potassium dihydrogen phosphate (1.36 g, 0.01 mol) in water (100 mL) and adjusting the pH to 7.4 by adding 45% aqueous KOH] and 10% palladium on charcoal (900 mg). The hydrogenation was conducted at 40 p.s.i. for 1 h after which the organic phase was separated and washed with water (2×5 mL). The combined aqueous phases were filtered and then concentrated under high vacuum. The residual solution was chromatographed on a reverse phase column (35×120 mm) eluted with water. Fractions containing the carbapenem were combined and lyophilized to afford 1.21 g of a pale greenish solid. This was then purified by HPLC (10×300 mm water microbondapack C-18 column, H$_2$O as eluent) to give pure title product, 480 mg (41%): $^1$HNMR (D$_2$O) δ1.23 (3H, d, J=6.4 Hz), 3.11 (2H, d, J=9 Hz), 3.37 (1H, q, J=3.0, 6.1 Hz), 4.02 (7H, m), 5.18 (2H, s), 8.53 (1H, s): IR (nujol mull) 1750 cm$^{-1}$: UV (phosphate buffer, pH 7.4)λ$_{max}$ 205 nm (ε=7,810).

EXAMPLE 19

3-[5-(1,4-Dimethyl-1,2,4-triazolium)methanethio]-6α-[1-(R)-hydroxyethyl]-7-oxo-1-azabicyclo[3.2.0]hept-2-ene-2-carboxylate

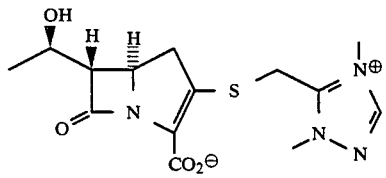

A. 1-methyl-5-methanethiolacetate-1,2,4-triazole

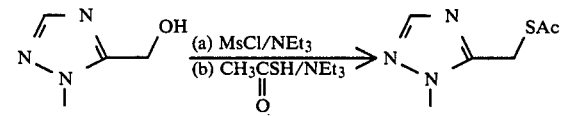

Methanesulfonyl chloride (0.46 mL, 6.0 mmol) was added dropwise to an ice-cooled, stirred, solution of 1-methyl-5-hydroxymethyl-1,2,4-triazole* (565 mg, 5.0 mmol) and triethylamine (0.91 mL, 6.5 mmol) in methylene chloride (5 mL). After 20 min, additional triethylamine (1.05 mL, 7.5 mmol) followed by thiolacetic acid (0.53 mL, 7.5 mmol) was added and stirring was continued for 45 min. The reaction was then diluted with methylene chloride and washed with water. The aqueous phase was extracted with methylene chloride (3×5 mL) and the combined organic phases were dried (MgSO$_4$) and the solvent removed. Column chromatography on silica gel afforded pure 1-methyl-5-methanethiolacetate-1,2,4-triazole (570 mg) as a yellow oil [in addition, an impure fraction (200 mg) was rechromatographed (preparative TLC, silica gel) to give a further 100 mg of pure material (total yield: 85%)]: $^1$HNMR (CDCl$_3$) δ2.38 (3H, s), 3.90 (3H, s), 4.25 (3H, s), 7.80 (1H, s).

* R. G. Jones and C. Ainsworth, *J. Amer. Chem. Soc.*, 1955, 77, 1938.

B.
3-[5-(1,4-dimethyl-1,2,4-triazolium)-methanethiol]-6α-[1-(R)-hydroxyethyl]-7-oxo-1-azabicyclo[3.2.0]hept-2-ene-2-carboxylate

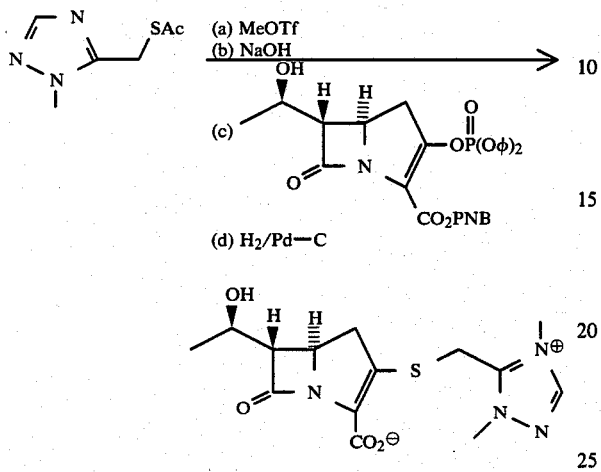

Methyl trifluoromethanesulfonate (1.20 mL, 10.7 mmol) was added dropwise to an ice-cooled solution of 1-methyl-5-methanethiolacetate-1,2,4-triazole (730 mg, 4.27 mmol) in methylene chloride (7 mL). The reaction mixture was slowly allowed to warm to room temperature over 3 h after which it was concentrated. The residual oil was triturated with ether to leave crude 1,4-dimethyl-5-methanethiolacetate-1,2,4-triazolium trifluoromethanesulfonate (1.46 g) which was used directly.

A solution of sodium hydroxide (512 mg, 12.8 mmol) in water (5 mL) was added to an ice-cooled solution of the triazolium salt (1.45 g, 4.35 mmol) in water (5 mL). After 45 min, this was diluted to 25 mL with water and the pH was adjusted to 7.6 with solid potassium dihydrogen phosphate. This solution was then added to an ice-cooled, stirred, solution of the enol phosphate (2.00 g, 3.45 mmol) in THF (25 mL). After 30 min, the reaction mixture was transferred to a pressure bottle containing ether (40 mL) and 10% palladium on charcoal (2.0 g). This was hydrogenated (45 p.s.i.) for 1.25 h. The reaction mixture was then diluted with ether (25 mL) and filtered. The organic phase was separated and washed with water (2×5 mL). The combined aqueous phases were washed with ether (3×25 mL) and then concentrated under vacuum. Column chromatography (reverse phase, 45×130 mm, water as eluent), followed by lyophilization of the carbapenem-containing fractions, afforded 650 mg of crude material. This was re-chromatographed to give pure title product (450 mg, 39%): $^1$HNMR (D$_2$O) δ1.24 (3H, d, J=6.4 Hz), 3.19 (2H, q, J=2.6, 9.2 Hz), 3.45 (1H, q, J=2.8, 6.0 Hz), 3.91 (3H, s), 4.06 (3H, s), 4.08–4.36 (2H, m), 4.54 (2H, d, J=2.8 Hz), 8.71 (1H, s); IR (nujol mull) 1755 cm$^{-1}$; UV (phosphate buffer, pH 7.4) λ$_{max}$ 294 nm (ε=8,202); T$_{\frac{1}{2}}$ (phosphate buffer, pH 7.4, M=0.067, T=37° C.) 9.1 h.

EXAMPLE 20

(1'R,5R,6S) 3-[(1,3-dimethyl-5-tetrazolium)-methylthio]-6-(1-hydroxyethyl)-7-oxo-1-azabicyclo[3.2.0]hept-2-ene-2-carboxylate

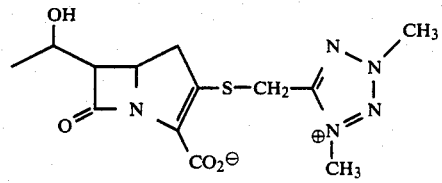

A. 5-carbethoxy-2-methyltetrazole and 5-carbethoxy-1-methyltetrazole

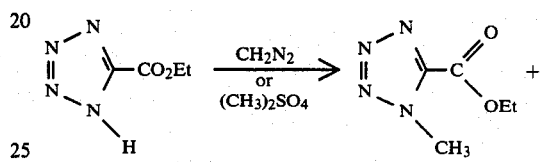

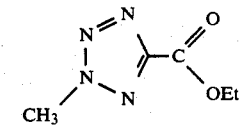

1a. Methylation with diazomethane

A solution of 5-carbethoxytetrazole[1] (9.17 g, 0.064 mmol) in ethyl ether[2] (80 mL) was cooled to 0° C. and treated

[1]D.Moderhack, Chem. Ber., 108, 887 (1975).
[2]The use of a mixture of ethanol and ether gave the same ratio of isomers. dropwise (15 min) with a solution of diazomethane (3 g, 0.071 mmol) in ether (200 mL). The light yellow solution was stirred for 30 min and the excess of diazomethane was destroyed by addition of acetic acid (1 mL). Evaporation of the solvent and distillation of the residue gave a clear oil: bp 95°–100° C./0.5 torr; 9.64 g, (96%). $^1$Hmr indicated a mixture of 1-methyl and 2-methyl isomers in a ratio 6:4. Separation of the two isomers could not be done by distillation nor hplc: ir (film) ν$_{max}$: 1740 cm$^{-1}$ (C=O of ester); $^1$Hmr (CDCl$_3$) δ: 1.53 (3H, two overlapping t, J=7.0, CH$_2$e,uns/CH/ $_3$), 4.46 and 4.53 (3H, 2S, CH$_3$ of 1-methyl and 2-methyl tetrazoles, ratio 6:4. The methyl of the 2-isomer is at lower field and is the minor product), 4.5 ppm (2H, two overlapping g, CH$_2$CH$_3$).

1b. 5-Carbethoxy-2-methyltetrazole

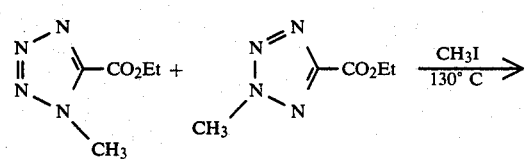

A mixture of 5-carbethoxy-2-methyltetrazole and 5-carbethoxy-1-methyltetrazole (0.252 g, 1.61 mmol, ratio of the two isomers 1:1) in iodomethane (0.5 mL) was selaed in a glass tube and heated at 100° C. for 15 h and at 130° C. for 6 h. Distillation of the reaction mixture gave the title compound as a light yellow oil: 0.139 g (55%); bp 95°–100° C/0.5 torr (air bath temperature): ir (film) $v_{max}$: 1740 cm$^{-1}$ (C=O of ester); $^1$Hmr (CDCl$_3$) δ: 1.46 (3H, t, J=7.0, CH$_3$ CH$_2$), 4.53 (3H, s, CH$_3$-2), 4.5 (2H, q, J=7.0, CH$_2$CH$_3$).

2. Methylation with dimethyl sulfate

A solution of 5-carbethoxytetrazole (1.42 g, 0.01 mol) in dry acetone (20 mL) was treated with anhydrous potassium carbonate (1.38 g, 0.01 mol) and dimethyl sulfate (1.26 g, 0.01 mol). The mixture was heated under reflux for 12 h. The carbonate was filtered and the solvent evaporated under reduced pressure. The residue was diluted with dichloromethane (30 mL), washed with saturated sodium bicarbonate (10 mL), brine (10 mL) and dried over anydrous sodium sulfate. Evaporation of the solvent and distillation under vacuum gave a clear oil: 1.45 g (93%); b.p. 85°–110° C./0.5 torr. $^1$Hmr indicated the presence of two isomers in a ratio 1:1.

B. 5-Hydroxymethyl-2-methyltetrazole

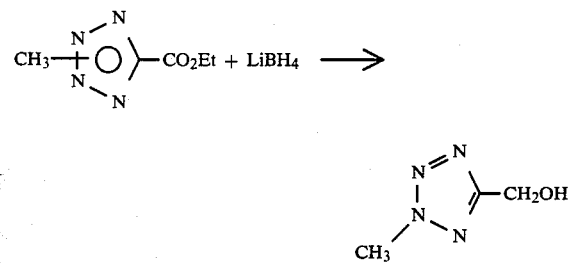

1. By reduction of the mixture of esters

A mixture of 5-carbethoxy-1-methyltetrazole and 5-carbethoxy-2-methyltetrazole (ratio 6:4) (7.60 g, 0.049 mol) in dry tetrahydrofuran (50 mL) was cooled to 0° C. and treated with lithium borohydride (1.06 g, 0.049 mmol) added in small portions over 15 min. The mixture was maintained at 10° C. for 30 addition min and then stirred at 20° C. for 4 h. The mixture was cooled to 0° C. and the excess hydride was carefully destroyed by addition of 6N HCl (pH of 7 after no more gas was evolved). The solvent was concentrated under vacuum and the residual oil diluted with dichloromethane (200 mL), washed with brine (10 mL) and finally dried over Na$_2$SO$_4$. Concentration of the solvent and distillation of the residue under vacuum gave 1.83 g (33%) of a clear oil. $^1$Hmr of this material indicated the product was 5-hydroxymethyl-2-methyltetrazole.

2. By reduction of 5-carbethoxy-2-methyltetrazole

To a solution of 5-carbethoxy-2-methyltetrazole (0.139 g, 0.89 mmol, obtained by isomerization of the mixture of esters with methyl iodide) in dry tetrahydrofuran (1 mL) at 10° C. was added solid lithium borohydride (0.019 g, 0.87 mmol). The mixture was slowly warmed up to room temperature and stirred for 4 h. The excess borohydride was destroyed by careful addition of 6N HCl at 0° C. (pH 7). The solvent was evaporated and the residue dissolved in dichloromethane (25 mL) and dried over anhydrous sodium sulfate. Evaporation of the solvent gave the title compound as a clear oil: 0.092 g (91%); bp 90°–120° C./0.5 torr with decomposition; ir (film) $v_{max}$: 3350 cm$^{-1}$ (broad, OH); $^1$Hmr (CDCl$_3$) δ: 4.4 (2H, s, CH$_3$−2), 4.93 (2H, s, CH$_2$−5).

C. 5-Acetylmercaptomethyl-2-methyltetrazole

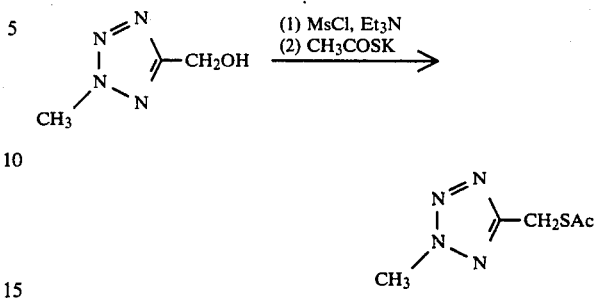

To a solution of 5-hydroxymethyl-2-methyltetrazole (1.83 g, 11.7 mmol) in dry dichloromethane (25 mL) at 0° C. was added methanesulfonyl chloride (1.47 g, 12.9 mmol) followed by triethylamine (1.30 g, 12.9 mmol) added dropwise over five min. The mixture was stirred at 0° C. for 1 h, and then treated with a solution of potassium thioacetate (1.60 g, 14.0 mmol) in dry N,N-dimethylformamide (10 mL). The resulting gel was stirred at 0° C. for 3 h. The reaction mixture was diluted with dichloromethane (200 mL), washed with brine (20 mL) and dried over anhydrous sodium sulfate. Evaporation of the solvent under vacuum and chromatography of the resulting oil over silica gel (2×15 cm, eluting with dichloromethane and dichloromethaneacetone 5%) gave the title compound as a clear oil: 1.31 g (65%); ir (film) $v_{max}$: 1696 cm$^{-1}$ (C=O of thioester); $^1$Hmr (CDCl$_3$) δ: 2.43 (3H, s, SAc), 4.36 (3H, s, 2-CH$_3$), 4.38 ppm (2H, s, 5-CH$_2$).

D. 5-Mercaptomethyl-1,3-dimethyltetrazolium trifluoromethanesulfonate

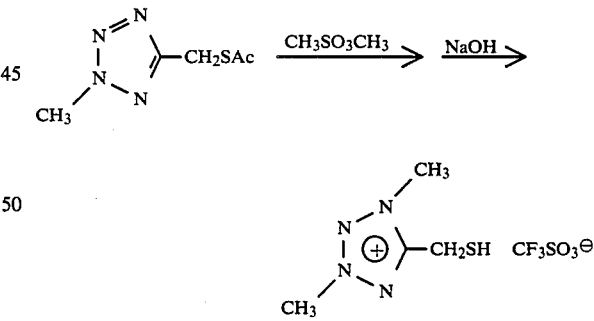

A solution of 5-acetylmercaptomethyl-2-methyltetrazole (0.400 g, 2.32 mmol) in dry dichloromethane (3 mL) was treated with methyltriflate (0.76 g, 4.64 mmol) and stirred at 22° C. for 16 h. Evaporation of the solvent under vacuum gave a red oil. This salt was dissolved in cold oxygen-free water (5 mL) and treated with 4M sodium hydroxide (0.8 mL, 3.2 mmol). The mixture was stirred at 0° C. for 40 min, diluted with water (7 mL), and the pH was adjusted to 7.3 with saturated KH$_2$PO$_4$. The clear resulting solution was maintained under nitrogen and used immediately for the following step.

E. (1'R,5R,6S) 3-[1,3-dimethyl-5-tetrazolium)-methylthio]-6-(1-hydroxyethyl)-7-oxo-1-azabicyclo(3.2.0)hept-2-ene-2-carboxylate

EXAMPLE 21

Alternate Procedure for Preparation of 3-(N-Methylpyridine-2-ylmethanethio)-6α-[1-(R)-hydroxyethyl]-7-oxo-1-azabicyclo[3.2.0]hept-2-ene-2-carboxylate

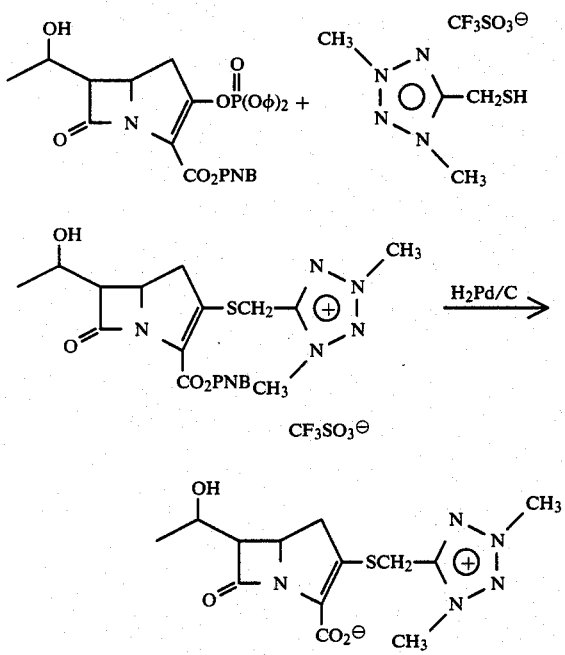

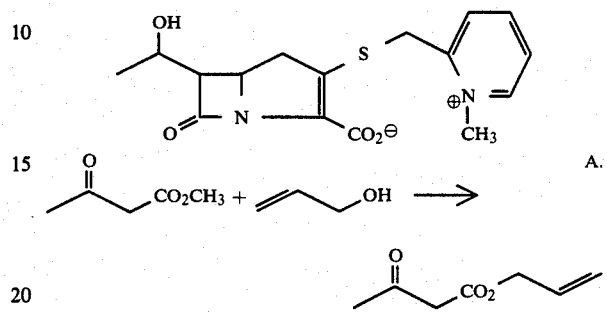

A solution of enol phosphate (0.915 g, 1.58 mmol) in tetrahydrofuran (8 mL) was cooled to 0° C. and treated dropwise with the solution of 5-mercaptomethyl-1,3-dimethyltetrazolium trifluoromethanesulfonate (2.32 mmol, prepared above) over a period of 20 min. The pH of the reaction mixture was stable at 6.5 throughout the addition. After 20 additional min. the pH of the solution was adjusted to 7.0 with saturated sodium bicarbonate. The mixture was transferred to a hydrogenation bottle, diluted with THF (10 mL), ether (20 mL) and ice (20 g). The carbapenem was hydrogenated over 10% palladium on activated carbon under 45 psi while slowly increasing the temperature to 22° C. for 90 min. The catalyst was filtered and washed with cold water (5 mL) and ether (20 mL). The aqueous phase was washed with ether (20 mL) and maintained under vacuum for 20 min to remove traces of organic solvent. Chromatography on PrePak 500-C/18 and elution with water gave the title compound as a white powder after lyophilization 0.266 g (49%); $[\alpha]_D^{23}+13°$ (c, 1.04, H$_2$O); UV (H$_2$O, pH 7.4) $\lambda_{max}$: 294 nm ($\epsilon$7,500); ir (KBr) $\nu_{max}$: 1755 (C=O of β-lactam), 1600 cm$^{-1}$ (broad, C=O of carboxylate); $^1$Hmr (D$_2$O) δ: 1.24 (3H, d, J=6.4 Hz, CH$_3$CHOH), 3.0-3.3 (2H, m, H-4), 3.42 (1H, dd, J=5.8, J=2.9, H-6), 4-4.2 (2H, m, H-5 and CH$_3$CHOH), 4.34 and 4.57 (2×3H, 2S, CH$_3$-1 and 3 of tetrazole), 4.49 and 4.51 (2H, 2s, CH$_2$S). The product has a half life of 10.5 h at 37° C. (c of 10$^{-4}$M in pH 7.4 phosphate buffer.

In a 2 l flask equipped with a magnetic stirrer, equipped for a Vigreaux column for distillation, a heating mantle and N$_2$, there was added 4.0 mole (432 ml) of methyl acetoacetate and 8.0 mole (464.6 g) of allyl alcohol. The reaction mixture was distilled for 12 hours at 92° C. There was added 136 ml (2.0 mole) of allyl alcohol and the mixture was distilled 23 hours. There was then added 136 ml (2.0 mole) of allyl alcohol and the mixture was distilled 16 hours. The reaction mixture was then distilled under vacuum and product was collected at 105°-110° C./35 mm Hg. There was obtained 414 g of allyl acetoacetate (73% yield).

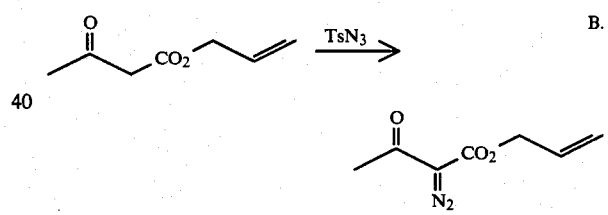

To a solution of allyl acetoacetate (226.5 g, 1.594 mole) in 3 l acetonitrile and triethylamine (243.4 ml, 1.753 mole), there was added p-toluenesulfonyl azide (345.3 ml, 1.753 mole) over a 1 hour period while keeping the temperature at ~20° C. with a cooling bath. The reaction mixture became yellow. The reaction mixture was then stirred at room temperature under a nitrogen atmosphere for 18 hours. The mixture was concentrated on a rotary evaporator. The residue was dissolved in diethyl ether (2.6 l) and 1M aqueous KOH (800 ml). The organic phase was washed five times with 1M KOH (500 ml) and once with brine (400 ml). After drying over MgSO$_4$ and concentration on a rotary evaporator (temp. ≦30° C.), there was obtained 260.2 g (97%) of the title product.

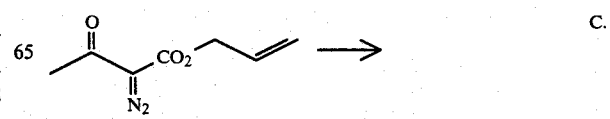

-continued

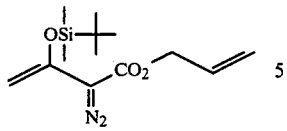

To a stirred suspension of allyl diazoacetoacetate (203 g, 1.195 mole) in 2 l methylene chloride and 199 ml (1.434 mole) triethylamine at 5° C., there was added 302 ml (1.315 mole) of t-butyldimethylsilyl triflate over a 45 minute period. The mixture was stirred 1 hour at 5° C. and then another 1 hour without cooling. The reaction mixture was washed 4 times with 500 ml H$_2$O and then once with 500 ml brine. It was then dried over Na$_2$SO$_4$ and concentrated to 344 g of orange oil. This oil was used directly in the next step.

D.

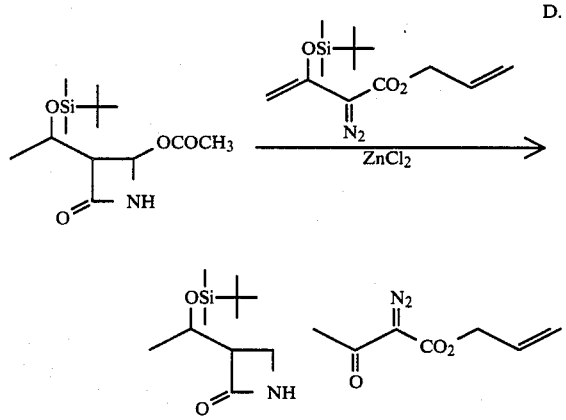

To a mixture of (1'R,3R,4R)-3-(1'-tert-butyldimethyl-silyloxyethyl)-4-acetoxy-azetidine-2-one (28.7 g, 0.1 mole) and freshly fused ZnCl$_2$ (6.8 g, 0.05 mole) in dry CH$_2$Cl$_2$ (700 ml), there was added dropwise a solution of allyl 2-diazo-3-tert-butyldimethylsilyloxy-3-butenoate (33.84 g, 0.12 mole) in CH$_2$Cl$_2$ (50 ml) over a 5 hour period. The mixture was stirred at room temperature for 2 hours at which time TLC (thin layer chromatography) showed a small amount of remaining starting material. An additional quantity of allyl 2-diazo-3-tert-butyl-dimethylsilyloxy-3-butenoate (4.23 g, 0.015 mole) in 10 ml of CH$_2$Cl$_2$ was added over a 1 hour period and stirring was continued at room temperature for 10 hours. The reaction was then diluted with ethyl acetate (750 ml), washed (2×300 ml saturated NaHCO$_3$, 300 ml brine), dried (MgSO$_4$) and evaporated to give 62.5 g of dark orange oil which was dissolved in methanol (500 ml) and treated with 1N aqueous HCl (110 ml). The resulting mixture was stirred at room temperature for 2 hours after which time there was added 10 ml 1N HCl followed by an additional 2 hours of stirring. The reaction mixture was concentrated to ½ volume and poured into a mixture of ethyl acetate (800 ml) and water (800 ml). The organic phase was separated, washed with water (800 ml) and the combined aqueous extracts washed with ethyl acetate (400 ml). The combined organic extracts were washed with brine (2×400 ml), dried (MgSO$_4$) and concentrated to 32 g of dark orange red oil. Flash chromatography afforded 9.33 g (33% yield) of tile product as a gold-yellow oil which solidified to a light yellow solid. $^1$H-nmr (CDCl$_3$) δ: 6.20–5.72 (m, 2H), 5.48–5.21 (m, 2H), 4.74 (dt, J=5.8, J'=1.2 Hz, 2H), 4.30–3.88 (m, 2H), 3.30–3.20 (m, 2H), 2.89 (dd, J=7.3, J'=2.1, 1H), 2.18 (s, 1H), 1.32 (d, J=6.2, 3H).

E.

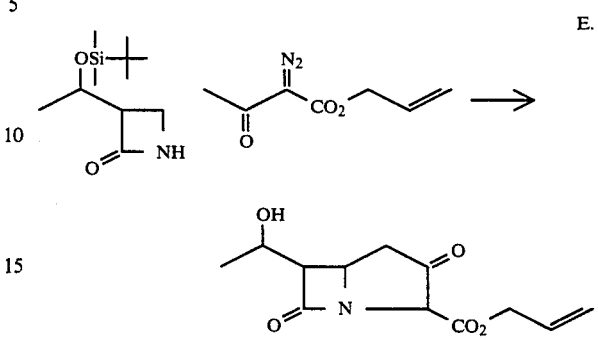

A mixture of α-diazo ester prepared in Step D above (9.2 g, 32.7 mmole) and rhodium acetate [Rh$_2$(OAc)$_4$] in benzene (1 l) was refluxed for 1 hour. The solution was treated with activated charcoal and filtered through a Celite pad. The pad was washed with 100 ml of hot benzene. Concentration of the filtrate afforded 8.08 g (97% yield) of title product as a light brown crystalline solid. H-nmr (CDCl$_3$) δ: 6.15–5.68 (m, 1H), 5.45–5.18 (m, 2H), 4.71–4.60 (m, 2H), 4.40–4.05 (m, 2H), 3.17 (dd, J=7.1, J'=2.0 1H), 2.95 (dd, J=6.9, J'=18.9, 1H), 2.42 (dd, J=7.6, J'−18.8, 1H), 1.88 (s, 1H), 1.39 (d, J=6.3, 3H).

F.

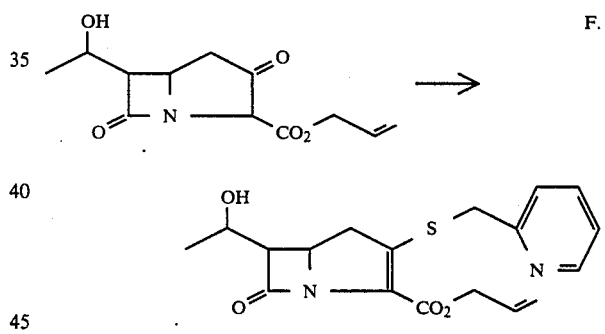

To a solution of keto ester prepared in Step E (7.5 g, 0.03 mole) there was added at 0° C. under a N$_2$ atmosphere diisopropylamine (6.08 ml, 0.035 mole) followed by diphenylphosphoryl chloride. After 15 minutes, TLC showed no remaining starting material. To the reaction mixture there was added diisopropylamine (6.26 ml, 0.036 mole) and a solution of freshly distilled 2-mercaptomethylpyridine (4.5 g, 0.036 mole) in 5 ml acetonitrile. After stirring at 0° C. for 2 hours, the mixture was poured into ethyl acetate (1 l), washed with water (2×150 ml), saturated NaHCO$_3$ (150 ml), H$_2$O (150 ml) and brine (200 ml). The organic phase was dried (MgSO$_4$) and concentrated to a dark orange-yellow gum. Flash chromatography afforded the product as a golden yellow oil. The product was dissolved in diethyl ether and cooled to 0° C. Filtration afforded 4.8 g (44% yield) of the purified title product as cream-colored crystals. $^1$H-nmr (CDCl$_3$) δ: 8.6–8.4 (m, 1H), 7.85–7.15 (m, 3H), 6.20–5.74 (m, 1H), 5.54–5.15 (m, 2H), 4.80–4.66 (m, 2H), 4.29–4.03 (m, 1H), 4.19 (s, 2H), 3.69–2.85 (m, 1H), 2.97 (s, 1H), 1.32 (d, J=6.2, 3H).

G.

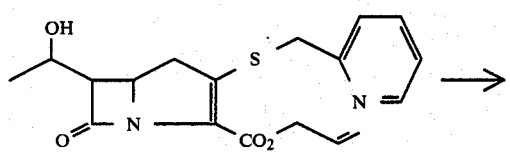

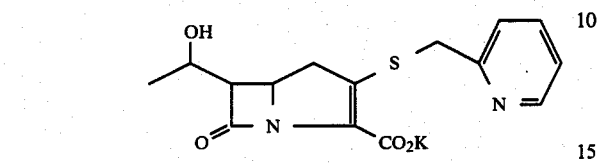

To a solution of the allyl ester prepared in Step F (1.79 g, 4.97 mmole), tetrakistriphenylphosphine palladium (175 mg, 0.15 mmole) and triphenylphosphine (175 mg, 0.67 mmole) in $CH_2Cl_2$ (25 ml), there was added a solution of potassium 2-ethylhexanoate (1.085 g, 5.96 mmole) in ethyl acetate (12 ml). After stirring at room temperature for 1 hour, TLC showed only a trace of starting material. The reaction mixture was diluted with anhydrous diethyl ether (150 ml) and the precipitate was collected by filtration, washed with ethyl acetate and then ether to give a light-brown solid. This solid was dissolved in $H_2O$ (10 ml) and purified by reversed phase chromatography to give 1.85 g of title product as a cream-colored solid. This material was further purified by slurrying in acetone to afford 1.47 g (83%) of pure title product. $^1$H-nmr ($D_2O$): 8.45–8.36 (m, 1H), 7.92–7.22 (m, 3H), 4.78–3.91 (m, 2H), 4.69 (s, 2H), 3.34–2.71 (m, 3H), 1.19 (d, J=6.4, 3H).

H.

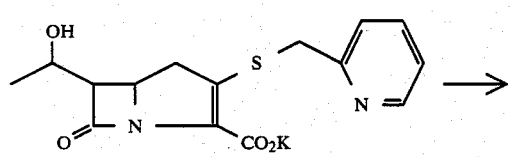

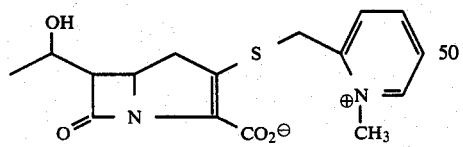

Toluenesulfonic acid (27.6 mg, 0.16 mmole) was added to a cooled (0° C.) suspension of potassium 6-hydroxyethyl-2-(2-pyridylmethylthio)-carbapenem-3-carboxylate (53.8 mg, 0.15 mmole) in acetone (2 ml). The mixture was stirred at 0° C. for 20 minutes and then treated with methyl triflate (0.02 ml). After stirring at 0° C. for 60 minutes, LA-1 resin was added followed by hexane (6 ml). The mixture was extracted with water (4×0.5 ml) and the combined aqueous phases purified by reversed phase HPLC to give 10 mg of the title product.

EXAMPLE 22

Preparation of 3-(N-Methylpyridine-2-yl-methanethio)-6α-[1-(R)-hydroxyethyl]-7-oxo-1-azabicyclo[3.2.0]-hept-2-ene-2-carboxylate Via "One Pot" Process

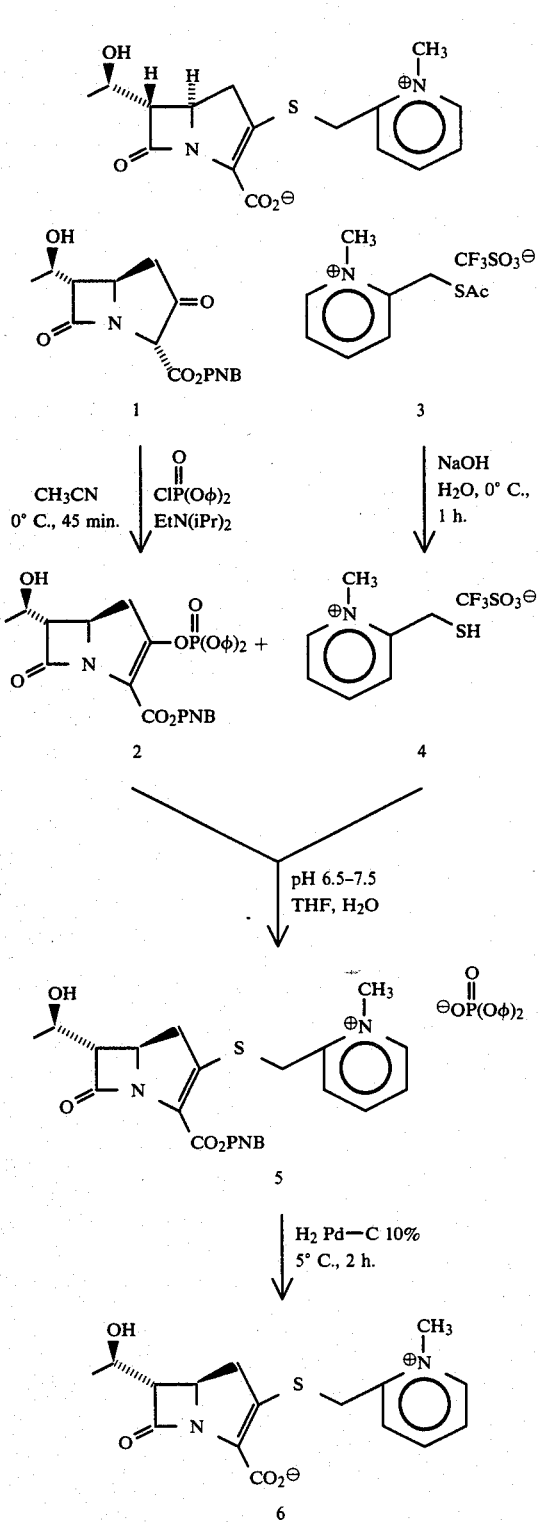

A. Preparation of enol phosphate (2)

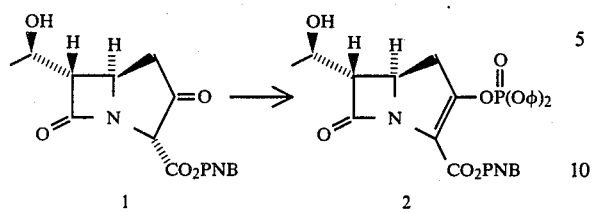

An ice-cooled solution of ketone 1 (3 g, 8.62 mmoles) in acetonitrile (30 ml) was treated with ethyl diisopropylamine (9 mmoles, 1.04 eq, 1.57 ml) (addition time ca. 2 minutes) and chlorodiphenyl phosphate (9 mmoles, 1.04 eq, 1.87 ml) (addition time ca. 2 minutes). The reaction was stirred for 45 minutes and TLC (ethyl acetate, silica gel) showed disappearance of ketone 1. The solution was diluted with ethyl acetate (60 ml), washed with cold water (2×50 ml) and brine, dried over sodium sulfate and concentrated (bath temperature below 20° C.) to give a foam which was used as such.

B. Preparation of thiol (4)

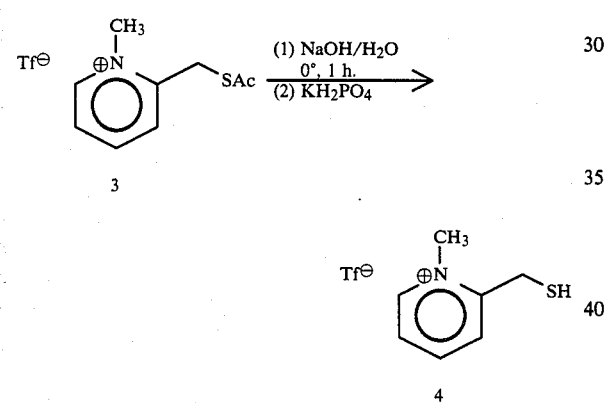

An ice-cooled solution of thioacetate 3 (3.31 g, 10 mmoles) in water purged with nitrogen for 5 minutes was treated dropwise (ca. 5 minutes) with a cooled solution of sodium hydroxide (1.75 eq, 17.5 mmoles, 0.7 g) in water (8 ml). The mixture became yellow. After 75 minutes under nitrogen the pH was adjusted to 7.4 with saturated aqueous solution of KH$_2$PO$_4$. The reaction mixture was diluted with water (15 ml). This aqueous solution of thiol 4 (50 ml, 0.2 mmoles/ml) was used as such.

C. Coupling

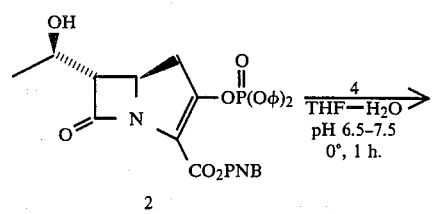

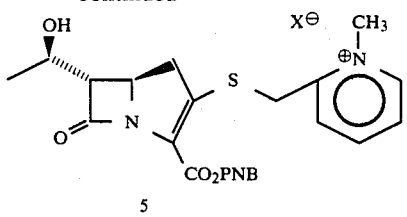

An ice-cooled solution of 2 (crude, prepared in A, 8.62 mmoles) in tetrahydrofuran (50 ml) was treated dropwise with the aqueous solution of thiol 4 prepared in B (5 ml of solution every 5 minutes). During the course of the reaction the pH of the reaction mixture was maintained around 6.5–7.5 (preferably 7) by adding cooled 2N sodium hydroxide solution. The reaction was followed by TLC (a) silicagel, ethyl acetate; (b) reversed phase Analtech RPSF, CH$_3$CN— pH 7 buffer (4:6).

At the end 1.15 eq of thiol was used (50 ml of solution). The reaction was complete after 1 hour at 0° C. and the mixture was used as such for the hydrogenation after the pH was adjusted to 7.

D. Hydrogenation

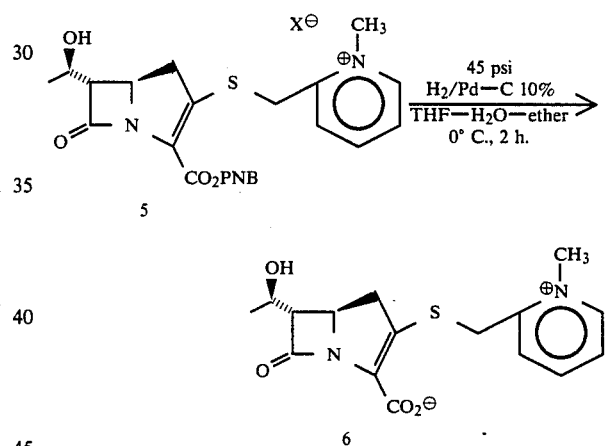

The reaction mixture containing 5 (prepared in C) was transferred into a Parr flask with THF (10 ml), phosphate buffer (pH 7. 0.1M) (10 ml), ether (75 ml) and Pd-C 10% (5 g) and hydrogenated at 45 psi at 3°–10° C. for 2 hours. Then the catalyst was filtered, washed with water (3×10 ml) and the pH adjusted to 6.2 carefully with cold 2N NaOH. Ether was added and the aqueous phase was separated and washed again with ether. The aqueous phase was purged of organic solvent under vacuum and then purified on Bondapak C-18 column (100 g, 4.5×13 cm) with cold distilled water. The light yellow fractions containing the product (checked by U.V. and TLC) were lyophilized to give 1.46 g (50%)* of 6 as a yellow powder. λ293, ε=9000, λ271, ε=11064.
*yield calculated from bicyclic ketone

EXAMPLE 23

Preparation of (5R,6S)-3-{[(1,3-dimethylpyridinium-4-yl)methyl]thio}-6-[1-(R)-hydroxyethyl]-7-oxo-1-azabicyclo[3.2.0]hept-2-ene-2-carboxylate (23A)

and (4R,5R,6S)-3-{[(1,3-dimethylpyridinium-4-yl)methyl]-thio}-6-[1-(R)-hydroxyethyl]-4-methyl-7-oxo-1-azabicyclo[3.2.0]hept-2-ene-2-carboxylate (23B)

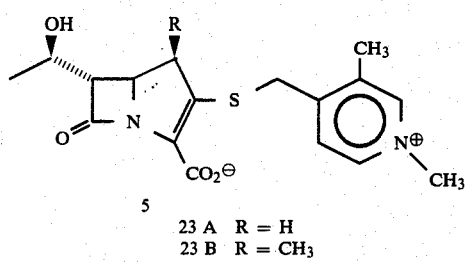

23 A  R = H
23 B  R = CH₃

A. Preparation of 4-Hydroxymethyl-3-methylpyridine

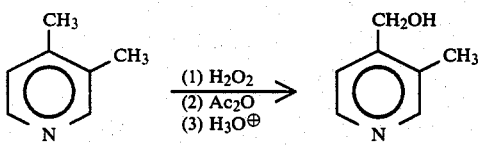

The general procedure of Boekelheide[1] for the preparation of hydroxymethylpyridines was used. Thus, a solution of freshly distilled 3,4-lutidine (46.0 g, 0.43 mol) in 120 mL of glacial acetic acid was cooled at 0° C. and then 64 mL of 30% $H_2O_2$ was added dropwise. The resulting solution was heated at 75° C. (oil-bath temperature) for 3 h. Another 20 mL of 30% $H_2O_2$ was then added and heating was continued for 18 h. Finally, 20 mL of 30% $H_2O_2$ was again added and the reaction was kept at 75° C. for another 3 h. The solution was then concentrated to about 100 mL under water-aspirator pressure, 50 mL of $H_2O$ was added and the mixture was concentrated to about one half volume. The resulting mixture was cooled (0°-5° C.) and basified to about pH 10 using cold 40% aqeuous NaOH. The mixture was then extracted with $CH_2Cl_2$ (5×) and the extract was dried ($Na_2CO_3 + Na_2SO_4$) and concentrated on the roto-vap to give a yellow solution. Dilution of this solution with hexane afforded a solid which was collected by filtration and then dried in vacuo to give 3,4-lutidine-N-oxide (48.0 g, 83%) as an off-white solid.

The N-oxide was added portionwise to 60 mL of acetic anhydride and the resulting dark orange solution was heated (water-bath) at about 90° C. for 1 h. The excess acetic anhydride was then distilled off under reduced pressure and the material boiling at 90°-120° C./0.1 torr (39.0 g) was collected. Chromatography of this oil (silica gel/ethyl acetate-pet.ether=2:3) afforded pure 4-acetoxymethyl-3-methylpyridine (19.0 g, 30%) as an oil: ir (neat) 1745 cm⁻¹.

The acetate was then taken up in 100 mL of 10% aqueous HCl and refluxed for 1 h. The resulting solution was cooled at 0° C., basified with solid $K_2CO_3$ and then extracted with $CH_2Cl_2$ (3×100 mL). The organic extract was washed (brine), dried ($Na_2SO_4$) and evaporated to give 11.0 g of an off-white solid, m.p. 70°-72° C. This solid was triturated with cold ether to give pure 4-hydroxymethyl-3-methylpyridine (9.5 g, 67%) as a white solid, m.p. 77°-80° C. (lit.[2] m.p. 81°-82° C.): ¹Hnmr (CDCl₃) δ 8.27, 7.41 (ABq, J=5 Hz, 2H), 8.18 (s, 1H), 5.63 (br s, —OH), 4.67 (s, CH₂), 2.20 (s, CH₃); ir (nujol) 3170 cm⁻¹.

1. V. Boekelheide, W. J. Linn, *JACS*, 76, 1286 (1954).

2. W. L. F. Armarego, B. A. Milloy, S. C. Milloy, S. C. Sharma, *JCS*, 2485 (1972).

B. Preparation of 4-(Acetylthiomethyl)-3-methylpyridine

To an ice-cold, mechanically stirred solution of triphenylphosphine (17.04 g, 0.065 mol) in 250 mL of dry THF was added dropwise diisopropyl azodicarboxylate (12.8 mL, 0.065 mol) and the resulting slurry was stirred at 0° C. for 1 h. To this mixture was added dropwise a solution of 4-hydroxymethyl-3-methylpyridine (4.0 g, 0.0325 mol) in 100 mL of dry THF, followed by freshly distilled thiolacetic acid (4.64 mL, 0.065 mol). The resulting mixture was stirred at 0° C. for 1 h and then at room temperature for 1 h to give an orange solution. The solution was concentrated (rotary evaporator) and then diluted with petroleum ether. The resulting mixture was filtered and the filtrate was evaporated to give an orange oil. Chromatography (silica gel/hexane then 10%→50% ethyl acetate-hexane) of this oil gave 7.0 g of a oil which was distilled (Kugelrohr) to give the pure product (6.0 g, 100%) as a yellow oil, b.p. (air-bath temperature) 95°-100° C./0.1 torr: ¹Hnmr (CDCl₃) δ8.40, 7.20 (ABq, J=5Hz, 2H), 8.37 (s, 1H), 4.08 (s, CH₂), 2.35 (s, CH₃), 2.32 (s, CH₃); ir (neat) 1695 cm⁻¹.

C. Preparation of 4-(Acetylthiomethyl)-1,3-dimethylpyridinium triflate

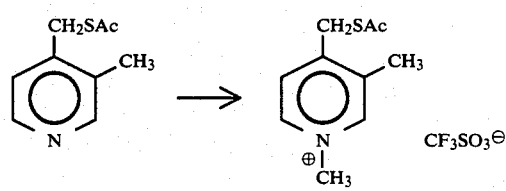

To an ice-cold solution of the thioacetate (2.95 g, 0.016 mol) in 10 mL of methylene chloride was added dropwise methyl trifluoromethanesulfonate (4.60 mL, 0.04 mol) and the mixture was stirred at 0° C. under $N_2$ for 1 h. The reaction mixture was then evaporated to dryness and the residue was triturated with ether. The resulting solid was collected by filtration and dried in vacuo to give the product (4.0 g, 72%) as a white solid: ¹Hnmr (CDCl₃) δ8.72 (s, 1H), 8.58, 7.87 (ABq, J=6Hz, 2H), 4.39 (s, N—CH₃), 4.17 (s, CH₂), 2.53 (s, CH₃), 2.36 (s, CH₃); ir (neat) 1700 cm⁻¹.

D. Preparation of (5R,6S)-3-{[(1,3-dimethylpyridinium-4-yl)methyl]thio}-6[1-(R)-hydroxyethyl]-7-oxo-1-azabicyclo[3.2.0.]hept-2-ene-2-carboxylate

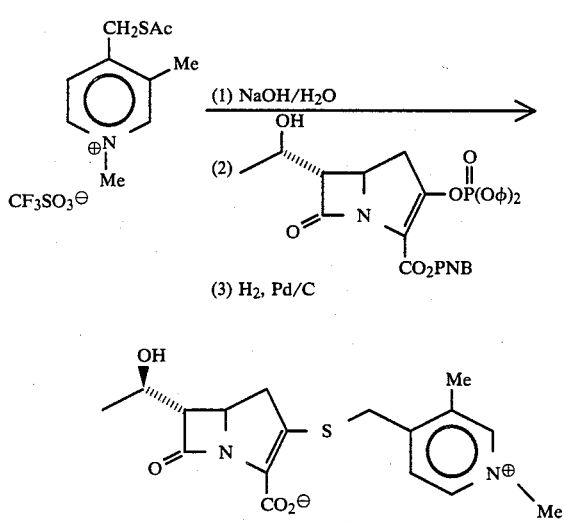

To an ice-cold, N₂-purged solution of NaOH (0.324 g, 0.008 mol) in 10 mL of H₂O was added the thioacetate (1.40 g, 0.004 mol) and the mixture was stirred at 0° C. under N₂ for 1 h. After the pH was adjusted to 7.2–7.3 using 10% aqueous potassium dihydrogen phosphate the resulting solution was added dropwise to an ice-cold solution of the enol phosphate (1.45 g, 0.0025 mol) in 20 mL of THF. The mixture was stirred at 0° for 1 h and was then transferred to a pressure bottle. To this mixture was added 20 mL of ether, 25 mL of 0.1M phosphate buffer (pH 7.4) and 1.4 g of 10% palladium-on-charcoal. The mixtures was then hydrogenated at 45 psi for 1 h. The reaction mixture was filtered through a pad of Celite and the pad was washed with additional ether and pH 7.4 phosphate buffer. The aqueous phase was separated and residual solvents were removed in vacuo. The resulting aqueous solution was applied to a reverse-phase column (C₁₈ BondaPak) which was eluted with H₂0 and then 10% acetonitrile-H₂O. Lyophilization of the relevant fractions gave 0.9 g of an orange solid. This material was rechromatographed using H₂O and then 2% acetonitrile-H₂O as eluant. Lyophilization afforded pure 23A (0.25 g, 57%) as a yellow solid: ¹Hnmr (D₂O) δ8.55 (s, 1H), 8.53, 7.96 (ABq, J=6.8 Hz, 2H), 4.30–3.99 (m, 2H), 4.27 (s, 5H), 3.35 (dd, J₁=2.8 Hz, J₂=6.0 Hz, 1H), 3.05 (d, J=8.8 Hz, 2H), 2.50 (s, 3H), 1.23 (d, J=6.3 Hz, 3H); ir (KBr) 1755, 1590 cm⁻¹; uv (phosphate buffer, pH 7) 295 nm (ε7180).

E. Preparation of (4R,5R,6S)-3{[(1,3-dimethylpyridinium-4-yl)methyl]-thio}-6-[1-(R)-hydroxyethyl]-4-methyl-7-oxo-1-azabicyclo[3.2.0]hept-2-ene-2-carboxylate

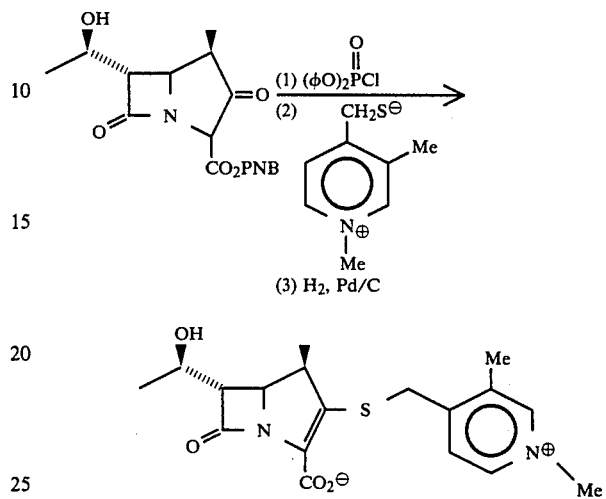

An ice-cold solution of the bicyclic ketone (0.906 g, 0.0025 mol) in 10 mL of acetonitrile was treated successively with diphenyl chlorophosphate (0.544 mL, 0.00263 mol), diisopropylethylamine (0.457 mL, 0.00263 mol) and 4-dimethylaminopyridine (0.3 mg). After 50 min the reaction mixture was diluted with cold ethyl acetate and then washed with cold water and brine. The organic phase was dried (Na₂SO₄) and evaporated at room temperature to give the enol phosphate as an off-white foam. This foam was take up in 20 mL of THF, cooled at −30° C. under N₂ and then treated with an aqueous solution of the thiolate [prepared as done previously from 0.3 g of NaOH (7.5 mmol) and 1.3 g of the thioacetate (3.76 mmol) in 10 mL of H₂O]. The reaction mixture was stirred at −30° C. for 30 min, then at 0° C. for 75 min and finally it was transferred to a pressure bottle containing 20 mL of ether, 30 mL of 0.1M phosphate buffer (pH 7.4) and 1.5 g of 10% palladium-on-charcoal. After hydrogenating at 45 psi for 1 h the mixture was filtered through Celite and the aqueous phase was separated and concentrated in vacuo. The resulting solution was applied to a reverse phase (C₁₈ BondaPak) column which was eluted with H₂O. Lyophilization of the relevant fractions gave 1.2 g of a yellow solid. This material was rechromatographed (eluting with H₂O to 4% acetonitrile-H₂O) to give, after lyophilization, pure 23B (0.250 g, 28%) as a yellow solid: ¹Hnmr (D₂O) δ8.53 (s, 1H), 8.49, 7.81 (ABq, J=6.2 Hz, 2H), 4.38–3.98 (m, 4H), 4.27 (s, 3H), 3.49–3.18 (m, 2H), 2.51 (s, 3H), 1.25 (d, J=6.7 Hz, 3H), 1.16 (d, J=7.6 Hz, 3H); ir (KBr) 1750, 1595 cm⁻¹; uv (phosphate buffer, pH 7) 292 nm (ε7930).

EXAMPLE 24

Preparation of (5R,6S)-3-{[(1,2-dimethylpyridinium-4-yl)methyl]thio}-6-[1-(R)-hydroxyethyl]-7-oxo-1-azabicyclo[3.2.0]hept-2-ene-2-carboxylate (24A)

and (4R,5R,6S)-3-{[(1,2-dimethylpyridinium-4-yl)methyl]-thio}-6-[1-(R)-hydroxyethyl]-4-methyl-7-oxo-1-azabicyclo[3.2.0]hept-2-ene-2-carboxylate (24B)

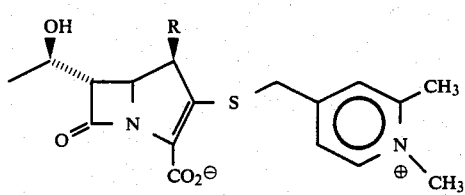

24A R = H
24B R = CH₃

A. Preparation of 4-Hydroxymethyl-2-methylpyridine

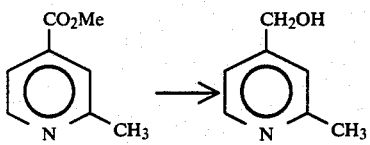

To a suspension of 95% lithium aluminum hydride (2.4 g, 0.06 mol) in 150 mL of anhydrous ether was added a solution of methyl 2-methylisonicotinate[1] (14.0 g, 0.093 mol) in 50 mL of anhydrous ether, at −5° C. under N₂. The resulting mixture was stirred at room temperature for 30 min and was then refluxed for 2 h. An additional 1.2 g (0.03 mole) of lithium aluminum hydride was added portionwise and refluxing was continued for 1 h. The reaction mixture was then cooled at 0° C. and treated successively with 3.75 mL H₂O, 3.75 mL 15% aqueous NaOH and finally 11.25 mL of H₂O. This suspension was then filtered and the filter cake was washed with ether and then ethyl acetate. The filtrate was evaporated to give a dark yellow oil which was taken up in acetonitrile and then filtered through a pad of silica gel (elution with acetonitrile and then acetone). This gave the product (7.7 g, 67%) as a yellow oil: ¹Hnmr (CDCl₃) δ8.30, 7.10 (ABq, J=5 Hz, 2H), 7.17 (s, 1H), 5.42 (s, —OH), 4.70 (s, CH₂), 2.50 (s, CH₃).
[1] O. Efimovsky, P. Rumpf, Bull. Soc. chim. Fr., 648 (1954).

B. Preparation of 4-(Acetylthiomethyl)-2-methylpyridine

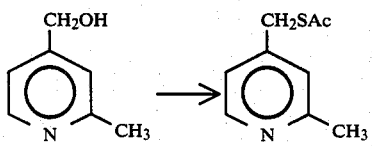

To a solution of triphenylphosphine (31.4 g, 0.12 mol) in 200 mL of dry THF, at −5° C. under N₂, was added dropwise diisopropyl azodicarboxylate (23.6 mL, 0.12 mol) and the mixture was stirred at −5° C. for 1 h. To the resulting slurry was added a solution of 4-hydroxymethyl-2-methylpyridine (7.60 g, 0.062 mol) and freshly distilled thiolacetic acid (8.60 mL, 0.12 mol) in 40 mL of dry THF over about 10 min. The reaction was stirred at 0° C. for 30 min and then at room temperature for 1 h. The resulting suspension was filtered and the filtrate was concentrated to give an orange-yellow liquid which was diluted with ether and filtered. The filtrate was evaporated and the residual oil was chromatographed (silica gel/ethyl acetate-hexane=1:1) to give the thioacetate (8.87 g, 79%) as a yellow oil: ¹Hnmr (CDCl₃) δ8.45, 7.03 (ABq, J=5 Hz, 2H), 7.08 (s, 1H), 4.04 (s, CH₂), 2.55 (s, CH₃), 2.39 (s, CH₃); ir (neat) 1695 cm⁻¹.

C. Preparation of 4-Mercaptomethyl-2-methylpyridine

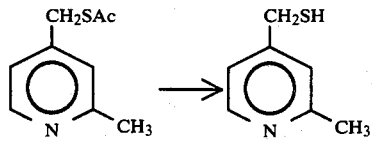

To 15 mL of ice-cold, N₂-purged 1N NaOH was added all at once 4-(acetylthiomethyl)-2-methylpyridine (1.358 g, 0.0075 mol). After stirring for 15 min at 0° C. the reaction mixture was washed with ether (2×5 mL), neutralized with concentrated HCl and extracted with methylene chloride (3×10 mL). Evaporation of the methylene chloride solution afforded the thiol (0.89 g, 96%) as a pale yellow oil which gradually became pink on standing: ¹Hnmr (CDCl₃) δ8.43, 7.37 (ABq, J=5 Hz, 2H), 7.43 (s, 1H), 3.63 (d, J=7.5 Hz, CH₂), 2.55 (s, CH₃), 1.81 (t, J=7.5 Hz, SH).

D. Preparation of Allyl (5R,6S)-3-{[(2-methylpyridin-4-yl)methyl]thio}-6-[1-(R)-hydroxyethyl]-7-oxo-1-azabicyclo[3.2.0]hept-2-ene-2-carboxylate

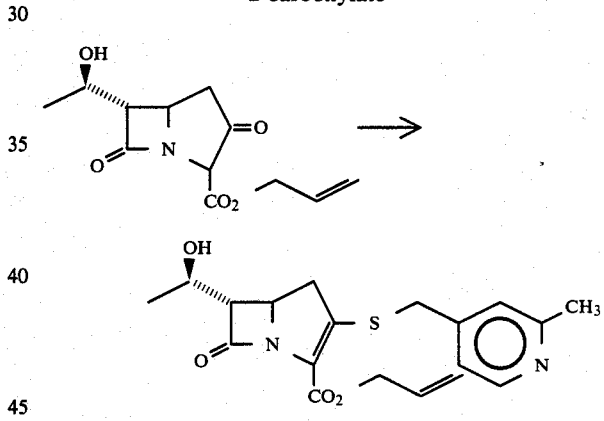

To an ice-cold solution of the bicyclic ketone (0.760 g, 0.003 mol) in 8 mL of acetonitrile was added successively diphenyl chlorophosphate (0.653 mL, 0.00315 mol), diisopropylethylamine (0.550 mL, 0.00315 mol), and dimethylaminopyridine (0.8 mg). After stirring the mixture at 0° C. for 1 h it was cooled at −20° C. and 4-mercaptomethyl-2-methylpyridine (0.620 g, 0.00446 mol), followed by diisopropylethylamine (0.550 mL, 0.00315 mol), was added. The reaction was stirred at −20° C. for 1.5 h and then allowed to warm to room temperature. The resulting mixture was diluted with 50 mL of ethyl acetate, washed (H₂O, sat. NaHCO₃, sat. NH₄Cl), dried (Na₂SO₄) and evaporated. The residual material was chromatographed on silica gel (eluted with ethyl acetate then acetonitrile) to give a solid which was triturated with ether to give the pure product (0.820 g, 73%) as a white solid: ¹Hnmr (CDCl₃) δ8.45, 7.09 (ABq, J ↑ 5 Hz, 2H), 7.15 (s, 1H), 6.25–5.80 (m, 1H), 5.60–5.20 (m, 2H), 4.82–4.68 (m, 2H), 4.55–4.05 (m, 2H), 3.97 (s, 2H), 3.16–2.93 (m, 3H), 2.55 (s, 3H), 1.84 (br s, 1H), 1.32 (d, J=6 Hz, 3H); ir (neat) 1777, 1695 cm⁻¹.

E. Preparation of (5R,6S)-3-{[(1,2-dimethylpyridinium-4-yl)methyl]thio}-6-[1-(R)-hydroxyethyl]-7-oxo-1-azabicyclo[3.2.0]hept-2-ene-2-carboxylate

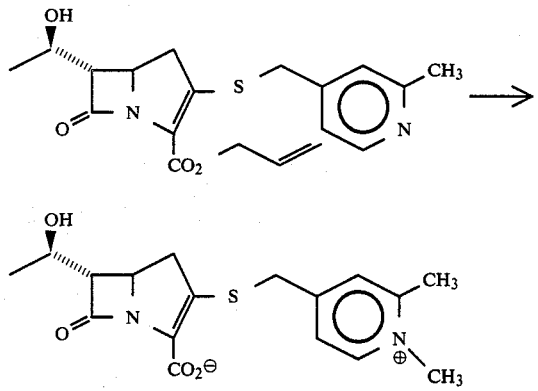

A solution of the allyl ester (0.350 g, 0.936 mmol) in 6mL of dry acetonitrile was cooled at −5° C. and treated with methyl trifluoromethanesulfonate (0.111 mL, 0.983 mmol). After 15 min a solution of tetrakis(triphenylphosphine)palladium (0.027 g, 2.5 mol%) and triphenylphosphine (0.027 g) was added. After stirring the reaction mixture for 5 min pyrrolidine (0.082 mL, 0.983 mmol) was added dropwise. A solid slowly began to separate from the resulting brown solution. The mixture was vigorously stirred at 0° C. for 20 min, then 15 mL of cold (0° C.) acetone was slowly added and stirring was continued at 0° C. for 20 min. The resulting suspension was filtered and the residue was washed with cold acetone and then dried in vacuo to give 0.345 g of a beige powder. This material was taken up in a small amount of pH 7 phosphate buffer (0.05M) and applied to a short reverse-phase (C$_{18}$ BondaPak) column. Elution with H$_2$O and lyophilization of the relevant fractions gave 0.255 g of a light yellow solid. This material was rechromatographed, as done before, to afford (after lyophilization) pure 24A (0.195 g, 60%) as a light yellow solid: $^1$Hnmr (D$_2$O) δ8.58, 7.83 (ABq, J=6.4 Hz, 2H), 7.87 (s, 1H), 4.32–3.95 (m, 2H), 4.22 (s, 2H), 4.17 (s, 3H), 3.32 (dd, J$_1$=2.6 Hz, J$_2$=6.1 Hz, 1H), 3.06–2.93 (m, 2H), 2.74 (s, 3H), 1.22 (d, J=6.4 Hz, 3H); ir (KBr) 1757, 1590 cm$^{-1}$; uv (phosphate buffer, pH 7.4) 296 nm (ε7446).

F. Preparation of Allyl (4R,5R,6S)-3-{[(2-methylpyridine-4-yl)methyl]thio}-6-[1-(R)-hydroxyethyl]-4-methyl-7-oxo-1-azabicyclo[3.2.0]hept-2-ene-2-carboxylate

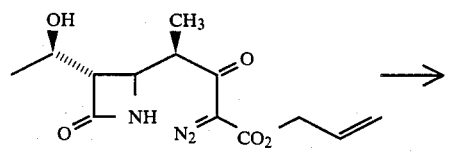

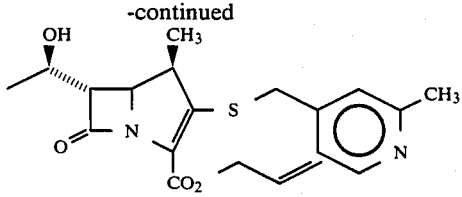

A solution of the α-diazo ester (1.50 g, 0.00508 mol) in 12 mL of ethyl acetate-hexane (3:1) was heated to a gentle reflux under N$_2$ and then 0.020 g of rhodium octanoate was added all at once. Rapid N$_2$ evolution was observed for about 5 min and after refluxing for another 10 min the reaction was complete (tlc). The solvents were subsequently removed under reduced pressure and the residual gum was taken up in 15 mL of acetonitrile. The solution was cooled at −5° C. and treated with diphenyl chlorophosphate (1.10 mL, 0.00533 mol), diisopropylethylamine (0.927 mL, 0.00533 mol) and 4-dimethylaminopyridine (0.6 mg, 0.1 mol %). The reaction mixture was stirred at 0° C. for 1 h and was then cooled to −20° C. and treated with a solution of 4-mercaptomethyl-2-methylpyridine (0.656 g, 0.00533 mol) in 1 mL of acetonitrile, followed by 0.927 mL (0.00533 mol) of diisopropylethylamine. The resulting mixture was stirred at −10° C. for 1.5 h and was then treated with additional thiol (0.066 g, 0.53 mmol) and diisopropylethylamine (0.093 mL, 0.53 mmol). The reaction was allowed to warm to about 10° C. over 1 h and was then diluted with 75 mL of cold ethyl acetate, washed (H$_2$O, brine), dried (Na$_2$SO$_4$) and evaporated (bath temperature <30° C.). The resulting gum was chromatographed on silica gel. Elution with ethyl acetate removed impurities and subsequent elution with acetonitrile afforded the product (1.04 g, 53%) which was obtained as a pale yellow foam: $^1$Hnmr (CDCl$_3$) δ8.43; 7.07 (ABq, J=5 Hz, 2H), 7.10 (s, 1H), 6.20–5.75 (m, 1H), 5.51–5.29 (m, 2H), 4.81–4.69 (m, 2H), 4.29–4.03 (m, 2H), 3.96 (s, 2H), 3.35–3.05 (m, 2H), 2.53 (s, 3H), 2.16 (br s, 1H), 1.33 (d, J=6.3 Hz, 3H), 1.22 (d, J=7.3 Hz, 3H); ir (neat) 1770, 1705 cm$^{-1}$.

G. Preparation of (4R,5R,6S)-3-{[(1,2-dimethylpyridinium-4-yl)methyl]thio}-6-[1-(R)-hydroxyethyl]-4-methyl-7-oxo-1-azabicyclo[3.2.0]hept-2-ene-2-carboxylate

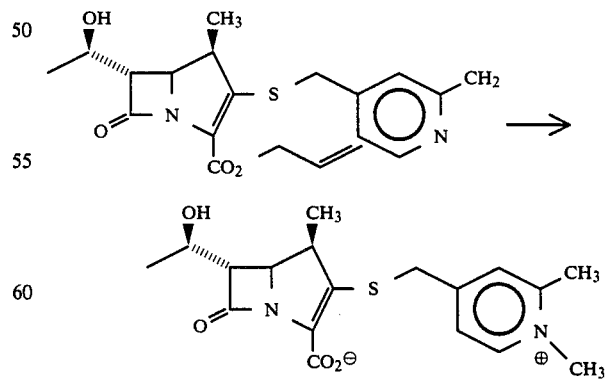

A solution of the allyl ester (0.582 g, 0.0015 mol) in 15 mL of dry acetonitrile was treated with methyl trifluoromethanesulfonate (0.178 mL, 1.575 mmol) at −5° under N$_2$. After 15 min a solution of tetrakis(triphenylphosphine)palladium (0.035 g, 2 mol %) and triphenylphosphine (0.035 g) in 1 mL of methylene chloride was added, followed after 5 min by 0.131 mL (1.575 mmol) of pyrrolidine. The resulting mixture was stirred at 0° C. for 20 min and then 30 mL of cold (0° C.) acetone was added. The mixture was vigorously stirred at 0° C. for 15 min and then the precipipate was collected by filtration, washed with cold acetone and dried in vacuo to give 0.520 g of a beige powder. By diluting the filtrate with ether another 0.041 g of the crude product was obtained. The combined solids were dissolved in a small amount of pH 7.4 phosphate buffer (0.05M) and applied to a reverse-phase (C$_{18}$ BondaPak) column. Elution with H$_2$O and then 2% acetonitrile-H$_2$O afforded, after lyophilization, 24B (0.413 g, 76%) as a yellow solid: $^1$Hnmr (D$_2$O) δ8.55, 7.76 (ABq, J=6.3 Hz, 2H), 7.81 (s, 1H, 4.4–3.7 (m, 2H), 4.19 (s, 2H), 4.16 (s, 3H), 3.47–3.14 (m, 2H), 2.73 (s, 3H), 1.24 (d, J=6.4 Hz, 3H), 1.16 (d, J=7.3 Hz, 3H), ir (KBr) 1750, 1595 cm$^{-1}$; uv (phosphate buffer, pH 7.4) 293 nm (ε7170).

EXAMPLE 25

Preparation of (5R,6S) 3-[1,6-dimethyl-pyridinium-2-yl)methylthio]-6-(1R-hydroxyethyl)-4R-methyl-7-oxo-1-azabicyclo[3.2.0-]hept-2-ene-2-carboxylate

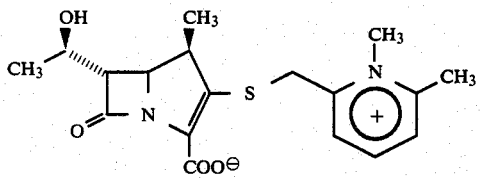

A. (1,6-dimethhylpyridinium-2-yl)methylthiol, trifluoromethanesulfonate salt

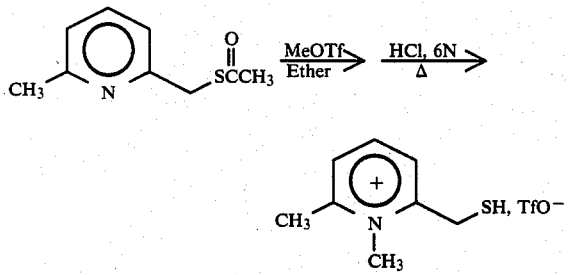

A solution of (6-methylpyridin-2-yl)methylthio acetate (1.0 g, 5.52 mmol) in dry ether (5 mL) kept under a nitrogen atmosphere was treated with methyl triflate (0.74 mL, 6.5 mmol) and stirred at 23° C. for 4 h. The ether was decanted and the white solid was washed twice with ether (2 mL) and dissolved into hydrochloric acid solution (15 mL, 6N, 90.0 mmol). The resulting solution was heated at 70° C. for 4 h under a nitrogen atmosphere and then concentrated under reduced pressure to a yellow syrup. Traces of hydrochloric acid were removed by codistillation with water (2×10 mL). The crude material was purified by reversed phase column chromatography (2.2×13.0 cm, PrepPak C-18) with water as eluting solvent. Appropriate fractions were combined and lyophylized to give a white powder; 1.43 g, 85.4%; ir (KBr) ν$_{max}$: 2565 (SH), 1626 (pyridinium), 1585 (pyridinium) cm$^{-1}$; uv (H$_2$O) λ$_{max}$: 278 (ε7355); Anal. calc'd for C$_9$H$_{12}$NO$_3$S$_2$F$_3$: C 35.64, H 3.99, N 4.62, S 21.14; found: C 35.49, H 4.05, N 4.56, S 20.99.

B. (5R,6S) 3-[1,6-dimethylpyridinium-2-yl)methylthio]-6-(1R-hydroxyethyl)-4R-methyl-7-oxo-1-azabicyclo[3.2.0-]hept-2-ene-2-carboxylate

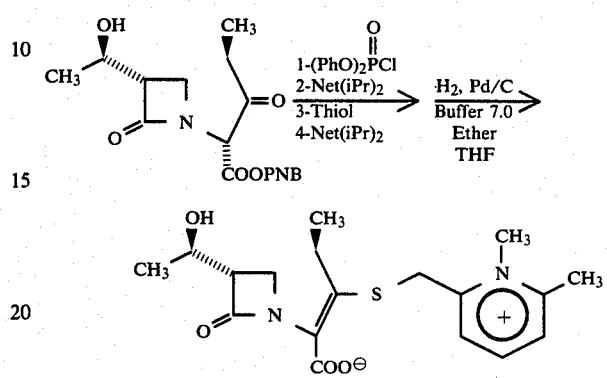

To a cold (5° C.) solution of (5R,6S) paranitrobenzyl 3,7-dioxo-6-(1R-hydroxyethyl)-4RS-methyl-1-azabicyclo[3.2.0]heptane-2-R-carboxylate (1.11 g, 3.06 mmol, R/S: 86/14) in dry acetonitrile (90 mL) kept under a nitrogen atmosphere was added simultaneously diphenyl chlorophosphate (0.68 mL, 3.3 mmol) and diisopropylethylamine (0.57 mL, 3.3 mmol) over 10 min period. The cold (5° C.) mixture was stirred for 1 h, cooled to −30° C. and treated simultaneously with a solution of (1,6-dimethylpyridinium-2-yl)methylthiol, trifluoromethanesulfonate salt (1.03 g, 3.4 mmol) in dry acetonitrile (2 mL) and diisopropylethylamine (0.59 mL, 3.4 mmol) over 15 min period. The resulting mixture was stirred for 0.5 h at −30° C., warmed up until 0° C. and stirred for 1.0 h before being diluted with cold water (35 mL). The resulting emulsion was poured on top of reversed phase column (prepPak C-18, 2.5×18 cm) which was then eluted with a mixture of 25–50% acetonitrile in water. Lyophilization of appropriate fractions gave a sticky yellow solid, 1.69 g which was solubilized into wet tetrahydrofuran (40 mL). To the resulting solution was added ether (70 mL), potassium dihydrogenphosphate-sodium hydroxide buffer (pH 7.0, 0.2M, 50 mL) and 10% palladium on charcoal (1.69 g) and the resulting mixture was hydrogenated under 42 psi at 23° C. for 2 h and then filtered on a Celite pad. The two phases were separated and an aqueous phase was washed with ether (2×20 mL) and concentrated under high vacuum at <23° C. to 15 mL which was applied on top of reversed phase column (prepPak C-18). Elution with a mixture of 4% acetronitrile in water gave after lyophilization of appropriate fractions 0.23 g of title compound mixed with potassium-sodium diphenylphosphate (24% in mole). Repurification on reversed phase column (2.5×14 cm, prepPak C-18) with water (400 mL) and a mixture of 10% acetonitrile in water (200 mL) as eluting solvent gave after lyophilization of appropriate fractions a yellow powder, 0.17 g, 15.3%; ir (KBr) ν$_{max}$: 1750 (C=O of β-lactam), 1625 (pyridinium), 1600 (C=O of carboxylate) cm$^{-1}$; $^1$Hmr (D$_2$) δ: 1.12 (d, J=7.2 Hz, CH$_3$ on C-4), 1.24 (d, J=6.2 Hz, CH$_3$CHOH), 2.80 (s, CH$_3$ on C-6 of pyridinium), 4.18 (CH$_3$ on N of pyridinium), 4.41 (center of AB quartet, CH$_2$S), 7.5–8.4 (H's on pyridinium); uv (Buffer 0.05M, pH 7.0) $\lambda_{max}$: 278 ($\epsilon$ 11504); $[\alpha]_D^{23} -256.4°$ (C 0.22, H$_2$O); $\tau_{\frac{1}{2}}=20.8$ h measured at 37° C. in buffer (pH 7.4) for a concentration of $10^{-4}$M.

EXAMPLE 26

Preparation of (5R,6S) 3-[(1,6-dimethylpyridinium-2-yl)methylthio]-6-(1R-hydroxyethyl)-7-oxo-1-azabicyclo[3.2.0]hept-2-ene-2-carboxylate

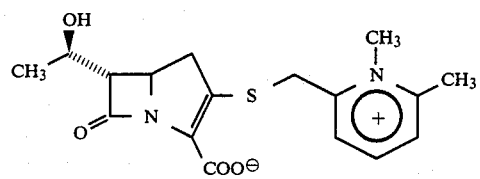

A. (5R,6S) paranitrobenzyl 3-[(1,6-dimethylpyridinium-2-yl)methylthio]-6-(1R-hydroxyethyl)-7-oxo-1-azabicyclo[3.2.0]hept-2-ene-2-carboxylate, trifluoromethanesulfonate and diphenylphosphate salt

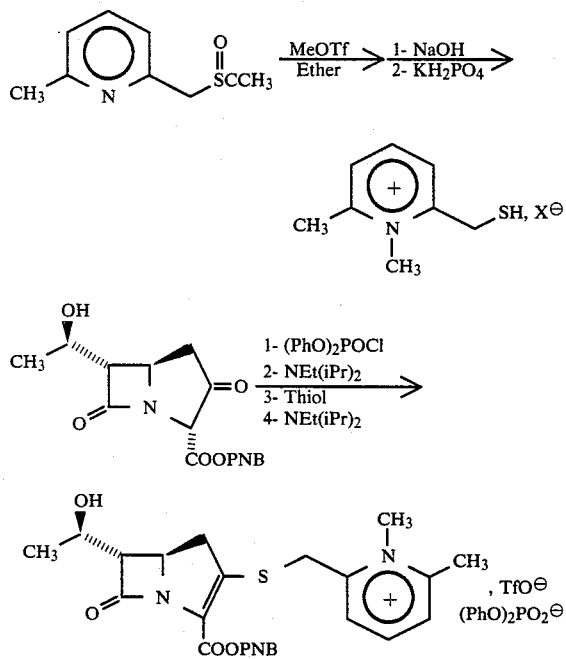

To a cold (5° C.) solution of (5R,6S) paranitrobenzyl 6-(1R-hydroxyethyl)-3,7-dioxo-1-azabicyclo[3.2.0]heptane-2R-carboxylate (2.14 g, 6.14 mmol) in dry acetonitrile (18 mL) kept under a nitrogen atmosphere was added diphenyl chlorophosphate (1.37 mL, 6.6 mmol), diisopropylethylamine (1.15 mL, 6.6 mmol) at such a rate that the temperature was kept at 5° C. (7–10 min) and 4-dimethylaminopyridine (6 mg, 0.05 mmol). The mixture was stirred for 1.5 h at 5° C. and, was used as it was; this mixture will be called 'solution A' further in the procedure. A solution of (6-methylpyridin-2-yl)methylthio acetate (1.23 g, 6.8 mmol) in dry ether (10 mL) kept under a nitrogen atmosphere was treated with methyl triflate (0.85 mL, 7.5 mmol) and stirred for 1.5 h at 23° C. The ether was decanted and the white powder was washed twice with ether (2×10 mL) and dissolved in water (20 mL). The resulting aqueous solution was cooled to 0° C. under oxygen free atmosphere and treated with sodium hydroxide (4N, 3.4 mL, 13.6 mmol). The mixture was stirred at 2° C. for 1 h and then the pH was adjusted at 7.6 by the addition of potassium dihydrogenphosphate; this mixture will be called 'solution B' further in the procedure. The cold (5° C.) 'solution A' was treated with 'solution B' over 0.5 h period while the pH was kept between 7.25–7.35 by the dropwise addition of 4N sodium hydroxide solution. The mixture was stirred for 0.5 h and poured on top of reversed phase column (4.0×18 cm), prePak C-18); the column was eluted with a mixture of 25–50% acetonitrile in water. Lyophilization of appropriate fractions gave the title compound as a yellow powder, 2.82 g (51% (PhO)$_2$PO$_2^-$, 49%, CF$_3$SO$_3^-$), 80%; ir (KBr) $\nu_{max}$: 3700–3000 (OH), 1772 (C=O of $\beta$-lactam), 1700 (C=O of ester), 1625 (pyridinium), 1590 (pyridinium) cm$^{-1}$; $^1$Hmr (DMSO, d-6) $\delta$: 1.15 (d, J=6.2 Hz, CH$_3$CHOH), 2.84 (s, CH$_3$ on C-6 of pyridinium), 4.16 (s, CH$_3$ on N of pyridinium), 4.79 (s, SCH$_2$), 6.6–7.5 [(PhO)$_2$PO$_2^-$], 7.5–8.7 (H's on pyridinium and H's of PNB ester).

B. (5R,6S) 3-[(1,6-dimethylpyridinium-2-yl)methylthio]-6-(1R-hydroxyethyl)-7-oxo-1-azabicyclo[3.2.0]hept-2-ene-2-carboxylate

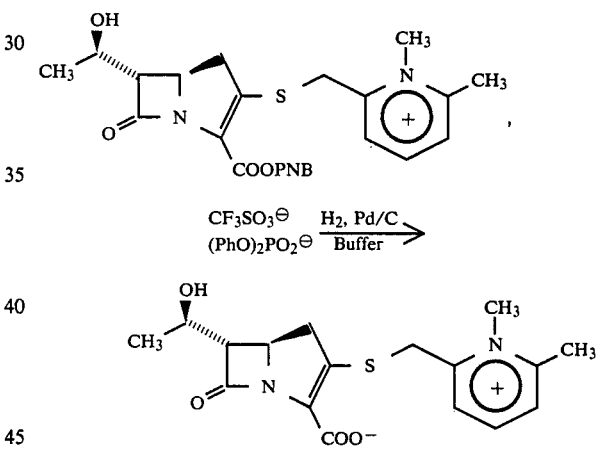

To a solution of (5R,6S) paranitrobenzyl 3-[(1,6-dimethylpyridinium-2-yl)methylthio]-6-(1R-hydroxyethyl)-7-oxo-1-azabicyclo[3.2.0]hept-2-ene-2-carboxylate, trifluoromethanesulfonate and diphenylphosphate (49:51) salt (0.87 g, 1.27 mmol) in wet tetrahydrofuran (50 mL) was added ether (50 mL), potassium dihydrogenphosphate-sodium hydroxide buffer (0.1M, 40 mL, pH 7.0) and 10% palladium on charcoal (0.87 g). The mixture was hydrogenated under 36 psi at 23° C. for 2 h and filtered on a Celite pad. The two phases were separated and aqueous phase was washed with ether (2×15 mL), concentrated under high vacuum until 30 mL and poured on top of reverse phase column (PrepPak C-18, 2.2×13 cm). Elution of the column was done with water. Appropriate fractions were combined and lyophilized to give a yellow powder, 0.179 g, 40%; ir (KBr) $\lambda_{max}$: 1755 (C=O of $\beta$-lactam), 1628 (pyridinium), 1590 (C=O of carboxylate) cm$^{-1}$; $^1$Hmr (D$_2$O) $\delta$:1.25 (d, J=6.4 Hz, CH$_3$CHOH), 2.82 (s, CH$_3$ on C-6 of pyridinium), 3.12 ('dd', J=9.2 Hz, J=2.9 Hz, H-4), 3.39 (dd, J=6.0 Hz, J=2.8 Hz, H-6), 3.7–4.4 (CH$_3$CHOH, H-5, CH$_3$ on N of pyridinium), 4.48 (s, CH₂S), 7.6–8.4 (H's on pyridinium); uv (H₂O) $\lambda_{max}$: 279 (ε9628) with shoulder at 296; $[\alpha]_D^{23}$ 55.0° C. (c 0.63, H₂O); $\tau_{\frac{1}{2}}=12.5$ h measured at 37° C. in buffer pH 7.4 for a concentration of $10^{-4}$M.

EXAMPLE 27

Preparation of 3-[2-(N-Methylpyridinium)methanethio]-6α-[1-(R)-hydroxyethyl]-4β-methyl-7-oxo-1-azabicyclo(3.2.0-)hept-2-ene-2-carboxylate

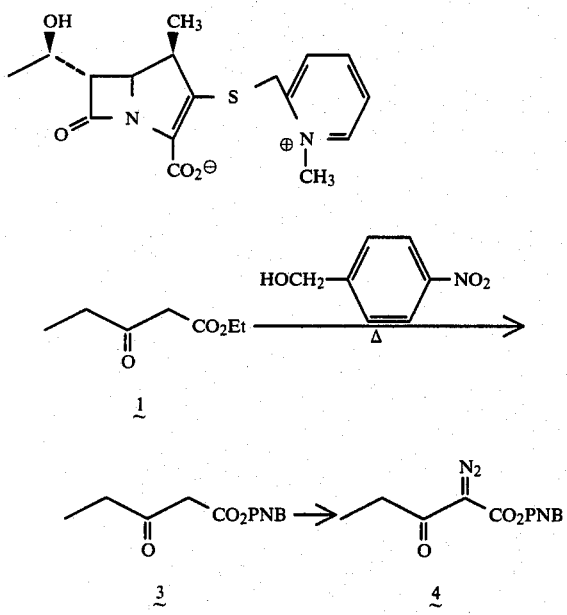

A. p-Nitrobenzyl-2-diazo-3-oxo-n-valerate(4)

A solution of 50 g (0.35M) of ethyl 3-oxo-n-valerate and 54 g (0.35M) of p-nitrobenzyl alcohol in 400 ml of toluene was heated at 130°–140° without a refluxing condenser for 18 h. Evaporation of solvent gave a yellow crystalline material which was recrystallized from Et₂O-pentane to produce 75 g (86% yield) of p-nitrobenzyl 3-oxo-n-valerate (3). m.p. 33°–34°. IR (KBr) γ 1740 and 1705 cm⁻¹. NMR (CDCl₃) δ 1.20(3H,t,J=7.0 Hz), 2.65(2H,q,J=7.0 Hz), 3.60(2H,s), 5.28(2H,s), 7.45(2H,d,J=9.5 Hz), and 8.18(2H,d,J=9.5 Hz). To a solution of 55.5 g (0.22M) of compound 3 in 500 ml of CH₃CN was added at 0° 45 g (0.44M) of TEA followed by 50 g (0.22M) of p-carboxybenzenesulfonyl azide. The ice bath was removed and the mixture was allowed to stir for 90 min. The precipitate was filtered, washed with CH₃CN and the filtrate was concentrated to ca 100 ml volume and diluted with 800 ml of EtOAc. The organic solution was washed with aq. NaHCO₃, brine and dried (MgSO₄). Evaporation of the dried solvent gave 55 g (90% yield) of compound 4 as a slightly yellow crystals. m.p. 96°–97°. IR (KBr) γ 2120 and 1710 cm⁻¹. NMR (CDCl₃) δ 1.20(3H,t,J=7.0 Hz), 2.85(2H,q,J=7.0 Hz), 5.40(2H,s), 7.50(2H,d,J=8.0 Hz), and 8.15(2H,d,J=8.0 Hz).

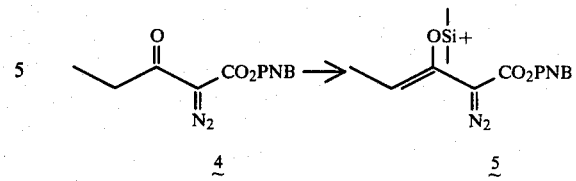

B. 1-p-Nitrobenzyloxycarbonyl-1-diazo-2-t-butyldimethylsilyloxy-2-buten (5)

To a cooled (0°) solution of 54 g (0.2M) of compound 4 in 400 ml of CH₂Cl₂ was added 41.4 g (0.4M) of TEA followed by 56 g (0.21M) of t-butyldimethylsilyl chloride in 30 ml of CH₂Cl₂ over 40 min. The solution was stirred for 120 min, then washed with ice-water. The CH₂Cl₂ was dried (MgSO₄), filtered and evaporated in vacuo to give 68 g (89% yield) of compound 5 as yellow solids. m.p.54°–55°. IR (KBr) γ 2080 and 1695 cm⁻¹. The NMR of compound 5 indicated that compound 5 was obtained as a E/Z mixture at the olefinic position in a ratio of 9:1. NMR (CDCl₃ major isomer) δ 0.15(6H,s), 0.90(9H,s), 1.58(3H,d,J=7.0 Hz), 5.15(2H,s), 7.30(2H,d,J=9.0 Hz) and 8.0(2H, d, J=9.0 Hz).

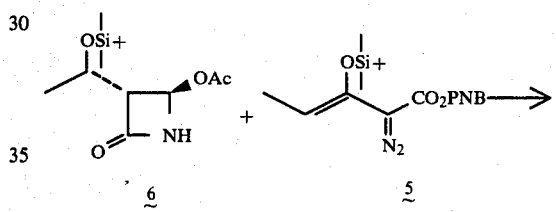

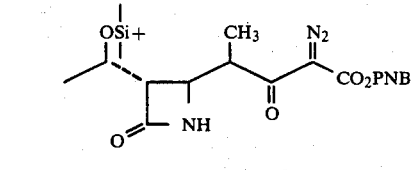

C. 4β-1-Methyl-3-diazo-3-p-nitrobenzyloxycarbonyl-2-oxo-propyl)-3α-[1-(R)-t-butyldimethylsilyloxy ethyl]-azetidin-2-one (7)

To a suspended solution of 12.5 g (0.1M) of anhydrous ZnCl₂ in 700 ml of CH₂Cl₂ was added 60.4 g (0.21M) of compound 6 and stirred for 15 min at 23° then cooled to 0°. A solution of 106 g (0.27M) of compound 5 in 200 ml of CH₂Cl₂ was added dropwise to the above reaction solution over 90 min, then stirred for 120 min without the cooling bath. The reaction mixture was washed with aq. NaHCO₃ (4×150 ml), water, brine and dried (MgSO₄). Evaporation of dried solvent gave a dark oil, which was purified by SiO₂ column; elution of the column with EtOAc-CH₂Cl₂ (1:9) gave 51.5 g (54%) of compound 7 as a white crystalline material. m.p. 112°–114°. IR (KBr) γ 2130,1760 and 1720 cm⁻¹. The 360 MHz nmr of compound 7 indicated that compound 7 was obtained as a mixture at the 1-methyl position in a ratio of 2:1. NMR (CDCl₃) δ 0.3–0.6(6H, 2s), 0.8Z(9H,2s), 1.05–1.15(6H,m), 2.68(0.66H,q,J=6.6 and 2.0 Hz), 2.88 (0.34H,q,J=6.6 and 2.0 Hz) 3.57(1H,m), 3.84 (1H,m), 4.09(1H,m), 517(2H,twos), 5.84(0.66H,s), 5.95(0.34H,s), 7.52(2H,d,J=8.5 Hz) and 8.23(2H,d,J=8.5 Hz).

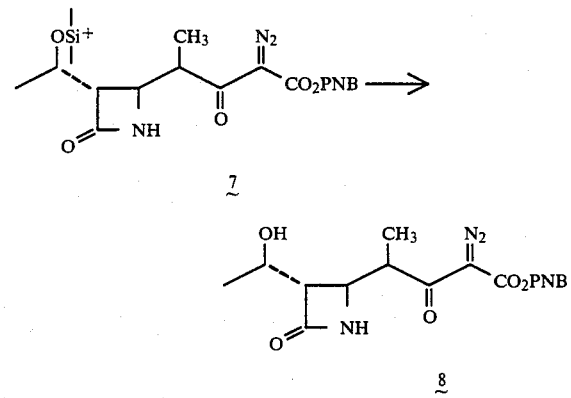

D.
4β-(1-Methyl-3-diazo-3-p-nitrobenzyloxycarbonyl-2-oxo-propyl)-3α-[1-(R)-hydroxyethyl]-azetidin-2-one (8)

To a solution of 30 g (59.5 mmol) of compound 7 in 400 ml of MeOH was added at 23° 150 ml of 1N-HCl and stirred for 18 h. The reaction was concentrated to ca 200 ml of volume and extracted with EtOAc (3×200 ml). The combined EtOAc was washed with water, aq. NaHCO₃ and brine. Evaporation of dried (MgSO₄) solvent gave 22.3 g (96%) of compound 8 as a white crystalline material. m.p. 147°–148°. IR (KBr) γ 3400, 2135, and 1750 cm⁻¹. The 360 MHz nmr of compound 8 indicated that compound 8 was obtained as a mixture at the 4-methyl position in a ratio of 2:1. NMR (DMSO-d) δ 1.07–1.10(6H,m), 2.75(0.66H,q,J=6.6 and 2.0 Hz), 2.85(0.34H,J=6.6 and 2.0 Hz), 3.55–3.90(3H,m), 5.25(2H,s) 7.70(2H,d,J=9.0 Hz), 8.05(0.66H,s), 8.10(0.34H,s) and 8.27(2H,d,J=9.0 Hz).

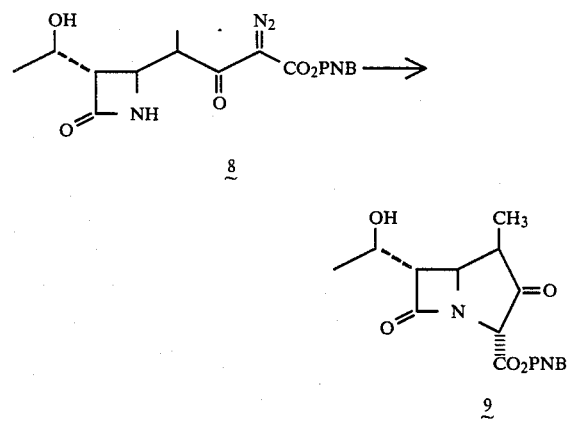

E.
p-Nitrobenzyl-6α-[1-(R)-hydroxyethyl]-4-methyl-3-,7-dioxo-1-azabicyclo[3.2.0]heptane-2-carboxylate (9)

A solution of 14.0 g (35.86 mmol) of compound 8 and 70 mg of rhodium(II) octanatate in ethylacetate was heated at reflux for 20 min under N₂. The mixture was evaporated in vacuo to give compound 9 as a form. IR (CHCl₃) γ 3400 and 1750 cm⁻¹. The 360 MHz nmr of compound 9 indicated that compound 9 was obtained as a mixture as the 4-methyl position in a ratio of 2:1. Nuclear Overhauser Effects (NOE) was used to determine the configuration of the 4-methyl. When the H₅ of major isomer is irradiated, an approximately 7% signal increase for the 4-methyl protons was observed, indicating the cis relationship of the H₅ and the 4-methyl. On the other hand, when the H₅ of minor isomer is irradiated, no signal increase was observed for the 4-methyl, indicating the trans relationship of the H₅ and the 4-methyl for the minor isomer. NMR (CDCl₃) for the major isomer δ 1.24(3H,d,J=7.35 Hz), 1.40(3H,d,J=6.3 Hz), 2.40(1H,m), 3.24(1H,q,J=6.6 and 7.2 Hz), 3.67(1H,q, J=8.0 and 2.2 Hz), 4.18(1H,m)) 4.82(1H,s), 5.24(1H,d,J=6.3 Hz), 6.18 (1H,d,J=6.3 Hz), 7.60(1H,d,J=8.5 Hz), and 8.22(1H,d,J=8.5 Hz), NMR (CDCl₃) for the minor isomer δ 1.0(3H,d,H=7.35 Hz), 1.40(3H,d,J=6.3 Hz), 2.83(1H,m), 3.25(1H,q,J=6.6 and 1.50 Hz), 4.14(1H,q,J=7.36 and 1.50 Hz), 4.67(1H,s), 5.24(1H,d,J=6.3 Hz), 6.18(1H,d,J=6.3 Hz) and 7.60(1H,d,J=8.5 Hz) and 8.22(1H,d,J=8.5 Hz).

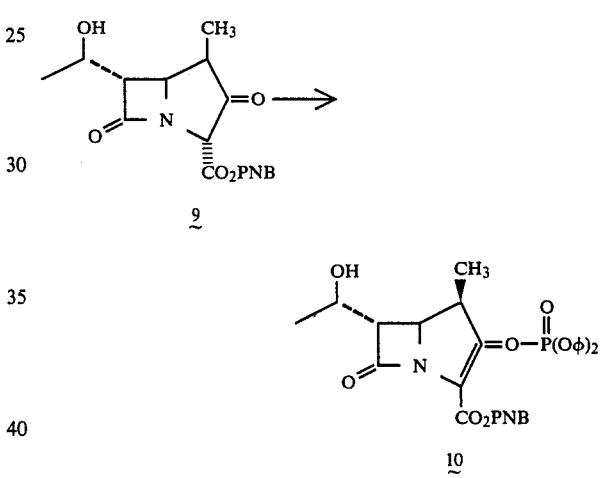

F.
p-Nitrobenzyl-3-diphenoxyphosphinyl-6α-[1-(R)-hydroxyethyl]-4β-methyl-7-oxo-1-azabicyclo(3.2.0)hept-2-ene-2-carboxylate (10)

To a cooled (0°) solution of 20.0 g (55.2 mmol) of the keto intermediate 9 in 150 ml of CH₃CN was added 7.18 g (55 mmol) of diisopropylethylamine followed by 14.85 g (55 mmol) of diphenylchlorophosphonate in 20 ml of CH₃CN over 5 min. The resulting solution was stirred for 60 min at 0°, then diluted with 600 ml of ETOAc, washed with ice cold 10% H₃PO₄ and brine. Evaporation of the dried (MgSO₄) solvent gave a crude oil which was purified by SiO₂ column; elution of the column with 10% EtOAc in CH₂Cl₂ gave 3.7 g (11.5%) of the phosphonate 10 as a white form. IR (CHCl₃) γ 3400, 1790 and 1720 cm⁻¹.

NMR (CDCl₃) δ 1.20(3H,d,J=7.2 Hz), 1.38(3H,d,H=7.3 Hz), 3.35(1H,l,J=6.7 and 2.0 Hz), 3.50(1H,m), 4.2–4.25(2H,m), 5.20(1H,d,J=10.5 Hz), 5.37 (1H,d,J=10.5 Hz), 7.1–7.4(10H,m), 7.56(1H,d,J=9.0 Hz), and 8.10 (1H,d,J=9.0 Hz). Nuclear Overhauser Effects were used to determine the configuration of the 4-methyl of compound 10. When the H₅ is irradiated, no signal increase was observed for the 4-methyl, indicating the trans relationship of the H5 and the 4-methyl.

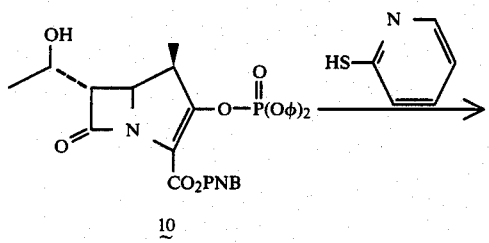

10

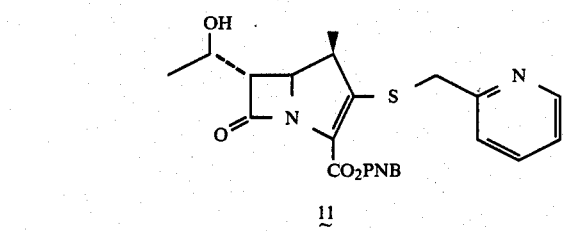

11

G.
p-Nitrobenzyl-3-[pyridine-2-yl-methanethio]-6α[1-(R)-hydroxyethyl]-4β-methyl-7-oxo-1-azabicyclo(3.2.0-)hept-2-ene-2-carboxylate (11)

To a cooled (−15°) solution of 1.2 g (2 mmol) of the phosphonate 10 in 10 ml of CH₃CN was added 390 mg (3 mmol) of diisopropylethylamine followed by 370 mg (3 mmol) of 2-mercaptomethylpyridine under N₂. The reaction mixture was allowed to stir for 60 min at −15° then additional 60 min at 0°. The reaction was diluted with EtOAc, washed with ice water, brine and dried (MgSO₄). Evaporation of solvents in vacuo gave a yellow oil which was purified by SiO₂ column; elution of the column with 20% EtOAc in CH₂Cl₂ gave 375 mg (40% yield) of compound 11 as a white amorphous foam. IR (KBr) γ 3400,1775, and 1710 cm⁻¹. NMR (CDCl₃) δ 2.14 (3H,d,J=6.7 HzH), 2.19(3H,d,J=6.7Hz), 3.14(1H,q,J=6.2 and 2.0 Hz), 3.40 (1H,m), 4.0(1H,d,J=7.6 Hz) 4.12(1H,d,J=7.6 Hz), 4.18(1H,q,J=6.7 and 2.0 Hz) 4.25(1H,m), 5.25(1H,d,J=11.3 Hz), 5.40(1H,d,J=11.3 Hz), 7.15-8.2(4H,m).

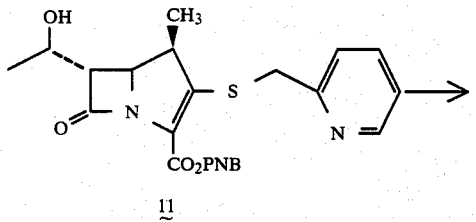

11

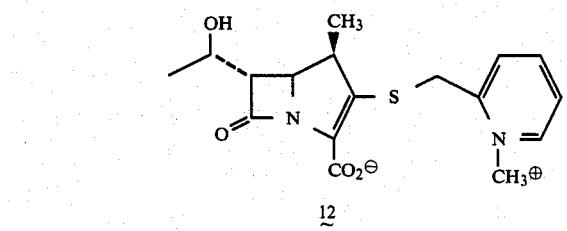

12

H. 3-[2-(N-Methylpyridinium)methane thio]-6α-[1-(R)-hydroxyethyl]-4β-methyl-7-oxo-1-azabicyclo(3.2.0)hept-2-ene-2-carboxylate (12)

To a solution of 1.0 g (2 mmol) of compound 11 in 10 ml of CH₂Cl₂ was added 450 mg (3.3 mmol) of methyltrifluoromethanesulfonate and stirred at 23° for 90 min. Evaporation of CH₂Cl₂ in vacuo gave the quaternized pyridine as a foam which wash hydrogenated immediately without any further purification. The crude pyridinium salt was dissolved into TMF-ether-PH 7 buffer (1:1:1, 100 ml each) followed by 600 mg of 10% palladium on charcoal. The mixture was hydrogenated at 35 psi on the per shaker for 45 min. The mixture was filtered through a celite pad and the catalyst was washed with water (2 × 10 ml). The combined filtrate and washings were extracted with ether (2 × 100 ml) and lypholized to give a yellow powder which was purified on a C₁₈ BONDPAK reverse phase column (10 g), eluting with 5% CH₃CN in water under 8 psi pressure. Each 15 ml fraction was assayed by high pressure liquid chromatography and fractions having an ultraviolet absorption at λ max 300 nm were collected and lyophilized to give 58 mg (11% yield) of the title compound as a pale yellow powder. IR (KBr) γ 3400,1750, and 1590 cm⁻¹. λ max (H₂O) 292 nm (ϵ 7081). NMR (D₂O) δ 1.13(3H,d,J=6.5 Hz), 1.23(3H,d,J=6.5 Hz), 3.18(1H,m), 3.45(1H,q,J=6.0 and 2.1 Hz), 4.0-4.4 (4H,m), 4.65(3H,s), 7.79(2H,m), 8.30(1H,m), and 8.60(1H,m).

EXAMPLE 28

Preparation of 3-[2-(1,4-Dimethylpyridinium)methane thio]-6α-[1-1R)-hydroxyethyl]-4β-methyl-7-oxo-1-azabicyclo(3.2.0)hept-2-ene-2-carboxylate

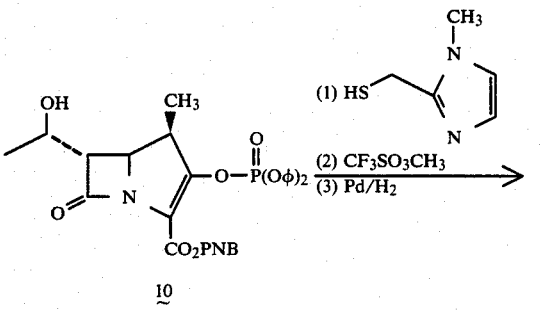

10

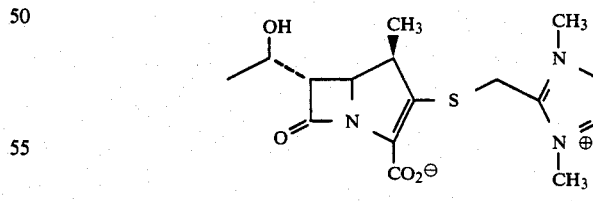

13

3-[2-(1,4-Dimethylpyridinium)methane thio]-6α-[1-(R)-hydroxyethyl]-4β-methyl-7-oxo-1-azabicyclo(3.2.0)hept-2-ene-2-carboxylate (13)

This compound was obtained as yellow powder in 17% yield from compound 10 in the same manner as that described in Example 27.

IR γ 3400, 1755, and 1600 cm⁻¹. UV λ max (H₂O) 300 nm (ϵ 7600). NMR (D₂O) δ 1.20 (3H, d, J=6.7 Hz), 1.28 (3H, d, J=6.7 Hz), 2.60 (3H, s), 3.4–3.5 (2H, m), 4.2–4.4 (4H, m), 4.52 (3H, s), 7.82 (1H, t, J=6.5 and 4.2 Hz), 8.32 (1H, d, J=6.5 Hz), and 8.60 (1H, d, J=4.2 Hz).

EXAMPLE 29

Preparation of 3-[4-(1-methylpyridiniummethanethio]-6α-[1-(R)-hydroxyethyl]-4β-methyl-7-oxo-1-azabicyclo(3.2.0-)hept-2-ene-2-carboxylate

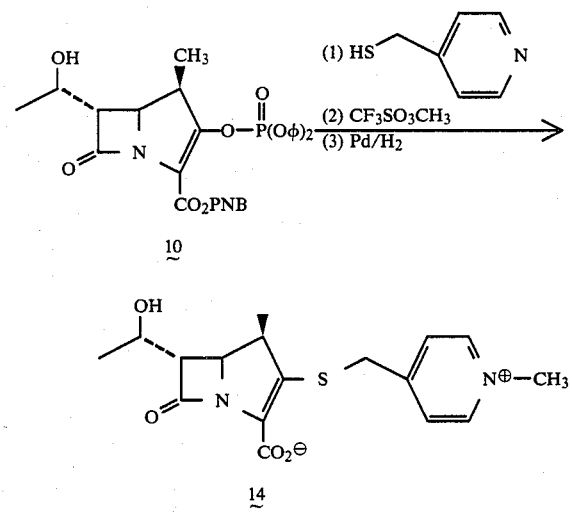

3-[4-(1-methylpyridinium methane thio]-6α-[1-(R)-hydroxyethyl]-4β-methyl-7-oxo-1-azabicyclo(3.2.0)hept-2-ene-2-carboxylate (14)

This compound was obtained as yellow powder in 15% yield from compound 10 in the same manner as that described in Example 27.

IR (KBr) γ 3410, 1750 and 1650 cm$^{-1}$ UV λmax (H$_2$O) 293 nm (ε 7295). NMR (D$_2$O) δ 1.15 (3H, d, J=6.5 Hz), 1.20 (3H, d, J=6.5 Hz), 3.20 (1H, m), 3.45 (1H, q, J=6.0 and 2.0 Hz), 4.11 (1H, q, J=8.0 and 2.0 Hz), 4.20 (1H, m), and 4.35 (3H, s), 7.95 (2H, d, J=5.2 Hz) and 8.72 (2H, d, J=5.2 Hz).

EXAMPLE 30

Preparation of 3-[3-(1-methylpyridinium)methanethio]-6α-[1-(R)-hydroxyethyl]-4β-methyl-7-oxo-1-azabicyclo(3.2.0-)hept-2-ene-2-carboxylate

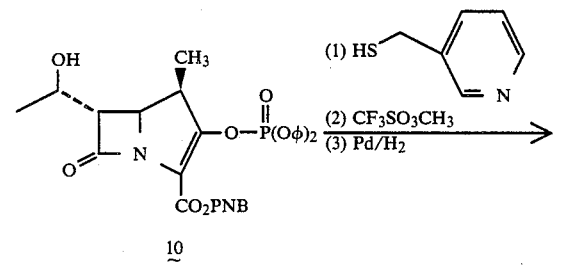

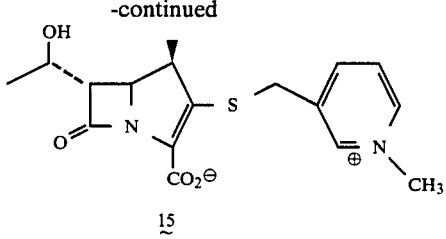

3-[3-(1-Methylpyridinium)methanethio]-6α[1-(R)-hydroxyethyl]-4β-methyl-7-oxo-1-azabicyclo(3.2.0-)hept-2-ene-2-carboxylate (15)

This compound was obtained as yellow powder in 27% yield from compound 10 in the same manner as that described in Example 27.

IR (KBr) γ 3420, 1750 and 1610 cm$^{-1}$. UV λmax (H$_2$O) 295 nm (ε 8750) NMR (D$_2$O) δ 1.10 (3H, d, J=6.9 Hz), 1.25 (3H, d, J=6.9 Hz), 1.27 (1H, m), 1.43 (1H, q, J=6.2 and 1.8 Hz), 4.1–4.35 (4H, m), 4.39 (3H, s), 8.0 (1H, t, J=8.5 and 6.2 Hz), 8.45 (1H, d, J=8.5 Hz), 8.70 (1H, d, J=6.2 Hz), and 8.82 (1H, s).

Anal. Calcd for C$_{17}$H$_{20}$N$_2$O$_4$S.2½H$_2$O: C, 5190; H, 6.36; N, 7.12. Found: C, 51.92; H, 5.71; N, 6.88.

EXAMPLE 31

Preparation of 3-[3-(1,2-Dimethylpyridinium)methanethio]-6α-[1-(R)-hydroxyethyl]-4β-methyl-7-oxo-1-azabicyclo(3.2.0-)hept-2-ene-2-carboxylate

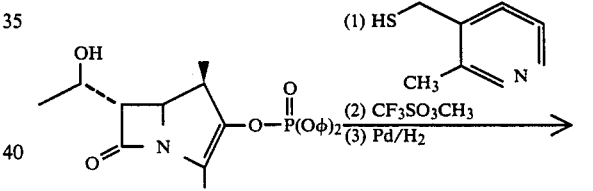

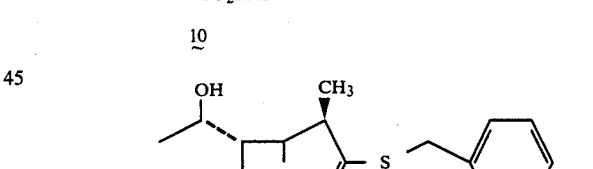

3-[3-(1,2-Dimethylpyridinium)methanethio]-6α-[1-(R)-hydroxyethyl]4β-methyl-7-oxo-1-azabicyclo(3.2.0-)hept-2-ene-2-carboxylate (16)

This compound was obtained as yellow powder in 14% yield from compound 10 in the same manner as that described in Example 27.

IR (KBr) γ 3400, 1750 and 1600 cm$^{-1}$. UV λmax (H$_2$O) 296 nm (ε 8500).

NMR (D$_2$O) δ 1.25 (3H, d, J=6.5 Hz), 1.30 (3H, d, J=6.5 Hz), 2.95 (3H, s), 3.40 (1H, m), 3.50 (1H, q, J=6.2 and 1.8 Hz), 4.2–4.4 (4H, m), 4.35 (3H, s), 7.82 (1H, t, J=8.5 and 6.3 Hz), 8.40 (1H, d, J=8.5 Hz) and 8.72 (1H, d, J=6.3 Hz).

EXAMPLE 32

Preparation of
[3-(2,4-Dimethyl-1,2,4-triazolium)methanethio]-6α-[1-(R)-hydroxyethyl]-4β-methyl-7-oxo-1-azabicyclo(3.2.0)hept-2-ene-2-carboxylate

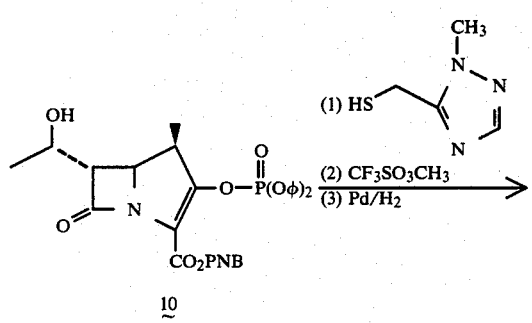

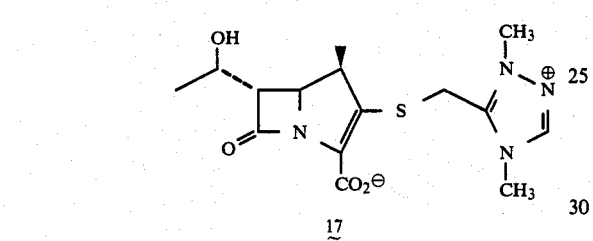

[3-(2,4-Dimethyl-1,2,4-triazolium)methanethio]-6α-[1-(R)-hydroxyethyl]-4β-methyl-7-oxo-1-azabicyclo(3.2.0)hept-2-ene-2-carboxylate (17)

This compound was obtained as yellow powder in 9% yield from compound 10 in the same manner as that described in Example 27. IR (KBr) γ 3420, 1756, and 1605 cm$^{-1}$. UV λmax (H$_2$O) 291 nm (ε 7850). NMR (D$_2$O) δ 1.15 (3H, d, J=6.3 Hz), 1.22 (3H, d, J=6.3 Hz), 3.35 (1H, m), 3.48 (1H, q, J=6.0 and 1.8 Hz), 3.90 (3H, s), 4.05 (3H, s), 4.2–4.4 (4H, m), and 8.80 (1H, s).

EXAMPLE 33

Preparation of
3-[2-(1,3-Dimethylimidazoliummethanethio)-6α-[1-(R)-hydroxyethyl]-4β-methyl-7-oxo-1-azabicyclo(3.2.0-)hept-2-ene-2-carboxylate

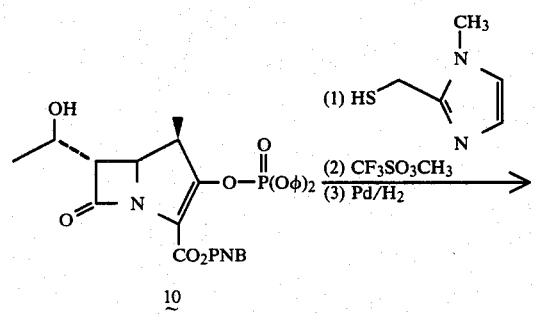

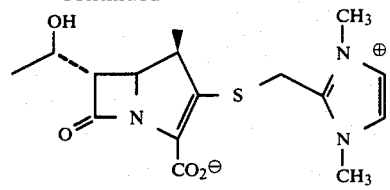

3-[2-(1,3-Dimethylimidazolium methanethio)-6α-[1-(R)-hydroxyethyl]-4β-methyl-7-oxo-1-azabicyclo(3.2.0)hept-2-ene-2-carboxylate (18)

This compound was obtained as yellow powder in 32% yield from compound 10 in the same manner as that described in Example 27.

IR (KBr) γ 3400, 1758 and 1600 cm$^{-1}$. UV λmax (H$_2$O) 294 nm (ε 7194). NMR (D$_2$O) δ 1.10 (3H, d, J=6.3 Hz), 1.25 (3H, d, J=6.3 Hz), 3.30 (1H, m), 3.42 (1H, 1, J=6.0 and 2.2 Hz) 3.85 (6H, s), 4.2–4.6 (4H, m) and 7.40 (2H, s).

EXAMPLE 34

Following the general procedure of Examples 1–33, the following carbapenem products are made by using the intermediate of the formula

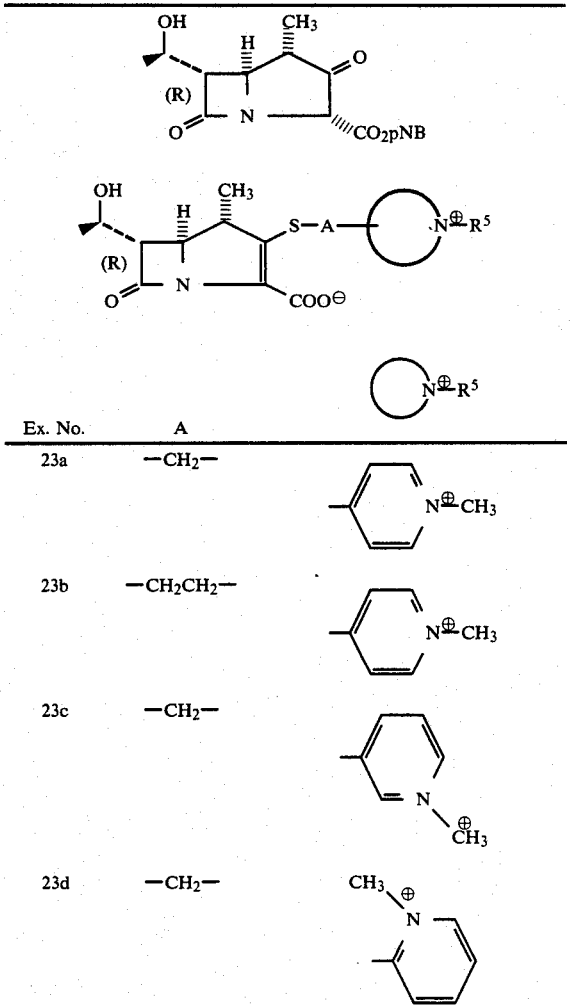

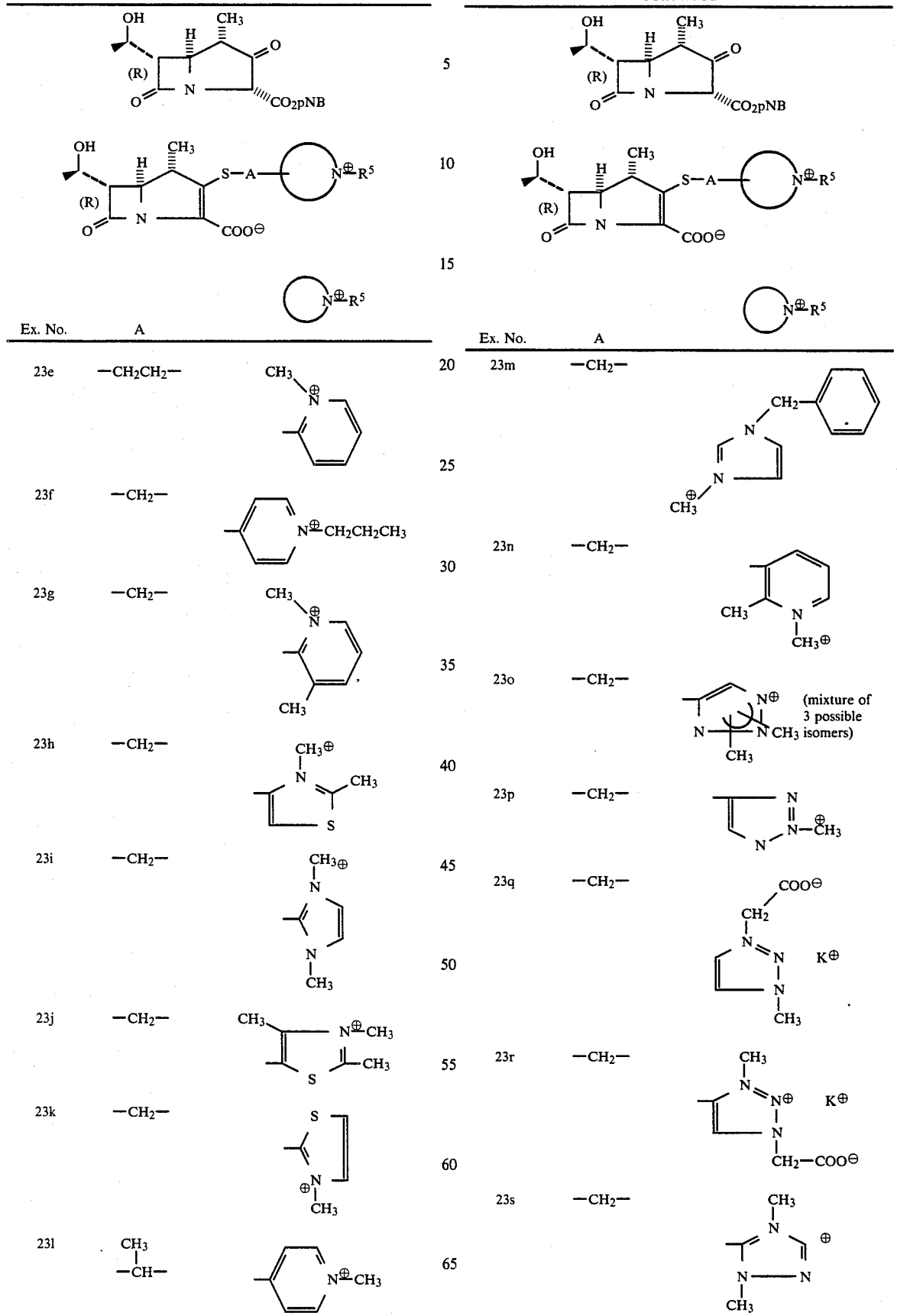

-continued

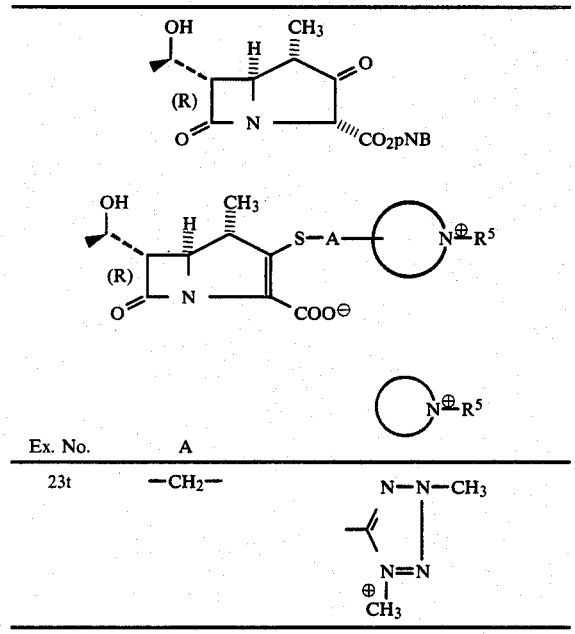

| Ex. No. | A | (ring) |
|---|---|---|
| 23t | —CH₂— | triazolium with N—N—CH₃ and ⊕CH₃ |

EXAMPLE 35

Following the general procedures of Examples 1–33, the following carbapenem products are made using the intermediate of the formula

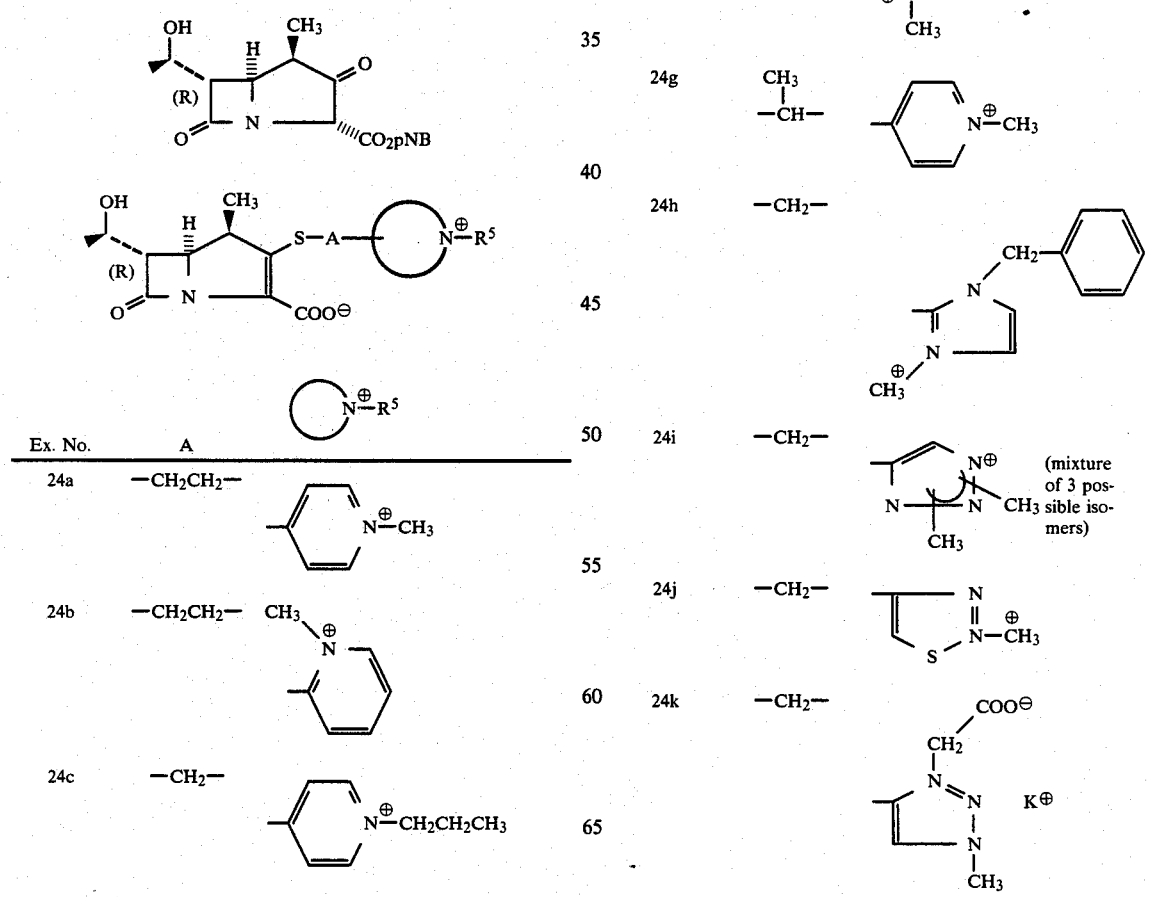

| Ex. No. | A | (ring) |
|---|---|---|
| 24a | —CH₂CH₂— | N-methylpyridinium (4-) |
| 24b | —CH₂CH₂— | N-methylpyridinium (2-) |
| 24c | —CH₂— | N-propylpyridinium |

-continued

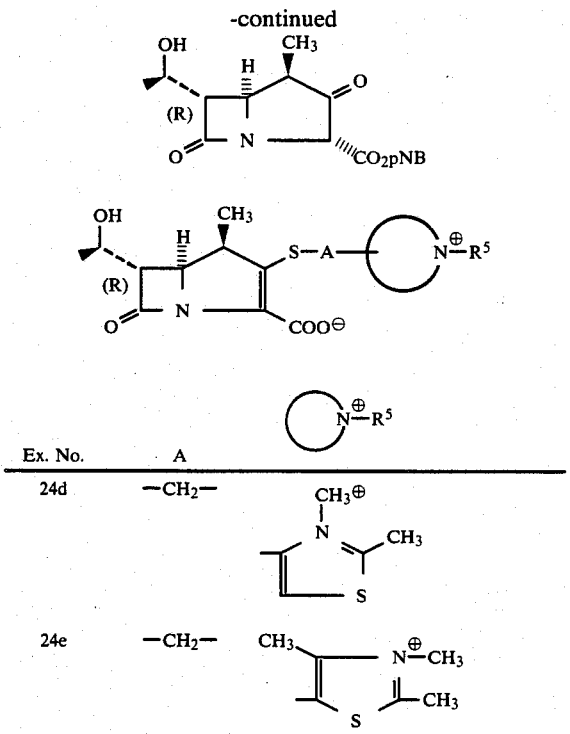

| Ex. No. | A | (ring) |
|---|---|---|
| 24d | —CH₂— | N-methyl thiazolinium with CH₃ |
| 24e | —CH₂— | dimethyl thiazolinium (N⊕—CH₃) |
| 24f | —CH₂— | N-methyl thiazolium |
| 24g | —CH(CH₃)— | N-methylpyridinium |
| 24h | —CH₂— | 1-benzyl-3-methylimidazolium |
| 24i | —CH₂— | dimethyltriazolium N⊕—CH₃ (mixture of 3 possible isomers) |
| 24j | —CH₂— | N-methyl isothiazolium |
| 24k | —CH₂— | methylpyrazolium-CH₂COO⊖ K⊕ |

-continued

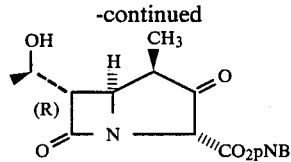

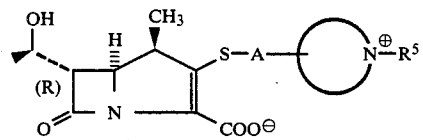

| Ex. No. | A | 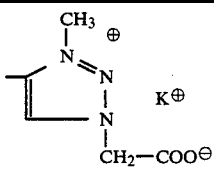 |
|---|---|---|
| 241 | —CH$_2$— | 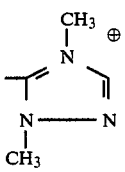 |
| 24m | —CH$_2$— | 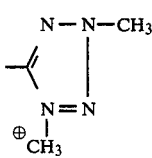 |
| 24n | —CH$_2$— | 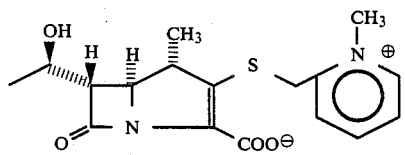 |

EXAMPLE 36

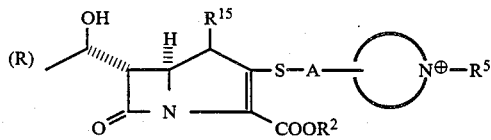

If in the procedure of Example 22, the keto intermediate 1 is replaced by an equimolar amount of the corresponding 1α-methyl intermediate, there is obtained the carbapenem end product indicated above.

We claim:

1. A compound of the formula

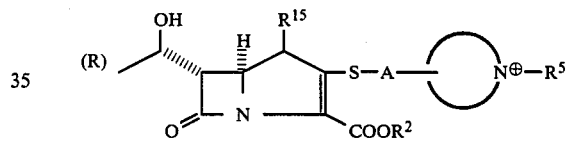

wherein $R^{15}$ is hydrogen or methyl; A is $C_1$–$C_6$ straight or branched chain alkylene; $R^2$ is hydrogen, an anionic charge or a conventional readily removable carboxyl protecting group, providing that when $R^2$ is hydrogen or a protecting group, there is also present a counter ion; and

represents a radical of the formula

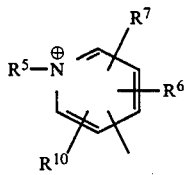

wherein $R^5$ is $C_1$–$C_4$ alkyl and $R^6$, $R^7$ and $R^{10}$ are independently selected from hydrogen; $C_1$–$C_4$ alkyl; $C_1$–$C_4$ alkyl substituted by hydroxy; $C_1$–$C_4$ alkoxy; $C_1$–$C_4$ alkylthio; halo; carboxy; carbamoyl or sulfo; or a pharmaceutically acceptable salt thereof.

2. A compound of claim 1 wherein $R^{15}$ is hydrogen.
3. A compound of claim 1 wherein $R^{15}$ is methyl.
4. A compound of claim 3 wherein $R^{15}$ is β-methyl.
5. A compound according to claim 1, 2, 3 or 4 wherein A is —CH$_2$— or —CH$_2$CH$_2$—.
6. A compound of the formula

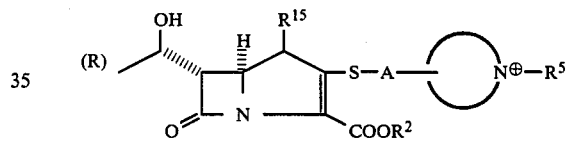

wherein $R^{15}$ is hydrogen or methyl; A is $C_1$–$C_6$ straight or branched chain alkylene; $R^2$ is hydrogen, an anionic charge or a conventional readily removable carboxyl protecting group, providing that when $R^2$ is hydrogen or a protecting group, there is also present a counter ion; and

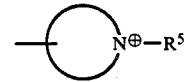

represents a radical of the formula

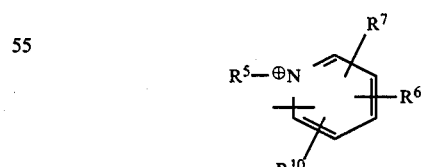

wherein $R^5$ is $C_1$–$C_4$ alkyl and $R^6$, $R^7$ and $R^{10}$ are independently selected from the group consisting of hydrogen, $C_1$–$C_4$ alkyl, $C_1$–$C_4$ alkoxy, carboxy and carbamoyl; or a pharmaceutically acceptable salt thereof.

7. A compound of claim 6 wherein $R^{15}$ is hydrogen.
8. A compound of claim 6 wherein $R^{15}$ is methyl.
9. A compound of claim 8 wherein $R^{15}$ is β-methyl.

10. A compound of claim 6, 7, 8 or 9 wherein A is —CH$_2$— or —CH$_2$CH$_2$—.

11. A compound having the formula

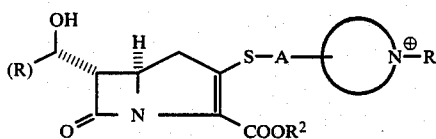

wherein A is C$_1$-C$_6$ straight or branched chain alkylene; R$^2$ is hydrogen, an anionic charge or a conventional readily removable carboxyl protecting group, providing that when R$^2$ is hydrogen or a protecting group, there is also present a counter ion; and

represents a radical of the formula

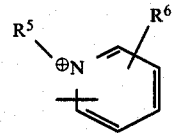
(a)

wherein R$^5$ is C$_1$-C$_4$ alkyl and R$^6$ represents hydrogen or C$_1$-C$_4$ alkyl.

12. A compound having the formula

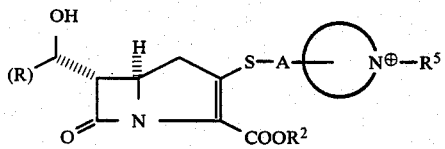

wherein A is C$_1$-C$_6$ straight or branched chain alkylene; R$^2$ is hydrogen, an anionic charge or a conventional readily removable carboxyl protecting group, providing that when R$^2$ is hydrogen or a protecting group, there is also present a counter ion; and

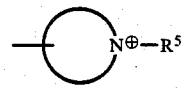

represents a radical of the formula

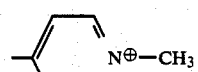
(a)

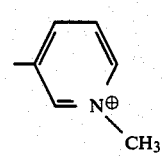
(b)

-continued

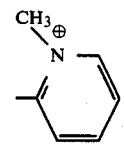
(c)

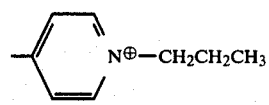
(d)

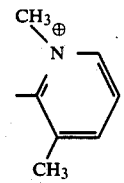
(e)

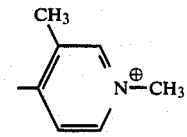
(r)

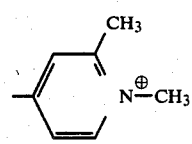
(s)

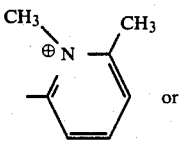
(t)

or

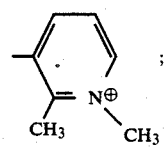
(u)

;

or a pharmaceutically acceptable salt thereof.

13. A compound having the formula

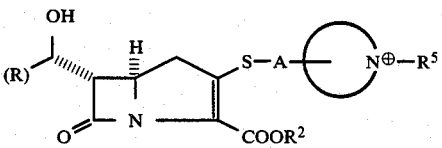

wherein R$^2$ is hydrogen, an anionic charge or a conventional readily removable carboxyl protecting group, providing that when R$^2$ is hydrogen or a protecting group, there is also present a counter ion and wherein

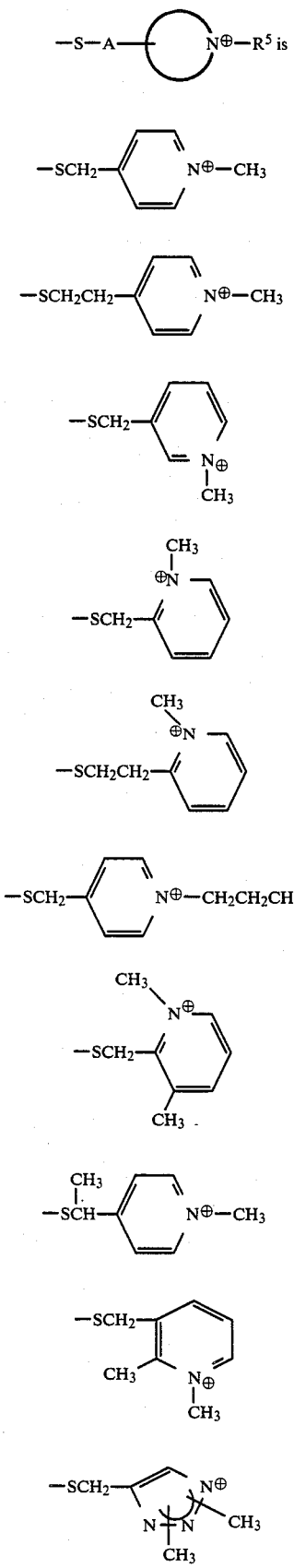

(a)
(b)
(c)
(d)
(e)
(f)
(g)
(l)
(n)
(p)

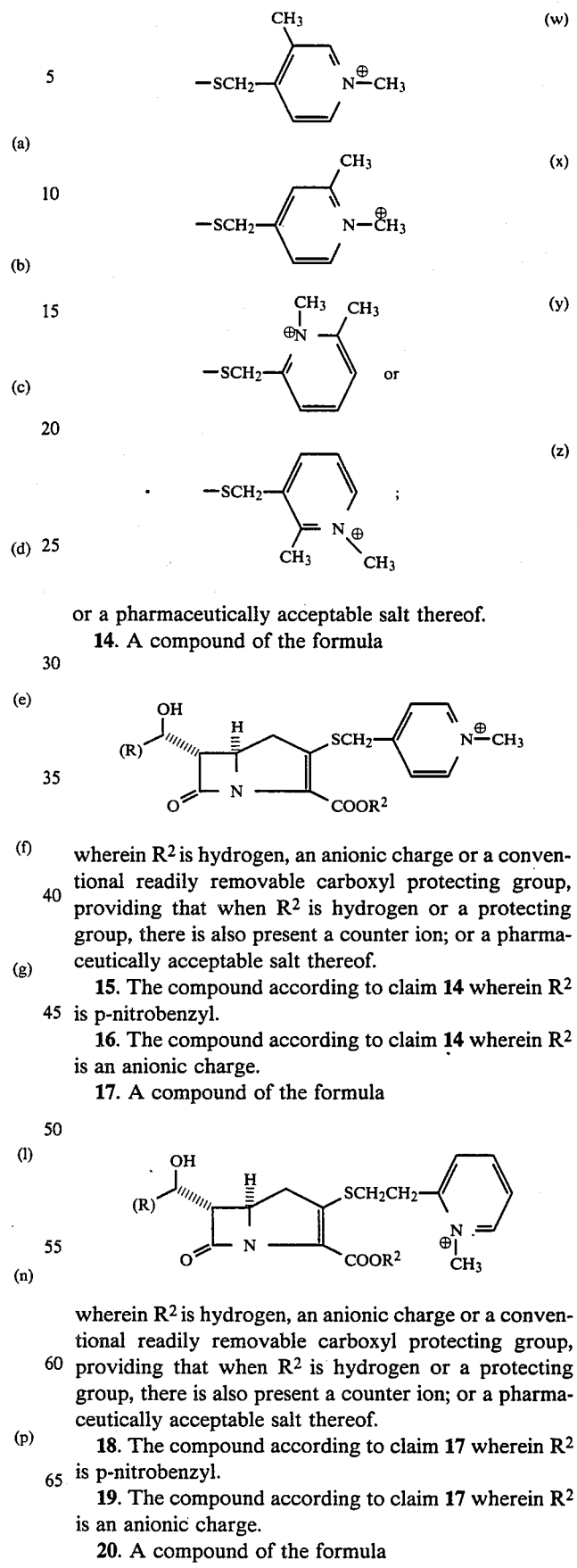

(w)
(x)
(y)
(z)

or a pharmaceutically acceptable salt thereof.

14. A compound of the formula wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

15. The compound according to claim 14 wherein $R^2$ is p-nitrobenzyl.

16. The compound according to claim 14 wherein $R^2$ is an anionic charge.

17. A compound of the formula wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

18. The compound according to claim 17 wherein $R^2$ is p-nitrobenzyl.

19. The compound according to claim 17 wherein $R^2$ is an anionic charge.

20. A compound of the formula

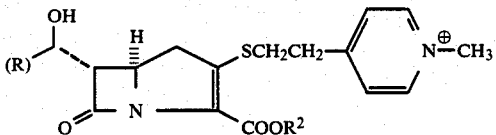

wherein R² is hydrogen, an anionic charge or a conventional readily removable carboxyl protecting group, providing that when R² is hydrogen or a protecting group, there is also present a counter ion; or a pharmaceutically acceptable salt thereof.

21. The compound according to claim 20 wherein R² is p-nitrobenzyl.

22. The compound according to claim 20 wherein R² is an anionic charge.

23. A compound of the formula

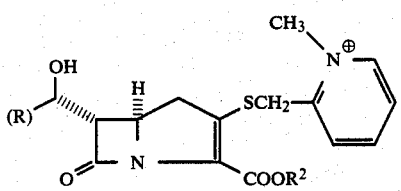

wherein R² is hydrogen, an anionic charge or a conventional readily removable carboxyl protecting group, providing that when R² is hydrogen or a protecting group, there is also present a counter ion; or a pharmaceutically acceptable salt thereof.

24. The compound according to claim 23 wherein R² is p-nitrobenzyl.

25. The compound according to claim 23 wherein R² is an anionic charge.

26. A compound of the formula

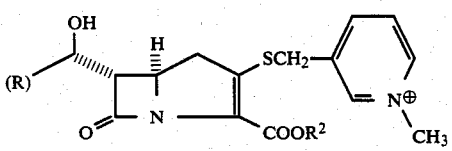

wherein R² is hydrogen, an anionic charge or a conventional readily removable carboxyl protecting group, providing that when R² is hydrogen or a protecting group, there is also present a counter ion; or a pharmaceutically acceptable salt thereof.

27. The compound according to claim 26 wherein R² is p-nitrobenzyl.

28. The compound according to claim 26 wherein R² is an anionic charge.

29. A compound of the formula

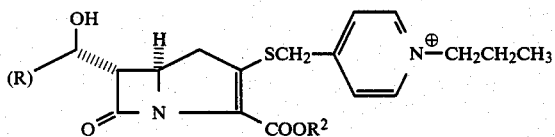

wherein R² is hydrogen, an anionic charge or a conventional readily removable carboxyl protecting group, providing that when R² is hydrogen or a protecting group, there is also present a counter ion; or a pharmaceutically acceptable salt thereof.

30. The compound according to claim 29 wherein R² is p-nitrobenzyl.

31. The compound according to claim 29 wherein R² is an anionic charge.

32. A compound of the formula

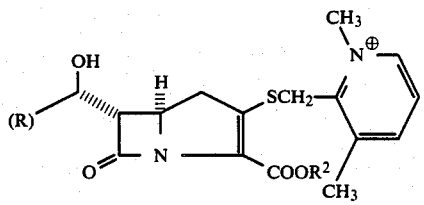

wherein R² is hydrogen, an anionic charge or a conventional readily removable carboxyl protecting group, providing that when R² is hydrogen or a protecting group, there is also present a counter ion; or a pharmaceutically acceptable salt thereof.

33. The compound according to claim 32 wherein R² is p-nitrobenzyl.

34. The compound according to claim 29 wherein R² is an anionic charge.

35. A compound of the formula

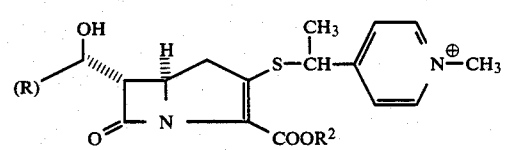

wherein R² is hydrogen, an anionic charge or a conventional readily removable carboxyl protecting group, providing that when R² is hydrogen or a protecting group, there is also present a counter ion; or a pharmaceutically acceptable salt thereof.

36. The compound according to claim 35 wherein R² is p-nitrobenzyl.

37. The compound according to claim 35 wherein R² is an anionic charge.

38. A compound of the formula

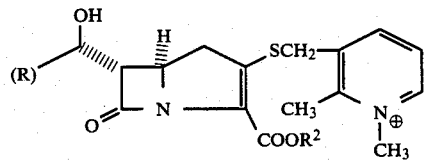

wherein R² is hydrogen, an anionic charge or a conventional readily removable carboxyl protecting group, providing that when R² is hydrogen or a protecting group, there is also present a counter ion; or a pharmaceutically acceptable salt thereof.

39. The compound according to claim 38 wherein R² is p-nitrobenzyl.

40. The compound according to claim 38 wherein R² is an anionic charge.

41. A compound of the formula

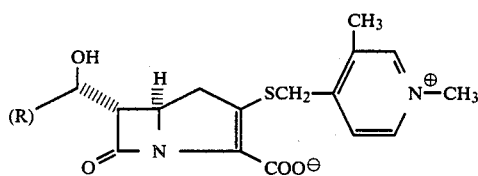

or a pharmaceutically acceptable salt or ester thereof.

42. A compound of the formula

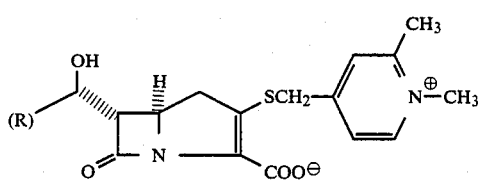

or a pharmaceutically acceptable salt or ester thereof.

43. A compound of the formula

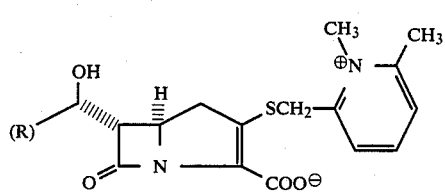

or a pharmaceutically acceptable salt or ester thereof.

44. A compound having the formula

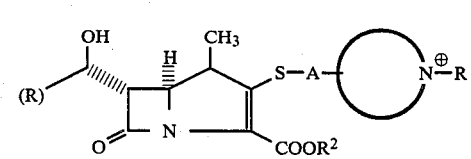

wherein A is $C_1$–$C_6$ straight or branched chain alkylene; $R^2$ is hydrogen, an anionic charge or a conventional readily removable carboxyl protecting group, providing that when $R^2$ is hydrogen or a protecting group, there is also present a counter ion; and

represents

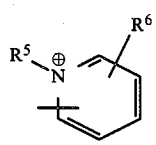

wherein $R^5$ is $C_1$–$C_4$ alkyl and $R^6$ represents hydrogen or $C_1$–$C_4$ alkyl; or a pharmaceutically acceptable salt thereof.

45. A compound having the formula

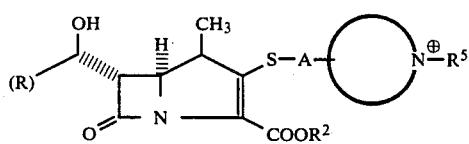

wherein A is $C_1$–$C_6$ straight or branched chain alkylene; $R^2$ is hydrogen, an anionic charge or a conventional readily removable carboxyl protecting group, providing that when $R^2$ is hydrogen or a protecting group, there is also present a counter ion; and

represents a radical of the formula

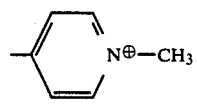 (a)

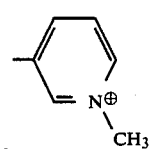 (b)

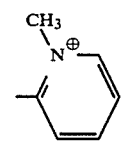 (c)

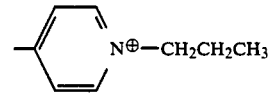 (d)

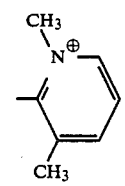 (e)

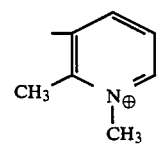 (k)

or

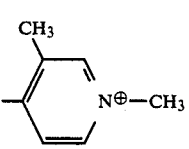 (r)

-continued

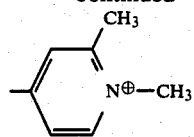 (s)

46. A compound of the formula

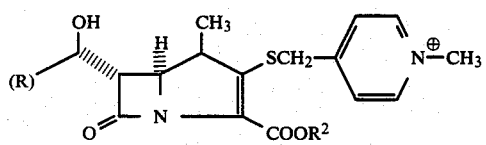

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

47. A compound of the formula

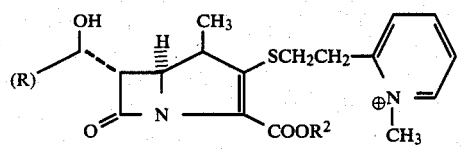

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

48. A compound of the formula

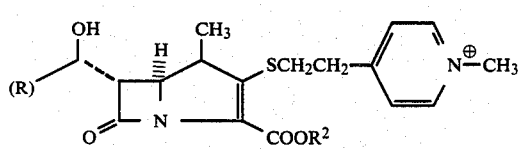

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

49. A compound of the formula

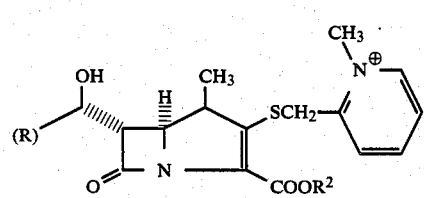

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

50. A compound of the formula

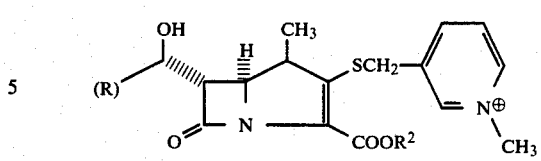

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

51. A compound of the formula

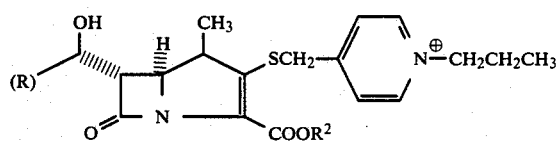

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

52. A compound of the formula

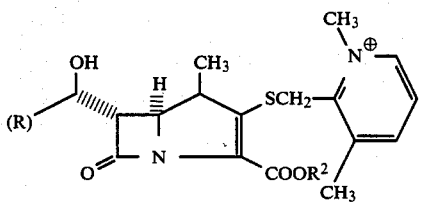

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

53. A compound of the formula

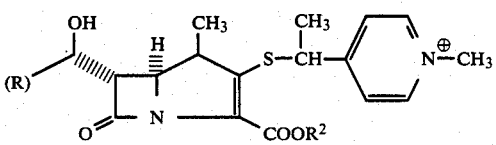

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

54. A compound of the formula

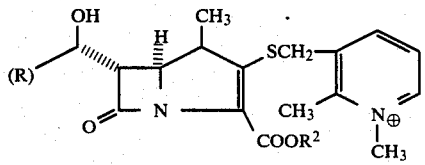

wherein $R^2$ is hydrogen, an anionic charge or a conventional readily removable carboxyl protecting group, providing that when $R^2$ is hydrogen or a protecting group, there is also present a counter ion; or a pharmacetically acceptable salt thereof.

55. A compound of the formula

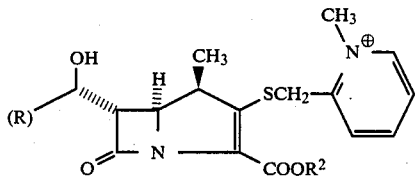

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

56. A compound of the formula

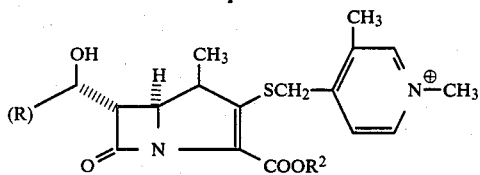

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

57. A compound of the formula

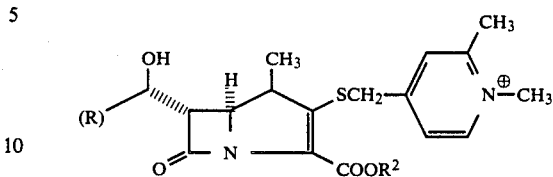

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

58. A compound of the formula

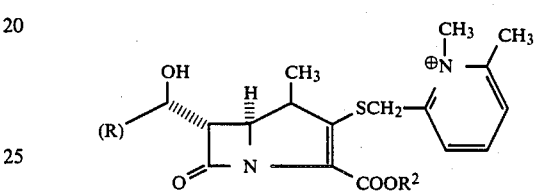

wherein $R^2$ is hydrogen, an anionic charge or a conventional readily removable carboxyl protecting group, providing that when $R^2$ is hydrogen or a protecting group, there is also present a counter ion; or a pharmaceutically acceptable salt thereof.

* * * * *